United States Patent
Allen et al.

(10) Patent No.: US 10,876,126 B2
(45) Date of Patent: Dec. 29, 2020

(54) METHODS FOR PRODUCING HYBRID SEED

(71) Applicant: Monsanto Technology LLC, St. Louis, MO (US)

(72) Inventors: Edwards Allen, O'Fallon, MO (US); Larry A. Gilbertson, Chesterfield, MO (US); James K. Roberts, Chesterfield, MO (US); Nancy M. Houmard, North Stonington, CT (US); Shihshieh Huang, Woodland, CA (US); Sergey Ivashuta, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 14/853,715

(22) Filed: Sep. 14, 2015

(65) Prior Publication Data

US 2016/0032300 A1    Feb. 4, 2016

Related U.S. Application Data

(63) Continuation of application No. 13/677,607, filed on Nov. 15, 2012, now Pat. No. 9,192,112, which is a continuation of application No. 12/089,891, filed as application No. PCT/US2006/036847 on Sep. 20, 2006, now Pat. No. 8,334,430.

(60) Provisional application No. 60/726,106, filed on Oct. 13, 2005, provisional application No. 60/836,246, filed on Aug. 7, 2006.

(51) Int. Cl.
*C12N 15/113* (2010.01)
*C12N 15/82* (2006.01)
*A01H 1/02* (2006.01)

(52) U.S. Cl.
CPC ..... *C12N 15/8218* (2013.01); *C12N 15/8274* (2013.01); *C12N 15/8286* (2013.01); *C12N 15/8287* (2013.01); *C12N 15/8289* (2013.01); *A01H 1/02* (2013.01); *C12N 15/8222* (2013.01); *C12N 15/8231* (2013.01); *C12N 15/8271* (2013.01); *C12N 15/8279* (2013.01)

(58) Field of Classification Search
None
See application file for complete search history.

(56) References Cited

U.S. PATENT DOCUMENTS

| | | |
|---|---|---|
| 4,535,060 A | 8/1985 | Comai |
| 4,735,649 A | 4/1988 | Dhingra et al. |
| 4,761,373 A | 8/1988 | Anderson et al. |
| 4,769,061 A | 9/1988 | Comai |
| 4,940,835 A | 7/1990 | Shah et al. |
| 4,971,908 A | 11/1990 | Kishore et al. |
| 5,034,322 A | 7/1991 | Rogers et al. |
| 5,068,193 A | 11/1991 | Comai |
| 5,094,945 A | 3/1992 | Comai |
| 5,188,642 A | 2/1993 | Shah et al. |
| 5,356,799 A | 10/1994 | Fabijanski et al. |
| 5,436,389 A | 7/1995 | Pfund |
| 5,484,956 A | 1/1996 | Lundquist et al. |
| 5,489,520 A | 2/1996 | Adams et al. |
| 5,554,798 A | 9/1996 | Lundquist et al. |
| 5,627,061 A | 5/1997 | Barry et al. |
| 5,633,435 A | 5/1997 | Barry et al. |
| 5,641,664 A | 6/1997 | D'Halluin et al. |
| 5,641,876 A | 6/1997 | McElroy et al. |
| 5,668,297 A | 9/1997 | Broer et al. |
| 6,040,497 A | 3/2000 | Spencer et al. |
| 6,046,382 A | 4/2000 | Mariani et al. |
| 6,057,496 A | 5/2000 | Conner |
| 6,072,110 A | 6/2000 | Henson |
| 6,255,564 B1 | 7/2001 | Fabijanski et al. |
| 6,384,304 B1 | 5/2002 | Quandt et al. |
| 6,448,476 B1 | 9/2002 | Barry |
| 6,476,291 B1 | 11/2002 | Conner |
| 6,646,186 B1 | 11/2003 | Stine et al. |
| 6,750,377 B1 | 6/2004 | Kaster, Jr. et al. |
| 6,762,344 B1 | 7/2004 | Spencer et al. |
| 6,825,400 B2 | 11/2004 | Behr et al. |
| 7,306,909 B2 | 12/2007 | Krieb et al. |
| 7,314,970 B2 | 1/2008 | Spencer et al. |
| 7,491,813 B2 | 2/2009 | Wu et al. |
| 7,554,012 B2 | 6/2009 | Barry |
| 7,615,678 B2 | 11/2009 | Flasinski |
| 7,750,207 B2 | 7/2010 | Wu et al. |
| 7,919,321 B2 | 4/2011 | Flasinski |
| 7,939,709 B2 | 5/2011 | Hawkes et al. |
| 8,158,850 B2 | 4/2012 | Feng et al. |
| 8,212,113 B2 | 7/2012 | Beazley et al. |

(Continued)

FOREIGN PATENT DOCUMENTS

DE    4126414 A1    2/1993
EP    0218571 A2    4/1987

(Continued)

OTHER PUBLICATIONS

Jones-Rhoades et al. Molecular Cell 14: 787-799 (Jun. 2004).*

(Continued)

*Primary Examiner* — David T Fox

(74) *Attorney, Agent, or Firm* — Arnold & Porter Kaye Scholer LLP; Amanda Carmany-Rampey; David R. Marsh

(57) ABSTRACT

This invention provides methods for producing a non-natural hybrid seed. Also disclosed are specific miRNAs and miRNA recognition sites useful for conferring inducible sterility on a crop plant, and recombinant DNA construct including such exogenous miRNA recognition sites.

13 Claims, 14 Drawing Sheets
Specification includes a Sequence Listing.

(56) References Cited

U.S. PATENT DOCUMENTS

| | | | |
|---|---|---|---|
| 8,217,227 | B2 | 7/2012 | Allen et al. |
| 8,334,430 | B2 | 12/2012 | Allen et al. |
| 8,344,211 | B2 | 1/2013 | Alexandrov et al. |
| 8,466,270 | B2 | 6/2013 | Flasinski |
| 8,618,358 | B2 | 12/2013 | Feng et al. |
| 9,212,370 | B2 * | 12/2015 | Allen ............... C12N 15/8216 |
| 2001/0023501 | A1 | 9/2001 | Johal et al. |
| 2002/0062499 | A1 | 5/2002 | Conner et al. |
| 2003/0106096 | A1 | 6/2003 | Barry |
| 2004/0034888 | A1 | 2/2004 | Liu et al. |
| 2004/0053411 | A1 * | 3/2004 | Cullen ............... C12N 15/111 435/455 |
| 2004/0268441 | A1 * | 12/2004 | Vance ............... C12N 15/821 800/288 |
| 2005/0144669 | A1 * | 6/2005 | Reinhart ............ C12N 15/8218 800/285 |
| 2005/0150013 | A1 | 7/2005 | Hawkes et al. |
| 2006/0059581 | A1 | 3/2006 | Spencer et al. |
| 2006/0200878 | A1 | 9/2006 | Lutfiyya et al. |
| 2007/0011775 | A1 | 1/2007 | Allen et al. |
| 2007/0083947 | A1 | 4/2007 | Huang et al. |
| 2007/0083949 | A1 | 4/2007 | Huang et al. |
| 2007/0083950 | A1 | 4/2007 | Huang et al. |
| 2007/0083951 | A1 | 4/2007 | Huang et al. |
| 2007/0083952 | A1 | 4/2007 | Huang et al. |
| 2007/0089184 | A1 | 4/2007 | Huang et al. |
| 2007/0089185 | A1 | 4/2007 | Huang et al. |
| 2007/0089186 | A1 | 4/2007 | Huang et al. |
| 2007/0089187 | A1 | 4/2007 | Huang et al. |
| 2007/0089188 | A1 | 4/2007 | Huang et al. |
| 2007/0089189 | A1 | 4/2007 | Huang et al. |
| 2007/0089190 | A1 | 4/2007 | Huang et al. |
| 2007/0089191 | A1 | 4/2007 | Huang et al. |
| 2007/0089192 | A1 | 4/2007 | Huang et al. |
| 2007/0089193 | A1 | 4/2007 | Huang et al. |
| 2007/0089194 | A1 | 4/2007 | Huang et al. |
| 2007/0089195 | A1 | 4/2007 | Huang et al. |
| 2007/0089196 | A1 | 4/2007 | Huang et al. |
| 2007/0094748 | A1 | 4/2007 | Huang et al. |
| 2007/0113301 | A1 | 5/2007 | Huang et al. |
| 2007/0113302 | A1 | 5/2007 | Huang et al. |
| 2007/0118917 | A1 | 5/2007 | Huang et al. |
| 2007/0118918 | A1 | 5/2007 | Huang et al. |
| 2007/0130645 | A1 | 6/2007 | Wu et al. |
| 2007/0199095 | A1 | 8/2007 | Allen et al. |
| 2007/0209085 | A1 | 9/2007 | Wu et al. |
| 2007/0300329 | A1 | 12/2007 | Allen et al. |
| 2008/0229456 | A1 | 9/2008 | Huang et al. |
| 2009/0013434 | A1 | 1/2009 | Huang et al. |
| 2009/0165166 | A1 | 6/2009 | Feng et al. |
| 2009/0293148 | A1 | 11/2009 | Ren et al. |
| 2010/0223694 | A1 | 9/2010 | Lutfiyya et al. |
| 2011/0126310 | A1 | 5/2011 | Feng et al. |
| 2011/0150832 | A1 | 6/2011 | Nemunaitis et al. |
| 2012/0317680 | A1 | 12/2012 | Feng et al. |
| 2013/0007908 | A1 | 1/2013 | Huang et al. |
| 2013/0074213 | A1 | 3/2013 | Kim et al. |
| 2013/0291138 | A1 | 10/2013 | Feng et al. |
| 2014/0007288 | A1 | 1/2014 | Flasinski |
| 2014/0109250 | A1 | 4/2014 | Feng et al. |

FOREIGN PATENT DOCUMENTS

| | | | |
|---|---|---|---|
| EP | 0242236 | A1 | 10/1987 |
| EP | 0242246 | A1 | 10/1987 |
| EP | 0290395 | A2 | 11/1988 |
| EP | 0329308 | A2 | 8/1989 |
| EP | 0348348 | A2 | 12/1989 |
| EP | 0353908 | A2 | 2/1990 |
| EP | 0360750 | A2 | 3/1990 |
| EP | 0242236 | B1 | 10/1990 |
| EP | 0426641 | A2 | 5/1991 |
| EP | 0469273 | A1 | 2/1992 |
| EP | 0242246 | B1 | 11/1992 |
| EP | 0218571 | B1 | 2/1993 |
| EP | 0290395 | B1 | 1/1994 |
| EP | 0353908 | B1 | 5/1995 |
| EP | 0348348 | B1 | 8/2000 |
| EP | 0426641 | B1 | 9/2000 |
| EP | 0329308 | B1 | 10/2001 |
| EP | 0469273 | B1 | 12/2003 |
| EP | 0975778 | B1 | 6/2007 |
| FR | 2661421 | A1 | 10/1991 |
| WO | WO 87/05629 | A1 | 9/1987 |
| WO | WO 90/08828 | A2 | 8/1990 |
| WO | WO 91/02071 | A2 | 2/1991 |
| WO | WO 91/09948 | A1 | 7/1991 |
| WO | WO 91/10725 | A1 | 7/1991 |
| WO | WO 92/04449 | A1 | 3/1992 |
| WO | WO 95/06128 | A2 | 3/1995 |
| WO | WO 97/04103 | A2 | 2/1997 |
| WO | WO 97/04114 | A2 | 2/1997 |
| WO | WO 97/06269 | A1 | 2/1997 |
| WO | WO 97/23634 | A2 | 7/1997 |
| WO | WO 97/46690 | A1 | 12/1997 |
| WO | WO 99/46396 | A2 | 9/1999 |
| WO | WO 99/46396 | A3 | 10/1999 |
| WO | WO 01/44457 | A2 | 6/2001 |
| WO | WO 02/26995 | A1 | 4/2002 |
| WO | WO 02/078427 | A2 | 10/2002 |
| WO | WO 2004/009779 | A2 | 1/2004 |
| WO | WO 2005/035769 | A2 | 4/2005 |
| WO | WO 2006/073727 | A2 | 7/2006 |
| WO | WO 2006/074400 | A2 | 7/2006 |
| WO | WO 2006/111512 | A1 | 10/2006 |
| WO | WO 2006/138638 | A1 | 12/2006 |
| WO | WO 2007/047016 | A2 | 4/2007 |
| WO | WO 2007/047016 | A3 | 2/2008 |
| WO | WO 2009/085982 | A1 | 7/2009 |
| WO | WO 2010/099084 | A2 | 9/2010 |
| WO | WO 2010/117735 | A1 | 10/2010 |
| WO | WO 2010/117737 | A8 | 6/2011 |

OTHER PUBLICATIONS

Cheng et al. Proc. Natl. Acad. Sci. USA 95: 2767-2772 (1998).*
Park et al. Current Biology 12: 1484-1495 (2002).*
Jesse et al. Oecologia 125: 241-248 (2000).*
Reinhart et al. Genes and Development 16: 1616-1626 (2002).*
Rhoades et al. Cell 110: 513-520 (2002).*
Axtell et al., "Antiquity of MicroRNAs and Their Targets in Land Plants," *The Plant Cell*, 17:1658-1673 (2005).
Achard et al., "Modulation of floral development by a gibberellin-regulated microRNA," *Development*, 131:3357-3365 (2004).
Advisory Action dated Mar. 27, 2015, in U.S. Appl. No. 13/677,607 (3 pgs.).
Allen et al., "Evolution of microRNA genes by inverted duplication of target gene sequences in *Arabidopsis thaliana*," *Nature Genetics*, 36(12):1282-1290 (2004).
Amrhein, et al., "Biochemical basis for glyphosate-tolerance in a bacterium and a plant tissue culture," *FEBS*,157(1):191-196 (1983).
Anderson, "Spread of Perennial Weeds," *Weed Science*, 13-15 (1983).
Appeal Brief filed Jan. 30, 2012, in U.S. Appl. No. 12/089,891 (23 pgs.).
Ashton, et al., "Mode of Action of Herbicides," *John Wiley & Sons*, vii-viii (1981).
Balthazor et al., "Glyphosate-Degrading Microorganisms from Industrial Activated Sludge," *Applied Environ. Microbiol.*, 51(2):432-434 (1986).
Bishop, "Two Teams Place Genes Into Corn," *The Wall Street Journal*, B1 (1990).
Chasan, "Transforming Maize Transformation," *The Plant Cell*, 4:1463-1464 (1992).
Chen et al., "Expression of CP4 EPSPS in microspores and tapetum cells of cotton (*Gossypium hirsutum*) is critical for male reproductive development in response to late-stage glyphosate applications," *Plant Biotech. J.*, 4:477-487 (2006).

(56) References Cited

OTHER PUBLICATIONS

Christou et al., "Stable Transformation of Soybean Callus by DNA-Coated Gold Particles," *Plant Physiol*, 87:671-674 (1988).
Christou, "Genetic transformation of crop plants using microprojectile bombardment," *The Plant Journal*, 2(3):275-281 (1992).
Clark, "Biotech Advance in Corn," *AG Consultant*, 12 (1990).
Cocking et al., "Gene Transfer in Cereals," *Science Mag.*, 236:1259-1262 (1987).
Comai et al., "An Altered aroA Gene Product Confers Resistance to the Herbicide Glyphosate," 221:370-371 (1983).
Comai et al., "Expression in plants of a mutant aroA gene from *Salmonella typhimurium* confers tolerance to glyphosate," *Nature*, 317:741-744 (1985).
Communication pursuant to Article 94(3) EPC dated Apr. 24, 2014, as received in European Patent Application No. 06 815 113.3 (4 pgs.).
Communication pursuant to Article 94(3) EPC dated Aug. 5, 2010, as received in European Patent Application No. 06 815 113.3 (4 pgs.).
Communication pursuant to Article 94(3) EPC dated Dec. 23, 2014, as received in European Patent Application No. 06 815 113.3 (4 pgs.).
Communication pursuant to Article 94(3) EPC dated Nov. 11, 2011, as received in European Patent Application No. 06 815 113.3 (4 pgs.).
Communication pursuant to Article 94(3) EPC dated Nov. 12, 2012, as received in European Patent Application No. 06 815 113.3 (4 pgs.).
d'Amato et al., "Subcellular localization of chorismate-mutase isoenzymes in protoplasts from mesophyll and suspension-cultured cells of *Nicotiana silvestris,*" *Planta*, 162:104-108 (1984).
D'Halluin et al., "Transgenic Maize Plants by Tissue Electroporation," *The Plant Cell*, 4:1495-1505 (1992).
De Block et al., "Engineering herbicide resistance in plants by expression of a detoxifying enzyme," *The EMBO Journal*, 6(9):2513-2518 (1987).
De Block et al., "Transformation of *Brassica napus* and *Brassica oleracea* Using *Agrobacterium tumefaciens* and the Expression of the bar and neo Genes in the Transgenic Plants," *Plant Physiol.*, 91:694-701 (1989).
Devine, "Why are there not more herbicide-tolerant crops?" *Pest Manag. Sci.*, 61:312-317 (2005).
EMBL Online Database Accession No. BZ797057, "PUGBJ25TD ZM_0.6_1.0_KB *Zea mays* genomic clone ZMMBTa329F02, DNA sequence," pp. 1 (2003).
Esquela-Kerscher et al., "The age of high-throughput microRNA profiling," *Nature Methods*, 1(2): 106-107 (2004).
Evans, "Somaclonal Variation—Genetic Basis and Breeding Applications," *Trends in Genetics*, 5:46-50 (1989).
Examiner's Report dated Aug. 5, 2010, as received in Australian Patent Application No. 2006302969 (2 pgs.).
Final Office Action dated Jan. 2, 2015, in U.S. Appl. No. 13/677,607 (23 pgs.).
Final Office Action dated Mar. 11, 2010 in U.S. Appl. No. 11/524,564 (11 pgs.).
Final Office Action dated Mar. 29, 2011, in U.S. Appl. No. 12/089,891 (18 pgs.).
First Office Action dated Oct. 12, 2010, as received in Chinese Patent Application No. 200680046237.7 (17 pgs.).
Fraley et al., "Expression of bacterial genes in plant cells," *PNAS*, 80:4803-4807 (1983).
Fransz et al., Isozymes as biochemical and cytochemical markers in embryogenic callus cultures of maize (*Zea mays* L.), *Plant Cell Reports*, 8:67-70 (1989).
Frascaroli et al., "Variability of pollen and plant responses to glyphosate in maize," *J. Genet. & Breed*, 46:4-56 (1992).
Fromm et al., "Inheritance and Expression of Chimeric Genes in the Progeny of Transgenic Maize Plants," *Biotechnology*, 8:833-839 (1990).
Fromm, "Gene guns succeed in altering corn," *Biotechnology*, 10(11):2-3 (1990).
Gandikota et al., "The miRNA 156/157 recognition element in the 3' UTR of the *Arabidopsis* SBP box gene SPL3 prevents early flowering by translational inhibition in seedlings," *The Plant Journal*, 49:683-693 (2007).
Fujiyama, GenBank Accession No. AG057893, pp. 1-2 (2001).
Goodman et al., "Gene Transfer in Crop Improvement," *Science*, 236(4797):48-54 (1987).
Gordon-Kamm et al., "Transformation of Maize Cells and Regeneration of Fertile Transgenic Plants," *The Plant Cell*, 2:603-618 (1990).
Guilley et al., "Transcription of Cauliflower Mosaic Virus DNA: Detection of Promoter Sequences, and Characterization of Transcripts," *Cell*, 30:763-773 (1982).
Gunset, "Corn Farmers See Economic, Environmental Gold in Designer Genes," *Chicago Tribune*, (1991).
Gunset, "Genetic Advance May Transform Corn," *Chicago Tribune*, (1990).
Hallas et al., "Characterization of microbial traits associated with glyphosate biodegradation in industrial activated sludge," *J. Industrial Microbiol.*, 3:377-385 (1988).
Hamilton et al., "Two classes of short interfering RNA in RNA silencing," *The EMBO Journal*, 21(17):4671-4679 (2002).
Han et al., "Relationship between small antisense RNAs and aberrant RNAs associated with sense transgene mediated gene silencing in tomato," *The Plant Journal*, 29(4):509-519 (2002).
Hansen et al., "Recent advances in the transformation of plants," *Trends in Plant Science*, 4(6)226-231 (1999).
Howe et al., Development of Glyphosate as a Selectable Marker for the Production of Fertile Transgenic Corn Plants, *In Vitro Cellular & Develop. Biol.*, 28(3)(2):124a (1992).
International Search Report dated Oct. 19, 2007, in International Patent Appln. No. PCT/US2006/036847 (7 pgs.).
International Search Report dated Sep. 28, 2012, in International Patent Appln. No. PCT/US2012/045040 (10 pgs.).
Jacob et al., "Metabolism o glyphosate in *Pseudomonas* sp. Strain LBr.," *Applied Environ. Microbiol.*, 54(12):2953-2958 (1988).
Jensen, "The shikimate/arogenate pathway: Link between carbohydrate metabolism and secondary metabolism," *Physiol Plant*, 66:164-168 (1985).
Johnson et al., "CSRDB: a small RNA integrated database and browser resource for cereals," *Nucleic Acids Research*, Database Issue:D829-D833 (2007).
Keystone Crops, "Ecogen and Evans Biocontrol: The Failure of a "Low-Risk" Strategy," *Agricultural Genetics Report*, 9:2-3 (1990).
Kidner et al., "Spatially restricted microRNA directs leaf polarity through ARGONAUTE1," *Nature*, 428:81-84 (2004).
Klahre et al., "High molecular weight RNAs and small interfering RNAs induce systemic posttranscriptional gene silencing in plants," *PNAS*, 99(18):11981-11986 (2002).
Klein et al., "Applications of the Particle Gun in Plant Biology," *Progress in plant, papers*, 56-66 (1990).
Klein et al., "Genetic Transformation of Maize Cells by Particle Bombardment," *Plant Physiol.*, 91:440-444 (1989).
Klein et al., "Genetic Transformation of Maize Cells by Particle Bombardment and the Influence of Methylation on Foreign-Gene Expression," *Pletnum Press*, 265-288 (1990).
Kumpatla et al., "Genome intruder scanning and modulation systems and transgene silencing," *Trends in Plant Science*, 3(3):97-104 (1998).
Leemans, "Genetic engineering for fertility control," *In Vitro Cellular & Develop. Biol.*, 28(3):51A (1992).
Lemaux et al., "Selection of Stable Transformants from Maize Suspension Cultures using the Herbicide Bialaphos," *J. Cellular Biochem.*, 44(14E):304 (1990).
Liu et al., "Degradation of the Herbicide Glyphosate by Members of the Family Rhizobiaceae," *Applied Environ. Microbiol.*, 57(6):1799-1804 (1991).
Mallory et al., "MicroRNA-Directed Regulation of *Arabidopsis* Auxin Response Factor17 is Essential for Proper Development and Modulates Expression of Early Auxin Response Genes," *The Plant Cell*, 17:1360-1375 (2005).

(56) References Cited

OTHER PUBLICATIONS

Mansoor et al., "Engineering novel traits in plants through RNA interference," *Trends Plant Sci.*, 11(11):559-565 (2006).

Marshall et al., "Studies on the Mode of Action of Asulam, Aminotriazole and Glyphosate in *Equisetum arvense* L. (Field Horsetail). II: The Metabolism of [$^{14}$C]Asulam, [$^{14}$C]Aminotriazole and [$^{14}$C]Glyphosate," *Pestic. Sci.*, 18:65-77 (1987).

McElroy et al., "Isolation of an Efficient Actin Promoter for Use in Rice Transformation," *The Plant Cell*, 2:163-171 (1990).

Meyer, "Understanding and controlling transgene expression," *Trends in Biotech.*, 13(9):332-337 (1995).

Millar et al., "The *Arabidopsis* GAMYB-Like Genes, MYB33 and MYB65, Are MicroRNA-Regulated Genes That Redundantly Facilitate Anther Development," *The Plant Cell*, 17:705-721 (2005).

miRBase Online Database Accession No. MI0001773, "Stem-loop sequence gma-MIR159a," undated.

Moffat, "Corn Transformed," *Science*, 249:630 (1990).

Molnar et al., "Silencing signals in plants: a long journey for small RNAs," *Genome Biology*, 12:215, pp. 1-8 (2011).

Mousdale et al., "Subcellular localization of the common shikimate-pathway enzymes in *Pisum sativum* L.," *Planta*, 163:241-249 (1985).

Murakami et al., "The bialaphos biosynthetic genes of *Streptomyces hygroscopicus*: Molecular cloning and characterization of the gene cluster," *Mol Gen Genet*, 205:42-50 (1986).

Murray et al., "Codon usage in plant genes," *Nucleic Acids Research*, 17(2):477-498 (1989).

Nafziger et al., "Selection and Characterization of a Carrot Cell Line Tolerant to Glyphosate," *Plant. Physiol.*, 76:571-574 (1984).

Netzer, "A tobacco plant that has been induced to regenerate in a flask," *BioTechnology*, 2(11):937-944 (1984).

Nobuta et al., "Distinct size distribution of endogeneous siRNAs in maize: Evidence from deep sequencing in the mop1-1 mutant," *PNAS*, 105(39):14958-14963 (2008).

Non-Final Office Action dated Apr. 20, 2012, in U.S. Appl. No. 12/089,891 (19 pgs.).

Non-Final Office Action dated Aug. 18, 2009, in U.S. Appl. No. 11/303,745 (8 pgs.).

Non-Final Office Action dated Jul. 1, 2009, in U.S. Appl. No. 11/524,564 (15 pgs.).

Non-Final Office Action dated Jul. 29, 2010, in U.S. Appl. No. 12/089,891 (17 pgs.).

Non-Final Office Action dated Jul. 3, 2014, in U.S. Appl. No. 13/677,607 (17 pgs.).

Non-Final Office Action dated Nov. 28, 2008, in U.S. Appl. No. 11/303,745 (28 pgs.).

Notice of Non-Compliant Amendment dated Oct. 13, 2010, in U.S. Appl. No. 12/089,891 (2 pgs.).

Notice of Reexamination dated Apr. 9, 2015, as received in Chinese Patent Application No. 200680046237.7 (11 pgs.).

Notification dated Apr. 28, 2015, as received in Eurasian Patent Application No. 200801074 (3 pgs.).

Nuovo et al., "A methodology for the combined in situ analyses of the precursor and mature forms of microRNAs and correlation with their putative targets," *Nat Protoc.*, 4(1):107-115 (2009).

Official Action dated Mar. 16, 2010, as received in Eurasian Patent Application No. 200801074 (6 pgs.).

Office Action dated Oct. 12, 2010, as received in Ukrainian Patent Application No. 200806024 (7 pgs.).

Office Action dated Feb. 13, 2012, as received in Canadian Patent Application No. 2,625,031 (3 pgs.).

Office Action dated Mar. 26, 2013, as received in Canadian Patent Application No. 2,625,031 (2 pgs.).

Office Action dated Jul. 30, 2014, as received in Canadian Patent Application No. 2,625,031 (2 pgs.).

Omirulleh et al.," Activity of a chimeric promoter with the doubled CaMV 35S enhancer element in protoplast-derived cells and transgenic plants in maize," *Plant Molecular Biology*, 21:415-428 (1993).

Oommen et al., "The Elicitor-Inducible Alfalfa Isoflavone Reductase Promoter Confers Different Patterns of Developmental Expression in Homologous and Heterologous Transgenic Plants," *The Plant Cell*, 6:1789-1803 (1994).

Padgette et al., "New Weed Control Opportunities: Development of Soybeans with a Roundup Ready™ Gene," *Herbicide-Resistant Crops*, 4:53-84 (1996).

Pang et al., "Nontarget DNA sequences reduce the transgene length necessary for RNA-mediated tospovirus resistance in transgenic plants," *Proc. Natl. Acad. Sci.*, 94:8261-8266 (1997).

Parizotto et al., "In vivo investigation of the transcription, processing, endonucleolytic activity, and functional relevance of the spatial distribution of a plant miRNA," *Genes Dev.*, 18:2237-2242 (2004).

Phillips et al., "Cell/tissue Culture and In Vitro Manipulation," *Corn and Corn Improvement*, 345-387 (1988).

Pipke et al., "Degradation of the Phosphonate Herbicide Glyphosate by *Arthrobacter atrocyaneus* ATCC 13752," *Applied Environ. Microbiol.*, 54(5):1293-1296 (1988).

Privalle et al., "Development of an Agricultural Biotechnology Crop Product: Testing from Discovery to Commercialization," *J. Agric. Food Chem.*, 60:10179-10187 (2012).

Puchta et al., "From centiMorgans to base pairs: homologous recombination in plants," *Trends in Plant Science*, 1(10):340-348 (1996).

Record of Interview, Preliminary Amendment and Supplemental Response to Restriction Requirement filed Apr. 24, 2009, in U.S. Appl. No. 11/524,564 (29 pgs.).

Response to Notice of Non-Compliant Reply and Amendment filed Feb. 14, 2011, in U.S. Appl. No. 12/089,891 (17 pgs.).

Response to Office Action and Amendment filed Dec. 1, 2009, in U.S. Appl. No. 11/524,564 (16 pgs.).

Response to Office Action and Amendment filed Jul. 20, 2012, in U.S. Appl. No. 12/089,891 (7 pgs.).

Response to Office Action and Amendment filed Oct. 3, 2014, in U.S. Appl. No. 13/677,607 (17 pgs.).

Response to Restriction Requirement dated Feb. 10, 2009 filed Apr. 10, 2009, in U.S. Appl. No. 11/524,564 (5 pgs.).

Restriction Requirement dated Feb. 10, 2009, in U.S. Appl. No. 11/524,564 (6 pgs.).

Rogers et al., "Amplification of the aroA gene from *Escherichia coli* results in tolerance to the herbicide glyphosate," *Applied Environ. Microbiol.*, 46(1):37-43 (1983).

Ross et al., "Transient and Stable Transgenic Cells and Calli of Tobacco and Maize following Microprojectile Bombardment," *J. Cellular Biochem.*, 41(13D):268 (1989).

Rothe et al., "Evidence for an intra- and extraplastidic prechorismate pathway," *Planta*, 157:358-366 (1983).

Rubin et al., "Enzymological Basis for Herbicidal Action of Glyphosate," *Plant Physiol.*, 70:833-839 (1982).

Rubin et al., "Glyphosate Inhibition of 5-Enolpyruvylshikimate 3-Phospate Synthase from Suspension-Cultured Cells of *Nicotiana silvestris,*" *Plant Physiol.*, 75:839-845 (1984).

Saijo et al., "Some properties of the Initial Four Enzymes Involved in Shikimic Acid Biosynthesis in Tea Plant," *Agric. Biol. Chem.*, 43(7):1427-1432 (1979).

Schmidt et al., "Rapid degradation of unassembled ribulose 1,5-bisphosphate carboxylase small subunits in chloroplasts," *PNAS*, 80:2632-2636 (1983).

Schowanek et al., "Phosphonate utilization by bacterial cultures and enrichments from environmental samples," *Appl. Environ. Microbiol.*, 56(4):895-903 (1990).

Second Office Action dated Mar. 19, 2012, as received in Chinese Patent Application No. 200680046237.7 (17 pgs.).

Second Preliminary Amendment filed Aug. 2, 2010, in U.S. Appl. No. 12/089,891 (7 pgs.).

Shah et al., "Engineering Herbicide Tolerance in Transgenic Plants," *Science*, 233:478-481 (1986).

Simon et al., "Small RNA-mediated epigenetic modifications in plants," *Current Opinion in Plant Biology*, 14:148-155 (2011).

Singh et al., "Chorismate Mutase Isoenzymes from *Sorghum bicolor*: Purification and Properties," *Archives of Biochem. & Biophysics*, 243(2):374-384 (1985).

(56) References Cited

OTHER PUBLICATIONS

Smart et al., "Selective Overproduction of 5-enol-Pyruvylshikimic Acid 3-Phosphate Synthase in a Plant Cell Culture Which Tolerates High Doses of the Herbicide Glyphosate," *J. Biol. Chem.*, 260(30):16338-16346 (1985).
Spencer et al., "Bialaphos selection of stable transformants from maize cell culture," *Theor Appl Genet*, 79:625-631 (1990).
Spencer et al., "Segregation of transgenes in maize," *Plant Molecular Biol.*, 18:201-210 (1992).
Stalker et al., "A Single Amino Acid Substitution in the Enzyme 5-Enolpyruvylshikimate-3-phospate Synthase Confers Resistance to the Herbicide Glyphosate," *J. Biol. Chem.*, 260(8):4724-4728 (1985).
Sun, "Engineering Crops to Resist Weed Killers," *Science*, 231:1360-1361 (1986).
Supplementary European Search Report dated Feb. 18, 2015, in European Patent Application No. 12 80 7530.6 (8 pgs.).
Supplementary European Search Report dated Jul. 29, 2009, as received in European Patent Application No. 06 815 113.3 (8 pgs.).
Thierry et al., "Sequence homology requirements for transcriptional silencing of 35S transgenes and post-transcriptional silencing of nitrite reductase (trans)genes by the tobacco 271 locus", *Plant Molecular Biol.*, 32:1075-1083 (1996).
Third Office Action dated Nov. 16, 2012, as received in Chinese Patent Application No. 200680046237.7 (14 pgs.).
Thomas et al., "Size constraints for targeting post-transcriptional gene silencing and for RNA-directed methylation in *Nicotiana benthamiana* using a potato virus X vector," *The Plant Journal*, 25(4):417-425 (2001).
Thompson et al., "Characterization of the herbicide-resistance gene bar from *Streptomyces hygroscopicus*," *The EMBO Journal*, 6(9):2519-2523 (1987).
Tones, "Practical and Applied Biotechnology: How to Make a Transgenic Plant," Bioreactorcrc, *WordPress*, pp. 1-22 (2008) <https://bioreactorcrc.wordpress.com/2008/02/02/comosehaceunaplantatransgenica/>.
Válóczi et al., "Spatio-temporal accumulation of mircoRNAs is highly coordinated in developing plant tissues," *The Plant Journal*, 47:140-151 (2006).
Van den Broek et al., "Targeting of a foreign protein to chloroplasts by fusion to the transit peptide from the small subunit of ribulose 1,5-biphosphate carboxylase," *Nature*, 313:358-363 (1985).
Wan et al., "Generation of Large Numbers of Independently Transformed Fertile Barley Plants," *Plant Physiol.*, 104:37-48 (1994).
Wang et al., "Control of Root Cap Formation by MicroRNA-Targeted Auxin Response Factors in *Arabidopsis*," *The Plant Cell*, 17:2204-2216 (2005).
Wang et al., "Development and validation of vectors containing multiple siRNA expression cassettes for maximizing the efficiency of gene silencing," *BMS Biotech.*, 6:50 (2006).
Weidhase et al., "Utilization of Glyphosate by *Pseudomonas spec.* GS," *Zentralbl. Mikrobiol.*, 145:433-438 (1990).
Weising et el., "Foreign Genes in Plants: Transfer, Structure, Expression, and Applications," *Annu. Rev. Genet.*, 22:421-477 (1988).
White et al., "A cassette containing the bar gene of *Streptomyces hygroscopicus*: a selectable marker for plant transformation," *Nucleic Acids Research*, 18(4):1062 (1990).
Wu et al., "Temporal regulation of Shoot Development in *Arabidopsis thaliana* by Mir156 and Its Target SPL3," *Development*,133(18):3539-3547 (2006).
Xie et al, "Expression of *Arabidopsis* MIRNA Genes," *Plant Phys.*, 138:2145-2154 (2005).
Extended European Search Report dated Apr. 19, 2018, in European Patent Application No. 17199834.7.

* cited by examiner

FIGURE 1
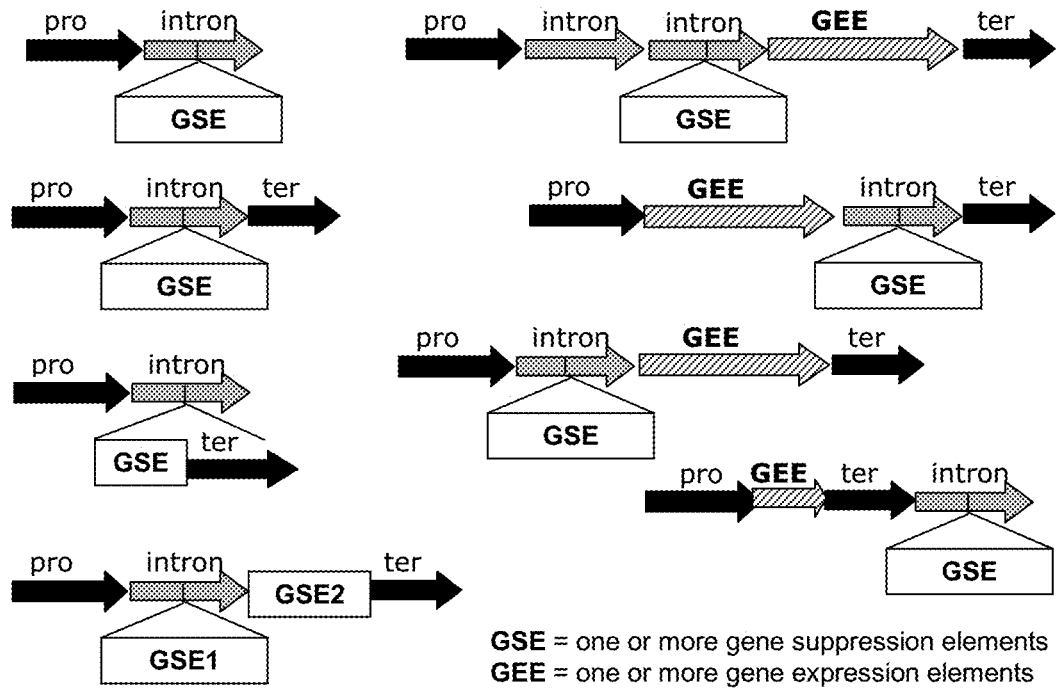
A
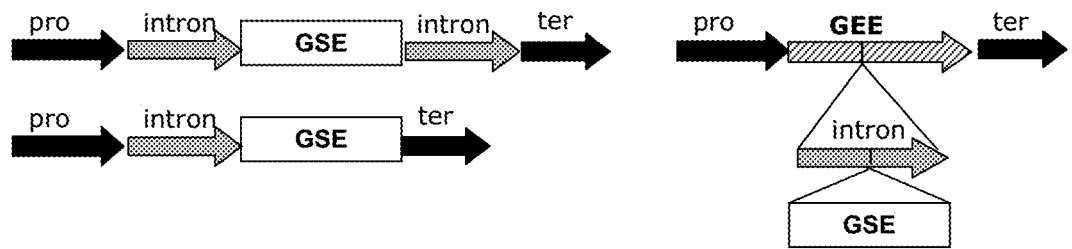
B

FIGURE 4

```
    ---------|---------|---------|---------|---------|
  1 acacgctgaaaccatcttccacacactcaagccacactattggagaacac  50

51 acagggacaacacaccataaccgccgccgccggtagaagATGGCGCCCAC 100
                                           M  A  P  T   5

101 CGTGATGATGGCCTCGTCGGCCACCGCCGTCGCTCCGTTCCaGGGGCTCA 150
  6  V  M  M  A  S  S  A  T  A  V  A  P  F  Q  G  L  K 22

151 AGTCCACCGCCAGCCTCCCCGTCGCCCGCCGCTCCTCCAGAAGCCTCGGC 200
 23  S  T  A  S  L  P  V  A  R  R  S  S  R  S  L  G   38

201 AACGTCAGCAACGGCGGAAGGATCCGGTGCATGCAGGTGTGGCCggcCTA 250
 39  N  V  S  N  G  G  R  I  R  C  M  Q  V  W  P  A  Y 55

251 CGGCAACAAGAAGTTCGAGACGCTGTCGTACCTGCCGCCGCTGTCGAccG 300
 56  G  N  K  K  F  E  T  L  S  Y  L  P  P  L  S  T  G 72

301 GCGGgcgcatccgctgcatgcaggcCATGgccTTCTTCAAcCGGGTgATc 350
 73  G  R  I  R  C  M  Q  A  M  A  F  F  N  R  V  I   88

351 ACCCTcACgGTgCCgTCgTCAGACGTGGTCAACTACTCgGAgATcTAcCA 400
 89  T  L  T  V  P  S  S  D  V  V  N  Y  S  E  I  Y  Q 105

401 GGTgGCTCCTCAGTATGTcAACCAgGCcCTGACccTGGCcAAGTAcTTcC 450
106  V  A  P  Q  Y  V  N  Q  A  L  T  L  A  K  Y  F  Q 122

451 AgGGCGCcATcGACGGcAGCACCCTgAGGTTCGAcTTCGAgAAgGCGTTA 500
123  G  A  I  D  G  S  T  L  R  F  D  F  E  K  A  L   138

501 CAgATcGCCAACGACATcCCCGCAggCcGCggTgGTcAACACCCTgAAcCA 550
139  Q  I  A  N  D  I  P  Q  A  A  V  V  N  T  L  N  Q 155

551 GACCGTCCAGCAGGGGACCGTCCAGGTCAGCGTcATGATCGAcAAGATcG 600
156  T  V  Q  Q  G  T  V  Q  V  S  V  M  I  D  K  I  V 172

601 TGGACATCATGAAgAATGTCCTGTCCATCGTGATAGAcAACAAGAAGTTT 650
173  D  I  M  K  N  V  L  S  I  V  I  D  N  K  K  F   188

651 TGGGATCAGGTCACGGCTGCcATcACcAAcACCTTCACGAAcCTGAACag 700
189  W  D  Q  V  T  A  A  I  T  N  T  F  T  N  L  N  S 205

701 cCAgGAgTCgGAggccTGGATCTTCTATTAcAAgGAgGACGCCCACAAGA 750
206  Q  E  S  E  A  W  I  F  Y  Y  K  E  D  A  H  K  T 222

751 CGTCcTAcTAtTAcAACATCCTCTTCGCcATCCAGGACGAAGAGACGGGt 800
223  S  Y  Y  Y  N  I  L  F  A  I  Q  D  E  E  T  G   238

801 GGcGTGATGGCcACgcTGCCCATCGCCTTCGACATCAGTGTgGACATCGA 850
239 G  V  M  A  T  L  P  I  A  F  D  I  S  V  D  I  E  255

851 GAAgGAgAAgGTCCTGTTCGTgACcATcAAGGAcACTGAGAATTACGCCG 900
256  K  E  K  V  L  F  V  T  I  K  D  T  E  N  Y  A  V 272

901 TCACCGTCAAGGCGATCAACGTGGTcCAGGCACTccAgTCTAGCAGGGAT 950
273  T  V  K  A  I  N  V  V  Q  A  L  Q  S  S  R  D   288

951 TCTAAGGTGGTTGATGCGTTCAAATCGCCaCGGCACTTACCCCGGAAGAG 1000
289 S  K  V  V  D  A  F  K  S  P  R  H  L  P  R  K  R  305

1001 GCATAAGATTTGCTCTAACTCGtgatgActgcTGGATGCAGAGGTATTAT 1050
306  H  K  I  C  S  N  *  *            miRNA162 site 1051 CGatgcgtttggacgtatgctcattcaggttggagccaatttggttgatg 1100

1101 tgtgtgcgagttcttgcgagtctgatgagacatctctgtattgtgtttct 1150

1151 ttccccagtgttttctgtacttgtgtaatcggctaatcgccaacagattc 1200

1201 ggcgatgaataaatgagaaataaattgttctgattttgagtg 1242
     ---------|---------|---------|---------|---------|
```

SEQ ID NO. 176

FIGURE 5

```
        ----------|----------|----------|----------|----------|
  1 ACACGCTGAcaagctGACTCTAGcagatCctctagaaccatcttccacac  50

51 actcaagccacactattggagaacacacagggacaacacaccataaGATC 100

101 CAAGGGAGGCCTCCGCCGCCGCCGGTAGAAGTGATCAACcATGgccTTCT 150
                                            M  A  F   6

151 TCAAcCGGGTgATcACCCTcACgGTgCCgTCgTCAGACGTGGTCAACTAC 200
  7  N  R  V  I  T  L  T  V  P  S  S  D  V  V  N  Y  22

201 TCgGAgATcTAcCAGGTgGCTCCTCAGTATGTcAACCAgGCcCTGACccT 250
 23  S  E  I  Y  Q  V  A  P  Q  Y  V  N  Q  A  L  T  L  39

251 GGCcAAGTAcTTcCAgGGCGCcATcGACGGcAGCACCCTgAGGTTCGAcT 300
 40  A  K  Y  F  Q  G  A  I  D  G  S  T  L  R  F  D  F  56

301 TCGAgAAgGCGTTACAgATcGCCAACGACATcCCGCAgGCcGCgGTgGTc 350
 57  E  K  A  L  Q  I  A  N  D  I  P  Q  A  A  V  V  72

351 AACACCCTgAAcCAGACCGTCCAGCAGGGGACCGTCCAGGTCAGCGTcAT 400
 73  N  T  L  N  Q  T  V  Q  Q  G  T  V  Q  V  S  V  M  89

401 GATCGAcAAGATcGTGGACATCATGAAgAATGTCCTGTCCATCGTGATAG 450
 90  I  D  K  I  V  D  I  M  K  N  V  L  S  I  V  I  D 106

451 AcAACAAGAAGTTTTGGGATCAGGTCACGGCTGCcATcACcAAcACCTTC 500
107  N  K  K  F  W  D  Q  V  T  A  A  I  T  N  T  F  122

501 ACGAAcCTGAACagcCAgGAgTCgGAGgccTGGATCTTCTATTAcAAgGA 550
123  T  N  L  N  S  Q  E  S  E  A  W  I  F  Y  Y  K  E  139

551 gGACGCCCACAAGACGTCcTAcTAtTAcAACATCCTCTTCGCcATCCAGG 600
140  D  A  H  K  T  S  Y  Y  Y  N  I  L  F  A  I  Q  D 156

601 ACGAAGAGACGGGtGGcGTGATGGCcACgcTGCCCATCGCCTTCGACATC 650
157  E  E  T  G  G  V  M  A  T  L  P  I  A  F  D  I  172

651 AGTGTgGACATCGAGAAgGAgAAgGTCCTGTTCGTgACcATCAAGGAcAC 700
173  S  V  D  I  E  K  E  K  V  L  F  V  T  I  K  D  T  189

701 TGAGAATTACGCCGTCACCGTCAAGGCGATCAACGTGGTcCAGGCACTcc 750
190  E  N  Y  A  V  T  V  K  A  I  N  V  V  Q  A  L  Q 206

751 AgTCTAGCAGGGATTCTAAGGTGGTTGATGCGTTCAAATCGCCaCGGCAC 800
207  S  S  R  D  S  K  V  V  D  A  F  K  S  P  R  H  222

801 TTACCCCGGAAGAGGCATAAGATTTGCTCTAACTCGtgatgAATgTACGT 850
223  L  P  R  K  R  H  K  I  C  S  N  S  *  *     miRNA164

851 GCCCTGCTTCTCCATCTGCATGCGTTTGGACGTATGCTCATTCAGGTTGG 900

901 AGCCAATTTGGTTGATGTGTGTGCGAGTTCTTGCGAGTCTGATGAGACAT 950

951 CTCTGT 956
        ----------|----------|----------|----------|----------|
```

SEQ ID NO. 177

FIGURE 6
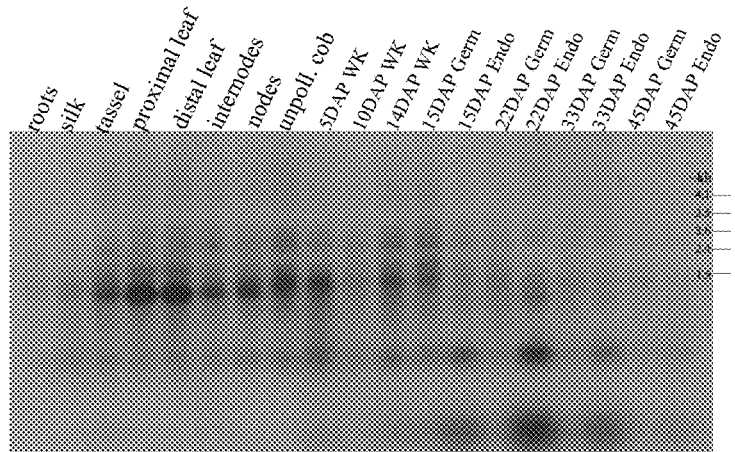
A
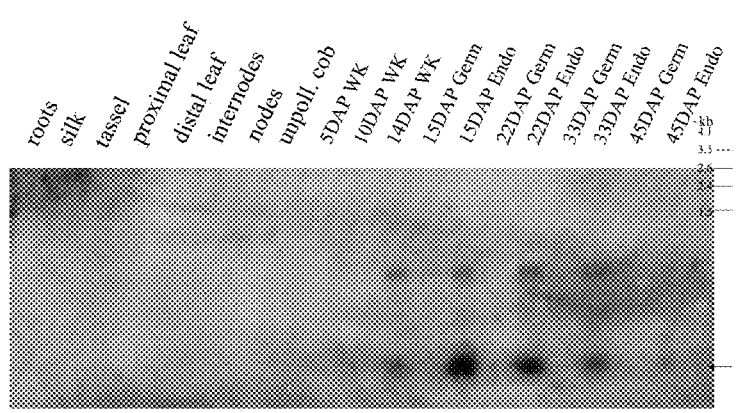
B
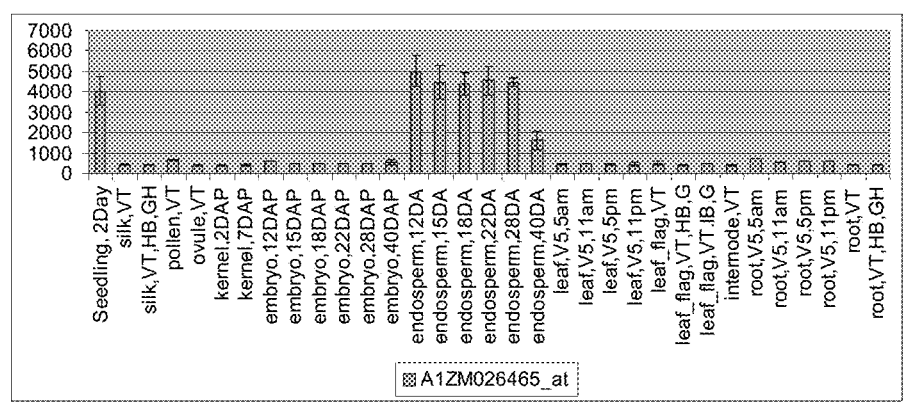
C

FIGURE 8
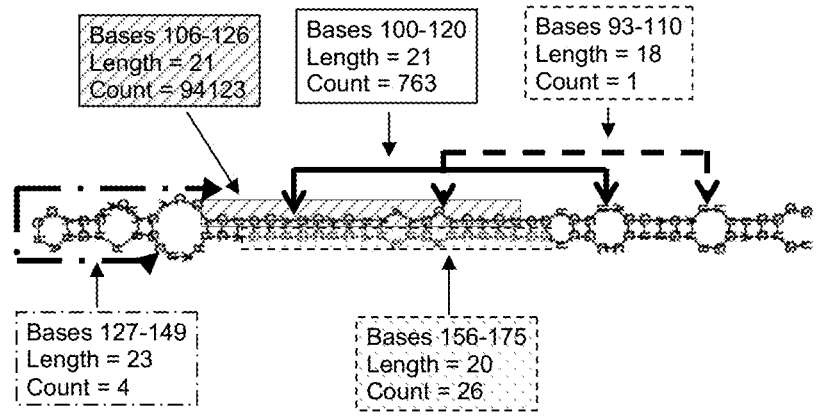
A
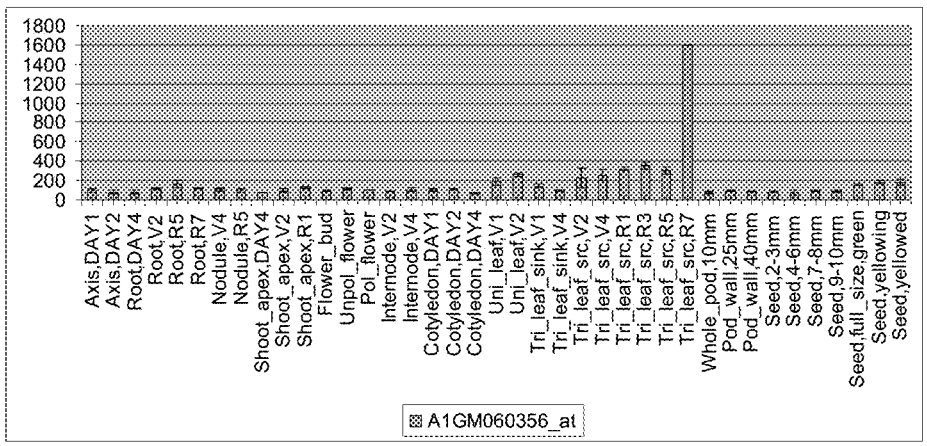
B
miRNA (3' - 5')    AGUCGACGAGUAAACCAGAGU (SEQ ID NO. 184)
Target (5' - 3') (bases 153-173)    Ccagcugcucauuuggcacu (SEQ ID NO. 200)
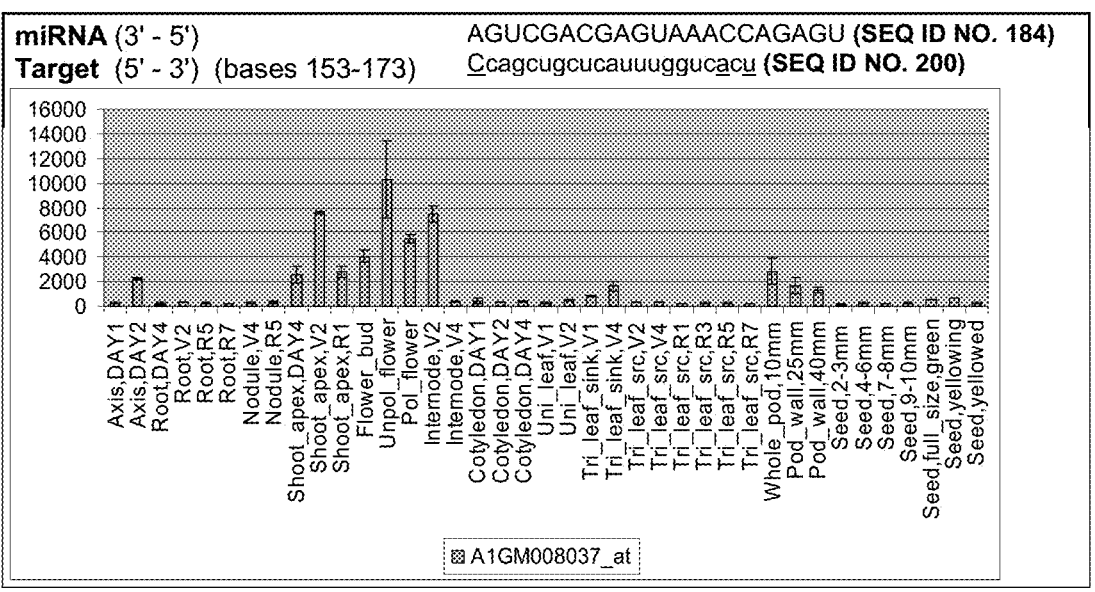
C

FIGURE 9
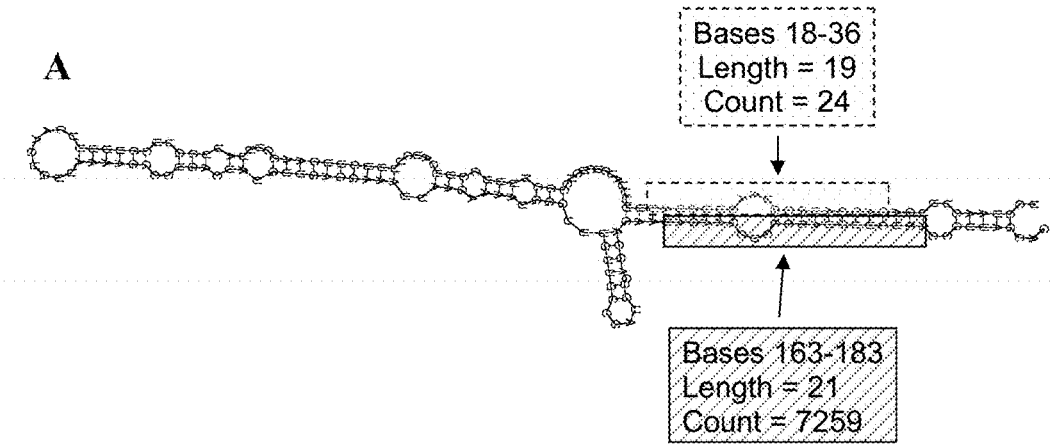
| | | |
|---|---|---|
| miRNA (3' - 5') | ACUCUUGUACCCCUCGAAGAU | (SEQ ID NO. 187) |
| Target (5' - 3') (bases 1111-1131) | Agaggacaugggga gguucua | (SEQ ID NO. 201) |
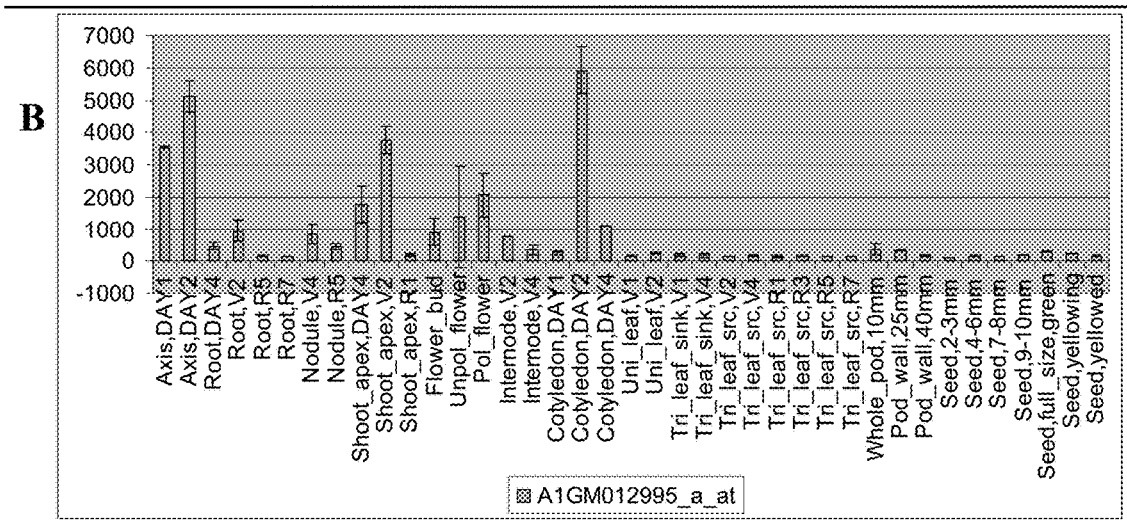

FIGURE 12
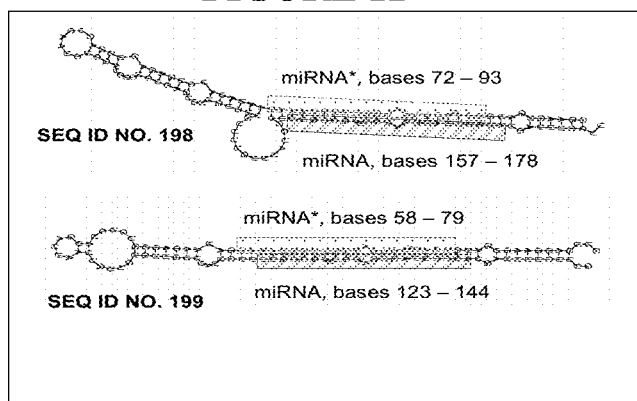
A
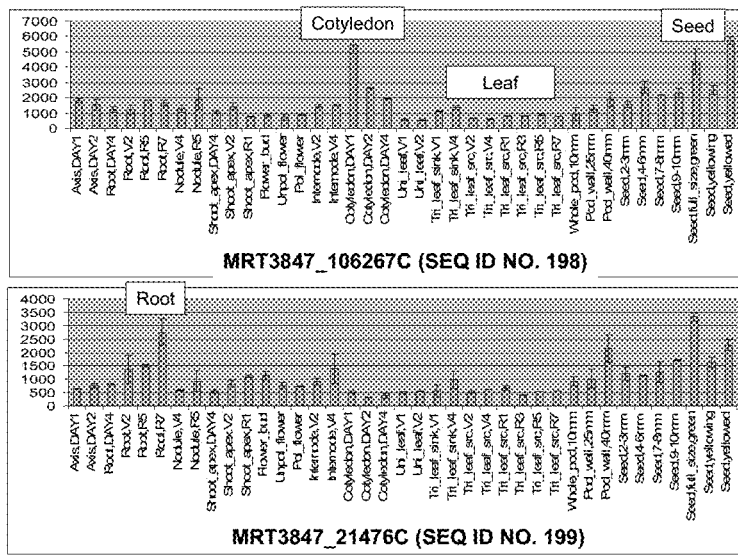
B

FIGURE 13
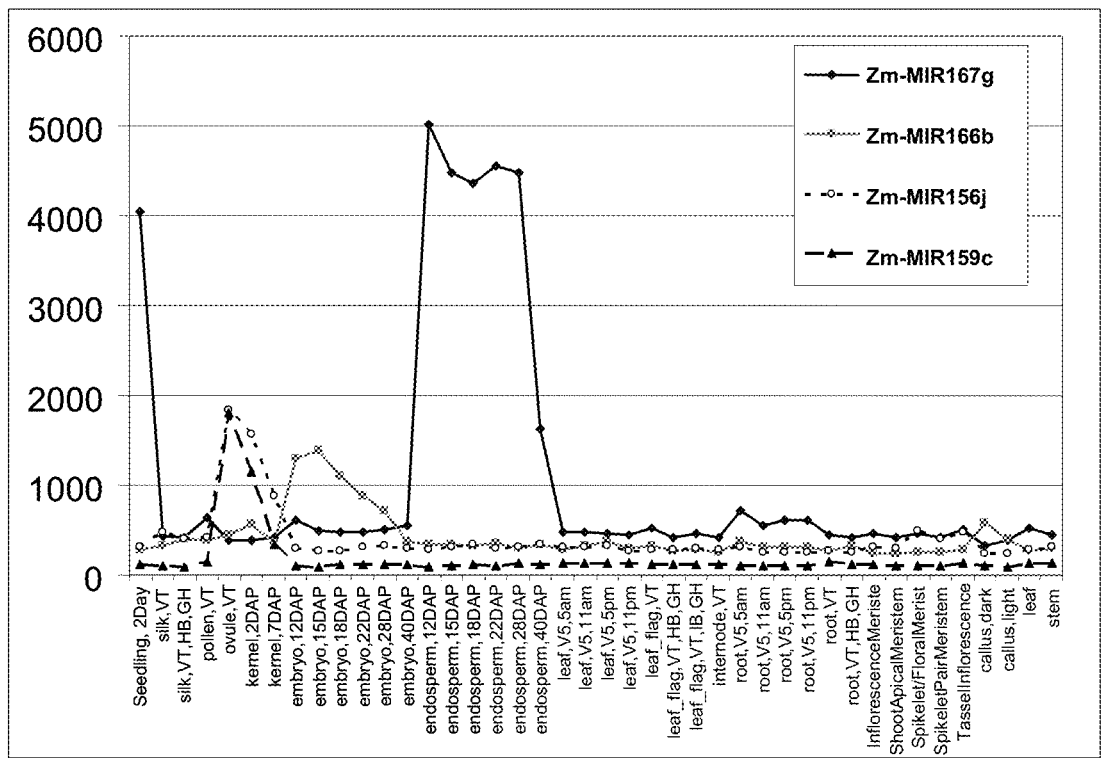
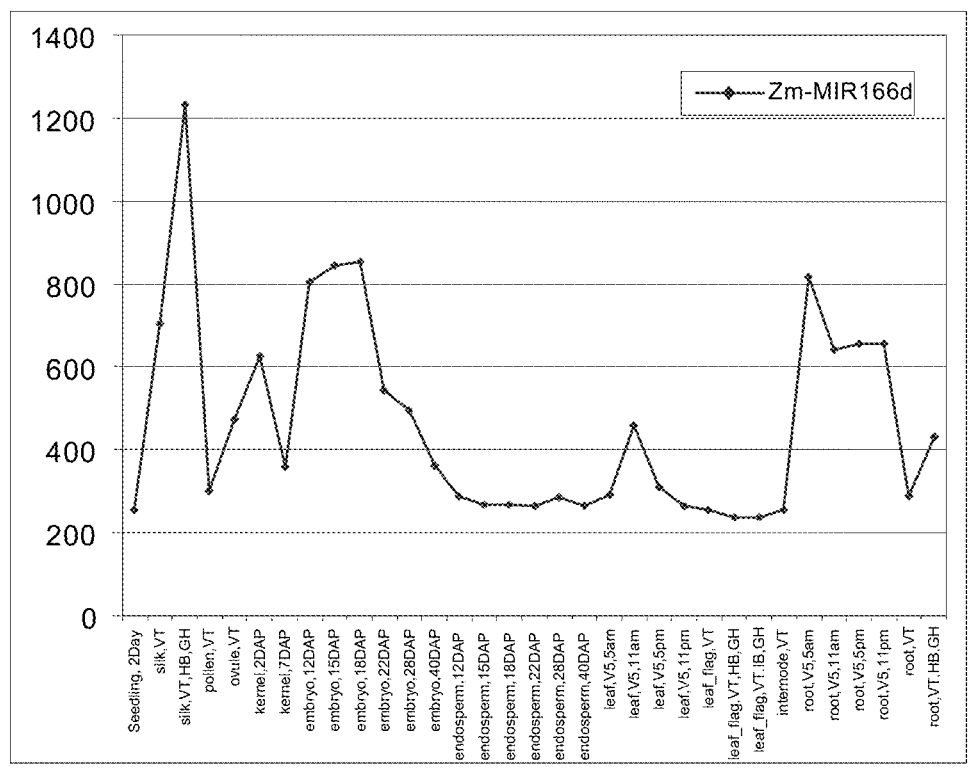

METHODS FOR PRODUCING HYBRID SEED

PRIORITY CLAIMS AND REFERENCE TO RELATED APPLICATIONS

This application is a continuation of U.S. patent application Ser. No. 13/677,607 filed Nov. 15, 2012 (U.S. Pat. No. 9,192,112), which is a continuation of U.S. patent application Ser. No. 12/089,891 filed on Oct. 14, 2008 (U.S. Pat. No. 8,334,430). U.S. patent application Ser. No. 12/089,891 is a U.S. National Stage Application of PCT/US2006/036847 filed on Sep. 20, 2006, which claims the benefit of priority to U.S. Provisional Patent Application Nos. 60/726,106 filed on Oct. 13, 2005, and 60/836,246 filed on Aug. 7, 2006, which are incorporated by reference in their entirety herein.

INCORPORATION OF SEQUENCE LISTINGS

A computer readable form of a sequence listing is filed with this application by electronic submission and is incorporated into this application by reference in its entirety. The sequence listing is contained in the file named P30837US05_SEQ.txt, which is 75,496 bytes in size (measured in operating system MS windows) and was created on Sep. 14, 2015.

FIELD OF THE INVENTION

This invention discloses methods for producing hybrid seed, and inducibly sterile, transgenic plants and molecular constructs useful in such methods.

BACKGROUND OF THE INVENTION

Hybrid seed, that is, seed produced by hybridization or cross-fertilization of closely related plants, can be grown into progeny hybrid plants possessing "hybrid vigor" or a desirable combination of traits not possessed by either parent plant (which are typically inbred plants). Hybrid plants can display superior agronomic performance characteristics, including improvement of plant size, yield, nutritional composition, disease resistance, herbicide tolerance, stress (heat, cold, drought, nutrient, salt) tolerance, climatic adaptation, and other desirable traits.

Efficient hybrid seed production requires that cross-pollination predominates over self-pollination. A major limitation in the production of hybrid seed for many crop species is the lack of simple, reliable and economical methods of generating sterility in at least one parent (especially the male parent, to result in male-sterility while leaving female gametes intact and accessible for pollination by a suitable pollen donor). Male sterility is also useful where pollen spread is not desirable, e.g., from a domestic plant to its wild relatives, or where flower fertilization is not desirable, e.g., in the case of ornamental flowers which deteriorate in condition after pollination.

Male sterility can be accomplished, for example, by physical removal of the organs containing the male gametes. In some species, this is a straightforward although labor-intensive and therefore expensive process (e.g., detasselling in maize). In other species, such physical emasculation is difficult because of the plant's anatomy. Alternative techniques that do not involve manual or physical emasculation could provide substantial economic savings.

Chemical gametocides have been also described as a method of generating male-sterile plants. Typically, such a chemical gametocide is an herbicidal compound that when applied to a plant at an appropriate developmental stage or before sexual maturity is capable of killing or effectively terminating the development of a plant's male gametes while leaving the plant's female gametes, or at least a significant proportion of them, capable of under going cross-pollination. For example, glyphosate tolerance has been genetically engineered into corn (U.S. Pat. No. 5,554,798), and use of the herbicide glyphosate (N-phosphonomethylglycine) as a gametocide, and transgenic plants that are vegetatively- and female-tolerant of glyphosate but male-sensitive to glyphosate, are disclosed in U.S. Pat. No. 4,735,649 and in PCT International Patent Application Publication WO99/46396A2. However, the levels of glyphosate necessary to kill most of the male gametes while leaving a sufficient number of female gametes still capable of fertilization often resulted in stunting or chlorosis of the plants. Thus, a major drawback of using glyphosate as a gametocide, as is generally true with most chemical gametocides, is the phytotoxic side effects resulting from lack of sufficient selectivity for gametes.

Commercial production of hybrid seed using chemical gametocides is limited primarily by their lack of selectivity for gametes in general. Compounds that possess some selectivity in targeting gametes to a greater extent than vegetative tissues are generally non-discriminating regarding the sex of the gametes destroyed. Thus, methods for improving the selectivity of a chemical gametocide would be highly desirable. Even more desirable would be methods that provide a first parent plant that is male-sterile, and a second parent plant that is female-sterile, thus ensuring that the seed produced are the result of hybridization between the two parent plants, and not of self-fertilization.

This invention provides methods of producing hybrid seed, and additionally provides recombinant DNA constructs, transgenic plant chromosomes, cells, plants, and seeds containing such constructs useful in these methods. The recombinant DNA constructs, transgenic plant chromosomes, cells, plants, and seeds, and methods for their use in making hybrid seed provide a greatly improved way to use herbicides as chemical gametocides. The recombinant DNA constructs of this invention include an exogenous microRNA recognition site, allowing expression of a messenger RNA encoding a protein imparting tolerance to an herbicide to be controlled by a microRNA endogenous to a plant in which the recombinant DNA construct is transcribed.

MicroRNAs (miRNAs) are non-protein coding RNAs, generally of between about 19 to about 25 nucleotides (commonly about 20-24 nucleotides in plants), that guide cleavage in trans of target transcripts, negatively regulating the expression of genes involved in various regulation and development pathways (Bartel (2004) *Cell*, 116:281-297). In some cases, miRNAs serve to guide in-phase processing of siRNA primary transcripts (see Allen et al. (2005) *Cell*, 121:207-221).

Some microRNA genes (MIR genes) have been identified and made publicly available in a database ('miRBase", available on line at microrna.sanger.ac.uk/sequences). The applicants have disclosed novel MIR genes, mature miRNAs, and miRNA recognition sites in U.S. patent application Ser. No. 11/303,745, filed 15 Dec. 2005. Additional MIR genes and mature miRNAs are also described in U.S. Patent Application Publications 2005/0120415 and 2005/144669A1. MIR genes have been reported to occur in inter-genic regions, both isolated and in clusters in the genome, but can also be located entirely or partially within introns of other genes (both protein-coding and non-protein-coding). For a recent review of miRNA biogenesis, see Kim (2005) *Nature Rev. Mol. Cell Biol.,* 6:376-385. Transcription of MIR genes can be, at least in some cases, under promotional control of a MIR gene's own promoter. MIR gene transcription is probably generally mediated by RNA polymerase II (see, e.g., Aukerman. and Sakai (2003) *Plant Cell,* 15:2730-2741; Parizotto et al. (2004) *Genes Dev.,* 18:2237-2242), and therefore could be amenable to gene silencing approaches that have been used in other polymerase II-transcribed genes. The primary transcript (which can be polycistronic) termed a "pri-miRNA", a miRNA precursor molecule that can be quite large (several kilobases) and contains one or more local double-stranded or "hairpin" regions as well as the usual 5' "cap" and polyadenylated tail of an mRNA. See, for example, FIG. 1 in Kim (2005) *Nature Rev. Mol. Cell Biol.,* 6:376-385.

In plant cells, microRNA precursor molecules are believed to be largely processed in the nucleus. In plants, miRNAs and siRNAs are formed by distinct DICER-like (DCL) enzymes, and in *Arabidopsis* a nuclear DCL enzyme is believed to be required for mature miRNA formation (Xie et al. (2004) *PLoS Biol.,* 2:642-652). Additional reviews on microRNA biogenesis and function are found, for example, in Bartel (2004) *Cell,* 116:281-297; Murchison and Hannon (2004) *Curr. Opin. Cell Biol.,* 16:223-229; and Dugas and Bartel (2004) *Curr. Opin. Plant Biol.,* 7:512-520. MicroRNAs can thus be described in terms of RNA (e.g., RNA sequence of a mature miRNA or a miRNA precursor RNA molecule), or in terms of DNA (e.g., DNA sequence corresponding to a mature miRNA RNA sequence or DNA sequence encoding a MIR gene or fragment of a MIR gene or a miRNA precursor).

MIR gene families are estimated to account for 1% of at least some genomes and capable of influencing or regulating expression of about a third of all genes (see, e.g., Tomari et al. (2005) *Curr. Biol.,* 15:R61-64; G. Tang (2005) *Trends Biochem. Sci.,* 30:106-14; Kim (2005) *Nature Rev. Mol. Cell Biol.,* 6:376-385). Because miRNAs are important regulatory elements in eukaryotes, including animals and plants, transgenic suppression of miRNAs could, for example, lead to the understanding of important biological processes or allow the manipulation of certain pathways (e.g., regulation of cellular differentiation, proliferation, and apoptosis) useful, for example, in biotechnological applications. See, for example, O'Donnell et al. (2005) *Nature,* 435:839-843; Cai et al. (2005) *Proc. Natl. Acad. Sci. USA,* 102:5570-5575; Morris and McManus (2005) *Sci. STKE,* pe41 (stke-.sciencemag.org/cgi/reprint/sigtrans;2005/297/pe41.pdf). MicroRNA (MIR) genes have identifying characteristics, including conservation among plant species, a stable foldback structure, and processing of a specific miRNA/miRNA* duplex by Dicer-like enzymes (Ambros et al. (2003) *RNA,* 9:277-279). These characteristics have been used to identify miRNAs and their corresponding genes in plants (Xie et al. (2005) *Plant Physiol.,* 138:2145-2154; Jones-Rhoades and Bartel (2004) *Mol. Cell,* 14:787-799; Reinhart et al. (2002) *Genes Dev.,* 16:1616-1626; Sunkar and Zhu (2004) *Plant Cell,* 16:2001-2019). Publicly available microRNA genes are catalogued at miRBase (Griffiths-Jones et al. (2003) *Nucleic Acids Res.,* 31:439-441).

MiRNAs are expressed in very specific cell types in *Arabidopsis* (see, for example, Kidner and Martienssen (2004) *Nature,* 428:81-84, Millar and Gubler (2005) *Plant Cell,* 17:705-721). Suppression can be limited to a side, edge, or other division between cell types, and is believed to be required for proper cell type patterning and specification (see, e.g., Palatnik et al. (2003) *Nature,* 425:257-263). Suppression of a GFP reporter gene containing an endogenous miR171 recognition site was found to limit expression to specific cells in transgenic *Arabidopsis* (Parizotto et al. (2004) *Genes Dev.,* 18:2237-2242). Recognition sites of miRNAs have been validated in all regions of an mRNA, including the 5' untranslated region, coding region, and 3' untranslated region, indicating that the position of the miRNA target site relative to the coding sequence may not necessarily affect suppression (see, e.g., Jones-Rhoades and Bartel (2004). *Mol. Cell,* 14:787-799, Rhoades et al. (2002) *Cell,* 110:513-520, Allen et al. (2004) *Nat. Genet.,* 36:1282-1290, Sunkar and Zhu (2004) *Plant Cell,* 16:2001-2019).

The mature miRNAs disclosed herein are processed from MIR genes that generally belong to canonical families conserved across distantly related plant species. These MIR genes and their encoded mature miRNAs are also useful, e.g., for modifying developmental pathways, e.g., by affecting cell differentiation or morphogenesis (see, for example, Palatnik et al. (2003) *Nature,* 425:257-263; Mallory et al. (2004) *Curr. Biol.,* 14:1035-1046), to serve as sequence sources for engineered (non-naturally occurring) miRNAs that are designed to silence sequences other than the transcripts targetted by the naturally occurring miRNA sequence (see, for example, Parizotto et al. (2004) *Genes Dev.,* 18:2237-2242; also see U.S. Patent Application Publications 2004/3411A1 and 2005/0120415), and to stabilize dsRNA. A MIR gene itself (or its native 5' or 3' untranslated regions, or its native promoter or other elements involved in its transcription) is useful as a target gene for gene suppression (e.g., by methods of the present invention), where suppression of the miRNA encoded by the MIR gene is desired. Promoters of MIR genes can have very specific expression patterns (e.g., cell-specific, tissue-specific, or temporally specific), and thus are useful in recombinant constructs to induce such specific transcription of a DNA sequence to which they are operably linked.

This invention provides methods for producing hybrid seed, using recombinant DNA constructs including recognition sites corresponding to novel mature miRNAs having specific expression patterns in crop plants. The recombinant DNA constructs of the invention transcribe to RNA including: (a) at least one exogenous miRNA recognition site recognizable by a mature miRNA that is specifically expressed in reproductive tissue of the plant; and (b) messenger RNA encoding a protein imparting tolerance to an herbicide. These constructs are useful for making and using transgenic plant chromosomes, cells, plants, and seeds, including inducibly sterile transgenic plants, useful, e.g. in producing hybrid seed.

SUMMARY OF THE INVENTION

In one aspect, this invention provides a method for producing a non-natural hybrid seed, including the steps of: (a) providing an inducibly sterile, transgenic first parent plant containing in its genome a recombinant DNA construct that transcribes to RNA including: (i) at least one exogenous miRNA recognition site recognizable by a mature miRNA that is specifically expressed in reproductive tissue of the first parent plant; and (ii) a first messenger RNA encoding a protein imparting tolerance to a first herbicide, wherein the mature miRNA specifically suppresses expression of the protein in the reproductive tissue, and wherein sterility of the first parent plant is inducible by application of the first herbicide to the first parent plant; (b) crossing the first parent plant with a second parent plant under conditions where sterility has been induced in the first parent plant, thereby producing non-natural hybrid seed.

In another aspect, this invention provides a method for producing a hybrid seed, including the steps of: (a) providing a first parent plant including a transgenic plant grown from a first transgenic plant cell containing in its genome a first recombinant DNA construct that transcribes to RNA including (i) at least one exogenous miRNA recognition site recognizable by a first mature miRNA, and (ii) a first messenger RNA encoding a protein imparting tolerance to a first herbicide, wherein the first mature miRNA is specifically expressed in male reproductive tissue of the first parent plant, thereby specifically suppressing expression of the protein in the male reproductive tissue, and wherein male sterility of the first parent plant is inducible by application of the first herbicide to the first parent plant; (b) providing a second parent plant including a transgenic plant grown from a second transgenic plant cell containing in its genome a second recombinant DNA construct that transcribes to RNA including (i) at least one exogenous miRNA recognition site recognizable by a second mature miRNA, and (ii) a second messenger RNA encoding a protein imparting tolerance to a second herbicide, wherein the second mature miRNA is specifically expressed in female reproductive tissue of the second parent plant, thereby specifically suppressing expression of the protein in the female reproductive tissue, and wherein female sterility of the second parent plant is inducible by application of the second herbicide to the second parent plant; (c) applying the first herbicide and the second herbicide to the parent plants, thereby inducing male sterility in the first parent plant and female sterility in the second parent plant; (d) crossing the first and second parent plants, wherein ovules of the first parent plant is pollinated by pollen of the second parent plant, thereby producing hybrid seed.

In an independent aspect, this invention provides an inducibly sterile, transgenic plant containing in its genome a recombinant DNA construct that transcribes to RNA including: (a) at least one exogenous miRNA recognition site recognizable by a mature miRNA that is specifically expressed in reproductive tissue of the plant; and (b) messenger RNA encoding a protein imparting tolerance to an herbicide; wherein the mature miRNA specifically suppresses expression of the protein in the reproductive tissue, and wherein sterility of the transgenic plant is inducible by application of the herbicide to the plant.

In yet a further aspect, this invention provides a recombinant DNA construct that transcribes to RNA including: (a) at least one exogenous miRNA recognition site recognizable by a mature miRNA that is specifically expressed in reproductive tissue of the plant; and (b) messenger RNA encoding a protein imparting tolerance to an herbicide.

Other specific embodiments of the invention are disclosed in the following detailed description.

BRIEF DESCRIPTION OF THE DRAWINGS

FIG. 1A schematically depicts non-limiting recombinant DNA constructs of the invention as described in Example 1. For use in *Agrobacterium*-mediated transformation of plant cells, at least one T-DNA border is generally included in each construct (not shown). These constructs include a promoter element ("pro"), an intron flanked on one or on both sides by non-protein-coding DNA, an optional terminator element ("ter"), at least one first gene suppression element ("GSE" or "GSE1") for suppressing at least one first target gene, and can optionally include at least one second gene suppression element ("GSE2") for suppressing at least one second target gene, at least one gene expression element ("GEE") for expressing at least one gene of interest, or both. In embodiments containing a gene expression element, the gene expression element can be located adjacent to (outside of) the intron. In one variation of this embodiment (not shown), the gene suppression element (embedded in an intron flanked on one or on both sides by non-protein-coding DNA) is located 3' to the terminator. In other constructs of the invention (not shown), a gene suppression element (not intron-embedded) is located 3' to the terminator (see Example 22). FIG. 1B schematically depicts examples of recombinant DNA constructs distinct from those of the present invention. These constructs can contain a gene suppression element that is located adjacent to an intron or between two discrete introns (that is to say, not embedded within a single intron), or can include a gene expression element including a gene suppression element embedded within an intron which is flanked on both sides by protein-coding DNA (e.g., protein-coding exons that make up a gene expression element).

These gene suppression elements and transcribable exogenous DNAs can include: DNA that includes at least one anti-sense DNA segment that is anti-sense to at least one segment of the at least one first target gene, or DNA that includes multiple copies of at least one anti-sense DNA segment that is anti-sense to at least one segment of the at least one first target gene (FIG. 2A); DNA that includes at least one sense DNA segment that is at least one segment of the at least one first target gene, or DNA that includes multiple copies of at least one sense DNA segment that is at least one segment of the at least one first target gene (FIG. 2B); DNA that transcribes to RNA for suppressing the at least one first target gene by forming double-stranded RNA and includes at least one anti-sense DNA segment that is anti-sense to at least one segment of the at least one target gene and at least one sense DNA segment that is at least one segment of the at least one first target gene (FIG. 2C); DNA that transcribes to RNA for suppressing the at least one first target gene by forming a single double-stranded RNA and includes multiple serial anti-sense DNA segments that are anti-sense to at least one segment of the at least one first target gene and multiple serial sense DNA segments that are at least one segment of the at least one first target gene (FIG. 2D); DNA that transcribes to RNA for suppressing the at least one first target gene by forming multiple double strands of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of inverted repeats (FIG. 2E); and DNA that includes nucleotides derived from a miRNA, or DNA that includes nucleotides of a siRNA (FIG. 2F). FIG. 2F depicts various non-limiting arrangements of double-stranded RNA (dsRNA) that can be transcribed from embodiments of the gene suppression elements and transcribable exogenous DNAs useful in the recombinant DNA constructs of the invention. When such dsRNA is formed, it can suppress one or more target genes, and can form a single double-stranded RNA or multiple double strands of RNA, or a single dsRNA "stem" or multiple "stems". Where multiple dsRNA "stems" are formed, they can be arranged in "hammerheads" or "cloverleaf" arrangements. Spacer DNA is optional and can include sequence that transcribes to an RNA (e.g., a large loop of antisense sequence of the target gene or an aptamer) that assumes a secondary structure or three-dimensional configuration that confers on the transcript a desired characteristic, such as increased stability, increased half-life in vivo, or cell or tissue specificity.

FIG. 4 depicts a non-limiting example of transcribable DNA sequence including an exogenous miRNA recognition site, chloroplast-targeted TIC809 with a miRNA162 recognition site (in bold text) located in the 3' untranslated region (SEQ ID NO. 176), as described in detail in Example 3. The translated amino acid sequence is also shown.

FIG. 5 depicts a non-limiting example of transcribable DNA sequence including an exogenous miRNA recognition site, non-chloroplast-targeted TIC809 with a miRNA164 recognition site (in bold text) located in the 3' untranslated region (SEQ ID NO. 177), as described in detail in Example 3. The translated amino acid sequence is also shown.

FIGS. 6A-6C depict the strong and specific endosperm expression of the miR167g microRNA (SEQ ID NO. 178) cloned from maize endosperm, as described in detail in Example 4. Northern blots of RNA from maize (LH59) tissues probed with an end-labeled mature miR167 22-mer LNA probe specific for SEQ ID NO. 178 (FIG. 6A) or with a ~400 bp miR167g gene-specific probe (FIG. 6B). Transcription profiling of maize tissues corroborated the Northern blot results (FIG. 6C); the transcript corresponding to miR167g was abundantly and specifically expressed in endosperm tissue (abundances are categorized as follows: >5000, high abundance, $97^{th}$ percentile; 700-5000, moderate abundance, $20^{th}$ percentile; 400-700, average abundance; 200-400, low abundance; <200, not detected). Selected abbreviations: "DAP" or "DA", days after pollination; "WK", whole kernel, "endo", endosperm.

FIGS. 8A-8C depict results described in detail in Example 5. FIG. 8A depicts the fold-back structure of SEQ ID NO. 186, the predicted miRNA precursor for SEQ ID NO. 184; the mature miRNA is located at bases 106-126, the corresponding miRNA* at bases 156-175, and another abundant miRNA was also found to be located at bases 100-120 in the stem of the fold-back structure. "Count" refers to the number of occurrences of a small RNA in the filtered set of 381,633 putative miRNA sequences that was analyzed. FIG. 8B depicts a transcription profile in soy tissues for the miRNA precursor SEQ ID NO. 186. FIG. 8C depicts a transcription profile in soy tissues for a predicted target, polyphenol oxidase (SEQ ID NO. 200) for the mature miRNA (SEQ ID NO. 184).

FIGS. 9A-9B depict results described in detail in Example 5. FIG. 9A depicts the fold-back structure of SEQ ID NO. 189, the predicted miRNA precursor for SEQ ID NO. 187; the mature miRNA is located at bases 163-183, and the miRNA* at bases 18-63. "Count" refers to the number of occurrences of a small RNA in the filtered set of 381,633 putative miRNA sequences that was analyzed. FIG. 9B depicts a transcription profile in soy tissues for a predicted target, polyphenol oxidase (SEQ ID NO. 251) for the mature miRNA (SEQ ID NO. 187).

FIG. 10 depicts the fold-back structure of SEQ ID NO. 192, the predicted miRNA precursor for SEQ ID NO. 190; the mature miRNA is located at bases 87-107, and the miRNA* at bases 150-169. "Count" refers to the number of occurrences of a small RNA in the filtered set of 381,633 putative miRNA sequences that was analyzed.

FIG. 11 depicts the fold-back structure of SEQ ID NO. 195, the predicted miRNA precursor for SEQ ID NO. 193; the mature miRNA is located at bases 61-81, and the miRNA* at bases 109-129. "Count" refers to the number of occurrences of a small RNA in the filtered set of 381,633 putative miRNA sequences that was analyzed.

FIGS. 12A-12B depict results described in detail in Example 5. FIG. 12A (top) depicts the fold-back structure of SEQ ID NO. 198, one of the predicted miRNA precursors for SEQ ID NO. 196; the mature miRNA is located at bases 157-178, and the miRNA* at bases 72-93. FIG. 12A (bottom) depicts the fold-back structure of SEQ ID NO. 199, another predicted miRNA precursors for SEQ ID NO. 196; the mature miRNA is located at bases 123-144, and the miRNA* at bases 58-79. "Count" refers to the number of occurrences of a small RNA in the filtered set of 381,633 putative miRNA sequences that was analyzed. FIG. 12B (top) depicts a transcription profile in soy tissues for the miRNA precursor SEQ ID NO. 198. FIG. 12B (bottom) depicts a transcription profile in soy tissues for the miRNA precursor SEQ ID NO. 199.

FIGS. 13 and 14 depict the transcription profiles of probeset sequences that were identified as including miRNA genes (given in Table 6) especially useful in methods of this invention and having the desired expression patterns, i.e., in female reproductive tissue (FIG. 13) or in male reproductive tissue (FIG. 14), as described in detail in Example 6.

DETAILED DESCRIPTION OF THE INVENTION

Figure 2:
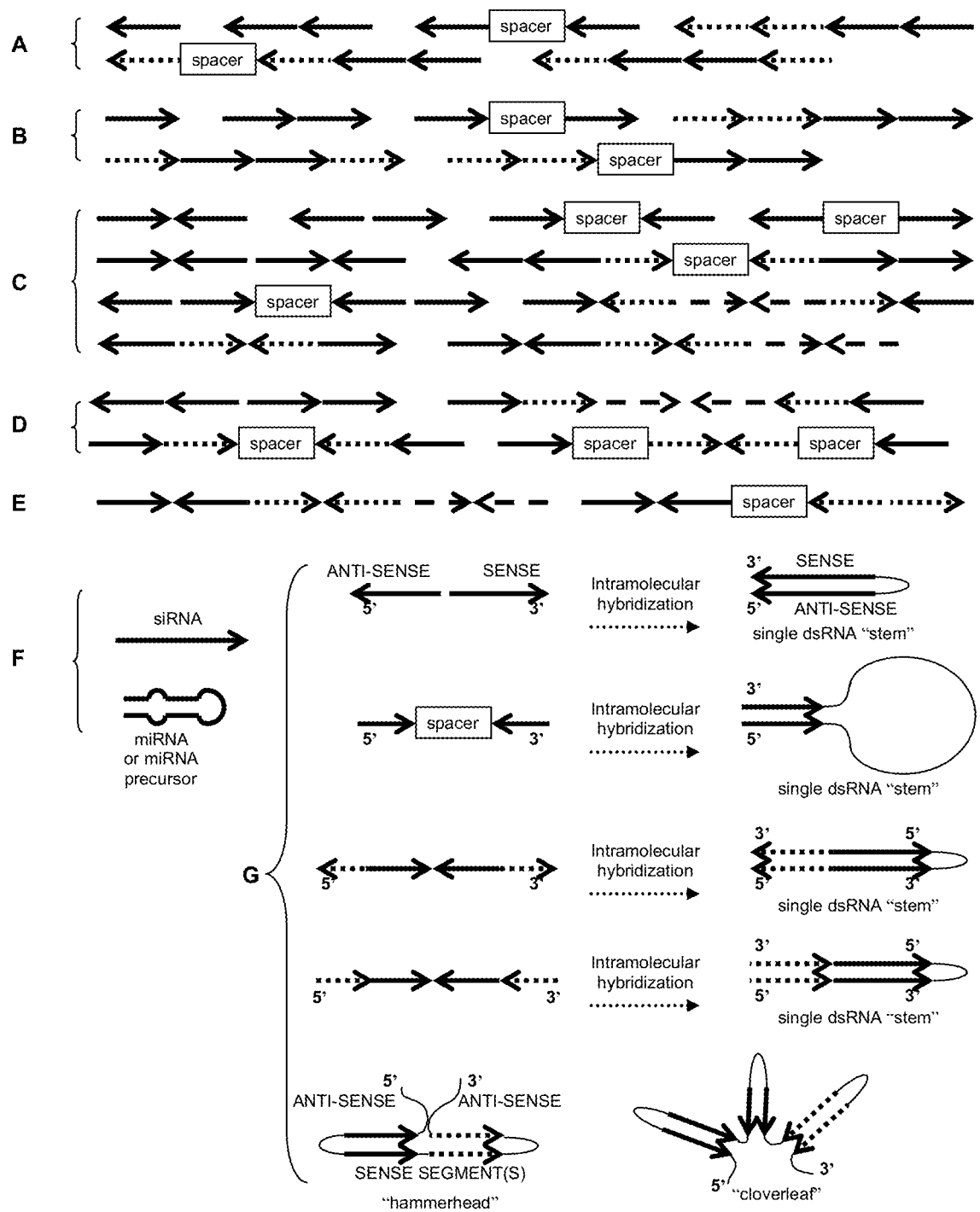
FIGS. 2A-2F depict various non-limiting examples of gene suppression elements and transcribable exogenous DNAs useful in the recombinant DNA constructs of the invention as described in Example 1. Where drawn as a single strand (FIGS. 2A through 2E), these are conventionally depicted in 5' to 3' (left to right) transcriptional direction, where the arrows indicate anti-sense sequence (arrowhead pointing to the left), or sense sequence (arrowhead pointing to the right). Where drawn as double-stranded (anti-parallel) transcripts (FIGS. 2F and 2G), the 5' and 3' transcriptional directionality is as shown. Solid lines, dashed lines, and dotted lines indicate sequences that target different target genes.

Unless defined otherwise, all technical and scientific terms used have the same meaning as commonly understood by one of ordinary skill in the art to which this invention belongs. Generally, the nomenclature used and the manufacturing or laboratory procedures described below are well known and commonly employed in the art. Conventional methods are used for these procedures, such as those provided in the art and various general references. Unless otherwise stated, nucleic acid sequences in the text of this specification are given, when read from left to right, in the 5' to 3' direction. Where a term is provided in the singular, the inventors also contemplate aspects of the invention described by the plural of that term. Where there are discrepancies in terms and definitions used in references that are incorporated by reference, the terms used in this application shall have the definitions given. Other technical terms used have their ordinary meaning in the art that they are used, as exemplified by a variety of technical dictionaries. The inventors do not intend to be limited to a mechanism or mode of action. Reference thereto is provided for illustrative purposes only.

Method for Producing Non-Natural Hybrid Seed

A first aspect of this invention provides a method for producing a non-natural hybrid seed, including the steps of: (a) providing an inducibly sterile, transgenic first parent plant containing in its genome a recombinant DNA construct that transcribes to RNA including: (i) at least one exogenous miRNA recognition site recognizable by a mature miRNA that is specifically expressed in reproductive tissue of the first parent plant; and (ii) a first messenger RNA encoding a protein imparting tolerance to a first herbicide, wherein the mature miRNA specifically suppresses expression of the protein in the reproductive tissue, and wherein sterility of the first parent plant is inducible by application of the first herbicide to the first parent plant; (b) crossing the first parent plant with a second parent plant under conditions where sterility has been induced in the first parent plant, thereby producing non-natural hybrid seed.

Plants:

The method of this invention includes providing an inducibly sterile, transgenic plant, useful as a parent plant, which is preferably a crop plant propagated by seed, such as those described below under the heading "Making and Using Transgenic Plant Cells and Transgenic Plants". Non-limiting examples of preferred plants include maize, rice, wheat, oat, barley, rye, triticale, millet, sorghum, quinoa, amaranth, buckwheat, forage grasses, turf grasses, alfalfa, cotton, safflower, sunflower, soybean, canola, rapeseed, flax, peanuts, beans, peas, lentils, alfalfa, lettuce, asparagus, artichoke, celery, carrot, radish, cabbage, kale, mustard, broccoli, cauliflower, Brussels sprouts, turnip, kohlrabi, cucumber, melons, summer squashes, winter squashes, onions, garlic, leeks, shallots, chives, tomatoes, eggplants, peppers, groundcherries, beet, chard, spinach, ornamental plants, and forest trees. Particularly preferred plants include maize, rice, wheat, cotton, safflower, sunflower, soybean, canola, and rapeseed. In a particularly preferred embodiment, the method is useful for producing the non-natural hybrid maize seed.

Sterility:

By "sterility" is meant the inability to successfully produce viable progeny seed. Male sterility includes, for example, the inability to produce male gametes (e.g., mature, fertile pollen grains) capable of fertilizing female gametes, or the inability to produce the male reproductive structures (e g., anthers, stamens, filaments) necessary for male gametes to be capable of normal fertilization of female gametes. Female sterility includes, for example, the inability to produce female gametes capable of being fertilized, or the inability to produce a fully developed seed (whether viable or sterile), or the inability to produce viable progeny seed capable of being germinated and developing into a normal progeny plant.

Reproductive Tissue:

In embodiments of the inducibly sterile, transgenic plant where the sterility is male sterility, the reproductive tissue is male reproductive tissue. Male reproductive tissue includes any tissue that is necessary for development of male gametes to fertility (i.e., having the ability to fertilize a female gamete), for example, pollen or male gametes at any developmental stage, anthers, stamens, filaments, tassels, and other male floral parts, nutritive tissues, and other structures involved in the ability of a male parent plant to fertilize a female parent plant.

In embodiments of the inducibly sterile, transgenic plant where the sterility is female sterility, the reproductive tissue is female reproductive tissue. Female reproductive tissue includes any tissue that is necessary for development of female gametes to fertility (i.e., having the ability be fertilized by a male gamete, more preferably having the ability to produce a fully developed seed (whether viable or sterile), and in many embodiments most preferably having the ability to produce viable progeny seed capable of being germinated and developing into a normal progeny plant). Female reproductive tissue includes, for example, ovules or female gametes at any developmental stage, silks, pistils and other female floral parts, seed coats, fruits, rachis, or cobs or other nutritive, supportive, or protective tissues, and any other structures involved in the ability of a female parent plant to be fertilized by a male parent plant, produce a fully developed seed, or produce a viable progeny seed. In certain embodiments, sterility results in failure of a fertilized ovule to develop to a viable seed, and "reproductive tissue" refers to a fertilized ovule (e. g., a zygote or an embryo of any developmental stage, or the maternal tissues required for the development of a fertilized ovule into a seed such as endosperm or other nutritive tissues).

Mature miRNA:

By "mature miRNA" is meant the small RNA ("microRNA") processed from a miRNA precursor (e.g., pri-miRNA or pre-miRNA), that is capable of recognizing and binding to a specific sequence ("miRNA recognition site") within an RNA transcript, and guiding the cleavage of that transcript. Preferred mature miRNAs include mature miRNAs that are specifically expressed in reproductive tissue of a plant. In a non-limiting embodiment of the invention, the mature miRNA is a crop plant miRNA, such as a maize miRNA or a soy miRNA. Non-limiting examples of miRNAs useful in this invention are provided in the working Examples and include, but are not limited to, the miRNAs identified in Tables 1, 2, 3, 4, 5, and 6, including the miRNAs having SEQ ID NO. 297, SEQ ID NO. 302, SEQ ID NO. 314, SEQ ID NO. 319, SEQ ID NO. 323, SEQ ID NO. 328, SEQ ID NO. 333, or SEQ ID NO. 338.

miRNA Recognition Sites:

The recombinant DNA construct transcribes to RNA including one or more exogenous miRNA recognition sites, which can be one or more copies of the same exogenous miRNA recognition site or one or more copies of different exogenous miRNA recognition sites. The exogenous miRNA recognition site may be located anywhere in the transcribed RNA where, when the mature miRNA is not present, transcription produces a messenger RNA that is translatable to the desired herbicide tolerance protein, and, where the mature miRNA is present, the mature miRNA binds to the RNA transcript and suppresses expression of the messenger RNA. One or more exogenous miRNA recognition sites can be located in coding regions or in non-coding regions of the messenger RNA. In various embodiments, the exogenous miRNA recognition site is located within at least one of (a) a region 5' to coding sequence of the messenger RNA; (b) a region 3' to coding sequence of the messenger RNA; and (c) the messenger RNA. In one preferred embodiment, the at least one miRNA recognition site is located in the 3' untranslated region of the messenger RNA. In various embodiments, the recombinant DNA construct further includes at least one element selected from: (a) a plant promoter; (b) a gene suppression element; (c) an intron; (d) a gene expression element; (e) DNA that transcribes to an RNA aptamer capable of binding to a ligand; (f) DNA that transcribes to an RNA aptamer capable of binding to a ligand and DNA that transcribes to regulatory RNA capable of regulating expression of a target sequence, characterized in that the regulation is dependent on the conformation of the regulatory RNA, and the conformation of the regulatory RNA is allosterically affected by the binding state of the RNA aptamer; and (g) at least one T-DNA border. These additional elements are described in detail below under the heading "Inducibly Sterile, Transgenic Plants Containing a Recombinant DNA Construct".

Any miRNA recognition site that is recognized by a mature miRNA having the desired expression pattern (i.e., specific expression in male or in female reproductive tissue) is useful in embodiments of this invention. Multiple miRNA recognition sites may be used to specifically suppresses expression of the protein in a desired combination of reproductive tissues. For example, a recombinant DNA construct can include multiple recognition sites, wherein each of which is recognized by a miRNA that has specific expression in a different male (or female) reproductive tissue (e.g., a miRNA expressed in pollen and a miRNA expressed in tassel). Selection of an appropriate mature miRNA or its corresponding miRNA recogntion site is carried out by methods known to those skilled in the art, including those illustrated in detail in the working examples provided herein. Methods include cloning of mature miRNA or miRNA precursor molecules (pre-miRNAs, pri-miRNAs) from whole plants or seeds or from selected tissues, bioinformatics-based miRNA identification, Southern blots of miRNA or miRNA precursor molecules, determining miRNA promoter expression patterns, etc. In non-limiting embodiments, the miRNA recognition site is recognized by a mature miRNA derived from the fold-back structure of a MIR sequence identified in Tables 1 through 6; particularly preferred are the miRNA recognition sites recognized by the mature miRNAs identified in Table 6.

Cleavage of a target RNA transcript and the subsequent suppression of the target RNA is dependent on base pairing between the mature miRNA and its cognate miRNA recognition site. Thus, the at least one exogenous miRNA recognition site is designed to have sufficient sequence complementarity to the mature miRNA to allow recognition and binding by the mature miRNA. In plants, sequence complementarity of a miRNA and its recognition site is typically high, e.g., perfect complementarity between 19, 20, or 21 out of 21 nucleotides (in the case of a mature miRNA that is 21 nucleotides in length), that is, complementarity of about 90% or greater. A similar degree of complementarity is preferable for recognition sites for plant miRNAs of any length (e.g., 20, 21, 22, 23, and 24 nucleotides). The sequence requirements for mature miRNA binding to a recognition site, and methods for predicting miRNA binding to a given sequence, are discussed, for example, in Llave et al. (2002) *Science*, 297:2053-2056, Rhoades et al. (2002) *Cell*, 110:513-520, Jones-Rhoades and Bartel (2004) *Mol. Cell*, 14:787-799, Schwab et at (2005) *Developmental Cell*, 8:517-527, and Xie et al. (2005) *Plant Physiol.*, 138:2145-2154. When designing a miRNA recognition site as well as its exact location in or adjacent to a messenger RNA, it is also preferable to avoid sequences that have undesirable characteristics, such sequences encoding undesirable polypeptides, as described below under the heading "Target Genes". When designing messenger RNA as a transgene to be expressed, the unintentional introduction of an exogenous miRNA recognition site is avoided where suppression by a mature miRNA is not desired.

Specific Expression:

By "specifically expressed in reproductive tissue" is meant that the mature miRNA is transcribed in reproductive tissue at a level sufficient to allow the miRNA to specifically suppresses expression of the protein in the reproductive tissue, that is, to substantially suppress expression in the reproductive tissue of the protein imparting tolerance to an herbicide, but not substantially suppress expression of the same protein in tissues other than the reproductive tissues. Substantial suppression of expression includes at least 30, at least 50, at least 60, at least 70, at least 80, at least 85, at least 90, at least 95, or at least 98 percent suppression of expression, relative to that in control cells (i.e., cells that include an analogous recombinant DNA construct, e.g., a recombinant DNA construct that transcribes to RNA including the same messenger RNA encoding a protein imparting tolerance to an herbicide but not including an exogenous miRNA recognition site recognizable by the mature miRNA specifically expressed in reproductive tissue of the plant). In preferred embodiments, the mature miRNA specifically suppresses expression of the protein in the reproductive tissue to a degree sufficient to result in sterility of the reproductive tissue when the herbicide is applied. Those of skill in the art will recognize that, in certain cases, tolerance to an herbicide can be adequately achieved at moderate or even low expression levels of an herbicide tolerance protein. Therefore it is not a requirement that the mature miRNA be completely absent in tissues other than the reproductive tissue, nor is it a requirement that the expression of the herbicide tolerance protein be completely suppressed in the reproductive tissue.

Protein Imparting Herbicide Tolerance:

Any protein imparting tolerance by a plant to an herbicide can be used. In many embodiments, the herbicide is a systemic herbicide. Non-limiting examples of herbicides useful in aspects of this invention include glyphosate, dicamba, glufosinate, sulfonylureas, imidazolinones, bromoxynil, dalapon, dicamba, cyclohezanedione, protoporphyrinogen oxidase inhibitors, and isoxaflutole herbicides. Non-limiting examples of proteins imparting tolerance to glyphosate include 5-enolpyruvylshikimate-3-phosphate synthase ("EPSPS" or "aroA", see U.S. Pat. Nos. 5,627,061, 5,633,435, 6,040,497, and 5,094,945), glyphosate oxidoreductase ("GOX", see U.S. Pat. No. 5,463,175), glyphosate decarboxylase (see U.S. Patent Application Publication 2004/0177399), glyphosate N-acetyl transferase ("GAT", see U.S. Patent Application Publication 2003/0083480) or any other gene that provides resistance to glyphosate. One particularly preferred embodiment is "epsps-cp4" or 5-enolpyruvylshikimate-3-phosphate synthase from *Agrobacterium tumefaciens* strain CP4; U.S. Pat. No. 5,633,435 discloses nucleic acid sequences and amino acid sequences of epsps-cp4, transformation vectors containing this gene, and methods of making glyphosate-resistant plants. Non-limiting examples of proteins imparting tolerance to other herbicides include dicamba monooxygenase, which confers tolerance to auxin-like herbicides such as dicamba (see U.S. Patent Application Publications 2003/0115626, 2003/0135879); phosphinothricin acetyltransferase ("pat" or "bar"), which confers tolerance to phosphinothricin or glufosinate (see U.S. Pat. Nos. 5,646,024, 5,561,236, 5,276, 268 5,637,489, and U.S. Pat. No. 5,273,894; also see European Patent application EP 275,957;); 2,2-dichloropropionic acid dehalogenase, which confers tolerance to 2,2-dichloropropionic acid ("Dalapon") (see PCT Patent Application Publication WO99/27116); acetohydroxyacid synthase or acetolactate synthase, which confers tolerance to acetolactate synthase inhibitors such as sulfonylurea, imidazolinone, triazolopyrimidine, pyrimidyloxybenzoates, and phthalide (see U.S. Pat. Nos. 6,225,105, 5,767,366, 4,761,373, 5,633,437, 6,613,963, 5,013,659, 5,141,870, 5,378,824 and 5,605,011); haloarylnitrilase ("Bxn"), which confers tolerance to bromoxynil (see U.S. Pat. No. 4,810,648; also see PCT Patent Application Publications WO89/00193 and WO87/04181A1); modified acetyl-coenzyme A carboxylase, which confers tolerance to cyclohexanedione ("sethoxydim") and aryloxyphenoxypropionate ("haloxyfop") (see U.S. Pat. No. 6,414,222); dihydropteroate synthase ("sul I"), which confers tolerance to sulfonamide herbicides (see U.S. Pat. Nos. 5,597,717, 5,633,444, and 5,719,046); 32 kDa photosystem II polypeptide ("psbA"), which confers tolerance to triazine herbicides (see Hirschberg et al. (1983) *Science,* 222:1346-1349); anthranilate synthase, which confers tolerance to 5-methyltryptophan (see U.S. Pat. No. 4,581,847); dihydrodipicolinic acid synthase ("dap A"), which confers to tolerance to aminoethyl cysteine (see PCT Patent Application Publication WO89/11789); phytoene desaturase ("crtl"), which confers tolerance to pyridazinone herbicides such as norflurazon (see Japanese Patent Publication JP06343473); hydroxyphenyl pyruvate dioxygenase, which confers tolerance to cyclopropylisoxazole herbicides such as isoxaflutole (see U.S. Pat. No. 6,268,549; also see PCT Patent Application Publication WO96/38567); modified protoporphyrinogen oxidase I ("protox"), which confers tolerance to protoporphyrinogen oxidase inhibitors (see U.S. Pat. No. 5,939,602); aryloxyalkanoate dioxygenase ("AAD-1"), which confers tolerance to an herbicide containing an aryloxyalkanoate moiety (see PCT Patent Application Publication WO05/107437), examples of which herbicides include phenoxy auxins (such as 2,4-D and dichlorprop), pyridyloxy auxins (such as fluroxypyr and triclopyr), aryloxyphenoxypropionates (AOPP) acetylcoenzyme A carboxylase (ACCase) inhibitors, (such as haloxyfop, quizalofop, and diclofop) and 5-substituted phenoxyacetate protoporphyrinogen oxidase IX inhibitors (such as pyraflufen and flumiclorac).

Combinations of Parent Plants:

The method of this invention can be carried out using various combinations of first parent plants and second parent plants. In many embodiments of the method, the second parent plant is tolerant to the first herbicide; for example, the second parent plant can contain in its genome a transgene conferring tolerance to the first herbicide. This invention encompasses embodiments of the method wherein: (a) the reproductive tissue is male reproductive tissue, the first parent plant is inducibly male-sterile, and the second parent plant is normally fertile; or (b) the reproductive tissue is male reproductive tissue, the first parent plant is inducibly male-sterile, and the second parent plant is female-sterile; or (c) the reproductive tissue is male reproductive tissue, the first parent plant is inducibly male-sterile, and the second parent plant is inducibly female-sterile; or (d) the reproductive tissue is female reproductive tissue, the first parent plant is inducibly female-sterile, and the second parent plant is normally fertile; or (e) the reproductive tissue is female reproductive tissue, the first parent plant is inducibly female-sterile, and the second parent plant is male-sterile; or (f) the reproductive tissue is female reproductive tissue, the first parent plant is inducibly female-sterile, and the second parent plant is inducibly male-sterile.

In one embodiment of the method, the reproductive tissue is male reproductive tissue, the first parent plant is inducibly male-sterile, and the second parent plant includes an inducibly female-sterile, transgenic second parent plant containing in its genome a recombinant DNA construct that transcribes to RNA including: (i) at least one exogenous miRNA recognition site recognizable by a second mature miRNA that is specifically expressed in female reproductive tissue of the second parent plant, and (ii) a second messenger RNA encoding a second protein imparting tolerance to a second herbicide; wherein the second mature miRNA specifically suppresses expression of the second protein in the female reproductive tissue, and wherein female sterility of the second parent plant is inducible by application of the second herbicide to the second parent plant. In another embodiment, the reproductive tissue is female reproductive tissue, the first parent plant is inducibly female-sterile, and the second parent plant includes an inducibly male-sterile, transgenic second parent plant containing in its genome a recombinant DNA construct that transcribes to RNA including: (i) at least one exogenous miRNA recognition site recognizable by a second mature miRNA that is specifically expressed in male reproductive tissue of the second parent plant, and (ii) a second messenger RNA encoding a second protein imparting tolerance to a second herbicide; wherein the second mature miRNA specifically suppresses expression of the second protein in the male reproductive tissue, and wherein male sterility of the second parent plant is inducible by application of the second herbicide to the second parent plant. In these embodiments, the first and the second messenger RNAs can be identical, or can be different. In these embodiments, the first herbicide and the second herbicide can be identical, or can be different. In some cases, at least one of the first herbicide and the second herbicide includes a systemic herbicide. In preferred embodiments, at least one of the first herbicide and the second herbicide include at least one herbicide selected from the group consisting of glyphosate, dicamba, glufosinate, sulfonylureas, imidazolinones, bromoxynil, 2,2-dichloropropionic acid, acetolactate synthase inhibitors, cyclohezanedione, aryloxyphenoxypropionate, sulfonamide herbicides, triazine herbicides, 5-methyltryptophan, aminoethyl cysteine, pyridazinone herbicides, cyclopropylisoxazole herbicides, protoporphyrinogen oxidase inhibitors, and herbicides containing an aryloxyalkanoate moiety.

In one embodiment of the method, the first parent plant is an inducibly sterile, transgenic plant containing in its genome a recombinant DNA construct that transcribes to RNA including: (i) at least one exogenous miRNA recognition site recognizable by a mature miRNA that is specifically expressed in male reproductive tissue of the plant; and (ii) messenger RNA encoding a protein imparting tolerance to an herbicide, wherein the mature miRNA specifically suppresses expression of the protein in the male reproductive tissue, and wherein male sterility of the transgenic plant is inducible by application of the herbicide to the plant, and the second parent plant is normally fertile. To induce male sterility of the first parent plant, the herbicide is preferably applied under a regime that results in the first parent plant's inability to produce male gametes (or the male reproductive structures) necessary for normal fertilization of the second parent plant. In such embodiments, the second parent plant is generally tolerant to the same herbicide used to induce male sterility of the first parent plant, and thus first and second parent plants can be treated with the same herbicide, preferably simultaneously (e.g., together in a field). A cross of the first and second parent plants yields seed that is the result of pollination of the first parent plant by the second parent plant.

In another embodiment of the method, the first parent plant is an inducibly sterile, transgenic plant containing in its genome a recombinant DNA construct that transcribes to RNA including: (i) at least one exogenous miRNA recognition site recognizable by a mature miRNA that is specifically expressed in female reproductive tissue of the plant; and (ii) messenger RNA encoding a protein imparting tolerance to an herbicide, wherein the mature miRNA specifically suppresses expression of the protein in the female reproductive tissue or in a fertilized ovum, and wherein female sterility of the transgenic plant is inducible by application of the herbicide to the plant, and the second parent plant is normally fertile. To induce female sterility of the first parent plant, the herbicide is preferably applied under a regime that results, for example, in the first parent plant's inability to produce female gametes capable of being fertilized, or the inability to produce a fully developed seed (whether viable or sterile), or the inability to produce viable progeny seed capable of being germinated and developing into a normal progeny plant. In such embodiments, the second parent plant is generally tolerant to the same herbicide used to induce female sterility of the first parent plant, and thus first and second parent plants can be treated with the same herbicide, preferably simultaneously. A cross of the first and second parent plants yields seed that is the result of pollination of the second parent plant by the first parent plant.

Another aspect of the invention provides a method for producing a non-natural, hybrid seed, including the steps of: (a) providing a first parent plant including a transgenic plant grown from a first transgenic plant cell (e.g., a first transgenic maize cell) containing in its genome a first recombinant DNA construct that transcribes to RNA including (i) at least one exogenous miRNA recognition site recognizable by a first mature miRNA, and (ii) a first messenger RNA encoding a protein imparting tolerance to a first herbicide, wherein the first mature miRNA is specifically expressed in male reproductive tissue of the first parent plant, thereby specifically suppressing expression of the protein in the male reproductive tissue, and wherein male sterility of the first parent plant is inducible by application of the first herbicide to the first parent plant; (b) providing a second parent plant including a transgenic plant grown from a second transgenic plant cell (e.g., a second transgenic maize cell) containing in its genome a second recombinant DNA construct that transcribes to RNA including (i) at least one exogenous miRNA recognition site recognizable by a second mature miRNA, and (ii) a second messenger RNA encoding a protein imparting tolerance to a second herbicide, wherein the second mature miRNA is specifically expressed in female reproductive tissue of the second parent plant, thereby specifically suppressing expression of the protein in the female reproductive tissue, and wherein female sterility of the second parent plant is inducible by application of the second herbicide to the second parent plant; (c) applying the first herbicide and the second herbicide to the parent plants, thereby inducing male sterility in the first parent plant and female sterility in the second parent plant; (d) crossing the first and second parent plants, wherein ovules of the first parent plant is pollinated by pollen of the second parent plant, thereby producing non-natural hybrid seed (e.g., non-natural, hybrid maize seed).

In practicing any of the methods for producing hybrid seed, "grown" refers to growing a transgenic plant by direct regeneration from the first transgenic plant cell or growing a transgenic progeny plant of the regenerated transgenic plant. Methods for directly regenerating a transgenic plant from a transgenic plant cell, or for growing transgenic progeny plants (including inbred progeny plants and hybrid progeny plants) are well known in the art, and are described herein under the heading "Making and Using Transgenic Plant Cells and Transgenic Plants".

The second messenger RNA can be the same or can be different from the first messenger RNA. In various embodiments, the first messenger RNA and the second messenger RNA (a) are identical; or (b) are different and encode different segments of the protein; (c) are different and encode segments of different proteins. In preferred embodiments, the first and second messenger RNA (whether the same or different) confer tolerance to the same herbicide, which provides the convenience of treating a field of mixed first and second parent plants with a single herbicide; when necessary, the herbicide is applied at one or more times in order to induce male sterility of the first parent plant and female sterility of the second parent plant. In some cases, the first messenger RNA encodes a first protein conferring tolerance to an herbicide, and the second messenger RNA encodes a second, different protein conferring tolerance to the same herbicide; a non-limiting example is where the first and second proteins are selected from a group (including 5-enolpyruvylshikimate-3-phosphate synthase, glyphosate acetyltransferase, and glyphosate decarboxylase) that all confer tolerance to glyphosate. In other embodiments, the first and second messenger RNA confer tolerance to two different herbicides, and preferably the first and second parent plants both contain in their genome DNA encoding two proteins, each conferring tolerance to one of the two herbicides, allowing a field of both first and second parent plants to be treated with the two herbicides (simultaneously or separately). In various embodiments of the method, the first herbicide and the second herbicide (a) are identical; or (b) are different (wherein the first and second parents preferably have tolerance to both first and second herbicides).

Herbicide application regimes are used whereby inducible sterility is achieved, preferably without loss of yield or other undesirable results. Herbicide application(s) is timed so as to induce sterility. In an analogous example, a line of transgenic cotton (RR1445) containing EPSPS under the control of an FMV 35S constitutive promoter, was found to have high EPSPS expression in most vegetative cells, but low EPSPS expression in certain male reproductive tissue types (pollen mother cells, male gametophytes, and tapetum); applications of glyphosate after the four-leaf stage results in male sterility (see Chen et al. (2006) *Plant Biotechnol. J.,* 4:477-487, published early online on 7 Jun. 2006, doi: 10.1111/j.1467-7652.2006.00203.x).

In preferred embodiments, the method is useful for producing non-natural, hybrid seed of a crop plant propagated by seed, such as those described under the heading "Making and Using Transgenic Plant Cells and Transgenic Plants", e.g., maize, rice, wheat, oat, barley, rye, triticale, millet, sorghum, quinoa, amaranth, buckwheat, forage grasses, turf grasses, alfalfa, cotton, safflower, sunflower, soybean, canola, rapeseed, flax, peanuts, beans, peas, lentils, alfalfa, lettuce, asparagus, artichoke, celery, carrot, radish, cabbage, kale, mustard, broccoli, cauliflower, Brussels sprouts, turnip, kohlrabi, cucumber, melons, summer squashes, winter squashes, onions, garlic, leeks, shallots, chives, tomatoes, eggplants, peppers, groundcherries, beet, chard, spinach, ornamental plants, and forest trees. In a particularly preferred embodiment, the non-natural, hybrid seed is maize seed. Non-natural, hybrid seed produced using human activity including any of the embodiments of the method are specifically further claimed.

Inducibly Sterile, Transgenic Plants Containing a Recombinant DNA Construct

An independent aspect of this invention includes an inducibly sterile, transgenic plant containing in its genome a recombinant DNA construct that transcribes to RNA including: (a) at least one exogenous miRNA recognition site recognizable by a mature miRNA that is specifically expressed in reproductive tissue of the plant; and (b) messenger RNA encoding a protein imparting tolerance to an herbicide; wherein the mature miRNA specifically suppresses expression of the protein in the reproductive tissue, and wherein sterility of the transgenic plant is inducible by application of the herbicide to the plant. In one embodiment, the reproductive tissue is male reproductive tissue and the sterility is male sterility. In another embodiment, the reproductive tissue is female reproductive tissue and the sterility is female sterility. In a further embodiment, the reproductive tissue includes a fertilized ovule, and the sterility results in failure of fertilized ovule to develop to a viable seed.

In preferred embodiments, the inducibly sterile, transgenic plant is a crop plant propagated by seed, for example, maize, rice, wheat, oat, barley, rye, triticale, millet, sorghum, quinoa, amaranth, buckwheat, forage grasses, turf grasses, alfalfa, cotton, safflower, sunflower, soybean, canola, rapeseed, flax, peanuts, beans, peas, lentils, alfalfa, lettuce, asparagus, artichoke, celery, carrot, radish, cabbage, kale, mustard, broccoli, cauliflower, Brussels sprouts, turnip, kohlrabi, cucumber, melons, summer squashes, winter squashes, onions, garlic, leeks, shallots, chives, tomatoes, eggplants, peppers, groundcherries, beet, chard, spinach, ornamental plants, and forest trees.

Recombinant DNA Constructs:

The inducibly sterile, transgenic plant provided by this invention has in its genome a recombinant DNA construct that transcribes to RNA including: (a) at least one exogenous miRNA recognition site recognizable by a mature miRNA that is specifically expressed in reproductive tissue of the plant; and (b) messenger RNA encoding a protein imparting tolerance to an herbicide; wherein the mature miRNA specifically suppresses expression of the protein in the reproductive tissue, and wherein sterility of the transgenic plant is inducible by application of the herbicide to the plant. This recombinant DNA construct is useful for making transgenic plant chromosomes, cells, plants, and seeds containing such a construct, all of which are useful particularly for the production of hybrid seed.

In various embodiments of this invention, including embodiments of the inducibly sterile, transgenic plant, the recombinant DNA construct further includes at least one element selected from: (a) a plant promoter; (b) a gene suppression element; (c) an intron; (d) a gene expression element; (e) DNA that transcribes to an RNA aptamer capable of binding to a ligand; (f) DNA that transcribes to an RNA aptamer capable of binding to a ligand and DNA that transcribes to regulatory RNA capable of regulating expression of a target gene, characterized in that the regulation is dependent on the conformation of the regulatory RNA, and the conformation of the regulatory RNA is allosterically affected by the binding state of the RNA aptamer; and (g) at least one T-DNA border. These and other elements (e.g., terminators and spacer DNA) useful in this invention are described in detail below under the headings "Promoters", "Gene Suppression Elements", "Introns", "Gene Expression Elements", "Aptamers", "Ligands", "Regulatory RNA", "T-DNA Borders", "Terminators", and "Spacer DNA", and elsewhere in this disclosure. Non-limiting examples of how these various elements can be arranged are depicted in FIGS. 1 and 2A-2F. Techniques for making and using recombinant DNA constructs of the invention, for making transgenic plant cells containing the recombinant DNA constructs and transgenic plants, seeds, and progeny plants derived therefrom, and for assaying the effects of transcribing the recombinant DNA constructs, are described in detail under the headings "Making and Using Recombinant DNA Constructs", "Making and Using Transgenic Plant Cells and Transgenic Plants", and elsewhere in this disclosure.

Promoters:

Generally, the recombinant DNA construct includes a promoter operably linked to the transcribable DNA. Suitable promoters include any promoter that is capable of transcribing DNA in the plant cell where transcription is desired. Non-constitutive promoters suitable for use with the recombinant DNA constructs of the invention include spatially specific promoters, temporally specific promoters, and inducible promoters. Spatially specific promoters can include organelle-, cell-, tissue-, or organ-specific promoters functional in a plant (e.g., a plastid-specific, a root-specific, a pollen-specific, or a seed-specific promoter for suppressing expression of the first target RNA in plastids, roots, pollen, or seeds, respectively). In many cases a seed-specific, embryo-specific, aleurone-specific, or endosperm-specific promoter is especially useful. Temporally specific promoters can include promoters that tend to promote expression during certain developmental stages in a plant's growth or reproductive cycle, or during different times of day or night, or at different seasons in a year. Inducible promoters include promoters induced by chemicals (e.g., exogenous or synthetic chemicals as well as endogenous pheromones and other signaling molecules) or by environmental conditions such as, but not limited to, biotic or abiotic stress (e.g., water deficit or drought, heat, cold, high or low nutrient or salt levels, high or low light levels, or pest or pathogen infection). An expression-specific promoter can also include promoters that are generally constitutively expressed but at differing degrees or "strengths" of expression, including promoters commonly regarded as "strong promoters" or as "weak promoters". Because the miRNA recognition site provides tissue-selective expression control of the messenger RNA, in many preferred embodiments the promoter is simply a constitutive promoter.

Non-limiting specific examples of promoters useful in plants include an opaline synthase promoter isolated from T-DNA of *Agrobacterium*, and a cauliflower mosaic virus 35S promoter, among others, as well as enhanced promoter elements or chimeric promoter elements, e. g., an enhanced cauliflower mosaic virus (CaMV) 35S promoter linked to an enhancer element (an intron from heat shock protein 70 of *Zea mays*). Many expression-specific promoters functional in plants and useful in aspects of the invention are known in the art. For example, U.S. Pat. Nos. 5,837,848; 6,437,217 and 6,426,446 disclose root specific promoters; U.S. Pat. No. 6,433,252 discloses a maize L3 oleosin promoter; U.S. Patent Application Publication 2004/0216189 discloses a promoter for a plant nuclear gene encoding a plastid-localized aldolase; U.S. Pat. No. 6,084,089 discloses cold-inducible promoters; U.S. Pat. No. 6,140,078 discloses salt inducible promoters; U.S. Pat. No. 6,294,714 discloses light-inducible promoters; U.S. Pat. No. 6,252,138 discloses pathogen-inducible promoters; and U.S. Patent Application Publication 2004/0123347 A1 discloses water deficit-inducible promoters.

The promoter element can include nucleic acid sequences that are not naturally occurring promoters or promoter elements or homologues thereof but that can regulate expression of a gene. Examples of such "gene independent" regulatory sequences include naturally occurring or artificially designed RNA sequences that include a ligand-binding region or aptamer and a regulatory region (which can be cis-acting or trans-acting). See, for example, Isaacs et al. (2004) *Nat. Biotechnol.*, 22:841-847, Bayer and Smolke (2005) *Nature Biotechnol.*, 23:337-343, Mandal and Breaker (2004) *Nature Rev. Mol. Cell Biol.*, 5:451-463, Davidson and Ellington (2005) *Trends Biotechnol.*, 23:109-112, Winkler et al. (2002) *Nature*, 419:952-956, Sudarsan et al. (2003) *RNA*, 9:644-647, and Mandal and Breaker (2004) *Nature Struct. Mol. Biol.*, 11:29-35. Such "riboregulators" could be selected or designed for specific spatial or temporal specificity, for example, to regulate translation of the exogenous gene only in the presence (or absence) of a given concentration of the appropriate ligand.

Gene Suppression Elements:

The gene suppression element can be transcribable DNA of any suitable length, and will generally include at least about 19 to about 27 nucleotides (for example 19, 20, 21, 22, 23, or 24 nucleotides) for every target gene that the recombinant DNA construct is intended to suppress. In many embodiments the gene suppression element includes more than 23 nucleotides (for example, more than about 30, about 50, about 100, about 200, about 300, about 500, about 1000, about 1500, about 2000, about 3000, about 4000, or about 5000 nucleotides) for every target gene that the recombinant DNA construct is intended to suppress. Target genes are described under the heading "Target Genes".

Suitable gene suppression elements useful in the recombinant DNA constructs of the invention include at least one element (and, in some embodiments, multiple elements) selected from the group consisting of:

(a) DNA that includes at least one anti-sense DNA segment that is anti-sense to at least one segment of at least one first target gene;

(b) DNA that includes multiple copies of at least one anti-sense DNA segment that is anti-sense to at least one segment of at least one first target gene;

(c) DNA that includes at least one sense DNA segment that is at least one segment of at least one first target gene;

(d) DNA that includes multiple copies of at least one sense DNA segment that is at least one segment of at least one first target gene;

(e) DNA that transcribes to RNA for suppressing at least one first target gene by forming double-stranded RNA and includes at least one anti-sense DNA segment that is anti-sense to at least one segment of the at least one first target gene and at least one sense DNA segment that is at least one segment of the at least one first target gene;

(f) DNA that transcribes to RNA for suppressing at least one first target gene by forming a single double-stranded RNA and includes multiple serial anti-sense DNA segments that are anti-sense to at least one segment of the at least one first target gene and multiple serial sense DNA segments that are at least one segment of the at least one first target gene;

(g) DNA that transcribes to RNA for suppressing at least one first target gene by forming multiple double strands of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of inverted repeats;

(h) DNA that includes nucleotides derived from a miRNA, preferably a plant miRNA;

(i) DNA that includes nucleotides of a siRNA;

(j) DNA that transcribes to an RNA aptamer capable of binding to a ligand; and (k) DNA that transcribes to an RNA aptamer capable of binding to a ligand, and DNA that transcribes to regulatory RNA capable of regulating expression of at least one first target gene, wherein the regulation is dependent on the conformation of the regulatory RNA, and the conformation of the regulatory RNA is allosterically affected by the binding state of the RNA aptamer.

Non-limiting representations of these gene suppression elements are illustrated in FIGS. 2A-2F. Any of these gene suppression elements, whether transcribing to a single double-stranded RNA or to multiple double-stranded RNAs, can be designed to suppress more than one target gene, including, e.g., more than one allele of a target gene, multiple target genes (or multiple segments of at least one target gene) from a single species, or target genes from different species. Aptamers, regulatory RNA, and ligands are described under their respective headings below.

Anti-Sense DNA Segments:

In one embodiment, the at least one anti-sense DNA segment that is anti-sense to at least one segment of the at least one first target gene includes DNA sequence that is anti-sense or complementary to at least a segment of the at least one first target gene, and can include multiple anti-sense DNA segments, that is, multiple copies of at least one anti-sense DNA segment that is anti-sense to at least one segment of the at least one first target gene. Multiple anti-sense DNA segments can include DNA sequence that is anti-sense or complementary to multiple segments of the at least one first target gene, or to multiple copies of a segment of the at least one first target gene, or to segments of multiple first target genes, or to any combination of these. Multiple anti-sense DNA segments can be fused into a chimera, e.g., including DNA sequences that are anti-sense to multiple segments of one or more first target genes and fused together.

The anti-sense DNA sequence that is anti-sense or complementary to (that is, can form Watson-Crick base-pairs with) at least a segment of the at least one first target gene has preferably at least about 80%, or at least about 85%, or at least about 90%, or at least about 95% complementarity to at least a segment of the at least one first target gene. In one preferred embodiment, the DNA sequence that is anti-sense or complementary to at least a segment of the at least one first target gene has between about 95% to about 100% complementarity to at least a segment of the at least one first target gene. Where the at least one anti-sense DNA segment includes multiple anti-sense DNA segments, the degree of complementarity can be, but need not be, identical for all of the multiple anti-sense DNA segments.

Sense DNA Segments: In another embodiment, the at least one sense DNA segment that is at least one segment of the at least one first target gene includes DNA sequence that corresponds to (that is, has a sequence that is identical or substantially identical to) at least a segment of the at least one first target gene, and can include multiple sense DNA segments, that is, multiple copies of at least one sense DNA segment that corresponds to (that is, has the nucleotide sequence of) at least one segment of the at least one first target gene. Multiple sense DNA segments can include DNA sequence that is or that corresponds to multiple segments of the at least one first target gene, or to multiple copies of a segment of the at least one first target gene, or to segments of multiple first target genes, or to any combination of these. Multiple sense DNA segments can be fused into a chimera, that is, can include DNA sequences corresponding to multiple segments of one or more first target genes and fused together.

The sense DNA sequence that corresponds to at least a segment of the target gene has preferably at least about 80%, or at least about 85%, or at least about 90%, or at least about 95% sequence identity to at least a segment of the target gene. In one preferred embodiment, the DNA sequence that corresponds to at least a segment of the target gene has between about 95% to about 100% sequence identity to at least a segment of the target gene. Where the at least one sense DNA segment includes multiple sense DNA segments, the degree of sequence identity can be, but need not be, identical for all of the multiple sense DNA segments.

Multiple Copies:

Where the gene suppression element includes multiple copies of anti-sense or multiple copies of sense DNA sequence, these multiple copies can be arranged serially in tandem repeats. In some embodiments, these multiple copies can be arranged serially end-to-end, that is, in directly connected tandem repeats. In some embodiments, these multiple copies can be arranged serially in interrupted tandem repeats, where one or more spacer DNA segment can be located adjacent to one or more of the multiple copies. Tandem repeats, whether directly connected or interrupted or a combination of both, can include multiple copies of a single anti-sense or multiple copies of a single sense DNA sequence in a serial arrangement or can include multiple copies of more than one anti-sense DNA sequence or of more than one sense DNA sequence in a serial arrangement.

Double-Stranded RNA:

In those embodiments wherein the gene suppression element includes either at least one anti-sense DNA segment that is anti-sense to at least one segment of the at least one target gene or at least one sense DNA segment that is at least one segment of the at least one target gene, RNA transcribed from either the at least one anti-sense or at least one sense DNA may become double-stranded by the action of an RNA-dependent RNA polymerase. See, for example, U.S. Pat. No. 5,283,184.

In yet other embodiments, the gene suppression element can include DNA that transcribes to RNA for suppressing the at least one first target gene by forming double-stranded RNA and includes at least one anti-sense DNA segment that is anti-sense to at least one segment of the at least one target gene (as described above under the heading "Anti-sense DNA Segments") and at least one sense DNA segment that is at least one segment of the at least one first target gene (as described above under the heading "Sense DNA Segments"). Such a gene suppression element can further include spacer DNA segments. Each at least one anti-sense DNA segment is complementary to at least part of a sense DNA segment in order to permit formation of double-stranded RNA by intramolecular hybridization of the at least one anti-sense DNA segment and the at least one sense DNA segment. Such complementarity between an anti-sense DNA segment and a sense DNA segment can be, but need not be, 100% complementarity; in some embodiments, this complementarity can be preferably at least about 80%, or at least about 85%, or at least about 90%, or at least about 95% complementarity.

The double-stranded RNA can be in the form of a single dsRNA "stem" (region of base-pairing between sense and anti-sense strands), or can have multiple dsRNA "stems". In one embodiment, the gene suppression element can include DNA that transcribes to RNA for suppressing the at least one first target gene by forming essentially a single double-stranded RNA and includes multiple serial anti-sense DNA segments that are anti-sense to at least one segment of the at least one first target gene and multiple serial sense DNA segments that are at least one segment of the at least one first target gene; the multiple serial anti-sense and multiple serial sense segments can form a single double-stranded RNA "stem" or multiple "stems" in a serial arrangement (with or without non-base paired spacer DNA separating the multiple "stems"). In another embodiment, the gene suppression element includes DNA that transcribes to RNA for suppressing the at least one first target gene by forming multiple dsRNA "stems" of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of dsRNA "stems" (such as, but not limited to "inverted repeats"). Such multiple dsRNA "stems" can further be arranged in series or clusters to form tandem inverted repeats, or structures resembling "hammerhead" or "cloverleaf" shapes. Any of these gene suppression elements can further include spacer DNA segments found within a dsRNA "stem" (for example, as a spacer between multiple anti-sense or sense DNA segments or as a spacer between a base-pairing anti-sense DNA segment and a sense DNA segment) or outside of a double-stranded RNA "stem" (for example, as a loop region separating a pair of inverted repeats). In cases where base-pairing anti-sense and sense DNA segment are of unequal length, the longer segment can act as a spacer. FIGS. 2A-2F depict illustrations of possible embodiments of these gene suppression constructs.

miRNAs: In a further embodiment, the gene suppression element can include DNA that includes nucleotides derived from a miRNA (microRNA), that is, a DNA sequence that corresponds to a miRNA native to a virus or a eukaryote of interest (including plants and animals, especially invertebrates), or a DNA sequence derived from such a native miRNA but modified to include nucleotide sequences that do not correspond to the native miRNA. While miRNAs have not to date been reported in fungi, fungal miRNAs, should they exist, are also suitable for use in the invention. One preferred embodiment includes a gene suppression element containing DNA that includes nucleotides derived from a viral or plant miRNA.

In a non-limiting example, the nucleotides derived from a miRNA can include DNA that includes nucleotides corresponding to the loop region of a native miRNA and nucleotides that are selected from a target gene sequence. In another non-limiting example, the nucleotides derived from a miRNA can include DNA derived from a miRNA precursor sequence, such as a native pri-miRNA or pre-miRNA sequence, or nucleotides corresponding to the regions of a native miRNA and nucleotides that are selected from a target gene sequence number such that the overall structure (e.g., the placement of mismatches in the stem structure of the pre-miRNA) is preserved to permit the pre-miRNA to be processed into a mature miRNA. In yet another embodiment, the gene suppression element can include DNA that includes nucleotides derived from a miRNA and capable of inducing or guiding in-phase cleavage of an endogenous transcript into trans-acting siRNAs, as described by Allen et al. (2005) *Cell*, 121:207-221. Thus, the DNA that includes nucleotides derived from a miRNA can include sequence naturally occurring in a miRNA or a miRNA precursor molecule, synthetic sequence, or both.

siRNAs: In yet another embodiment, the gene suppression element can include DNA that includes nucleotides of a small interfering RNA (siRNA). The siRNA can be one or more native siRNAs (such as siRNAs isolated from a non-transgenic eukaryote or from a transgenic eukaryote), or can be one or more DNA sequences predicted to have siRNA activity (such as by use of predictive tools known in the art, see, for example, Reynolds et al. (2004) *Nature Biotechnol.,* 22:326-330). Multiple native or predicted siRNA sequences can be joined in a chimeric siRNA sequence for gene suppression. Such a DNA that includes nucleotides of a siRNA preferably includes at least 19 nucleotides, and in some embodiments preferably includes at least 21, at least 22, at least 23, or at least 24 nucleotides. In other embodiments, the DNA that includes nucleotides of a siRNA can contain substantially more than 21 nucleotides, for example, more than about 50, about 100, about 300, about 500, about 1000, about 3000, or about 5000 nucleotides or greater.

Target Genes:

The gene suppression element can be designed to suppress any first target gene. In some embodiments, the construct further includes a second gene suppression element for suppressing at least one second target gene, wherein the second gene suppression element is located adjacent to the intron. Whether a first or a second target gene, the target gene can include a single gene or part of a single gene that is targetted for suppression or can include, e. g., multiple consecutive segments of a target gene, multiple non-consecutive segments of a target gene, multiple alleles of a target gene, or multiple target genes from one or more species.

The target gene can be translatable (coding) sequence, or can be non-coding sequence (such as non-coding regulatory sequence), or both, and can include at least one gene selected from the group consisting of a eukaryotic target gene, a non-eukaryotic target gene, a microRNA precursor DNA sequence, and a microRNA promoter. The target gene can be native (endogenous) to the cell (e.g., a cell of a plant or animal) in which the recombinant DNA construct of the invention is transcribed, or can be native to a pest or pathogen of the plant or animal in which the construct is transcribed. The target gene can be an exogenous gene, such as a transgene in a plant. A target gene can be a native gene targetted for suppression, with or without concurrent expression of an exogenous transgene, for example, by including a gene expression element in the same or in a separate recombinant DNA construct. For example, it can be desirable to replace a native gene with an exogenous transgene homologue.

The target gene can include a single gene or part of a single gene that is targetted for suppression, or can include, for example, multiple consecutive segments of a target gene, multiple non-consecutive segments of a target gene, multiple alleles of a target gene, or multiple target genes from one or more species. A target gene sequence can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans.

One aspect of the invention provides recombinant DNA constructs wherein the target gene is exogenous to the plant in which the construct is to be transcribed, but endogenous to a pest or pathogen (e.g., viruses, bacteria, fungi, oomycetes, and invertebrates such as insects, nematodes, and molluscs) of the plant. The target gene can include multiple target genes, or multiple segments of one or more genes. In one preferred embodiment, the target gene or genes is a gene or genes of an invertebrate pest or pathogen of the plant. These recombinant DNA constructs are particularly useful in providing transgenic plants having resistance to one or more plant pests or pathogens, for example, resistance to a nematode such as soybean cyst nematode or root knot nematode or to a pest insect.

The target gene can be translatable (coding) sequence, or can be non-coding sequence (such as non-coding regulatory sequence), or both. Non-limiting examples of a target gene include non-translatable (non-coding) sequence, such as, but not limited to, 5' untranslated regions, promoters, enhancers, or other non-coding transcriptional regions, 3' untranslated regions, terminators, and introns. Target genes include genes encoding microRNAs, small interfering RNAs, RNA components of ribosomes or ribozymes, small nucleolar RNAs, and other non-coding RNAs (see, for example, non-coding RNA sequences provided publicly at rfam.wustl.edu; Erdmann et al. (2001) *Nucleic Acids Res.,* 29:189-193; Gottesman (2005) *Trends Genet.,* 21:399-404; Griffiths-Jones et al. (2005) *Nucleic Acids Res.,* 33:121-124). One specific example of a target gene includes a microRNA recognition site (that is, the site on an RNA strand to which a mature miRNA binds and induces cleavage). Another specific example of a target gene includes a microRNA precursor sequence native to a pest or pathogen of the transgenic plant, that is, the primary transcript encoding a microRNA, or the RNA intermediates processed from this primary transcript (e.g., a nuclear-limited pri-miRNA or a pre-miRNA which can be exported from the nucleus into the cytoplasm). See, for example, Lee et al. (2002) *EMBO Journal,* 21:4663-4670; Reinhart et al. (2002) *Genes & Dev.,* 16:161611626; Lund et al. (2004) *Science,* 303:95-98; and Millar and Waterhouse (2005) *Funct. Integr Genomics,* 5:129-135. Target genes can also include translatable (coding) sequence for genes encoding transcription factors and genes encoding enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin).

In many preferred embodiments, the target gene is an essential gene of the plant pest or pathogen. Essential genes include genes that are required for development of the pest or pathogen to a fertile reproductive adult. Essential genes include genes that, when silenced or suppressed, result in the death of the organism (as an adult or at any developmental stage, including gametes) or in the organism's inability to successfully reproduce (e.g., sterility in a male or female parent or lethality to the zygote, embryo, or larva). A description of nematode essential genes is found, e.g., in Kemphues K. "Essential Genes" (Dec. 24, 2005), WormBook, ed. The *C. elegans* Research Community, WormBook, doi/10.1895/wormbook.1.57.1, available on line at www.wormbook.org. Non-limiting examples of nematode essential genes include major sperm protein, RNA polymerase II, and chitin synthase (see, e.g., U.S. Patent Application Publication US20040098761 A1); additional soybean cyst nematode essential genes are provided in U.S. patent application Ser. No. 11/360,355, filed 23 Feb. 2006. A description of insect genes is publicly available at the *Drosophila* genome database (available on line at flybase.bio.indiana.edu/). The majority of predicted *Drosophila* genes have been analyzed for function by a cell culture-based RNA interference screen, resulting in 438 essential genes being identified; see Boutros et al. (2004) *Science*, 303:832-835, and supporting material available on line at www.sciencemag.org/cgi/content/full/303/5659/832/DC1. A description of bacterial and fungal essential genes is provided in the Database of Essential Genes ("DEG", available on line at tubic.tju.edu.cn/deg/); see Zhang et al. (2004) *Nucleic Acids Res.*, 32:D271-D272.

Plant pest invertebrates include, but are not limited to, pest nematodes, pest molluscs (slugs and snails), and pest insects. Plant pathogens of interest include fungi, oomycetes, bacteria (e.g., the bacteria that cause leaf spotting, fireblight, crown gall, and bacterial wilt), mollicutes, and viruses (e.g., the viruses that cause mosaics, vein banding, flecking, spotting, or abnormal growth). See also G. N. Agrios, "Plant Pathology" (Fourth Edition), Academic Press, San Diego, 1997, 635 pp., for descriptions of fungi, bacteria, mollicutes (including mycoplasmas and spiroplasmas), viruses, nematodes, parasitic higher plants, and flagellate protozoans, all of which are plant pests or pathogens of interest. See also the continually updated compilation of plant pests and pathogens and the diseases caused by such on the American Phytopathological Society's "Common Names of Plant Diseases", compiled by the Committee on Standardization of Common Names for Plant Diseases of The American Phytopathological Society, 1978-2005, available online at www.apsnet.org/online/common/top.asp.

Non-limiting examples of fungal plant pathogens of particular interest include, e. g., the fungi that cause powdery mildew, rust, leaf spot and blight, damping-off, root rot, crown rot, cotton boll rot, stem canker, twig canker, vascular wilt, smut, or mold, including, but not limited to, *Fusarium* spp., *Phakospora* spp., *Rhizoctonia* spp., *Aspergillus* spp., *Gibberella* spp., *Pyricularia* spp., and *Alternaria* spp., Specific examples of fungal plant pathogens include *Phakospora pachirhizi* (Asian soy rust), *Puccinia sorghi* (corn common rust), *Puccinia polysora* (corn Southern rust), *Fusarium oxysporum* and other *Fusarium* spp., *Alternaria* spp., *Penicillium* spp., *Rhizoctonia solani*, *Exserohilum turcicum* (Northern corn leaf blight), & polaris maydis (Southern corn leaf blight), *Ustilago maydis* (corn smut), *Fusarium graminearum* (*Gibberella zeae*), *Fusarium verticilliodes* (*Gibberella moniliformis*), *F. proliferatum* (*G. fujikuroi* var. *intermedia*), *F. subglutinans* (*G. subglutinans*), *Diplodia maydis*, *Sporisorium holci-sorghi*, *Colletotrichum graminicola*, *Setosphaeria turcica*, *Aureobasidium zeae*, *Sclerotinia sclerotiorum*, and the numerous fungal species provided in Tables 4 and 5 of U.S. Pat. No. 6,194,636. Non-limiting examples of plant pathogens include pathogens previously classified as fungi but more recently classified as oomycetes. Specific examples of oomycete plant pathogens of particular interest include members of the genus *Pythium* (e.g., *Pythium aphanidermatum*) and *Phytophthora* (e.g., *Phytophthora infestans*, *Phytophthora sojae*,) and organisms that cause downy mildew (e.g., *Peronospora farinosa*).

Non-limiting examples of bacterial pathogens include the mycoplasmas that cause yellows disease and spiroplasmas such as *Spiroplasma kunkelii*, which causes corn stunt, eubacteria such as *Pseudomonas avenae*, *Pseudomonas andropogonis*, *Erwinia stewartii*, *Pseudomonas syringae* pv. *syringae*, *Xylella fastidiosa*, and the numerous bacterial species listed in Table 3 of U.S. Pat. No. 6,194,636.

Non-limiting examples of viral plant pathogens of particular interest include maize dwarf mosaic virus (MDMV), sugarcane mosaic virus (SCMV, formerly MDMV strain B), wheat streak mosaic virus (WSMV), maize chlorotic dwarf virus (MCDV), barley yellow dwarf virus (BYDV), banana bunchy top virus (BBTV), and the numerous viruses listed in Table 2 of U.S. Pat. No. 6,194,636.

Invertebrate pests of particular interest, especially in but not limited to southern hemisphere regions (including South and Central America) include aphids, corn rootworms, spodoptera, noctuideae, potato beetle, *Lygus* spp., any hemipteran, homopteran, or heteropteran, any lepidopteran, any coleopteran, nematodes, cutworms, earworms, armyworms, borers, leaf rollers, and others. Arthropod pests specifically encompassed by this invention include various cutworm species including cutworm (*Agrotis repleta*), black cutworm (*Agrotis ipsilon*), cutworm (*Anicla ignicans*), granulate cutworm (*Feltia subterranea*), "gusano áspero" (*Agrotis malefida*); Mediterranean flour moth (*Anagasta kuehniella*), square-necked grain beetle (*Cathartus quadricollis*), flea beetle (*Chaetocnema* spp), rice moth (*Corcyra cephalonica*), corn rootworm or "vaquita de San Antonio" (*Diabotica speciosa*), sugarcane borer (*Diatraea saccharalis*), lesser cornstalk borer (*Elasmopalpus lignosellus*), brown stink bug (*Euschistus* spp.), corn earworm (*Helicoverpa zea*), flat grain beetle (*Laemophloeus minutus*), grass looper moth (*Mocis latipes*), sawtoothed grain beetle (*Oryzaephilus surinamensis*), meal moth (*Pyralis farinalis*), Indian meal moth (*Plodia interpunctella*), corn leaf aphid (*Rhopalosiphum maidis*), brown burrowing bug or "chinche subterránea" (*Scaptocoris castanea*), greenbug (*Schizaphis graminum*), grain weevil (*Sitophilus zeamais*), Angoumois grain moth (*Sitotroga cerealella*), fall armyworm (*Spodoptera frugiperda*), cadelle beetle (*Tenebroides mauritanicus*), two-spotted spider mite (*Tetranychus urticae*), red flour beetle (*Triboleum castaneum*), cotton leafworm (*Alabama argillacea*), boll weevil (*Anthonomus grandis*), cotton aphid (*Aphis gossypii*), sweet potato whitefly (*Bemisia tabaci*), various thrips species (*Frankliniella* spp.), cotton earworm (*Helicoverpa zea*), "oruga bolillera" (e.g., *Helicoverpa geletopoeon*), tobacco budworm (*Heliothis virescens*), stinkbug (*Nezara viridula*), pink bollworm (*Pectinophora gossypiella*), beet armyworm (*Spodoptera exigua*), spider mites (*Tetranychus* spp.), onion thrips (*Thrips tabaci*), greenhouse whitefly (*Trialeurodes vaporarium*), velvetbean caterpillar (*Anticarsia gemmatalis*), spotted maize beetle or "astilo moteado" (*Astylus atromaculatus*), "oruga de la alfalfa" (*Colias lesbia*), "chinche marrón" or "chinche de los cuernos" (*Dichelops furcatus*), "alquiche chico" (Edessa miditabunda), blister beetles (*Epicauta* spp.), "barrenador del brote" (*Epinotia aporema*), "oruga verde del yuyo colorado" (*Loxostege bifidalis*), rootknot nematodes (*Meloidogyne* spp.), "oruga cuarteadora" (*Mocis repanda*), southern green stink bug (*Nezara viridula*), "chinche de la alfalfa" (*Piezodorus guildinii*), green cloverworm (*Plathypena scabra*), soybean looper (*Pseudoplusia includens*), looper moth "isoca medidora del girasol" (*Rachiplusia nu*), yellow woolybear (*Spilosoma virginica*), yellowstriped armyworm (*Spodoptera ornithogalli*), various root weevils (family Curculionidae), various wireworms (family Elateridae), and various white grubs (family Scarabaeidae). Nematode pests specifically encompassed by this invention include nematode pests of maize (*Belonolaimus* spp., *Trichodorus* spp., *Longidorus* spp., *Dolichodorus* spp., *Anguina* spp., *Pratylenchus* spp., *Meloidogyne* spp., *Heterodera* spp.), soybean (*Heterodera glycines*, *Meloidogyne* spp., *Belonolaimus* spp.), bananas (*Radopholus similis*, *Meloidogyne* spp., *Heli-

*cotylenchus* spp.), sugarcane (*Heterodera sacchari*, *Pratylenchus* spp., *Meloidogyne* spp.), oranges (*Tylenchulus* spp., *Radopholus* spp., *Belonolaimus* spp., *Pratylenchus* spp., *Xiphinema* spp.), coffee (*Meloidogyne* spp., *Pratylenchus* spp.), coconut palm (*Bursaphelenchus* spp.), tomatoes (*Meloidogyne* spp., *Belonolaimus* spp., *Nacobbus* spp.), grapes (*Meloidogyne* spp., *Xiphinema* spp., *Tylenchulus* spp., *Criconemella* spp.), lemon and lime (*Tylenchulus* spp., *Radopholus* spp., *Belonolaimus* spp., *Pratylenchus* spp., *Xiphinema* spp.), cacao (*Meloidogyne* spp., *Rotylenchulus reniformis*), pineapple (*Meloidogyne* spp., *Pratylenchus* spp., *Rotylenchulus reniformis*), papaya (*Meloidogyne* spp., *Rotylenchulus reniformis*), grapefruit (*Tylenchulus* spp., *Radopholus* spp. *Belonolaimus* spp., *Pratylenchus* spp., *Xiphinema* spp., and broad beans (*Meloidogyne* spp.).

Target genes from pests can include invertebrate genes for major sperm protein, alpha tubulin, beta tubulin, vacuolar ATPase, glyceraldehyde-3-phosphate dehydrogenase, RNA polymerase II, chitin synthase, cytochromes, miRNAs, miRNA precursor molecules, miRNA promoters, as well as other genes such as those disclosed in U.S. Patent Application Publication 2006/0021087 A1, PCT Patent Application PCT/US05/11816, and in Table II of U.S. Patent Application Publication 2004/0098761 A1. Target genes from pathogens can include genes for viral translation initiation factors, viral replicases, miRNAs, miRNA precursor molecules, fungal tubulin, fungal vacuolar ATPase, fungal chitin synthase, fungal MAP kinases, fungal Pac1 Tyr/Thr phosphatase, enzymes involved in nutrient transport (e.g., amino acid transporters or sugar transporters), enzymes involved in fungal cell wall biosynthesis, cutinases, melanin biosynthetic enzymes, polygalacturonases, pectinases, pectin lyases, cellulases, proteases, genes that interact with plant avirulence genes, and other genes involved in invasion and replication of the pathogen in the infected plant. Thus, a target gene need not be endogenous to the plant in which the recombinant DNA construct is transcribed. A recombinant DNA construct of the invention can be transcribed in a plant and used to suppress a gene of a pathogen or pest that may infest the plant.

Specific, non-limiting examples of suitable target genes also include amino acid catabolic genes (such as, but not limited to, the maize LKR/SDH gene encoding lysine-ketoglutarate reductase (LKR) and saccharopine dehydrogenase (SDH), and its homologues), maize zein genes, genes involved in fatty acid synthesis (e.g., plant microsomal fatty acid desaturases and plant acyl-ACP thioesterases, such as, but not limited to, those disclosed in U.S. Pat. Nos. 6,426, 448, 6,372,965, and 6,872,872), genes involved in multi-step biosynthesis pathways, where it may be of interest to regulate the level of one or more intermediates, such as genes encoding enzymes for polyhydroxyalkanoate biosynthesis (see, for example, U.S. Pat. No. 5,750,848); and genes encoding cell-cycle control proteins, such as proteins with cyclin-dependent kinase (CDK) inhibitor-like activity (see, for example, genes disclosed in International Patent Application Publication Number WO 05007829A2). Target genes can include genes encoding undesirable proteins (e.g., allergens or toxins) or the enzymes for the biosynthesis of undesirable compounds (e.g., undesirable flavor or odor components). Thus, one embodiment of the invention is a transgenic plant or tissue of such a plant that is improved by the suppression of allergenic proteins or toxins, e.g., a peanut, soybean, or wheat kernel with decreased allergenicity. Target genes can include genes involved in fruit ripening, such as polygalacturonase. Target genes can include genes where expression is preferably limited to a particular cell or tissue or developmental stage, or where expression is preferably transient, that is to say, where constitutive or general suppression, or suppression that spreads through many tissues, is not necessarily desired. Thus, other examples of suitable target genes include genes encoding proteins that, when expressed in transgenic plants, make the transgenic plants resistant to pests or pathogens (see, for example, genes for cholesterol oxidase as disclosed in U.S. Pat. No. 5,763,245); genes where expression is pest- or pathogen-induced; and genes which can induce or restore fertility (see, for example, the barstar/barnase genes described in U.S. Pat. No. 6,759,575).

The recombinant DNA constructs of the invention can be designed to be more specifically suppress the target gene, by designing the gene suppression element or elements to include regions substantially non-identical to a non-target gene sequence. Non-target genes can include any gene not intended to be silenced or suppressed, either in a plant transcribing the recombinant DNA construct or in organisms that may come into contact with RNA transcribed from the recombinant DNA construct. A non-target gene sequence can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans).

In one embodiment, the target gene is a gene endogenous to a given species, such as a given plant (such as, but not limited to, agriculturally or commercially important plants, including monocots and dicots), and the non-target gene can be, e.g., a gene of a non-target species, such as another plant species or a gene of a virus, fungus, bacterium, invertebrate, or vertebrate, even a human. One non-limiting example is where the gene suppression element is designed to suppress a target gene that is a gene endogenous to a single species (e.g., Western corn rootworm, *Diabrotica virgifera virgifera* LeConte) but to not suppress a non-target gene such as genes from related, even closely related, species (e.g., Northern corn rootworm, *Diabrotica barberi* Smith and Lawrence, or Southern corn rootworm, *Diabrotica undecimpunctata*).

In other embodiments (e.g., where it is desirable to suppress a target gene across multiple species), it may be desirable to design the gene suppression element to suppress a target gene sequence common to the multiple species in which the target gene is to be silenced. Thus, a gene suppression element can be selected to be specific for one taxon (for example, specific to a genus, family, or even a larger taxon such as a phylum, e.g., arthropoda) but not for other taxa (e. g., plants or vertebrates or mammals). In one non-limiting example of this embodiment, a gene suppression element for gene silencing can be selected so as to target pathogenic fungi (e.g., a *Fusarium* spp.) but not target any gene sequence from beneficial fungi.

In another non-limiting example of this embodiment, a gene suppression element for gene silencing in corn rootworm can be selected to be specific to all members of the genus *Diabrotica*. In a further example of this embodiment, such a *Diabrotica*-targetted gene suppression element can be selected so as to not target any gene sequence from beneficial coleopterans (for example, predatory coccinellid beetles, commonly known as ladybugs or ladybirds) or other beneficial insect species.

The required degree of specificity of an RNA for silencing a target gene depends on various factors. For example, the RNA for silencing a target gene includes double-stranded RNA (dsRNA), and thus factors can include the size of the smaller dsRNA fragments that are expected to be produced by the action of Dicer or dicer-like proteins, and the relative importance of decreasing the dsRNA's potential to suppress non-target genes. For example, where the dsRNA fragments are expected to be 21 base pairs in size, one particularly preferred embodiment includes RNA for silencing a target gene that encodes regions substantially non-identical to a non-target gene sequence, such as regions within which every contiguous fragment including at least 21 nucleotides matches fewer than 21 (e.g., fewer than 21, or fewer than 20, or fewer than 19, or fewer than 18, or fewer than 17) out of 21 contiguous nucleotides of a non-target gene sequence. In another embodiment, regions substantially non-identical to a non-target gene sequence include regions within which every contiguous fragment including at least 19 nucleotides matches fewer than 19 (e.g., fewer than 19, or fewer than 18, or fewer than 17, or fewer than 16) out of 19 contiguous nucleotides of a non-target gene sequence.

In some embodiments, it may be desirable to design the RNA for silencing a target gene to include regions predicted to not generate undesirable polypeptides, for example, by screening the RNA for silencing a target gene for sequences that may encode known undesirable polypeptides or close homologues of these. Undesirable polypeptides include, but are not limited to, polypeptides homologous to known allergenic polypeptides and polypeptides homologous to known polypeptide toxins. Publicly available sequences encoding such undesirable potentially allergenic peptides are available, for example, the Food Allergy Research and Resource Program (FARRP) allergen database (available at allergenonline.com) or the Biotechnology Information for Food Safety Databases (available at www.iit.edu/~sgendel/fa.htm) (see also, for example, Gendel (1998) *Adv. Food Nutr. Res.*, 42:63-92). Undesirable sequences can also include, for example, those polypeptide sequences annotated as known toxins or as potential or known allergens and contained in publicly available databases such as GenBank, EMBL, SwissProt, and others, which are searchable by the Entrez system (www.ncbi.nih.gov/Entrez). Non-limiting examples of undesirable, potentially allergenic peptide sequences include glycinin from soybean, oleosin and agglutinin from peanut, glutenins from wheat, casein, lactalbumin, and lactoglobulin from bovine milk, and tropomyosin from various shellfish (allergenonline.com). Non-limiting examples of undesirable, potentially toxic peptides include tetanus toxin tetA from *Clostridium tetani*, diarrheal toxins from *Staphylococcus aureus*, and venoms such as conotoxins from *Conus* spp. and neurotoxins from arthropods and reptiles (www.ncbi.nih.gov/Entrez).

In one non-limiting example, an RNA for silencing a target gene is screened to eliminate those transcribable sequences encoding polypeptides with perfect homology to a known allergen or toxin over 8 contiguous amino acids, or with at least 35% identity over at least 80 amino acids; such screens can be performed on any and all possible reading frames in both directions, on potential open reading frames that begin with AUG (ATG in the corresponding DNA), or on all possible reading frames, regardless of whether they start with an AUG (or ATG) or not. When a "hit" or match is made, that is, when a sequence that encodes a potential polypeptide with perfect homology to a known allergen or toxin over 8 contiguous amino acids (or at least about 35% identity over at least about 80 amino acids), is identified, the nucleic acid sequences corresponding to the hit can be avoided, eliminated, or modified when selecting sequences to be used in an RNA for silencing a target gene.

Avoiding, elimination of, or modification of, an undesired sequence can be achieved by any of a number of methods known to those skilled in the art. In some cases, the result can be novel sequences that are believed to not exist naturally. For example, avoiding certain sequences can be accomplished by joining together "clean" sequences into novel chimeric sequences to be used in an RNA for silencing a target gene.

Since the RNA for silencing a target gene includes double-stranded RNA (dsRNA), applicants recognize that in some dsRNA-mediated gene silencing, it is possible for imperfectly matching dsRNA sequences to be effective at gene silencing. For example, it has been shown that mismatches near the center of a miRNA complementary site has stronger effects on the miRNA's gene silencing than do more distally located mismatches. See, for example, FIG. 4 in Mallory et al. (2004) *EMBO J.*, 23:3356-3364. In another example, it has been reported that, both the position of a mismatched base pair and the identity of the nucleotides forming the mismatch influence the ability of a given siRNA to silence a target gene, and that adenine-cytosine mismatches, in addition to the G:U wobble base pair, were well tolerated (see Du et al. (2005) *Nucleic Acids Res.*, 33:1671-1677). Thus, the dsRNA that is included in the RNA for silencing a target gene need not always have 100% sequence identity with the intended target gene, but generally would preferably have substantial sequence identity with the intended target gene, such as about 95%, about 90%, about 85%, or about 80% sequence identity with the intended target gene. One skilled in the art would be capable of judging the importance given to screening for regions predicted to be more highly specific to the target gene or predicted to not generate undesirable polypeptides, relative to the importance given to other criteria, such as, but not limited to, the percent sequence identity with the intended target gene or the predicted gene silencing efficiency of a given sequence. For example, it may be desirable for an RNA for silencing a target gene to be active across several species, and therefore one skilled in the art can determine that it is more important to include in the RNA for silencing a target gene regions specific to the several species of interest, but less important to screen for regions predicted to have higher gene silencing efficiency or for regions predicted to generate undesirable polypeptides.

RNA Aptamers:

Nucleic acid aptamers are nucleic acid molecules that bind to a ligand through binding mechanism that is not primarily based on Watson-Crick base-pairing (in contrast, for example, to the base-pairing that occurs between complementary, anti-parallel nucleic acid strands to form a double-stranded nucleic acid structure). See, for example, Ellington and Szostak (1990) *Nature*, 346:818-822. A nucleic acid aptamer generally includes a primary nucleotide sequence that allows the aptamer to form a secondary structure (e.g., by forming stem-loop structures) that allows the aptamer to bind to its ligand. Binding of the aptamer to its ligand is preferably specific, allowing the aptamer to distinguish between two or more molecules that are structurally similar (see, for example, Bayer and Smolke (2005) *Nature Biotechnol.*, 23:337-343). Aptamers useful in the invention can, however, be monovalent (binding a single ligand) or multivalent (binding more than one individual ligand, e.g., binding one unit of two or more different ligands). See, for example, Di Giusto and King (2004) *J. Biol. Chem.*, 279:46483-46489, describing the design and construction of multivalent, circular DNA aptamers.

Aptamers useful in the invention can include DNA, RNA, nucleic acid analogues (e.g., peptide nucleic acids), locked nucleic acids, chemically modified nucleic acids, or combinations thereof. See, for example, Schmidt et al. (2004) *Nucleic Acids Res.*, 32:5757-5765, who describe locked nucleic acid aptamers. In a preferred embodiment of the invention, the aptamer is an RNA aptamer. In a particularly preferred embodiment, the aptamer is produced by transcription in planta. Examples of aptamers can be found, for example, in the public Aptamer Database, available on line at aptamer.icmb.utexas.edu (Lee et al. (2004) *Nucleic Acids Res.*, 32(1):D95-100).

Aptamers can be designed for a given ligand by various procedures known in the art, including in vitro selection or directed evolution techniques. See, for example, "SELEX" ("systematic evolution of ligands by exponential enrichment"), as described in Tuerk and Gold (1990) *Science*, 249:505-510, Ellington and Szostak (1990) *Nature*, 346: 818-822, Ellington and Szostak (1992) *Nature*, 355:850-852, selection of bifunctional RNA aptamers by chimeric SELEX, as described by Burke and Willis (1998), *RNA*, 4:1165-1175, selection using ligands bound to magnetic particles as described by Murphy et al. (2003) *Nucleic Acids Res.*, 31:e110, an automated SELEX technique described by Eulberg et al. (2005) *Nucleic Acids Res.*, 33(4):e45, and a SELEX-type technique for obtaining aptamers raised against recombinant molecules expressed on cell surfaces, as descried by Ohuchi et al. (2005) *Nucleic Acid Symposium Series*, 49:351-352 Selection can begin with a random pool of RNAs, from a partially structured pool of RNAs (see, for example, Davis and Szostak (2002) *Proc. Natl. Acad. Sci. USA*, 99: 11616-11621), or from a pool of degenerate RNAs (see, for example, Geiger et al. (1996) *Nucleic Acids Res.*, 24: 1029-1036). Secondary structure models, folding, and hybridization behavior for a given RNA sequence can be predicted using algorithms, e.g., as described by Zuker (2003) *Nucleic Acids Res.*, 31: 3406-3415. Thus, aptamers for a given ligand can be designed de novo using suitable selection. One non-limiting example of aptamer design and selection is described in detail in Weill et al. (2004) *Nucleic Acids Res.*, 32:5045-5058, which describes isolation of various ATP-binding aptamers and secondary selection of aptamers that bind cordycepin (3' deoxyadenosine). Another non-limiting example of aptamer design is given in Huang and Szostak (2003) RNA, 9:1456-1463, which describes the in vitro evolution of novel aptamers with new specificities and new secondary structures from a starting aptamer.

Ligands:

Ligands useful in the invention can include amino acids or their biosynthetic or catabolic intermediates, peptides, proteins, glycoproteins, lipoproteins, carbohydrates, fatty acids and other lipids, steroids, terpenoids, hormones, nucleic acids, aromatics, alkaloids, natural products or synthetic compounds (e.g., dyes, pharmaceuticals, antibiotics, herbicides), inorganic ions, and metals, in short, any molecule (or part of a molecule) that can be recognized and be bound by a nucleic acid secondary structure by a mechanism not primarily based on Watson-Crick base pairing. In this way, the recognition and binding of ligand and aptamer is analogous to that of antigen and antibody, or of biological effector and receptor. Ligands can include single molecules (or part of a molecule), or a combination of two or more molecules (or parts of a molecule), and can include one or more macromolecular complexes (e.g., polymers, lipid bilayers, liposomes, cellular membranes or other cellular structures, or cell surfaces). See, for example, Plummer et al. (2005) *Nucleic Acids Res.*, 33:5602-5610, which describes selection of aptamers that bind to a composite small molecule-protein surface; Zhuang et al. (2002) *J. Biol. Chem.*, 277:13863-13872, which describes the association of insect mid-gut receptor proteins with lipid rafts, which affects the binding of *Bacillus thuringiensis* insecticidal endotoxins; and Homann and Goringer (1999) *Nucleic Acids Res.*, 27:2006-2014, which describes aptamers that bind to live trypanosomes.

Non-limiting examples of specific ligands include vitamins such as coenzyme $B_{12}$ and thiamine pyrophosphate, flavin mononucleotide, guanine, adenosine, S-adenosylmethionine, S-adenosylhomocysteine, coenzyme A, lysine, tyrosine, dopamine, glucosamine-6-phosphate, caffeine, theophylline, antibiotics such as chloramphenicol and neomycin, herbicides such as glyphosate and dicamba, proteins including viral or phage coat proteins and invertebrate epidermal or digestive tract surface proteins, and RNAs including viral RNA, transfer-RNAs (t-RNAs), ribosomal RNA (rRNA), and RNA polymerases such as RNA-dependent RNA polymerase (RdRP). Ligands suitable for use in this invention include the insect mid-gut brush border receptor proteins that are recognized by *Bacillus thuringiensis* insecticidal endotoxins. See, for example, Knight et al. (1995) *J. Biol. Chem.*, 270:17765-17770, and Gill et al. (1995) *J. Biol. Chem.*, 270:27277-27282, which describe the isolation, identification, and cloning of examples of such receptor proteins; Gomez et al. (2001) *J. Biol. Chem.*, 276:28906-28912, and Daniel et al. (2002) *Appl. Env. Microbiol.*, 68:2106-2112, which describe techniques for identifying binding epitopes of such receptor proteins and for studying their binding affinities; Jurat-Fuentes and Adang (2001) *Appl. Env. Microbiol.*, 67:323-329, and Jurat-Fuentes et al. (2001), *Appl. Env. Microbiol.*, 67:872-879, which describe endotoxin-receptor binding assays involving either membrane blots or surface plasmon resonance measured binding of brush border membrane vesicles to endotoxin. Other examples of suitable ligands to which RNA aptamers of the invention bind include steroid receptors, such as estrogen receptors, androgen receptors, retinoid receptors, and ecdysone receptors (see, for example, Saez et al. (2000) *Proc. Natl. Acad. Sci. USA*, 97:14512-14517. Where ligands are receptor molecules or receptor complexes, RNA aptamers of the invention can optionally act as antagonists or as agonists. One class of RNA aptamers useful in the invention are "thermoswitches" that do not bind a ligand but are thermally responsive, that is to say, the aptamer's conformation is determined by temperature. See, for example, Box 3 in Mandal and Breaker (2004) *Nature Rev. Mol. Cell Biol.*, 5:451-463.

An aptamer can be described by its binding state, that is, whether the aptamer is bound (or unbound) to its respective ligand. The binding site (or three-dimensional binding domain or domains) of an aptamer can be described as occupied or unoccupied by the ligand. Similarly, a population of a given aptamer can be described by the fraction of the population that is bound or unbound to the ligand. The affinity of an aptamer for its ligand can be described in terms of the rate of association (binding) of the aptamer with the ligand and the rate of dissociation of the ligand from the aptamer, e.g., by the equilibrium association constant (K) or by its reciprocal, the affinity constant ($K_a$) as is well known in the art. These rates can be determined by methods similar to those commonly used for determining binding kinetics of ligands and receptors or antigens and antibodies, such as, but not limited to, equilibrium assays, competition assays, surface plasmon resonance, and predictive models. The affinity of an aptamer for its ligand can be selected, e.g., during in vitro evolution of the aptamer, or further modified by changes to the aptamer's primary sequence, where such changes can be guided by calculations of binding energy or by algorithms, e.g., as described by Zuker (2003) *Nucleic Acids Res.*, 31:3406-3415 or Bayer and Smolke (2005) *Nature Biotechnol.*, 23:337-343.

The binding state of an aptamer preferably at least partially determines the secondary structure (e.g., the formation of double-stranded or single stranded regions) and the three-dimensional conformation of the aptamer. In embodiments where the transcribable DNA further includes DNA that transcribes to regulatory RNA capable of regulating expression of a target sequence, the binding state of the aptamer allosterically affects the conformation of the regulatory RNA and thus the ability of the regulatory RNA to regulate expression of the target sequence.

In one preferred embodiments, the aptamer (transcribed RNA) is flanked by DNA that transcribes to RNA capable of forming double-stranded RNA (dsRNA). In some of these embodiments, the dsRNA is processed by an RNAi (siRNA or miRNA) mechanism, whereby the aptamer is cleaved from the rest of the transcript. In other, particularly preferred embodiments, the two transcribed RNA regions flanking the aptamer form at least partially double-stranded RNA "stem" between themselves, wherein the aptamer serves as a "spacer" or "loop" in a stem-loop structure; such an arrangement is expected to enhance the stability or half-life of the transcript in a manner analogous to that observed for DNA (see, for example, Di Giusto and King (2004) *J. Biol. Chem.*, 279:46483-46489). Transgenic plants having in their genome DNA that transcribes to such aptamers having enhanced stability are particularly desirable, e.g., where the aptamer functions to inhibit or kill a pathogen or pest of the transgenic plant.

Regulatory RNA:

In many embodiments, the transcribable DNA further includes DNA that transcribes to regulatory RNA capable of regulating expression of a target sequence, wherein the regulation of the target sequence is dependent on the conformation of the regulatory RNA, and the conformation of the regulatory RNA is allosterically affected by the binding state of the RNA aptamer. Such combinations of an aptamer with a regulator RNA domain are commonly known as riboswitches. The regulatory RNA is typically downstream of the aptamer but the two domains may overlap; see, e.g., Najafi-Shoushtari and Famulok (2005) RNA, 11:1514-1520, which describes a hairpin ribozyme that includes an aptamer domain and is competitively regulated by flavin mononucleotide and an oligonucleotide complementary to the aptamer domain. In some embodiments, the regulatory RNA is operably linked to the target sequence, and acts "in cis". In other embodiments, the regulatory RNA is not operably linked to the target sequence, and acts "in trans".

Any target sequence may be chosen, including one or more target sequences selected from a gene native to the transgenic plant of the invention, a transgene in the transgenic plant, and a gene native to a pest or pathogen of the transgenic plant. The target sequence can include a sequence that expresses a gene of interest (e.g., an RNA encoding a protein), or a sequence that suppresses a gene of interest (e.g., an RNA that is processed to an siRNA or miRNA that in turn suppresses the gene of interest). The target sequence can be translatable (coding) sequence, or can be non-coding sequence (such as non-coding regulatory sequence), or both. The target sequence can include at least one eukaryotic target sequence, at least one non-eukaryotic target sequence, or both. A target sequence can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans. Suitable target sequences are further described as "target genes" under the heading "Target Genes".

In riboswitch embodiments including an aptamer and a regulatory RNA, the riboswitch regulates expression of the target sequence by any suitable mechanism. One non-limiting mechanism is transcriptional regulation by the ligand-dependent formation of an intrinsic terminator stem (an extended stem-loop structure typically followed by a run of 6 or more U residues) that causes RNA polymerase to abort transcription, e.g., before a complete mRNA is formed. In "off" riboswitches, in the absence of sufficient ligand, the unbound aptamer domain permits formation of an "antiterminator stem", which prevents formation of the intrinsic terminator stem and thus allows transcription to proceed; thus, the default state of the riboswitch is "on" (i.e., transcription normally proceeds) and the ligand must be added to turn the riboswitch off. In "on" riboswitches that use this mechanism, the aptamer domain must be in the bound (ligand-occupied) conformation to permit formation of the "antiterminator stem" and allow transcription. Another mechanism is translation regulation, where ligand binding causes structural changes in full-length mRNAs and thereby permits (or prevents) ribosomes from binding to the ribosomal binding site (RBS); the formation of an "anti-anti-RBS" stem and an "anti-RBS" stem is also mutually exclusive. In "on" riboswitches that use this mechanism, absence of the ligand allows formation of an anti-anti-RBS, and thus a structurally unencumbered RBS to which the ribosome can bind. A combination of both transcriptional and translational regulation is also possible. For a detailed discussion of regulation mechanisms, see Mandal and Breaker (2004) *Nature Rev. Mol. Cell Biol.*, 5:451-463.

In some embodiments, the regulatory RNA includes a ribozyme, e.g., a self-cleaving ribozyme, a hammerhead ribozyme, or a hairpin ribozyme. Certain embodiments of the regulatory RNA include RNA sequence that is complementary or substantially complementary to the target sequence. One non-limiting example is where the regulatory RNA includes an anti-sense segment that is complementary or substantially complementary to the target sequence. See, for example, Bayer and Smolke (2005) *Nature Biotechnol.*, 23:337-343, where the regulatory RNA includes both an anti-sense segment complementary to the target sequence, and a sense segment complementary to the anti-sense segment, wherein the anti-sense segment and sense segment are capable of hybridizing to each other to form an intramolecular double-stranded RNA.

In some embodiments, regulation of a target sequence involves Watson-Crick base-pairing of the regulatory RNA to the target sequence (e.g., in trans-acting embodiments, see, e.g., Bayer and Smolke (2005) *Nature Biotechnol.*, 23:337-343). Particularly in the case of such trans-acting embodiments, suitable target sequences include the target genes described under the heading "Target Genes". A target sequence of interest can be more specifically targetted by designing the regulatory RNA to include regions substantially non-identical to a non-target sequence. Non-target sequences can include any gene for which the expression is preferably not modified, either in a plant transcribing the recombinant DNA construct or in organisms that may come into contact with RNA transcribed from the recombinant DNA construct. A non-target sequence can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans).

One embodiment provides a transgenic plant having in its genome a recombinant DNA construct including transcribable DNA including DNA that transcribes to an RNA aptamer capable of binding to a ligand, wherein the construct confers chemically inducible or suppressible male sterility or fertility for hybridization. Preferred examples use a riboswitch containing an aptamer that binds a ligand that is an already registered substance, e.g., an approved herbicide. In a non-limiting example, a transgenic plant harboring a male sterility gene under the control of a male-specific promoter and a glyphosate "off" riboswitch is male-sterile unless glyphosate is applied. In contrast, a transgenic plant harboring a male sterility gene under the control of a male-specific promoter and a glyphosate "on" riboswitch is male-sterile only when glyphosate is applied.

One application of the invention is to provide a ligand-activated, herbicide-resistant system for gene identity preservation ("gene lock") as well as to maintain herbicide-resistant volunteer control. In one embodiment, the DNA sequence encoding an "on" riboswitch is inserted into an expression cassette containing as the target sequence "CP4", a selectable marker conferring glyphosate resistance, epsps-cp4 (5-enolpyruvylshikimate-3-phosphate synthase from *Agrobacterium tumefaciens* strain CP4), to conditionally express CP4 in transgenic plants. Transgenic plants harboring the riboswitch-controlled CP4 cassette express CP4 only in the presence of the ligand, which is applied (e.g., by a foliar spray) to the plant by means of a proprietary glyphosate formulation containing the ligand. Upon application, the formulated glyphosate herbicide activates CP4 transcription/translation and renders the transgenic plant resistant to glyphosate. Transgenic plants are susceptible to generic glyphosate formulations that do not contain the ligand. Similarly, this approach can be applied to any other herbicide-resistance gene/herbicide combinations, for example, dicamba-degrading-oxygenase/dicamba, or antibiotic-resistance gene/antibiotic combination.

In another embodiment, the target sequence is a gene endogenous to a given species, such as a given plant (such as, but not limited to, agriculturally or commercially important plants, including monocots and dicots), and the non-target sequence can be, for example, a gene of a non-target species, such as another plant species or a gene of a virus, fungus, bacterium, invertebrate, or vertebrate, even a human. One non-limiting example is where it is desirable to design either the aptamer, or the regulatory RNA, or both, in order to modify the expression of a target sequence that is a gene endogenous to a single species (e.g., Western corn rootworm, *Diabrotica virgifera virgifera* LeConte) but to not modify the expression of a non-target sequence such as genes from related, even closely related, species (e.g., Northern corn rootworm, *Diabrotica barberi* Smith and Lawrence, or Southern corn rootworm, *Diabrotica undecimpunctata*).

In other embodiments (e.g., where it is desirable to modify the expression of a target sequence across multiple species), it may be desirable to design the aptamer, or the regulatory RNA, or both, to modify the expression of a target sequence common to the multiple species in which the expression of the target sequence is to be modified. Thus, the aptamer, or the regulatory RNA, or both, can be selected to be specific for one taxon (e.g., specific to a genus, family, or even a larger taxon such as a phylum, e.g., arthropoda) but not for other taxa (for example, plants or vertebrates or mammals). In one non-limiting example of this embodiment, a regulatory RNA can be selected so as to target pathogenic fungi (e.g., a *Fusarium* spp.) but not target any gene sequence from beneficial fungi (e.g., beneficial soil mycorrhizal fungi).

In another non-limiting example of this embodiment, the aptamer, or the regulatory RNA, or both, to regulate gene expression in corn rootworm can be selected to be specific to all members of the genus *Diabrotica*. For example, a regulatory RNA including a *Diabrotica*-targetted suppression element (e.g., anti-sense RNA, double-stranded RNA, microRNA, or tandem RNA repeats) can be selected so as to not target any gene sequence from beneficial coleopterans (for example, predatory coccinellid beetles, commonly known as ladybugs or ladybirds) or other beneficial insect species.

The required degree of specificity of a regulatory RNA that includes a gene suppression element (e.g., anti-sense RNA, double-stranded RNA, microRNA, or tandem RNA repeats) for suppression of a target sequence depends on various factors. For example, where the gene suppression element includes double-stranded RNA (dsRNA), factors can include the size of the smaller dsRNA fragments that are expected to be produced by the action of Dicer, and the relative importance of decreasing the dsRNA's potential to suppress non-target sequences. For example, where the dsRNA fragments are expected to be 21 base pairs in size, one particularly preferred embodiment can be to include in the regulatory RNA a sequence capable of forming dsRNA and encoding regions substantially non-identical to a non-target sequence, such as regions within which every contiguous fragment including at least 21 nucleotides matches fewer than 21 (e.g., fewer than 21, or fewer than 20, or fewer than 19, or fewer than 18, or fewer than 17) out of 21 contiguous nucleotides of a non-target sequence. In another embodiment, regions substantially non-identical to a non-target sequence include regions within which every contiguous fragment including at least 19 nucleotides matches fewer than 19 (e.g., fewer than 19, or fewer than 18, or fewer than 17, or fewer than 16) out of 19 contiguous nucleotides of a non-target sequence.

In some embodiments, it may be desirable to design the aptamer, the regulatory RNA, or both, to include regions predicted to not generate undesirable polypeptides, for example, by screening the aptamer, the regulatory RNA, or both, for sequences that may encode known undesirable polypeptides or close homologues of these. Undesirable polypeptides include, but are not limited to, polypeptides homologous to known allergenic polypeptides and polypeptides homologous to known polypeptide toxins. Publicly available sequences encoding such undesirable potentially allergenic peptides are available, for example, the Food Allergy Research and Resource Program (FARRP) allergen database (available at allergenonline.com) or the Biotechnology Information for Food Safety Databases (available at www.iit.edu/~sgendel/fa.htm) (see also, for example, Gendel (1998) *Adv. Food Nutr. Res.*, 42:63-92). Undesirable sequences can also include, for example, those polypeptide sequences annotated as known toxins or as potential or known allergens and contained in publicly available databases such as GenBank, EMBL, SwissProt, and others, which are searchable by the Entrez system (www.ncbi.nih.gov/Entrez). Non-limiting examples of undesirable, potentially allergenic peptide sequences include glycinin from soybean, oleosin and agglutinin from peanut, glutenins from wheat, casein, lactalbumin, and lactoglobulin from bovine milk, and tropomyosin from various shellfish (allergenonline.com). Non-limiting examples of undesirable, potentially toxic peptides include tetanus toxin tetA from *Clostridium tetani*, diarrheal toxins from *Staphylococcus aureus*, and venoms such as conotoxins from *Conus* spp. and neurotoxins from arthropods and reptiles (www.ncbi.nih.gov/Entrez).

In one non-limiting example, a proposed aptamer, regulatory RNA, or both, can be screened to eliminate those transcribable sequences encoding polypeptides with perfect homology to a known allergen or toxin over 8 contiguous amino acids, or with at least 35% identity over at least 80 amino acids; such screens can be performed on any and all possible reading frames in both directions, on potential open reading frames that begin with ATG, or on all possible reading frames, regardless of whether they start with an ATG or not. When a "hit" or match is made, that is, when a sequence that encodes a potential polypeptide with perfect homology to a known allergen or toxin over 8 contiguous amino acids (or at least about 35% identity over at least about 80 amino acids), is identified, the DNA sequences corresponding to the hit can be avoided, eliminated, or modified when selecting sequences to be used in the aptamer, the regulatory RNA, or both.

Avoiding, elimination of, or modification of, an undesired sequence can be achieved by any of a number of methods known to those skilled in the art. In some cases, the result can be novel sequences that are believed to not exist naturally. For example, avoiding certain sequences can be accomplished by joining together "clean" sequences into novel chimeric sequences to be used in a gene suppression element.

Where the regulatory RNA includes double-stranded RNA (dsRNA) for silencing a target gene, applicants recognize that in some dsRNA-mediated gene silencing, it is possible for imperfectly matching dsRNA sequences to be effective at gene silencing. For example, it has been shown that mismatches near the center of a miRNA complementary site has stronger effects on the miRNA's gene silencing than do more distally located mismatches. See, for example, FIG. 4 in Mallory et al. (2004) *EMBO J.*, 23:3356-3364. In another example, it has been reported that, both the position of a mismatched base pair and the identity of the nucleotides forming the mismatch influence the ability of a given siRNA to silence a target sequence, and that adenine-cytosine mismatches, in addition to the G:U wobble base pair, were well tolerated (see Du et al. (2005) *Nucleic Acids Res.*, 33:1671-1677). Thus, a regulatory RNA that includes double-stranded RNA need not always have 100% sequence identity with the intended target sequence, but generally would preferably have substantial sequence identity with the intended target sequence, such as about 95%, about 90%, about 85%, or about 80% sequence identity with the intended target sequence. One skilled in the art would be capable of judging the importance given to screening for regions predicted to be more highly specific to the first target sequence or predicted to not generate undesirable polypeptides, relative to the importance given to other criteria, such as, but not limited to, the percent sequence identity with the intended first target sequence or the predicted gene silencing efficiency of a given sequence. For example, it may be desirable for a given regulatory RNA that includes double-stranded RNA for gene silencing to be active across several species, and therefore one skilled in the art can determine that it is more important to include in the regulatory RNA regions specific to the several species of interest, but less important to screen for regions predicted to have higher gene silencing efficiency or for regions predicted to generate undesirable polypeptides.

In many embodiments, the transgenic plant cell has in its genome recombinant DNA including transcribable DNA including (a) DNA that transcribes to an RNA aptamer capable of binding to a ligand, and (b) DNA that transcribes to regulatory RNA capable of regulating expression of a target sequence, wherein the regulation is dependent on the conformation of the regulatory RNA, and the conformation of said regulatory RNA is allosterically affected by the binding state of said RNA aptamer. In these embodiments, binding of the aptamer to its ligand results in a specific change in the expression of the target sequence, which may be an increase or a decrease in expression, depending on the design of the recombinant DNA.

In one embodiment, binding of the ligand to the RNA aptamer results in an increase of expression of the target sequence relative to expression in the absence of the binding. In another embodiment, binding of the ligand to the RNA aptamer results in a decrease of expression of the target sequence relative to expression in the absence of the binding.

Some embodiments are characterized by "autoinducibility". In one such embodiment, binding of the ligand to the RNA aptamer results in an increase of expression of the target sequence relative to expression in the absence of the binding, wherein the increase of expression results in a level of the ligand sufficient to maintain the increase of expression. In another embodiment, binding of the ligand to the RNA aptamer results in a decrease of expression of the target sequence relative to expression in the absence of the binding, the decrease of expression resulting in a level of the ligand sufficient to maintain the increase of expression.

Thus, another aspect of the invention is a method of modifying expression of a gene of interest in a plant cell, including transcribing in a transgenic plant cell of the invention, or a plant, progeny plant, or seed or other plant tissue derived from such a transgenic plant cell, recombinant or heterologous DNA that transcribes to (a) an RNA aptamer capable of binding to a ligand, and (b) regulatory RNA capable of regulating expression of a target sequence, wherein the regulation is dependent on the conformation of the regulatory RNA, and wherein the conformation of the regulatory RNA is allosterically affected by the binding state of the RNA aptamer, whereby expression of the gene of interest is modified relative to its expression in the absence of transcription of the recombinant DNA construct.

Introns:

As used herein, "intron" or "intron sequence" generally means non-coding DNA sequence from a natural gene, which retains in the recombinant DNA constructs of this invention its native capability to be excised from pre-mRNA transcripts, e.g., native intron sequences found with associated protein coding RNA regions, wherein the native introns are spliced, allowing exons to be assembled into mature mRNAs before the RNA leaves the nucleus. Such an excisable intron has a 5' splice site and a 3' splice site. Introns can be self-splicing or non-self-splicing (that is, requiring enzymes or a spliceosome for splicing to occur) and can be selected for different splicing efficiency.

Introns suitable for use in constructs of the invention can be viral introns (e.g., Yamada et al. (1994) *Nucleic Acids*

Res., 22:2532-2537), eukaryotic introns (including animal, fungal, and plant introns), archeal or bacterial introns (e.g., Belfort et al. (1995) *J. Bacteriol.*, 177:3897-3903), or any naturally occurring or artificial (e.g., Yoshimatsu and Nagawa (1989) *Science,* 244:1346-1348) DNA sequences with intron-like functionality in the plant in which the recombinant DNA construct of the invention is to be transcribed. While essentially any intron can be used in the practice of this invention as a host for embedded DNA, particularly preferred are introns that are introns that enhance expression in a plant or introns that are derived from a 5' untranslated leader sequence. Where a recombinant DNA construct of the invention is used to transform a plant, plant-sourced introns can be especially preferred. Examples of especially preferred plant introns include a rice actin 1 intron (I-Os-Act1) (Wang et al. (1992) *Mol. Cell Biol.,* 12:3399-3406; McElroy et al. (1990) *Plant Cell,* 2:163-171), a maize heat shock protein intron (I-Zm-hsp70) (U.S. Pat. Nos. 5,593,874 and 5,859,347), and a maize alcohol dehydrogenase intron (I-Zm-adh1) (Callis et al. (1987) *Genes Dev.,* 1:1183-1200). Other examples of introns suitable for use in the invention include the tobacco mosaic virus 5' leader sequence or "omega" leader (Gallie and Walbot (1992) *Nucleic Acids Res.,* 20:4631-4638), the Shrunken-1 (Sh-1) intron (Vasil et al. (1989) *Plant Physiol.,* 91:1575-1579), the maize sucrose synthase intron (Clancy and Hannah (2002) *Plant Physiol.,* 130:918-929), the heat shock protein 18 (hsp18) intron (Silva et al. (1987) *J. Cell Biol.,* 105:245), and the 82 kilodalton heat shock protein (hsp82) intron (Semrau et al. (1989) J. Cell Biol., 109, p. 39A, and Mettler et al. (May 1990) N.A.T.O. Advanced Studies Institute on Molecular Biology, Elmer, Bavaria).

Gene Expression Elements:

The recombinant DNA constructs can further include a gene expression element. Any gene or genes of interest can be expressed by the gene expression element, including coding or non-coding sequence or both, and can include naturally occurring sequences or artificial or chimeric sequences or both. Where the gene expression element encodes a protein, such constructs preferably include a functional terminator element to permit transcription and translation of the gene expression element. In embodiments including inducibly sterile, transgenic plants, the gene expression element can include, or can be in addition to, the messenger RNA encoding an herbicide tolerance protein.

In embodiments where the recombinant DNA construct contains an intron, the construct can further include a gene expression element for expressing at least one gene of interest, wherein the gene expression element is located adjacent to the intron. In other embodiments, the recombinant DNA construct includes an intron in which is embedded a gene suppression element and a gene expression element for expressing at least one gene of interest, wherein the gene expression element is also located within the intron; in such cases, the gene expression element can be operably linked to a functional terminator element that is itself also within the intron. The gene of interest to be expressed by the gene expression element can include at least one gene selected from the group consisting of a eukaryotic target gene, a non-eukaryotic target gene, and a microRNA precursor DNA sequence. The gene of interest can include a single gene or multiple genes (such as multiple copies of a single gene, multiple alleles of a single gene, or multiple genes including genes from multiple species). In one embodiment, the gene expression element can include self-hydrolyzing peptide sequences, e.g., located between multiple sequences coding for one or more polypeptides (see, for example, the 2A and "2A-like" self-cleaving sequences from various species, including viruses, trypanosomes, and bacteria, disclosed by Donnelly et al. (2001), *J. Gen. Virol.,* 82:1027-1041). In another embodiment, the gene expression element can include ribosomal "skip" sequences, e.g., located between multiple sequences coding for one or more polypeptides (see, for example, the aphthovirus foot-and-mouth disease virus (FMDV) 2A ribosomal "skip" sequences disclosed by Donnelly et al. (2001), *J. Gen. Virol.,* 82:1013-1025).

A gene of interest can include any coding or non-coding sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, and mammals. Non-limiting examples of a non-coding sequence to be expressed by a gene expression element include, but not limited to, 5' untranslated regions, promoters, enhancers, or other non-coding transcriptional regions, 3' untranslated regions, terminators, intron, microRNAs, microRNA precursor DNA sequences, small interfering RNAs, RNA components of ribosomes or ribozymes, small nucleolar RNAs, and other non-coding RNAs. Non-limiting examples of a gene of interest further include, but are not limited to, translatable (coding) sequence, such as genes encoding transcription factors and genes encoding enzymes involved in the biosynthesis or catabolism of molecules of interest (such as amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin). A gene of interest can be a gene native to the plant in which the recombinant DNA construct of the invention is to be transcribed, or can be a non-native gene. A gene of interest can be a marker gene, for example, a selectable marker gene encoding antibiotic, antifungal, or herbicide resistance, or a marker gene encoding an easily detectable trait (e.g., phytoene synthase or other genes imparting a particular pigment to the plant), or a gene encoding a detectable molecule, such as a fluorescent protein, luciferase, or a unique polypeptide or nucleic acid "tag" detectable by protein or nucleic acid detection methods, respectively). Selectable markers are genes of interest of particular utility in identifying successful processing of constructs of the invention.

In some embodiments of the invention, the recombinant DNA constructs are designed to suppress at least one endogenous or exogenous gene and to simultaneously express at least one exogenous gene. In one non-limiting example, the recombinant DNA construct includes a gene suppression element for suppressing a endogenous (maize) lysine ketoglutarate reductase/saccharopine dehydrogenase (LKR/SDH) gene, a gene expression element for expressing an exogenous (bacterial) dihydrodipicolinic acid synthase protein, and DNA that transcribes to RNA including: (a) at least one exogenous miRNA recognition site recognizable by a mature miRNA that is specifically expressed in reproductive tissue of the plant; and (b) messenger RNA encoding epsps-CP4, wherein the mature miRNA specifically suppresses expression of epsps-CP4 in the reproductive tissue, and wherein sterility of the transgenic plant is inducible by application of glyphosate to the plant. Such a construct would be especially useful for providing maize with enhanced levels of lysine and general tolerance of glyphosate, wherein sterility of the maize is inducible by application of glyphosate at the appropriate developmental time(s). In another non-limiting example, the recombinant DNA construct includes a gene suppression element for suppressing a corn rootworm gene, and DNA that transcribes to RNA including: (a) at least one exogenous miRNA recognition site recognizable by a mature miRNA that is specifically expressed in reproductive tissue of the plant; and (b) messenger RNA encoding epsps-CP4, wherein the mature miRNA specifically suppresses expression of epsps-CP4 in the reproductive tissue, and wherein sterility of the transgenic plant is inducible by application of glyphosate to the plant. Such a construct would be especially useful for providing maize with resistance to corn rootworm and general tolerance of glyphosate, wherein sterility of the maize is inducible by application of glyphosate at the appropriate developmental time(s).

T-DNA Borders:

T-DNA borders refer to the DNA sequences or regions of DNA that define the start and end of an *Agrobacterium* T-DNA (tumor DNA) and function in cis for transfer of T-DNA into a plant genome by *Agrobacterium*-mediated transformation (see, e.g., Hooykaas and Schilperoort (1992) *Plant Mol. Biol.*, 19:15-38). Various embodiments include recombinant DNA construct with no T-DNA borders, a single T-DNA border, or more than one T-DNA border. For example, in embodiments where the recombinant DNA construct includes an intron in which is embedded a gene suppression element, the intron is preferably located between a pair of T-DNA borders, which can be a set of left and right T-DNA borders, a set of two left T-DNA borders, or a set of two right T-DNA borders. In another embodiment, the recombinant DNA construct includes a single T-DNA border, an intron-embedded gene suppression element, and at least one gene expression element.

Terminators:

Many embodiments, particularly where the recombinant DNA construct is designed to transcribed to messenger RNA, include both a promoter element and a functional terminator element that includes a functional polyadenylation signal and polyadenylation site, allowing RNA transcribed from the recombinant DNA construct to be polyadenylated and processed for transport into the cytoplasm.

In general embodiments as described under the heading "Recombinant DNA Constructs Including MicroRNA Recognition Sites", a functional terminator element can be present or absent. In embodiments where a functional terminator element is absent, at least one of a functional polyadenylation signal and a functional polyadenylation site is absent. In other embodiments, a 3' untranslated region is absent. In these cases, the recombinant DNA construct is transcribed as unpolyadenylated RNA and is preferably not transported into the cytoplasm.

Spacer DNA: Spacer DNA segments can include virtually any DNA (such as, but not limited to, translatable DNA sequence encoding a gene of interest, translatable DNA sequence encoding a marker or reporter gene; transcribable DNA derived from an intron, which upon transcription can be excised from the resulting transcribed RNA; transcribable DNA sequence encoding RNA that forms a structure such as a loop or stem or an aptamer capable of binding to a specific ligand; spliceable DNA such as introns and self-splicing ribozymes; transcribable DNA encoding a sequence for detection by nucleic acid hybridization, amplification, or sequencing; and a combination of these). Spacer DNA can be found, for example, adjacent to a gene expression element, between parts of a gene suppression element, or between different gene suppression elements. In some embodiments, spacer DNA is itself sense or anti-sense sequence of the target gene. In some preferred embodiments, the RNA transcribed from the spacer DNA (e.g., a large loop of antisense sequence of the target gene or an aptamer) assumes a secondary structure or three-dimensional configuration that confers on the transcript a desired characteristic, such as increased stability, increased half-life in vivo, or cell or tissue specificity.

Making and Using Recombinant DNA Constructs

The recombinant DNA constructs of the present invention can be made by any method suitable to the intended application, taking into account, for example, the type of expression desired and convenience of use in the plant in which the construct is to be transcribed. General methods for making and using DNA constructs and vectors are well known in the art and described in detail in, for example, handbooks and laboratory manuals including Sambrook and Russell, "Molecular Cloning: A Laboratory Manual" (third edition), Cold Spring Harbor Laboratory Press, N Y, 2001. An example of useful technology for building DNA constructs and vectors for transformation is disclosed in US Patent Application Publication 2004/0115642 A1. DNA constructs can also be built using the GATEWAY™ cloning technology (available from Invitrogen Life Technologies, Carlsbad, Calif.), which uses the site-specific recombinase LR cloning reaction of the Integrase/att system from bacteriophage lambda vector construction, instead of restriction endonucleases and ligases. The LR cloning reaction is disclosed in U.S. Pat. Nos. 5,888,732 and 6,277,608, and in U.S. Patent Application Publications 2001/283529, 2001/282319 and 2002/0007051. The GATEWAY™ Cloning Technology Instruction Manual, which is also supplied by Invitrogen, provides concise directions for routine cloning of any desired DNA into a vector comprising operable plant expression elements. Another alternative vector fabrication method employs ligation-independent cloning as disclosed by Aslandis et al. (1990) *Nucleic Acids Res.*, 18:6069-6074 and Rashtchian et al. (1992) *Biochem.*, 206:91-97, where a DNA fragment with single-stranded 5' and 3' ends is ligated into a desired vector which can then be amplified in vivo.

In certain embodiments, the DNA sequence of the recombinant DNA construct includes sequence that has been codon-optimized for the plant in which the recombinant DNA construct is to be expressed. For example, a recombinant DNA construct to be expressed in a plant can have all or parts of its sequence (e.g., the first gene suppression element or the gene expression element) codon-optimized for expression in a plant by methods known in the art. See, e.g., U.S. Pat. No. 5,500,365 for a description of codon-optimization for plants; see also De Amicis and Marchetti (2000) *Nucleic Acid Res.*, 28:3339-3346.

Transgenic Plant Cells and Transgenic Plants

An additional aspect of this invention provides a transgenic plant cell having in its genome any of the recombinant DNA constructs provided by this invention. Further provided is a transgenic plant containing the transgenic plant cell of this invention. The transgenic plant of the invention includes plants of any developmental stage, and includes a regenerated plant prepared from the transgenic plant cells claimed herein, or a progeny plant (which can be an inbred or hybrid progeny plant) of the regenerated plant, or seed of such a transgenic plant. Also provided and claimed is a transgenic seed having in its genome any of the recombinant DNA constructs provided by this invention.

One embodiment includes a transgenic plant having in its genome a recombinant DNA construct that transcribes to RNA including: (a) at least one exogenous miRNA recognition site recognizable by a mature miRNA that is specifically expressed in reproductive tissue of the plant (that is, a plant prepared from the transgenic plant cell); and (b) messenger RNA encoding a protein imparting tolerance to an herbicide; wherein the mature miRNA specifically suppresses expression of the protein in the reproductive tissue, and wherein sterility of a transgenic plant prepared from the transgenic plant cell is inducible by application of the herbicide to the plant.

The transgenic plant cell can be an isolated plant cell (e.g., individual plant cells or cells grown in or on an artificial culture medium), or can be a plant cell in undifferentiated tissue (e.g., callus or any aggregation of plant cells). The transgenic plant cell can be a plant cell in at least one differentiated tissue selected from the group consisting of leaf (e.g., petiole and blade), root, stem (e.g., tuber, rhizome, stolon, bulb, and corm) stalk (e.g., xylem, phloem), wood, seed, fruit (e.g., nut, grain, fleshy fruits), and flower (e.g., stamen, filament, anther, pollen, carpel, pistil, ovary, ovules).

The transgenic plant cell or transgenic plant of the invention can be any suitable plant cell or plant of interest. Both transiently transformed and stably transformed plant cells are encompassed by this invention. Stably transformed transgenic plants are particularly preferred. In many preferred embodiments, the transgenic plant is a fertile transgenic plant from which seed can be harvested, and the invention further claims transgenic seed of such transgenic plants, wherein the seed preferably also contains the recombinant construct of this invention.

Making and Using Transgenic Plant Cells and Transgenic Plants

Where a recombinant DNA construct is used to produce a transgenic plant cell, transgenic plant, or transgenic seed of this invention, transformation can include any of the well-known and demonstrated methods and compositions. Suitable methods for plant transformation include virtually any method by which DNA can be introduced into a cell, such as by direct delivery of DNA (e.g., by PEG-mediated transformation of protoplasts, by electroporation, by agitation with silicon carbide fibers, and by acceleration of DNA coated particles), by *Agrobacterium*-mediated transformation, by viral or other vectors, etc. One preferred method of plant transformation is microprojectile bombardment, for example, as illustrated in U.S. Pat. No. 5,015,580 (soy), U.S. Pat. No. 5,550,318 (maize), U.S. Pat. No. 5,538,880 (maize), U.S. Pat. No. 6,153,812 (wheat), U.S. Pat. No. 6,160,208 (maize), U.S. Pat. No. 6,288,312 (rice) and 6,399,861 (maize), and 6,403,865 (maize).

Another preferred method of plant transformation is *Agrobacterium*-mediated transformation. In one preferred embodiment of the invention, the transgenic plant cell of the invention is obtained by transformation by means of *Agrobacterium* containing a binary Ti plasmid system, wherein the *Agrobacterium* carries a first Ti plasmid and a second, chimeric plasmid containing at least one T-DNA border of a wild-type Ti plasmid, a promoter functional in the transformed plant cell and operably linked to a gene suppression construct of the invention. See, for example, the binary system described in U.S. Pat. No. 5,159,135. Also see De Framond (1983) *Biotechnology*, 1:262-269; and Hoekema et al., (1983) *Nature*, 303:179. In such a binary system, the smaller plasmid, containing the T-DNA border or borders, can be conveniently constructed and manipulated in a suitable alternative host, such as *E. coli*, and then transferred into *Agrobacterium*.

Detailed procedures for *Agrobacterium*-mediated transformation of plants, especially crop plants, include, for example, procedures disclosed in U.S. Pat. Nos. 5,004,863, 5,159,135, and 5,518,908 (cotton); U.S. Pat. Nos. 5,416,011, 5,569,834, 5,824,877 and 6,384,301 (soy); U.S. Pat. No. 5,591,616 (maize); U.S. Pat. No. 5,981,840 (maize); U.S. Pat. No. 5,463,174 (brassicas). Similar methods have been reported for many plant species, both dicots and monocots, including, among others, peanut (Cheng et al. (1996) *Plant Cell Rep.*, 15: 653); asparagus (Bytebier et al. (1987) *Proc. Natl. Acad. Sci. U.S.A.*, 84:5345); barley (Wan and Lemaux (1994) *Plant Physiol.*, 104:37); rice (Toriyama et al. (1988) *Bio/Technology*, 6:10; Zhang et al. (1988) *Plant Cell Rep.*, 7:379; wheat (Vasil et al. (1992) *Bio/Technology*, 10:667; Becker et al. (1994) *Plant J.*, 5:299), alfalfa (Masoud et al. (1996) *Transgen. Res.*, 5:313); and tomato (Sun et al. (2006) *Plant Cell Physiol.*, 47:426-431). See also U.S. Patent Application Publication 2003/0167537 A1 for a description of vectors, transformation methods, and production of transformed *Arabidopsis thaliana* plants where transcription factors are constitutively expressed by a CaMV35S promoter. Transgenic plant cells and transgenic plants can also be obtained by transformation with other vectors, such as, but not limited to, viral vectors (e.g., tobacco etch potyvirus (TEV), barley stripe mosaic virus (BSMV), and the viruses referenced in Edwardson and Christie, "The Potyvirus Group: Monograph No. 16, 1991, Agric. Exp. Station, Univ. of Florida), plasmids, cosmids, YACs (yeast artificial chromosomes), BACs (bacterial artificial chromosomes) or any other suitable cloning vector, when used with an appropriate transformation protocol, e.g., bacterial infection (e.g., with *Agrobacterium* as described above), binary bacterial artificial chromosome constructs, direct delivery of DNA (e.g., via PEG-mediated transformation, desiccation/inhibition-mediated DNA uptake, electroporation, agitation with silicon carbide fibers, and microprojectile bombardment). It would be clear to one of skill in the art that various transformation methodologies can be used and modified for production of stable transgenic plants from any number of plant species of interest.

Transformation methods to provide transgenic plant cells and transgenic plants containing stably integrated recombinant DNA are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos or parts of embryos, and gametic cells such as microspores, pollen, sperm, and egg cells. Any cell from which a fertile plant can be regenerated is contemplated as a useful recipient cell for practice of the invention. Callus can be initiated from various tissue sources, including, but not limited to, immature embryos or parts of embryos, seedling apical meristems, microspores, and the like. Those cells which are capable of proliferating as callus can serve as recipient cells for genetic transformation. Practical transformation methods and materials for making transgenic plants of this invention (e.g., various media and recipient target cells, transformation of immature embryos, and subsequent regeneration of fertile transgenic plants) are disclosed, for example, in U.S. Pat. Nos. 6,194,636 and 6,232,526 and U.S. Patent Application Publication 2004/0216189.

In general transformation practice, DNA is introduced into only a small percentage of target cells in any one transformation experiment. Marker genes are generally used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the antibiotics or herbicides to which a plant cell may be resistant can be a useful agent for selection. Potentially transformed cells are exposed to the selective agent. In the population of surviving cells will be those cells where, generally, the resistance-conferring gene is integrated and expressed at sufficient levels to permit cell survival. Cells can be tested further to confirm stable integration of the recombinant DNA. Commonly used selective marker genes include those conferring resistance to antibiotics such as kanamycin or paromomycin (nptll), hygromycin B (aph IV) and gentamycin (aac3 and aacC4) or resistance to herbicides such as glufosinate (bar or pat) and glyphosate (EPSPS). Examples of useful selective marker genes and selection agents are illustrated in U.S. Pat. Nos. 5,550,318, 5,633,435, 5,780,708, and 6,118,047. Screenable markers or reporters, such as markers that provide an ability to visually identify transformants can also be employed. Non-limiting examples of useful screenable markers include, for example, a gene expressing a protein that produces a detectable color by acting on a chromogenic substrate (e.g., beta-glucuronidase (GUS) (uidA) or luciferase (luc)) or that itself is detectable, such as green fluorescent protein (GFP) (gfp) or an immunogenic molecule. Those of skill in the art will recognize that many other useful markers or reporters are available for use.

Detecting or measuring the resulting change in expression of the target gene (or concurrent expression of a gene of interest) obtained by transcription of the recombinant construct in the transgenic plant of the invention can be achieved by any suitable methods, including protein detection methods (e.g., western blots, ELISAs, and other immunochemical methods), measurements of enzymatic activity, or nucleic acid detection methods (e.g., Southern blots, northern blots, PCR, RT-PCR, fluorescent in situ hybridization). Such methods are well known to those of ordinary skill in the art as evidenced by the numerous handbooks available; see, for example, Joseph Sambrook and David W. Russell, "Molecular Cloning: A Laboratory Manual" (third edition), Cold Spring Harbor Laboratory Press, N Y, 2001; Frederick M. Ausubel et al. (editors) "Short Protocols in Molecular Biology" (fifth edition), John Wiley and Sons, 2002; John M. Walker (editor) "Protein Protocols Handbook" (second edition), Humana Press, 2002; and Leandro Pena (editor) "Transgenic Plants: Methods and Protocols", Humana Press, 2004.

Other suitable methods for detecting or measuring the resulting change in expression of the target gene (or concurrent expression of a gene of interest) obtained by transcription of the recombinant DNA in the transgenic plant of the invention include measurement of any other trait that is a direct or proxy indication of expression of the target gene (or concurrent expression of a gene of interest) in the transgenic plant in which the recombinant DNA is transcribed, relative to one in which the recombinant DNA is not transcribed, e.g., gross or microscopic morphological traits, growth rates, yield, reproductive or recruitment rates, resistance to pests or pathogens, or resistance to biotic or abiotic stress (e.g., water deficit stress, salt stress, nutrient stress, heat or cold stress). Such methods can use direct measurements of a phenotypic trait or proxy assays (e.g., in plants, these assays include plant part assays such as leaf or root assays to determine tolerance of abiotic stress).

The recombinant DNA constructs of the invention can be stacked with other recombinant DNA for imparting additional traits (e.g., in the case of transformed plants, traits including herbicide resistance, pest resistance, cold germination tolerance, water deficit tolerance, and the like) for example, by expressing or suppressing other genes. Constructs for coordinated decrease and increase of gene expression are disclosed in U.S. Patent Application Publication 2004/0126845 A1.

Seeds of transgenic, fertile plants can be harvested and used to grow progeny generations, including hybrid generations, of transgenic plants of this invention that include the recombinant DNA construct in their genome. Thus, in addition to direct transformation of a plant with a recombinant DNA construct, transgenic plants of the invention can be prepared by crossing a first plant having the recombinant DNA with a second plant lacking the construct. For example, the recombinant DNA can be introduced into a plant line that is amenable to transformation to produce a transgenic plant, which can be crossed with a second plant line to introgress the recombinant DNA into the resulting progeny. A transgenic plant of the invention with one recombinant DNA (effecting change in expression of a target gene) can be crossed with a plant line having other recombinant DNA that confers one or more additional trait(s) (such as, but not limited to, herbicide resistance, pest or disease resistance, environmental stress resistance, modified nutrient content, and yield improvement) to produce progeny plants having recombinant DNA that confers both the desired target sequence expression behavior and the additional trait(s).

Typically, in such breeding for combining traits the transgenic plant donating the additional trait is a male line and the transgenic plant carrying the base traits is the female line. The progeny of this cross segregate such that some of the plant will carry the DNA for both parental traits and some will carry DNA for one parental trait; such plants can be identified by markers associated with parental recombinant DNA Progeny plants carrying DNA for both parental traits can be crossed back into the female parent line multiple times, e.g., usually 6 to 8 generations, to produce a progeny plant with substantially the same genotype as one original transgenic parental line but for the recombinant DNA of the other transgenic parental line.

Yet another aspect of the invention is a transgenic plant grown from the transgenic seed of the invention. This invention contemplates transgenic plants grown directly from transgenic seed containing the recombinant DNA as well as progeny generations of plants, including inbred or hybrid plant lines, made by crossing a transgenic plant grown directly from transgenic seed to a second plant not grown from the same transgenic seed.

Crossing can include, for example, the following steps:
(a) plant seeds of the first parent plant (e.g., non-transgenic or a transgenic) and a second parent plant that is transgenic according to the invention;
(b) grow the seeds of the first and second parent plants into plants that bear flowers;
(c) pollinate a flower from the first parent with pollen from the second parent; and
(d) harvest seeds produced on the parent plant bearing the fertilized flower.

It is often desirable to introgress recombinant DNA into elite varieties, e.g., by backcrossing, to transfer a specific desirable trait from one source to an inbred or other plant that lacks that trait. This can be accomplished, for example, by first crossing a superior inbred ("A") (recurrent parent) to a donor inbred ("B") (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent "B", and then the selected progeny are mated back to the superior recurrent parent "A". After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i.e., one or more transformation events.

Through a series of breeding manipulations, a selected DNA construct can be moved from one line into an entirely different line without the need for further recombinant manipulation. One can thus produce inbred plants which are true breeding for one or more DNA constructs. By crossing different inbred plants, one can produce a large number of different hybrids with different combinations of DNA constructs. In this way, plants can be produced which have the desirable agronomic properties frequently associated with hybrids ("hybrid vigor"), as well as the desirable characteristics imparted by one or more DNA constructs.

Genetic markers can be used to assist in the introgression of one or more DNA constructs of the invention from one genetic background into another. Marker assisted selection offers advantages relative to conventional breeding in that it can be used to avoid errors caused by phenotypic variations. Further, genetic markers can provide data regarding the relative degree of elite germplasm in the individual progeny of a particular cross. For example, when a plant with a desired trait which otherwise has a non-agronomically desirable genetic background is crossed to an elite parent, genetic markers can be used to select progeny which not only possess the trait of interest, but also have a relatively large proportion of the desired germplasm. In this way, the number of generations required to introgress one or more traits into a particular genetic background is minimized. The usefulness of marker assisted selection in breeding transgenic plants of the current invention, as well as types of useful molecular markers, such as but not limited to SSRs and SNPs, are discussed in PCT Application Publication WO 02/062129 and U.S. Patent Application Publications Numbers 2002/0133852, 2003/0049612, and 2003/0005491.

In certain transgenic plant cells and transgenic plants of the invention, it may be desirable to concurrently express (or suppress) a gene of interest while also regulating expression of a target gene. Thus, in some embodiments, the transgenic plant contains recombinant DNA further including a gene expression (or suppression) element for expressing at least one gene of interest, and regulation of expression of a target gene is preferably effected with concurrent expression (or suppression) of the at least one gene of interest in the transgenic plant.

Thus, as described herein, the transgenic plant cells or transgenic plants of the invention can be obtained by use of any appropriate transient or stable, integrative or non-integrative transformation method known in the art or presently disclosed. The recombinant DNA constructs can be transcribed in any plant cell or tissue or in a whole plant of any developmental stage. Transgenic plants can be derived from any monocot or dicot plant, such as, but not limited to, plants of commercial or agricultural interest, such as crop plants (especially crop plants used for human food or animal feed), wood- or pulp-producing trees, vegetable plants, fruit plants, and ornamental plants. Non-limiting examples of plants of interest include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; and ornamental plants including ornamental flowering plants, ornamental trees and shrubs, ornamental groundcovers, and ornamental grasses. Preferred dicot plants include, but are not limited to, canola, cotton, potato, quinoa, amaranth, buckwheat, safflower, soybean, sugarbeet, and sunflower, more preferably soybean, canola, and cotton. Preferred monocots include, but are not limited to, wheat, oat, barley, maize, rye, triticale, rice, ornamental and forage grasses, sorghum, millet, and sugarcane, more preferably maize, wheat, and rice.

The ultimate goal in plant transformation is to produce plants which are useful to man. In this respect, transgenic plants of the invention can be used for virtually any purpose deemed of value to the grower or to the consumer. For example, one may wish to harvest the transgenic plant itself, or harvest transgenic seed of the transgenic plant for planting purposes, or products can be made from the transgenic plant or its seed such as oil, starch, ethanol or other fermentation products, animal feed or human food, pharmaceuticals, and various industrial products. For example, maize is used extensively in the food and feed industries, as well as in industrial applications. Further discussion of the uses of maize can be found, for example, in U.S. Pat. Nos. 6,194, 636, 6,207,879, 6,232,526, 6,426,446, 6,429,357, 6,433,252, 6,437,217, and 6,583,338 and PCT Publications WO 95/06128 and WO 02/057471. Thus, this invention also provides commodity products produced from a transgenic plant cell, plant, or seed of this invention, including, but not limited to, harvested leaves, roots, shoots, tubers, stems, fruits, seeds, or other parts of a plant, meals, oils, extracts, fermentation or digestion products, crushed or whole grains or seeds of a plant, or any food or non-food product including such commodity products produced from a transgenic plant cell, plant, or seed of this invention. The detection of one or more of nucleic acid sequences of the recombinant DNA constructs of this invention in one or more commodity or commodity products contemplated herein is de facto evidence that the commodity or commodity product contains or is derived from a transgenic plant cell, plant, or seed of this invention.

In preferred embodiments, the transgenic plant having in its genome a recombinant DNA construct of this invention has at least one additional altered trait, relative to a plant lacking the recombinant DNA construct, selected from the group of traits consisting of:
(a) improved abiotic stress tolerance;
(b) improved biotic stress tolerance;
(c) modified primary metabolite composition;
(d) modified secondary metabolite composition;
(e) modified trace element, carotenoid, or vitamin composition;
(f) improved yield;
(g) improved ability to use nitrogen or other nutrients;
(h) modified agronomic characteristics;
(i) modified growth or reproductive characteristics; and
(j) improved harvest, storage, or processing quality.

In particularly preferred embodiments, the transgenic plant is characterized by: improved tolerance of abiotic stress (e.g., tolerance of water deficit or drought, heat, cold, non-optimal nutrient or salt levels, non-optimal light levels) or of biotic stress (e.g., crowding, allelopathy, or wounding); by a modified primary metabolite (e.g., fatty acid, oil, amino acid, protein, sugar, or carbohydrate) composition; a modified secondary metabolite (e.g., alkaloids, terpenoids, polyketides, non-ribosomal peptides, and secondary metabolites of mixed biosynthetic origin) composition; a modified trace element (e.g., iron, zinc), carotenoid (e.g., beta-carotene, lycopene, lutein, zeaxanthin, or other carotenoids and xanthophylls), or vitamin (e.g., tocopherols) composition; improved yield (e.g., improved yield under non-stress conditions or improved yield under biotic or abiotic stress); improved ability to use nitrogen or other nutrients; modified agronomic characteristics (e.g., delayed ripening; delayed senescence; earlier or later maturity; improved shade tolerance; improved resistance to root or stalk lodging; improved resistance to "green snap" of stems; modified photoperiod response); modified growth or reproductive characteristics (e.g., intentional dwarfing; intentional male sterility, useful, e.g., in improved hybridization procedures; improved vegetative growth rate; improved germination; improved male or female fertility); improved harvest, storage, or processing quality (e.g., improved resistance to pests during storage, improved resistance to breakage, improved appeal to consumers); or any combination of these traits.

In one preferred embodiment, transgenic seed, or seed produced by the transgenic plant, has modified primary metabolite (e.g., fatty acid, oil, amino acid, protein, sugar, or carbohydrate) composition, a modified secondary metabolite (e.g., alkaloids, terpenoids, polyketides, non-ribosomal peptides, and secondary metabolites of mixed biosynthetic origin) composition, a modified trace element (e.g., iron, zinc), carotenoid (e.g., beta-carotene, lycopene, lutein, zeaxanthin, or other carotenoids and xanthophylls), or vitamin (e.g., tocopherols,) composition, an improved harvest, storage, or processing quality, or a combination of these. For example, it can be desirable to modify the amino acid (e.g., lysine, methionine, tryptophan, or total protein), oil (e.g., fatty acid composition or total oil), carbohydrate (e.g., simple sugars or starches), trace element, carotenoid, or vitamin content of seeds of crop plants (e.g., canola, cotton, safflower, soybean, sugarbeet, sunflower, wheat, maize, or rice), preferably in combination with improved seed harvest, storage, or processing quality, and thus provide improved seed for use in animal feeds or human foods. In another instance, it can be desirable to change levels of native components of the transgenic plant or seed of a transgenic plant, for example, to decrease levels of proteins with low levels of lysine, methionine, or tryptophan, or to increase the levels of a desired amino acid or fatty acid, or to decrease levels of an allergenic protein or glycoprotein (e. g., peanut allergens including ara h 1, wheat allergens including gliadins and glutenins, soy allergens including P34 allergen, globulins, glycinins, and conglycinins) or of a toxic metabolite (e.g., cyanogenic glycosides in cassava, solanum alkaloids in members of the Solanaceae).

EXAMPLES

Example 1

This illustrates non-limiting examples of recombinant DNA constructs for suppression of at least one target gene; these constructs, when designed to include a miRNA recognition site, allow expression of the gene suppression element in specific tissues.

FIG. 1A schematically depicts non-limiting examples of recombinant DNA constructs of the invention for suppression of at least one target gene. These constructs include at least one first gene suppression element ("GSE" or "GSE1") for suppressing at least one first target gene, wherein the first gene suppression element is embedded in an intron flanked on one or on both sides by non-protein-coding DNA. These constructs utilize an intron (in many embodiments, an intron derived from a 5' untranslated region or an expression-enhancing intron is preferred) to deliver a gene suppression element without requiring the presence of any protein-coding exons (coding sequence). The constructs can optionally include at least one second gene suppression element ("GSE2") for suppressing at least one second target gene, at least one gene expression element ("GEE") for expressing at least one gene of interest (which can be coding or non-coding sequence or both), or both. In embodiments containing an optional gene expression element, the gene expression element can be located outside of (e.g., adjacent to) the intron. In some embodiments, the intron containing the first gene suppression element is 3' to a terminator.

To more clearly differentiate recombinant DNA constructs of the invention (containing at least one gene suppression element embedded within a single intron flanked on one or on both sides by non-protein-coding DNA) from the prior art, FIG. 1B schematically depicts examples of prior art recombinant DNA constructs. These constructs can contain a gene suppression element that is located adjacent to an intron flanked by protein-coding sequence, or between two discrete introns (wherein the gene suppression element is not embedded in either of the two discrete introns), or can include a gene expression element including a gene suppression element embedded within an intron which is flanked by multiple exons (e.g., exons including the coding sequence of a protein).

FIGS. 2A-2F depict various non-limiting examples of gene suppression elements and transcribable exogenous DNAs useful in the recombinant DNA constructs of the invention. Where drawn as a single strand (FIGS. 2A through 2E), these are conventionally depicted in 5' to 3' (left to right) transcriptional direction; the arrows indicate anti-sense sequence (arrowhead pointing to the left), or sense sequence (arrowhead pointing to the right). These gene suppression elements and transcribable exogenous DNAs can include: DNA that includes at least one anti-sense DNA segment that is anti-sense to at least one segment of the at least one first target gene, or DNA that includes multiple copies of at least one anti-sense DNA segment that is anti-sense to at least one segment of the at least one first target gene (FIG. 2A); DNA that includes at least one sense DNA segment that is at least one segment of the at least one first target gene, or DNA that includes multiple copies of at least one sense DNA segment that is at least one segment of the at least one first target gene (FIG. 2B); DNA that transcribes to RNA for suppressing the at least one first target gene by forming double-stranded RNA and includes at least one anti-sense DNA segment that is anti-sense to at least one segment of the at least one target gene and at least one sense DNA segment that is at least one segment of the at least one first target gene (FIG. 2C); DNA that transcribes to RNA for suppressing the at least one first target gene by forming a single double-stranded RNA and includes multiple serial anti-sense DNA segments that are anti-sense to at least one segment of the at least one first target gene and multiple serial sense DNA segments that are at least one segment of the at least one first target gene (FIG. 2D); DNA that transcribes to RNA for suppressing the at least one first target gene by forming multiple double strands of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of inverted repeats (FIG. 2E); and DNA that includes nucleotides derived from a miRNA, or DNA that includes nucleotides of a siRNA (FIG. 2F).

FIG. 2F depicts various non-limiting arrangements of double-stranded RNA that can be transcribed from embodiments of the gene suppression elements and transcribable exogenous DNAs useful in the recombinant DNA constructs of the invention. When such double-stranded RNA is formed, it can suppress one or more target genes, and can form a single double-stranded RNA or multiple double strands of RNA, or a single double-stranded RNA "stem" or multiple "stems". Where multiple double-stranded RNA "stems" are formed, they can be arranged in "hammerheads" or "cloverleaf" arrangements. In some embodiments, the double-stranded stems can form a "pseudoknot" arrangement (e.g., where spacer or loop RNA of one double-stranded stem forms part of a second double-stranded stem); see, for example, depictions of pseudoknot architectures in Staple and Butcher (2005) *PLoS Biol.*, 3(6):e213. Spacer DNA (located between or adjacent to dsRNA regions) is optional but commonly included and generally includes DNA that does not correspond to the target gene (although in some embodiments can include sense or anti-sense DNA of the target gene). Spacer DNA can include sequence that transcribes to single-stranded RNA or to at least partially double-stranded RNA (such as in a "kissing stem-loop" arrangement), or to an RNA that assumes a secondary structure or three-dimensional configuration (e.g., a large loop of antisense sequence of the target gene or an aptamer) that confers on the transcript an additional desired characteristic, such as increased stability, increased half-life in vivo, or cell or tissue specificity.

Example 2

This example describes one non-limiting method of determining the potential usefulness of a miRNA's recognition site, by determining the miRNA's expression pattern. Knowledge of the spatial or temporal distribution of a given miRNA's expression is useful, e.g., in designing recombinant constructs to be expressed in a spatially or temporally specific manner. This example discloses mature miRNA expression patterns in maize and provides sequences of recognition sites for these miRNAs that are suitable for inclusion in recombinant DNA constructs useful in maize and other plants.

Total RNA was isolated from LH244 maize plants using Trizol (Invitrogen, Carlsbad, Calif.). Seven developmental stages were used, including roots and shoot meristems from germinating seedlings, juvenile (V1 to V2) and adult leaves (V7 to V8), stalk internode, tassel before shedding, and immature (approximately 1") ears. Five micrograms total RNA was resolved on 17% PAGE-Urea as described by Allen et al. (2004) *Nat. Genet.*, 36:1282-1290. Blots were probed with DNA oligonucleotides that were antisense to the small RNA sequence and end-labelled with gamma $^{32}$P-ATP using Optikinase (USB). The probes used, and their respective sequences, are given in Table 1.

TABLE 1

| SEQ ID NO. | Sequence | miRNA |
| --- | --- | --- |
| 1 | GTGCTCACTCTCTTCTGTCA | miR156, miR157 |
| 2 | TAGAGCTCCCTTCAATCCAAA | miR159 |
| 3 | TGGCATCCAGGGAGCCAGGCA | miR160 |
| 4 | CTGGATGCAGAGGTTTATCGA | miR162 |
| 5 | TGCACGTGCCCTGCTTCTCCA | miR164 |
| 6 | GGGGAATGAAGCCTGGTCCGA | miR166 |
| 7 | TAGATCATGCTGGCAGCTTCA | miR167 |
| 8 | TTCCCGACCTGCACCAAGCGA | miR168 |
| 9 | TCGGCAAGTCATCCTTGGCTG | miR169 |
| 10 | GATATTGGCGCGGCTCAATCA | miR171 |
| 11 | CTGCAGCATCATCAAGATTCT | miR172 |
| 12 | GGCGCTATCCCTCCTGAGCTT | miR390 |
| 13 | GATCAATGCGATCCCTTTGGA | miR393 |
| 14 | TGGGGTCCTTACAAGGTCAAGA | TAS3 5'D7(+) |
| 15 | GGAGGTGGACAGAATGCCAA | miR394 |
| 16 | GAGTTCCCCCAAACACTTCAC | miR395 |
| 17 | CATCAACGCTGCGCTCAATGA | miR397 |
| 18 | CGGGGGCGACCTGAGAACACA | miR398 |
| 19 | AGCCAGGGAAGAGGCAGTGCA | miR408 |

Figure 3:
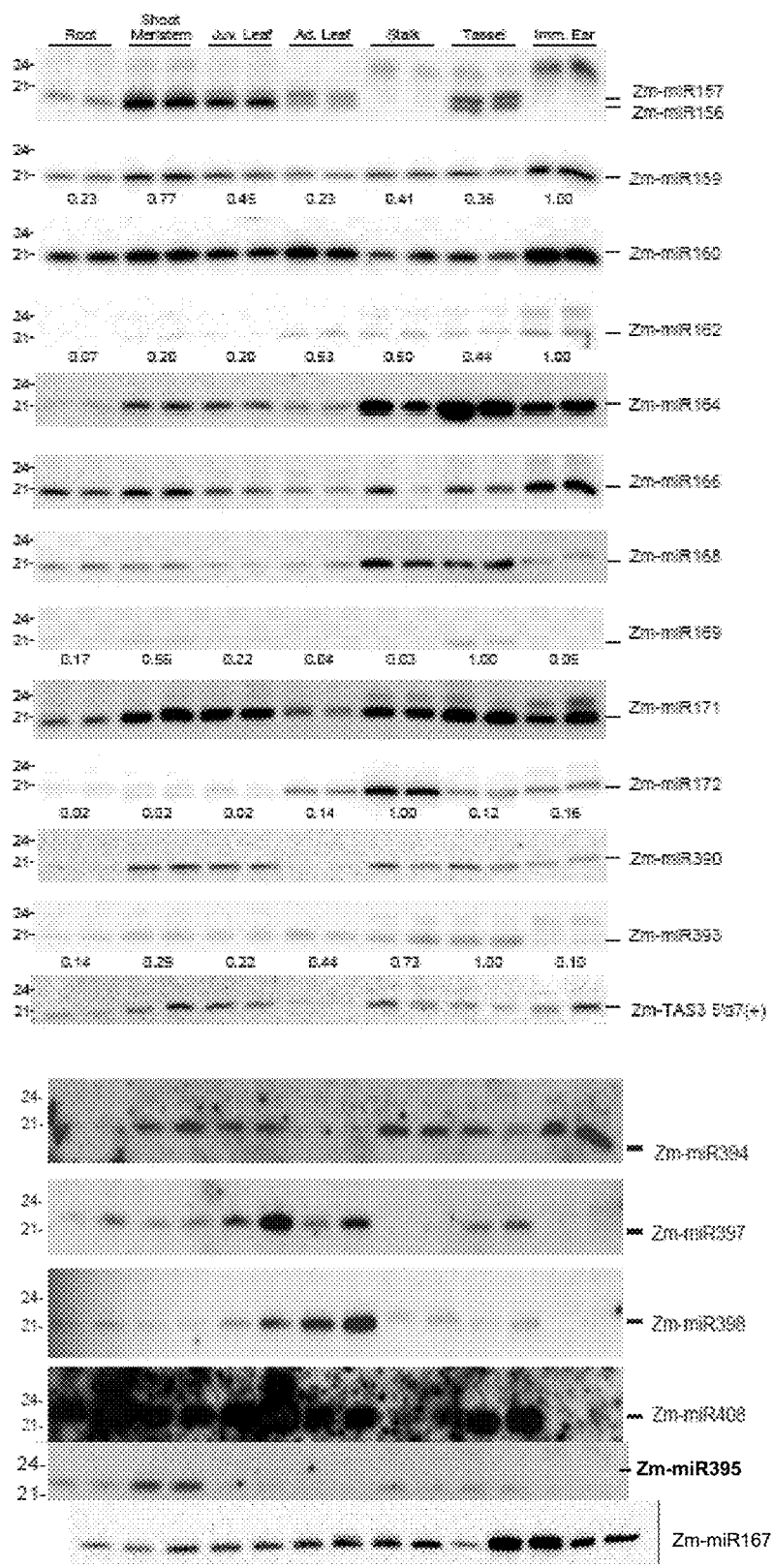
FIG. 3 depicts expression levels of the indicated mature miRNAs in various tissues from maize, as described in detail in Example 2.

The results are shown in FIG. 3. One probe (SEQ ID NO. 1) hybridized to mature miRNAs from two families (miR156 and miR157). Individual mature miRNAs were expressed at differing levels in specific cells or tissues. For example, Zm-miR390 was not expressed, or expressed only at low levels, in root and adult leaf.

Example 3

This non-limiting example describes recombinant DNA constructs of the invention, useful for suppressing expression of a target RNA in a specific cell of or derived from a multicellular eukaryote such as a plant cell or an animal cell, and methods for their use. The constructs include a promoter operably linked to DNA that transcribes to RNA including at least one exogenous miRNA recognition site recognizable by a mature miRNA expressed in a specific cell of a multicellular eukaryote, and target RNA to be suppressed in the specific cell, wherein said target RNA is to be expressed in cells of the multicellular eukaryote other than the specific cell.

Strong constitutive promoters that are expressed in nearly all plant cells have been identified (e.g., CaMC 35S, OsAct), but strong spatially specific (cell- or tissue-specific) and temporally specific promoters have been less well characterized. To limit target RNA or transgene expression to a specific cell or tissue type in the absence of a strong cell- or tissue-specific promoter, it may be desirable to suppress in selected cells or tissues the expression of a transcript under the control of a constitutive promoter. The invention provides methods that use recognition sequences of endogenous miRNAs to suppress expression of a constitutively expressed target RNA in specific cells.

Methods of the invention allow spatially or temporally specific post-transcriptional control of expression of a target RNA wherein transcription is driven by a non-specific (e.g., constitutive) promoter. The methods of the invention allow, for example, the restricted expression of a gene transcribed by a constitutive promoter or a promoter with expression beyond the desired cell or tissue type(s). Restricted expression may be spatially or temporally restricted, e.g., restricted to specific tissues or cell types or files, or to specific developmental, reproductive, growth, or seasonal stages. Where a miRNA is expressed under particular conditions (e.g., under biotic stress such as crowding, allelopathic interactions or pest or pathogen infestation, or abiotic stress such as heat or cold stress, drought stress, nutrient stress, heavy metal or salt stress), the corresponding miRNA recognition site can be used for conditionally specific suppression, i.e., to suppress a target RNA under the particular condition.

For example, Zm-miR162 is poorly expressed in maize roots (see Example 2 and FIG. 3), therefore, designing an expression construct to include an exogenous miRNA162 recognition site adjacent to, or within, a constitutively expressed target RNA, may limit target RNA transcript accumulation in all cells of a maize plant with the exception of roots. This method has utility for all gene expression applications in multicellular eukaryotes (plants and animals), where restricted expression is desired in cells wherein the given mature miRNA is expressed.

In multicellular eukaryotes, including plants, microRNAs (miRNAs) regulate endogenous genes by a post-transcriptional cleavage mechanism, which can spatially or temporally specific. The present invention provides methods by which the addition of a miRNA recognition site to a constitutively expressed transgene could be used to limit expression of the transgene to cells lacking, or distant to those expressing, the complementary mature miRNA either spatially or temporally (including conditionally). Manipulation of these miRNA recognition sites in new transcripts introduced into transgenic plant cells and transgenic plants derived from these cells, is useful for altering expression patterns for the new transgene.

In an alternative approach, an existing (native or endogenous) miRNA recognition site is mutated (e.g., by chemical mutagenesis) sufficiently to reduce or prevent cleavage (see Mallory et al. (2004) Curr. Biol., 14:1035-1046). In this way a target RNA sequence with desirable effects, e.g., increased leaf or seed size, can be expressed at levels higher than when the native or endogeous miRNA recognition site was present. One embodiment is to replace a native gene with an engineered homologue, wherein a native miRNA has been mutated or even deleted, that is less susceptible to cleavage by a given miRNA.

One embodiment of the method is the introduction of at least one exogenous miRNA recognition site (typically a 21 nucleotide sequence) into the 5' or into the 3' untranslated regions of a target RNA, or within the target RNA. Where the target RNA includes coding sequence, the at least one exogenous miRNA recognition site can be introduced into the coding region of the target RNA. This results in the reduced expression of the target RNA in tissues or cell types that express the corresponding mature miRNA. By including a recognition site corresponding to a mature miRNA in a target RNA transcript, it is possible to modulate the target RNA's expression in such a way that even under the control of a constitutive promoter, the target RNA is expressed only in selected cells or tissues or during selected temporal periods. This allows both the high levels of expression obtainable with strong constitutive promoters, and spatial or temporal limiting of such expression.

Any miRNA recognition site may be used, preferably where the expression of the corresponding mature miRNA has been determined to suit the desired expression or suppression of the target RNA. Numerous miRNA recognition sequences are known. See, for example, Jones-Rhoades and Bartel (2004). *Mol. Cell*, 14:787-799, Rhoades et al. (2002) *Cell*, 110:513-520, Allen et al. (2004) *Nat. Genet.*, 36:1282-1290). Also see the ASRP database online (Gustafson et al. (2005) *Nucleic Acids Res.*, 33:D6379-D640). Non-limiting examples of miRNA recognition sites useful in constructs and methods of the invention include those provided in Table 2, which gives the recognition site sequences for the indicated miRNA family and indicates the distribution among "all plants" (i.e., lower plants, monocots, and dicots), monocots and/or dicots. The plant species from which the miRNA was identified and the abbreviations used were: *Arabidopsis thaliana* (At), *Glycine max* (Gm), *Gossypium hirsutum* (Gh), *Hordeum vulgare* (Hv), *Lycopersicum esculentum* (Le), *Lotus corniculatus* var. *japonicus* (synonymous with "*Lotus japonicus*") (Lj), *Medicago truncatula* (Mt), *Mesembryanthemum crystallinum* (Mc), *Oryza sativa* (Os), *Pennisetum glaucum* (Pg), *Phaseolus vulgaris* (Pv), *Populus tremula* (Pt), *Saccharum officinarum* (So), *Sorghum bicolor* (Sb), *Theobroma cacao* (Tc), *Triticum aestivumi* (Ta), *Vitis vinifera* (Vv), and *Zea mays* (Zm).

TABLE 2

| SEQ ID NO. | miRNA Recognition Site | Recognition Site Sequence |
|---|---|---|
| miR156 family recognition sequence - all plants | | |
| 20 | At1g27370 | GUGCUCUCUCUCUUCUGUCA |
| 21 | At1g53160 | CUGCUCUCUCUCUUCUGUCA |
| 22 | At2g33810 | UUGCUUACUCUCUUCUGUCA |
| 23 | At3g15270 | CCGCUCUCUCUCUUCUGUCA |
| miR159 family recognition sequence - all plants | | |
| 24 | At5g06100 | UGGAGCUCCCUUCAUUCCAAU |
| 25 | At2g26960 | UCGAGUUCCCUUCAUUCCAAU |
| 26 | At4g26930 | AUGAGCUCUCUUCAAACCAAA |
| 27 | At2g26950 | UGGAGCUCCCUUCAUUCCAAG |
| 28 | At2g32460 | UAGAGCUUCCUUCAAACCAAA |
| 29 | At3g60460 | UGGAGCUCCAUUCGAUCCAAA |
| 30 | At5g55020 | AGCAGCUCCCUUCAAACCAAA |
| 31 | PvMYB | CAGAGCUCCCUUCACUCCAAU |
| 32 | VvMYB | UGGAGCUCCCUUCACUCCAAU |

TABLE 2-continued

| SEQ ID NO. | miRNA Recognition Site | Recognition Site Sequence |
|---|---|---|
| 33 | HvMYB33 | UGGAGCUCCCUUCACUCCAAG |
| 34 | OsMYB33 | UGGAGCUCCCUUUAAUCCAAU | miR160 family target sequences - all plants

| 35 | At1g77850 | UGGCAUGCAGGGAGCCAGGCA |
| 36 | At2g28350 | AGGAAUACAGGGAGCCAGGCA |
| 37 | At4g30080 | GGGUUUACAGGGAGCCAGGCA |
| 38 | OsARF | AGGCAUACAGGGAGCCAGGCA |
| 39 | LjARF | AAGCAUACAGGGAGCCAGGCA | miR161 family target sequences - *Arabidopsis*

| 40 | At5g41170 | ACCUGAUGUAAUCACUUUCAA |
| 41 | At1g06580 | CCCGGAUGUAAUCACUUUCAG |
| 42 | At1g63150 | UUGUUACUUUCAAUGCAUUGA |
| 43 | At5g16640 | CCCUGAUGUAUUUACUUUCAA |
| 44 | At1g62590 | UAGUCACGUUCAAUGCAUUGA |
| 45 | At1g62670 | CCCUGAUGUAUUCACUUUCAG |
| 46 | At1g62860 | CCCUGAUGUUGUUACUUUCAG |
| 47 | At1g62910 | UAGUCACUUUCAGCGCAUUGA |
| 48 | At1g62930 | UCCAAAUGUAGUCACUUUCAA |
| 49 | At1g63080 | UCCAAAUGUAGUCACUUUCAA |
| 50 | At1g63130 | UCCAAAUGUAGUCACUUUCAG |
| 51 | At1g63400 | UCCAAAUGUAGUCACUUUCAA |
| 52 | At1g63230 | UUGUUACUUUCAGUGCAUUGA |
| 53 | At1g63330 | UAGUCACGUUCAAUGCAUUGA |
| 54 | At1g63630 | UUGUUACUUUCAGUGCAUUGA |
| 55 | At1g64580 | CCCUGAUGUUGUCACUUUCAC |
| 56 | At2g41720 | UUGUUACUUACAAUGCAUUGA |
| 57 | At1g63070 | UAGUCUUUUCAACGCAUUGA | miR162 family target sequences - monocots and dicots

| 58 | At1g01040 | CUGGAUGCAGAGGUAUUAUCGA |
| 59 | PtDCL1 | CUGGAUGCAGAGGUCUUAUCGA |
| 60 | OsDCL1 | CUGGAUGCAGAGGUUUUAUCGA | miR163 family target sequences - *Arabidopsis*

| 61 | At1g66700 | AUCGAGUUCCAAGUCCUCUUCAA |
| 62 | At1g66720 | AUCGAGUUCCAGGUCCUCUUCAA |
| 63 | At3g44860 | AUCGAGUUCCAAGUUUUCUUCAA | miR164 family target sequences - monocots and dicots

| 64 | At1g56010 | AGCACGUACCCUGCUUCUCCA |
| 65 | At5g07680 | UUUACGUGCCCUGCUUCUCCA |
| 66 | At5g53950 | AGCACGUGUCCUGUUUCUCCA |
| 67 | At5g61430 | UCUACGUGCCCUGCUUCUCCA |
| 68 | At5g39610 | CUCACGUGACCUGCUUCUCCG |
| 69 | OsNAC1 | CGCACGUGACCUGCUUCUCCA |
| 70 | MtNAC | CUUACGUGUCCUGCUUCUCCA |
| 71 | GmNAC | CUUACGUGCCCUGCUUCUCCA |
| 72 | LeNAC | GCCACGUGCACUGCUUCUCCA | miR165/166 family target sequences - all plants

| 73 | At1g30490 | UUGGGAUGAAGCCUGGUCCGG |
| 74 | At5g60690 | CUGGGAUGAAGCCUGGUCCGG |
| 75 | At1g52150 | CUGGAUGAAGCCUGGUCCGG |
| 76 | PtHDZIPIII | CCGGGAUGAAGCCUGGUCCGG | miR167 family target sequences - monocots and dicots

| 77 | At1g30330 | GAGAUCAGGCUGGCAGCUUGU |
| 78 | At5g37020 | UAGAUCAGGCUGGCAGCUUGU |
| 79 | OsARF6 | AAGAUCAGGCUGGCAGCUUGU | miR168 family target sequences - all plants

| 80 | At1g48410 | UUCCCGAGCUGCAUCAAGCUA | miR169 family target sequences - all plants

| 81 | At1g17590 | AAGGGAAGUCAUCCUUGGCUG |
| 82 | At1g54160 | ACGGGAAGUCAUCCUUGGCUA |
| 83 | At1g72830 | AGGGGAAGUCAUCCUUGGCUA |
| 84 | At3g05690 | AGGCAAAUCAUCUUUGGCUCA |
| 85 | At3g20910 | GCGGCAAUUCAUUCUUGGCUU |
| 86 | At5g12840 | CCGGCAAAUCAUUCUUGGCUU |
| 87 | At3g14020 | AAGGGAAGUCAUCCUUGGCUA |
| 88 | ZmHAP2 | GUGGCAACUCAUCCUUGGCUC |
| 89 | VvHAP2 | UGGGCAAUUCAUCCUUGGCUU |
| 90 | OsHAP2 | AUGGCAAAUCAUCCUUGGCUU |
| 91 | GmHAP2 | UAGGGAAGUCAUCCUUGGCUC |
| 92 | GhHAP2 | CUGGGAAGUCAUCCUUGGCUC | miR170/171 family target sequences - all plants

| 93 | At2g45160 | GAUAUUGGCGCGGCUCAAUCA | miR172 family target sequences - all plants

| 94 | At4g36920 | CUGCAGCAUCAUCAGGAUUCU |
| 95 | At2g28550 | CAGCAGCAUCAUCAGGAUUCU |
| 96 | At5g60120 | AUGCAGCAUCAUCAGGAUUCU |
| 97 | At5g67180 | UGGCAGCAUCAUCAGGAUUCU |
| 97 | At2g39250 | UUGUAGCAUCAUCAGGAUUCC |
| 99 | At3g54990 | UUGCAGCAUCAUCAGGAUUCC | miR319 family target sequences - all plants

| 100 | At4g18390 | CAGGGGGACCCUUCAGUCCAA |
| 101 | At1g53230 | GAGGGGUCCCUUCAGUCCAU |
| 102 | At3g15030 | GAGGGGUCCCUUCAGUCCAG |
| 103 | At2g31070 | AAGGGUACCCUUCAGUCCAG |
| 104 | At1g30210 | UAGGGGGACCCUUCAGUCCAA |
| 105 | OsPCF5 | GAGGGGACCCUUCAGUCCAG |
| 106 | OsPCF8 | UCGGGGCACACUUCAGUCCAA | miR393 family target sequences - monocots and dicots

| 107 | At1g12820 | AAACAAUGCGAUCCCUUUGGA |
| 108 | At4g03190 | AGACCAUGCGAUCCCUUUGGA |
| 109 | At3g23690 | GGUCAGAGCGAUCCCUUUGGC |
| 110 | At3g62980 | AGACAAUGCGAUCCCUUUGGA | miR394 family target sequences - monocots and dicots

| 111 | At1g27340 | GGAGGUUGACAGAAUGCCAAA | miR395 family target sequences - monocots and dicots

| 112 | At5g43780 | GAGUUCCUCCAAACACUUCAU |
| 113 | At3g22890 | GAGUUCCUCCAAACUCUUCAU |
| 114 | At5g10180 | AAGUUCUCCCAAACACUUCAA | miR396 family target sequences - monocots and dicots

| 115 | At2g22840 | UCGUUCAAGAAAGCCUGUGGAA |
| 116 | At2g36400 | CCGUUCAAGAAAGCUGUGGAA |
| 117 | At4g24150 | UCGUUCAAGAAAGCAUGUGGAA |
| 118 | At2g45480 | ACGUUCAAGAAAGCUGUGGAA |
| 119 | At3g52910 | CCGUUCAAGAAAGCCUGUGGAA | miR397 family target sequences - monocots and dicots

| 120 | At2g29130 | AAUCAAUGCUGCACUCAAUGA |
| 121 | At2g38080 | AGUCAACGCUGCACUUAAUGA |
| 122 | At2g60020 | AAUCAAUGCUGCACUUAAUGA |

TABLE 2-continued

| SEQ ID NO. | miRNA Recognition Site | Recognition Site Sequence |
|---|---|---|
| miR398 family target sequences - monocots and dicots | | |
| 123 | At1g08830 | AAGGGGUUUCCUGAGAUCACA |
| 124 | At2g28190 | UGCGGGUGACCUGGGAAACAUA |
| 125 | At3g15640 | AAGGUGUGACCUGAGAAUCACA |
| miR173 family target sequences - Arabidopsis | | |
| 126 | AtTAS1a | GUGAUUUUCUCAACAAGCGAA |
| 127 | AtTAS1c | GUGAUUUUCUCUACAAGCGAA |
| 128 | AtTAS2 | GUGAUUUUCUCUCCAAGCGAA |
| miR399 family target sequences - monocots and dicots | | |
| 129 | At2g33770 | UAGGGCAUAUCUCCUUUGGCA |
| 130 | At2g33770 | UUGGGCAAAUCUCCUUUGGCA |
| 131 | At2g33770 | UCGAGCAAAUCUCCUUUGGCA |
| 132 | At2g33770 | UAGAGCAAAUCUCCUUUGGCA |
| 133 | At2g33770 | UAGGGCAAAUCUUCUUUGGCA |
| 134 | OsE2UBC | UAGGGCAAAUCUCCUUUGGCA |
| 135 | OsE2UBC | CUGGGCAAAUCUCCUUUGGCA |
| 136 | OsE2UBC | UCGGGCAAAUCUCCUUUGGCA |
| 137 | OsE2UBC | CCGGGCAAAUCUCCUUUGGCA |
| 138 | PtE2UBC | GCGGGCAAAUCUUCUUUGGCA |
| 139 | MtE2UBC | AAGGGCAAAUCUCCUUUGGCA |
| 140 | TaE2UBC | UAGGGCAAAUCUCCUUUGGCG |
| 141 | TaE2UBC | CUGGGCAAAUCUCCUUUGGCG |
| 142 | TaE2UBC | UUCGGCAAAUCUCCUUUGGCA |
| miR403 family target sequences - dicots | | |
| 143 | At1g31280 | GGAGUUUGUGCGUGAAUCUAAU |
| miR390 family target sequences - all plants | | |
| 144 | At3g17185 | CUUGUCUAUCCCUCCUGAGCUA |
| 145 | SbTAS3 | UAUGUCUAUCCCUUCUGAGCUG |
| 146 | SoTAS3 | UAUGUCUAUCCCUUCUGAGCUA |
| 147 | ZmTAS3 | UAUGUCUAUCCCUUCUGAGCUG |
| 148 | OsTAS3 | UCGGUCUAUCCCUCCUGAGCUG |
| 149 | PgTAS3 | UUAGUCUAUCCCUCCUGAGCUA |
| 150 | VvTAS3 | AUUGCCUAUCCCUCCUGAGCUG |
| 151 | TcTAS3 | CCUUGCUAUCCCUCCUGAGCUG |
| 152 | LeASR | CUUGCUCAUCCCUCCUGAGCUG |
| 153 | ZmTAS3 | CCCUUCUAUCCCUCCUGAGCUA |
| 154 | PtTAS3 | CUUGCUAUCCCUCCUGAGCUA |
| 155 | OsTAS3 | CCCUUCUAUCCCUCCUGAGCUA |
| 156 | TaTAS3 | CCCUUCUAUCCCUCCUGAGCUA |
| 157 | HvTAS3 | CCUUUCUAUCCCUCCUGAGCUA |
| 158 | PtTAS3 | CCUGUCUAUCCCUCCUGAGCUA |
| 159 | McTAS3 | UGUGUCUAUCCCUCCUGAGCUA |
| miR447 family target sequences - Arabidopsis | | |
| 160 | At5g60760 | UGACAAACAUCUCGUCCCCAA |
| 161 | At3g45090 | UGACAAACAUCUCGUUCCUAA |
| miR408 family target sequences - monocots and dicots | | |
| 162 | At2g02850 | CCAAGGGAAGAGGCAGUGCAU |
| 163 | At2g30210 | ACCAGUGAAGAGGCUGUGCAG |
| 164 | At2g47020 | GCCAGGGAAGAGGCAGUGCAU |
| 165 | At5g05390 | GCCGGUGAAGAGGCUGUGCAA |
| 166 | At5g07130 | GCCGGUGAAGAGGCUGUGCAG |
| TAS3 ta-siRNA target sequences - monocots and dicots | | |
| 167 | At2g33860a | AGGGUCUUGCAAGGUCAAGAA |
| 168 | At5g60450a | AAGGUCUUGCAAGGUCAAGAA |
| 169 | OsARF3-like | GAGGUCUUGCAAGGUCAAGAA |
| 170 | OsARF2-like | ACGGUCUUGCAAGGUCAAGAA |

TABLE 2-continued

| SEQ ID NO. | miRNA Recognition Site | Recognition Site Sequence |
|---|---|---|
| TAS1/TAS2 target sequences - Arabidopsis thaliana | | |
| 171 | Atg12770 | AGAACUAGAGAAAGCAUUGGA |
| 172 | Atg12770 | AGAGUAAGAUGGAGCUUGAUA |
| 173 | At1g63130 | AGAUGGUGGAAAUGGGAUAUC |
| 174 | At1g63230 | UUGUUGAUCGUAUGGUAGAAG |
| 175 | At1g62930 | GGUAUUCGAGUAUCUGCAAAA |

Thus, a transgenic plant expressing a recombinant DNA construct that, under the control of a constitutive promoter (e.g., a 35S promoter) transcribes to RNA containing a Zm-miR390 recognition site and a target RNA would be expected to show suppression of the target RNA expression in root and adult leaf, relative to expression in other tissues.

In another example, Zm-miR172 was expressed at high levels in stalk, and not expressed, or expressed only at low levels, in other tissues. A transgenic plant expressing a construct that, under the control of a strong constitutive promoter (e.g., a CaMV 35S promoter) transcribes to RNA containing a Zm-miR172 recognition site and a target RNA would be expected to express that target RNA at higher levels in tissues other than stalk (where expression of the target RNA would be suppressed).

To illustrate use of the constructs and methods of the invention to control expression of a gene of interest, a reporter gene is used as the gene of interest itself, or as a surrogate for the gene of interest. For example, where expression of a reporter gene (e.g., green fluorescent protein, GFP) is desired in maize stalk and immature ear tissue, a miR156 target site is included in a GFP expression cassette and expressed in a stably transgenic maize plant under the control of the CaMV 35S promoter. In other tissues (e.g., roots, leaves, and tassel), GFP expression is suppressed. The suppression phenotype may be limited to very specific cell types within the suppressed tissues, with neighboring cells showing expression or a gradient of expression of GFP adjacent to those cells expressing the mature miR156.

In another example, a strong constitutive promoter is used to drive expression of a *Bacillus thuringiensis* insecticidal protein or protein fragment ("Bt"), where a recognition site for a miRNA expressed specifically in pollen is included in the construct, resulting in strong Bt expression in tissues of the plant except for the pollen.

One specific, non-limiting example of the method is the inclusion of the recognition site for at least one miRNA that is not expressed (or expressed only at low levels) in roots to a recombinant DNA construct including a target RNA of which expression is desired only in the roots. A strong constitutive promoter (e.g., enhanced 35S) can still be used, but the target RNA's expression is now restricted to the cells that that do not express the corresponding mature miRNA. A specific example of this approach is the inclusion of a maize miRNA162, maize miRNA164, or maize miRNA390 recognition site (or any combination thereof) in a recombinant DNA construct for the expression of a *Bacillus thuringiensis* insecticidal protein or protein fragment ("Bt", see, for example, the *Bacillus thuringiensis* insecticidal sequences and methods of use thereof disclosed in U.S. Pat. No. 6,953,835 and in U.S. Provisional Patent Application No. 60/713,111, filed on 31 Aug. 2005) as the target RNA, e.g., in a construct including the expression cassette e35S/Bt/hsp17. These miRNAs (e.g., miRNA162, miRNA164, or miRNA390) are not substantially expressed in maize roots but are expressed in most other tissues. Including one or more of these recognition sites within the expression cassette reduces the expression of transcripts in most tissues other than root, but maintains high Bt target RNA expression levels in roots, such as is desirable for control of pests such as corn rootworm. In similar embodiments, combinations of different miRNA recognition sites are included in the construct in order to achieve the desired expression pattern in one or more specific tissues.

Non-limiting specific examples of transcribable DNA sequence including an exogenous miRNA recognition site are depicted in FIG. 4 and FIG. 5. FIG. 4 depicts chloroplast-targeted TIC809 with a miRNA162 recognition site (in bold text) located in the 3' untranslated region (SEQ ID NO. 176). FIG. 5 depicts non-targeted TIC809 with a miRNA164 recognition site (in bold text) located in the 3' untranslated region (SEQ ID NO. 177).

Example 4

This example describes identification of a crop plant MIR gene with tissue-specific expression, and identification of the miR gene promoter. More particularly, this example describes transcription profiling as a non-limiting method of identifying a miRNA specifically expressed in female reproductive tissue (endosperm), as well as identification of a maize miR167 promoter sequence with endosperm-specific expression. The recognition site corresponding to this miRNA is useful, e.g., in making transgenic plants with inducible female sterility according to this invention.

A member of the MIR167 gene family (SEQ ID NO. 178) was found to represent about a quarter of the small RNA population cloned from developing maize endosperm. To determine whether a single MIR167 gene family member is responsible for the observed strong endosperm expression, several MIR167 genes were analyzed by RT-PCR. Nine Zea mays MIR167 stem-loop sequences were found in the public miRNA registry ('miRBase", available on line at microrna.sanger.ac.uk/sequences), listed as miR167a through miR167i. Tissue-specific RT-PCR was performed for several of the Z. mays miR167 sequences using gene-specific primers for first strand cDNA synthesis followed by PCR with gene-specific primer pairs. Expression of miR167g was strong and tissue-specific for endosperm (15, 20 days after pollination).

To determine whether miR167g is abundantly expressed in endosperm, Northern blots of maize (LH59) were prepared. The blot was probed with an end-labeled mature miR167 22-mer LNA probe (FIG. 6A), stripped, and re-probed with a ~400 bp miR167g gene-specific probe (FIG. 6B). The strong endosperm signal observed indicated that miR167g is largely responsible for endosperm-enhanced expression. Transcription profiling of maize tissues corroborated the Northern blot results (FIG. 6C); the transcript corresponding to miR167g was abundantly and specifically expressed in endosperm tissue.

Figure 7:
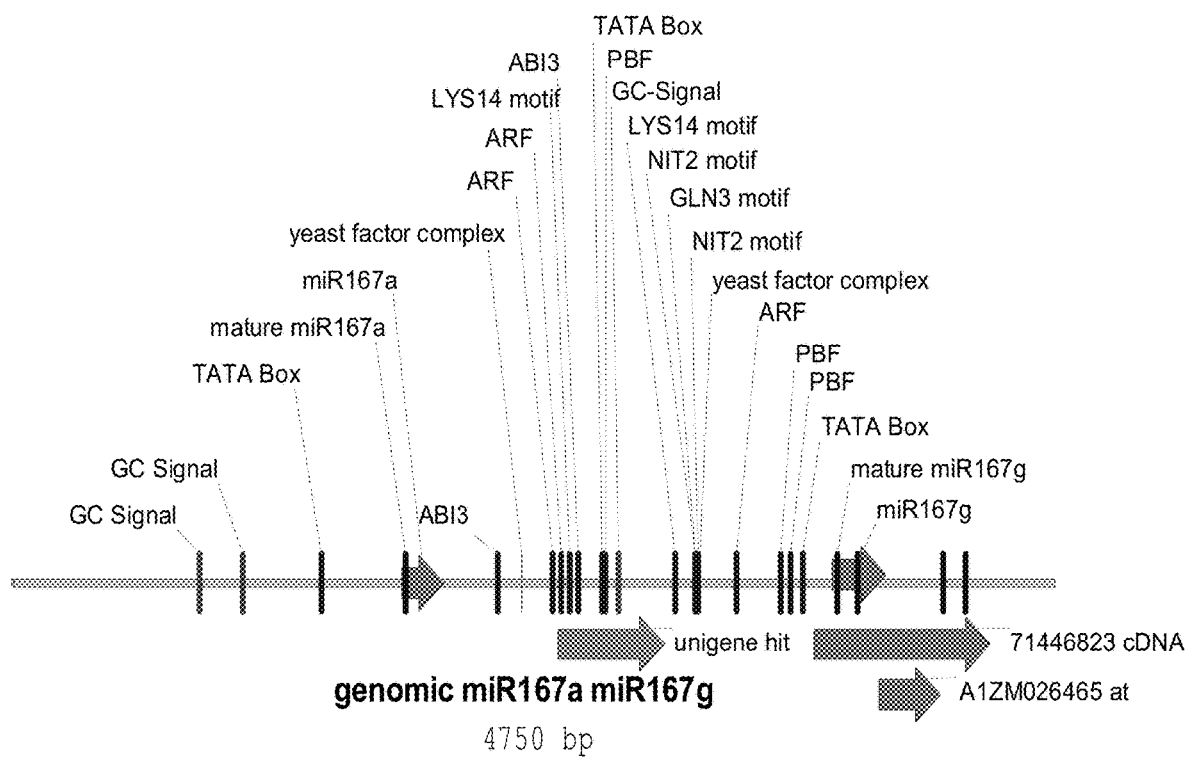
FIG. 7 depicts a partial annotation map, including locations of the miR167a and miR167g genes and mature miRNAs, and promoter elements (e.g., TATA boxes), of the genomic cluster within which was identified the miR167g promoter sequences as described in detail in Example 4. Abbreviations: "PBF", prolamin box binding factor; "ARF" auxin-responsive (auxin binding) factor; "NIT2", activator of nitrogen-related genes; "LYS14", element that binds to UASLYS, an upstream activating element conferring Lys14- and adipate semialdehyde-dependent activation and apparent repression; "GLN3", element that binds the nitrogen upstream activation sequence of glutamine synthetase.

A GenBank publicly available 804 base pair cDNA sequence (annotated as "ZM_BFb0071I20.r ZM_BFb Zea mays cDNA 5', mRNA sequence") and having the accession number DR827873.1 (GI:71446823) is incorporated here by reference. This sequence includes a segment (SEQ ID NO. 178) corresponding to the mature miR167g. Using the public sequence, bioinformatic analysis was performed on proprietary maize genomic sequence. A 4.75 kilobase genomic cluster including sequence from maize inbred line B73 was identified as containing predicted gene sequences for miR167a and miR167g. A 486 base pair region between the two MIR167 genes was identified as having homology to an expressed sequence tag (EST) sequence. Promoter motifs were identified in the upstream sequences of both (miR167a and miR167g) predicted transcripts. A region of 1682 base pairs (SEQ ID NO. 179) between the predicted miR167a and miR167g transcripts, and a smaller region of 674 base pairs (SEQ ID NO. 180) between the EST and the predicted miR167g transcript was identified as miR167g promoter sequences. Subsets of these sequences (e.g., at least about 50, about 100, about 150, about 200, about 250, or about 300 nucleotides of SEQ ID NO. 179 or SEQ ID NO. 180, or fragments of at least about 50, about 100, about 150, and about 200 contiguous nucleotides having at least 85%, at least 90%, or at least 95% identity to a segment of SEQ ID NO. 179 or SEQ ID NO. 180) are also useful as promoters; their promoter effects are demonstrable by procedures well known in the art (e.g., to drive expression of a reporter gene such as luciferase or green fluorescent protein). The annotation map, including locations of the miR167a and miR167g genes and mature miRNAs, and promoter elements (e.g., TATA boxes), of this genomic cluster is shown in FIG. 7. The annotation map also shows the location of auxin-responsive factor (ARF) motifs or auxin response elements with the sequence TGTCTC (SEQ ID NO. 181), which indicates that auxin may regulate expression of miR167g. Mature miR167 miRNAs are complementary to ARF6 and ARF8 (which encode activating ARFs) and have been proposed to regulate auxin homeostasis; see, for example, Rhoades et al. (2002) Cell, 110:513-520, Bartel and Bartel (2003) Plant Physiol., 132:709-717, Ulmasov et al. (1999) Proc. Natl. Acad. Sci. USA, 96:5844-5849, and Mallory et al. (2005) Plant Cell, 17:1360-1375.

In addition to the miR167g promoter sequences (SEQ ID NO. 179 and SEQ ID NO. 180) identified from maize inbred line B73, two additional miR167g promoter sequences (SEQ ID NO. 182 and SEQ ID NO. 183) were amplified from the maize inbred line LH244. The 3' ends of SEQ ID NO. 182 and SEQ ID NO. 183 were determined experimentally by 5' RACE (rapid amplification of cDNA ends, Invitrogen Corporation, Carlsbad, Calif.) of miR167g. The 5' end of the 768 base pairs sequence (SEQ ID NO. 182) corresponds to the end of a GenBank publicly available 481 base pair cDNA sequence (annotated as "QCG17c03.yg QCG Zea mays cDNA clone QCG17c03, mRNA sequence") and having the accession number CF035345.1 (GI:32930533). The 5' end of the 407 base pairs sequence (SEQ ID NO. 183) corresponds to the end of a GenBank publicly available 746 base pair cDNA sequence (annotated as "MEST991 A06.T7-1 UGA-ZmSAM-XZ2 Zea mays cDNA, mRNA sequence") and having the accession number DN214085.1 (GI:60347112).

The miR167g promoter sequences, miR167g gene, mature miR167g microRNA, and miR167g recognition site (examples of which are included below in Table 6) described herein have various utilities as described elsewhere in this disclosure. In particular, a miR167g promoter is useful as an endosperm-specific promoter, and can be used, for example to replace a maize B32 promoter. In another utility, the miR167g sequence or mature miR167g (or a precursor thereof) is engineered to suppress a target gene, especially where suppression is to be endosperm-specific. The miR167g recognition site is useful, e.g., in constructs for gene expression where the gene is to be expressed in tissues other than endosperm, and especially useful in making transgenic plants with inducible female sterility according to this invention.

Example 5

Current criteria for miRNA identification have emphasized phylogenetic conservation of miRNAs across species, and thus few non-conserved or species-specific miRNAs in plants have been characterized in plants. This example describes non-limiting methods for identifying miRNAs, their tissue expression patterns, their corresponding recognition sites, and examples of targets.

Five novel non-conserved miRNAs and the corresponding MIR sequences were identified from a size-fractionized cDNA library constructed from soybean leaves. Criteria for miRNA identification included: (1) a cloned 21-nt small RNA, and possible miRNA* (strand corresponding to the miRNA) at a lower abundance, (2) containment of the miRNA/miRNA* duplex wholly within a short, imperfect foldback structure, (3) derivation of the miRNA from an RNA Pol II non-protein-coding transcript, and (4) presence of a complementary target site in a coding gene; see Ambros et al. (2003) *RNA*, 9:277-279.

Small RNAs were extracted from adaptor-containing raw sequences and their strands were determined. This sequence set was filtered to remove small RNA sequences that were virus, tRNA, rRNA, chloroplast and mitochondria RNAs, and transgene, resulting in a filtered set of 381,633 putative miRNA sequences. Small RNAs not originating from the above sources and not homologous to known miRNAs were mapped to reference soybean cDNA sequences. For the mapped cDNA sequences with low protein-coding content, a cDNA sequence fragment of about 250 nucleotides, containing the putative miRNA, was folded using RNA Folder. The foldback structure was examined to check if the small RNA was located in the stem, and if an extensively (but not perfectly) complementary small RNA with lower abundance was located in the opposite side of the stem. The potential targets of the small RNA are predicted based on rules modified from Jones-Rhoades and Bartel (2004) *Mol. Cell*, 14:787-799, and Zhang (2005) *Nucleic Acids Res.*, 33:W701-704. Table 3 lists the five novel non-conserved miRNAs cloned from soy leaf tissue, and for each the corresponding miRNA* and precursor pri-miRNA(s); abundance ("abund") is given as the number of times the sequence occurred in a total of 381,633 sequences.

TABLE 3

| miRNA | | miRNA* | | miRNA |
| --- | --- | --- | --- | --- |
| SEQ ID NO. sequence | abund | SEQ ID NO. sequence | abund | precursor SEQ ID NO. |
| 184 UGAGACCAAAUGAGCAGCUGA | 94123 | 185 GCUGCUCAUCUGUUCUCAGG | 26 | 186 |
| 187 UAGAAGCUCCCCAUGUUCUCA | 7259 | 188 GAGCAUGGGUAACUUCUAU | 24 | 189 |
| 190 UGUUGCGGGUAUCUUUGCCUC | 4127 | 191 GGCGUAGAUCCCCACAACAG | 9 | 192 |
| 193 UGCGAGUGUCUUCGCCUCUGA | 3778 | 194 GGAGGCGUAGAUACUCACACC | 70 | 195 |
| 196 UUGCCGAUUCCACCCAUUCCUA | 3733 | 197 GCUGCUCAUCUGUUCUCAGG | 93 | 198, 199 |

For each novel soy miRNA, the fold-back structure of the miRNA precursor sequence(s) was predicted by an algorithm ("RNAFolder", based on RNAfold, publicly available at www.tbi.univie.ac.at/~ivo/RNA/RNAfold.html), and the miRNA precursor transcription profile obtained when available, as listed in Table 4. Examples of predicted targets (recognition sites) in soybean and their expression pattern identified were identified for two of the miRNAs (SEQ ID NO. 184 and SEQ ID NO. 187).

TABLE 4

Figure 10:
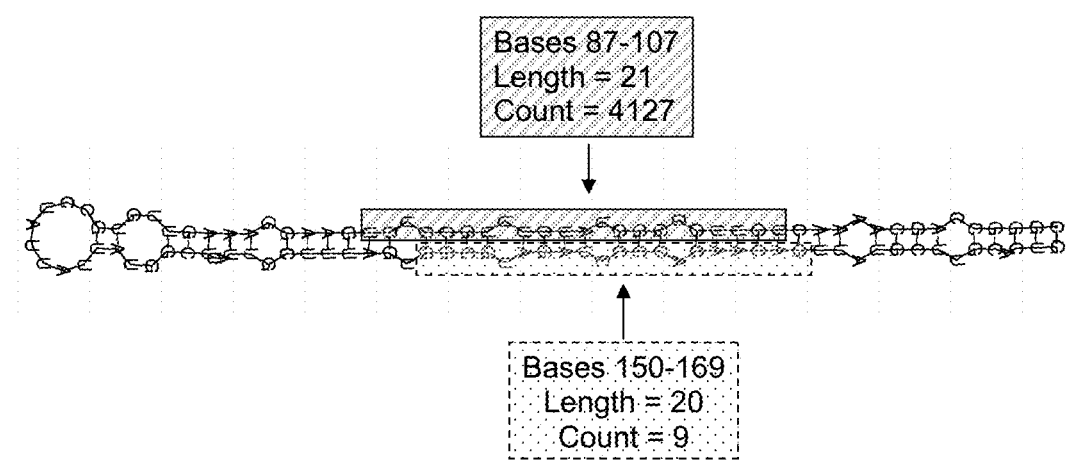
FIG. 10 depicts results described in detail in Example 5.
Figure 11:
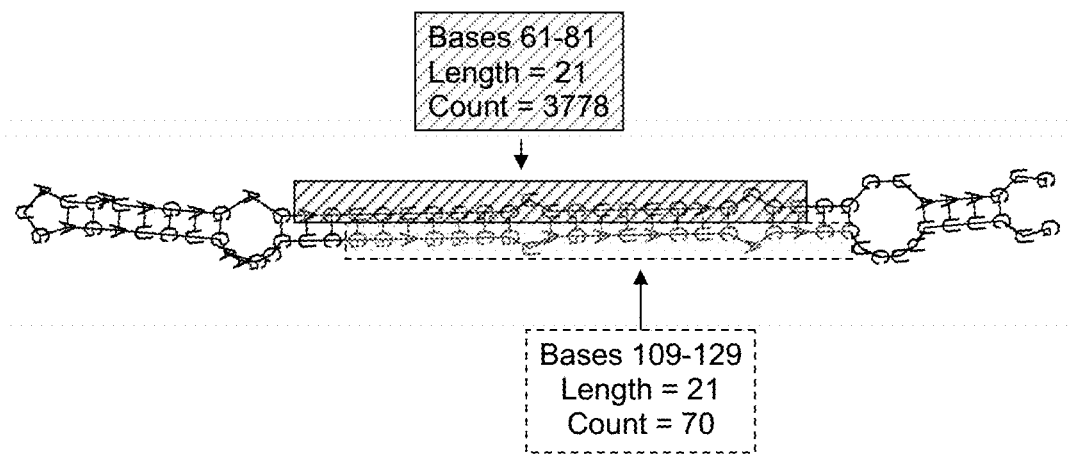
FIG. 11 depicts results described in detail in Example 5.

| miRNA SEQ ID NO. | miRNA precursor | miRNA precursor fold-back | miRNA precursor transcription profile | predicted *G. max* target (recognition site) sequence | predicted target expression pattern |
| --- | --- | --- | --- | --- | --- |
| 184 | 186 | see FIG. 8A | see FIG. 8B | polyphenol oxidase (SEQ ID NO. 200) | see FIG. 8C |
| 187 | 189 | see FIG. 9A | — | polyphenol oxidase (SEQ ID NO. 201) | see FIG. 9B |
| 190 | 192 | see FIG. 10 | — | — | — |
| 193 | 195 | see FIG. 11 | — | — | — |
| 196 | 198, 199 | see FIG. 12A | see FIG. 12B | — | — |

In addition, target (recognition site) sequences for each novel soy miRNA were identified from in-house ("MRTC") soy databases, as listed in Table 5. The number of mismatched nucleotides between each recognition site and the corresponding mature miRNA sequence range between 1 to 6 mismatches, which can include gaps or "missing" nucleotides. For example, a gap is found between nucleotides 7 and 8 in each of SEQ ID NO. 220, SEQ ID NO. 221, SEQ ID NO. 223, SEQ ID NO. 224, and SEQ ID NO. 225.

TABLE 5 miRNA SEQ ID NO. 184

| Glycine max target (recognition site) SEQ ID NO. | MRTC designation | Location of target (recognition site) | miRNA sequence (3'→5') AGUCGACGAGUAAACCAGAGU target (recognition site) sequence | score | mismatch |
|---|---|---|---|---|---|
| 202 | MRT3847_253879C.2 | 153 - 173 | ucagcugcucaucuguucuca | 2.5 | 2 |
| 203 | MRT3847_54392C.5 | 402 - 422 | ccagcugcucauuuggucacu | 2.5 | 3 |
| 204 | MRT3847_41382C.3 | 118 - 138 | ucagcucuucuuuuggucucu | 2.5 | 4 |
| 205 | MRT3847_319840C.1 | 408 - 428 | ucagcacugaucuggucuca | 3 | 3 |
| 206 | MRT3847_326146C.1 | 117 - 137 | ucagcuguccuuuguucucu | 3 | 4 |
| 207 | MRT3847_39543C.6 | 768 - 788 | ucagcuguuccuuuguucucu | 3 | 4 |
| 208 | MRT3847_253942C.4 | 1837 - 1857 | guagcuucucacuuggucuua | 3 | 5 |
| 209 | MRT3847_260486C.4 | 124 - 144 | uuagcugcuucuucggucucu | 3 | 5 |
| 210 | MRT3847_210520C.2 | 357 - 377 | uuagaugcuuguuuggucuuu | 3 | 6 | miRNA SEQ ID NO. 187

| Glycine max target (recognition site) SEQ ID NO. | MRTC designation | Location of target (recognition site) | miRNA sequence (3'→5') ACUCUUGUACCCCUCGAAGAU target (recognition site) sequence | score | mismatch |
|---|---|---|---|---|---|
| 211 | MRT3847_303349C.1 | 435 - 455 | ugagaacaugggggagccucua | 1.5 | 1 |
| 212 | MRT3847_14593C.6 | 1133 - 1153 | agaggacauggggagauucua | 2 | 3 |
| 213 | MRT3847_241913C.3 | 1111 - 1131 | agaggacauggggagguucua | 2 | 3 |
| 214 | MRT3847_32439C.4 | 1142 - 1162 | ugagaacaugggaaucuucua | 2.5 | 2 |
| 215 | MRT3847_187197C.5 | 689 - 709 | aaagaacaugggggagccucua | 2.5 | 3 |
| 216 | MRT3847_33448C.5 | 1047 - 1067 | ugagaacauggggagauucua | 2.5 | 3 |
| 217 | MRT3847_39693C.6 | 305 - 325 | ugugaaggugggagagcuucuu | 2.5 | 4 |
| 218 | MRT3847_50432C.5 | 89 - 109 | ggagaacaugcagagcuucug | 2.5 | 4 |
| 219 | MRT3847_95417C.1 | 308 - 328 | ugagaacuggggagcuuuc | 2.5 | 4 |
| 220 | MRT3847_115705C.2 | 82 - 101 | ugagaacuggugagcuucug | 3 | 3 | miRNA SEQ ID NO. 187

| Glycine max target (recognition site) SEQ ID NO. | MRTC designation | Location of target (recognition site) | miRNA sequence (3'→5') ACUCUUGUACCCCUCGAAGAU target (recognition site) sequence | score | mismatch |
|---|---|---|---|---|---|
| 221 | MRT3847_182667C.1 | 143 - 162 | ugaguacuggggagcuucuc | 3 | 3 |
| 222 | MRT3847_184995C.1 | 16 - 36 | ugagagcaugggguaacuucua | 3 | 3 |
| 223 | MRT3847_253437C.4 | 141 - 160 | ugagcacuggggagcuucuc | 3 | 3 |
| 224 | MRT3847_293395C.2 | 294 - 313 | ugagcacuggggagcuucuc | 3 | 3 |
| 225 | MRT3847_63512C.6 | 321 - 340 | ugagcacuggggagcuucuc | 3 | 3 |
| 226 | MRT3847_64829C.6 | 1087 - 1107 | ugagaacaugggaacuuucua | 3 | 3 |
| 227 | MRT3X47_80470C.3 | 15 - 35 | ugagagcaugggguaacuucua | 3 | 3 |
| 228 | MRT3847_136444C.5 | 312 - 332 | ugagaaccugguaagcuucug | 3 | 4 |
| 229 | MRT3847_231576C.1 | 360 - 380 | ugauaacaucgaaagcuucuu | 3 | 4 |
| 230 | MRT3847_263317C.1 | 90 - 110 | ugaggacaagggggagcuuaug | 3 | 4 |
| 231 | MRT3847_304409C.1 | 217 - 237 | cuaaaacauggggagcuucuu | 3 | 4 |
| 232 | MRT3847_247682C.3 | 1287 - 1307 | ugaggaaauagggaguuucug | 3 | 5 |
| 233 | MRT3847_251048C.2 | 280 - 300 | ugagaacauagugaguuuuuu | 3 | 5 |
| 234 | MRT3847_270705C.2 | 575 - 595 | uaggaucguuuguagcuucuc | 3 | 5 |
| 235 | MRT3847_304509C.2 | 592 - 612 | uaggaucgugggguagcuucuc | 3 | 5 |
| 236 | MRT3847_62576C.4 | 540 - 560 | uaggaucgugggggagcuucuc | 3 | 5 |
| 237 | MRT3847_67153C.3 | 661 - 681 | gaugaauauggggagcuuucua | 3 | 5 |

TABLE 5-continued miRNA SEQ ID NO. 190

| Glycine max target (recognition site) SEQ ID NO. | MRTC designation | Location of target (recognition site) | miRNA sequence (3'→5') CUCCGUUUCUAUGGGCGUUGU target (recognition site) sequence | score | mismatch |
|---|---|---|---|---|---|
| 238 | MRT3847_106868C.2 | 318 - 338 | ggggcaaggacauccgcaacg | 2.5 | 5 |
| 239 | MRT3847_307036C.1 | 171 - 191 | aagucaaaguugcccucgacg | 2.5 | 5 |
| 240 | MRT3847_308816C.2 | 719 - 739 | gaggcaaagaugcgagcaacg | 3 | 4 |
| 241 | MRT3847_6248C.3 | 584 - 604 | gcggcaaagauacucacaacc | 3 | 4 |
| 242 | MRT3847_104943C.2 | 177 - 197 | aacucaaagagaccuguaaca | 3 | 5 |
| 243 | MRT3847_290510C.2 | 181 - 201 | aaugcaaagaugccagcgacg | 3 | 5 |
| 244 | MRT3847_294184C.2 | 1090 - 1110 | gagccaaagagacccgugacg | 3 | 5 |
| 245 | MRT3847_321797C.1 | 847 - 867 | aaggcauagauagucgcagca | 3 | 5 |
| 246 | MRT3847_63653C.5 | 1096 - 1116 | aaggcaaagaugccagcaaug | 3 | 5 |
| 247 | MRT3847_9362C.2 | 481 - 501 | uagggaaagauacauguaaca | 3 | 5 |
| 248 | MRT3847_112761C.3 | 331 - 351 | gaggcaaaguuguucgcaaug | 3 | 6 |
| 249 | MRT3847_249731C.3 | 515 - 535 | caggcaaaagaugucugcaauu | 3 | 6 |
| 250 | MRT3847_313052C.1 | 253 - 273 | uagguauggauacuugcaaca | 3 | 6 |
| 251 | MRT3847_318082C.1 | 123 - 143 | aaggcaaagcugcccgcgaug | 3 | 6 | miRNA SEQ ID NO. 193

| Glycine max target (recognition site) SEQ ID NO. | MRTC designation | Location of target (recognition site) | miRNA sequence (3'→5') AGUCUCCGCUUCUGUGAGCGU target (recognition site) sequence | score | mismatch |
|---|---|---|---|---|---|
| 252 | MRT3847_160536C.3 | 182 - 202 | ucaggggaggagacacucgca | 2 | 3 |
| 253 | MRT3847_290017C.2 | 304 - 324 | uuagaggcaaagacacucguc | 2 | 4 |
| 254 | MRT3847_97323C.1 | 55 - 75 | ucagaggagaagauacucgug | 2 | 4 |
| 255 | MRT3847_182887C.1 | 43 - 63 | ucagaggagaagacacgcgca | 2.5 | 2 |
| 256 | MRT3847_290275C.2 | 177 - 197 | ucagagggagacacacgca | 2.5 | 3 |
| 257 | MRT3847_296312C.2 | 155 - 175 | ucagagggaagacacacgcu | 2.5 | 3 |
| 258 | MRT3X47_292252C.2 | 171 - 191 | ucagaggugaugacacacgcu | 2.5 | 4 |
| 259 | MRT3847_206250C.1 | 306 - 326 | ccagaggcggaugcauucgca | 2.5 | 5 |
| 26u | MRT3K47_240825C.3 | 436 - 456 | acagaggcagguacacuuga | 2.5 | 5 |
| 261 | MRT3847_250458C.2 | 776 - 796 | gcagaggugaagaagcuugca | 2.5 | 5 |
| 262 | MRT3847_36451C.4 | 87 - 107 | uuagaggagaggauacucgcg | 2.5 | 5 |
| 263 | MRT3847_48749C.4 | 715 - 735 | gcagaggugaagaagcuugca | 2.5 | 5 |
| 264 | MRT3847_97362C.3 | 566 - 586 | ucagaggcaaagauaccccgca | 3 | 3 |
| 265 | MRT3K47_20647C.2 | 143 - 163 | uuagagggaagacacgcgcu | 3 | 4 |
| 266 | MRT3847_219382C.1 | 147 - 167 | ucagagggaagacacccgug | 3 | 4 |
| 267 | MRT3847_243196C.3 | 73 - 93 | ucagaggcuaagagacuugua | 3 | 4 |
| 268 | MRT3847_248880C.3 | 760 - 780 | ucagagggaagacacgcgug | 3 | 4 |
| 269 | MRT3847_25201C.4 | 173 - 193 | ucagaugaagacacccgug | 3 | 4 |
| 270 | MRT3847_264555C.4 | 212 - 232 | ucagagggaagacacacguu | 3 | 4 |
| 271 | MRT3847_28447C.6 | 142 - 162 | ucagaggugaagacacgguu | 3 | 4 |
| 272 | MRT3847_32431C.4 | 59 - 79 | ucagggggaagacacacgua | 3 | 4 |
| 273 | MRT3847 99342C.1 | 116 - 136 | ucagagggaagacacccgug | 3 | 4 |
| 274 | MRT3847_210811C.2 | 273 - 293 | ucagaaacgaagacgcucguu | 3 | 5 |
| 275 | MRT3847 240A22C.2 | 92 - 112 | uccgagggaagauacucguu | 3 | 5 |
| 276 | MRT3847_254863C.2 | 175 - 195 | uccgagggaagauacucguc | 3 | 5 |
| 277 | MRT3847 255345C.3 | 113 - 133 | uccuaguggaagauacucguc | 3 | 5 |
| 278 | MRT3847 257424C.1 | 378 - 398 | gcagaggcuguggcacucgca | 3 | 5 |
| 279 | MRT3847_38012C.4 | 56 - 76 | uuagagucgaggacacguu | 3 | 5 |
| 280 | MRT3847_6951C.6 | 306 - 326 | uccuauuauaagauacucguu | 3 | 5 |
| 281 | MRT3847_263266C.4 | 163 - 183 | ucaguggcgaaggcguucguc | 3 | 6 |
| 282 | MRT3847_272810C.2 | 502 - 522 | uuagaggugaugucacucgug | 3 | 6 | miRNA SEQ ID NO. 196

| Glycine max target (recognition site) SEQ ID NO. | MRTC designation | Location of target (recognition site) | miRNA sequence (3'→5') AUCCUUACCCACCUUAGCCGUU target (recognition site) sequence | score | mismatch |
|---|---|---|---|---|---|
| 283 | MRT3847_302750C.1 | 259 - 280 | ggggaaugggguggaaacggcaa | 1.5 | 3 |
| 284 | MRT3847_136115C.3 | 661 - 682 | ugggaaugggguggauggguaa | 2.5 | 4 |
| 285 | MRT3847_235247C.2 | 694 - 715 | ugggaaugggguggauggguaa | 2.5 | 4 |
| 286 | MRT3847_21031C.3 | 1364 - 1385 | auggaacugguggaauuggcaa | 2.5 | 5 |
| 287 | MRT3847_297070C.2 | 280 - 301 | cgggaaagguuggaauuggcaa | 2.5 | 5 |
| 288 | MRT3847_248343C.3 | 392 - 413 | uaggaaugggguggauuugcaa | 3 | 3 |

TABLE 5-continued

| 289 | MRT3847_207469C.2 | 1 - 20 | ggaaugggguggcgugggcaa | 3 | 5 |
| 290 | MRT3847_216295C.4 | 537 - 558 | caggaaagggggaguuggcaa | 3 | 5 |
| 291 | MRT3847_287795C.2 | 141 - 162 | uagcaaugggguuggaucgguga | 3 | 5 |
| 292 | MRT3847_302511C.2 | 35 - 56 | guugaaugggguggaauuggaaa | 3 | 5 |
| 293 | MRT3847_312620C.1 | 46 - 67 | guugaaugggguggaauuggaaa | 3 | 5 |
| 294 | MRT3847_20416C.2 | 679 - 700 | aaggaauugggggaauugguac | 3 | 6 |
| 295 | MRT3847_297209C.1 | 289 - 310 | cacgagugggggggaaucggcgg | 3 | 6 |
| 296 | MRT3847_6639C.4 | 195 - 216 | guggaauggguggucuuggudaa | 3 | 6 |

Example 6

This example describes non-limiting methods for identifying miRNAs of use in making transgenic plants with inducible sterility usable in methods of this invention. More specifically, miRNAs having an expression pattern in the desired tissues (i.e., male or female reproductive tissues) were identified by evaluating transcription profile (TxP) data.

One general procedure for identifying miRNAs having an expression pattern in the desired tissues (i.e., male or female reproductive tissues) includes the steps of:

(a) providing an initial miR sequence including the stem-loop region, e.g., from the publicly available miR sequences at the 'miRBase" database (available on line at microrna-.sanger.ac.uk/sequences);

(b) applying sequence analysis algorithms, such as BLAST as is well known in the art (see Altschul et al. (1990) J. Mol. Biol., 215:403-410) to identify homologous or identical sequences (e.g., from proprietary sequences on microarray probesets made with corn whole genome DNA); and (c) analyzing the transcription profiles of the homologous probeset sequences identified in step (b) and identifying miRNAs having an expression pattern in the desired tissues (i.e., male or female reproductive tissues).

Preferably, a fourth step is added:

(d) for homologous probeset sequences found to have the desired transcription profiles, confirming identification of the miRNA gene by either aligning the stem-loop sequence of the initial miR sequence to the probeset sequence, or for potentially novel miRNAs, determining the sequence is predicted to fold into a stem-loop structure characteristic of a miRNA. Also preferably, an optional step is used, wherein one or more BLAST comparisons against additional sequence datasets other than the probeset sequence dataset is included (prior to step (b) above), allowing the further identification of probes that fall outside of the predicted fold-back region of the miR gene; false positives, e.g., due to matches in the additional sequence dataset(s) that include incorrectly spliced contigs, are identified by their lack of miRNA characteristics such as proper fold-back structure, and removed.

Figure 14:
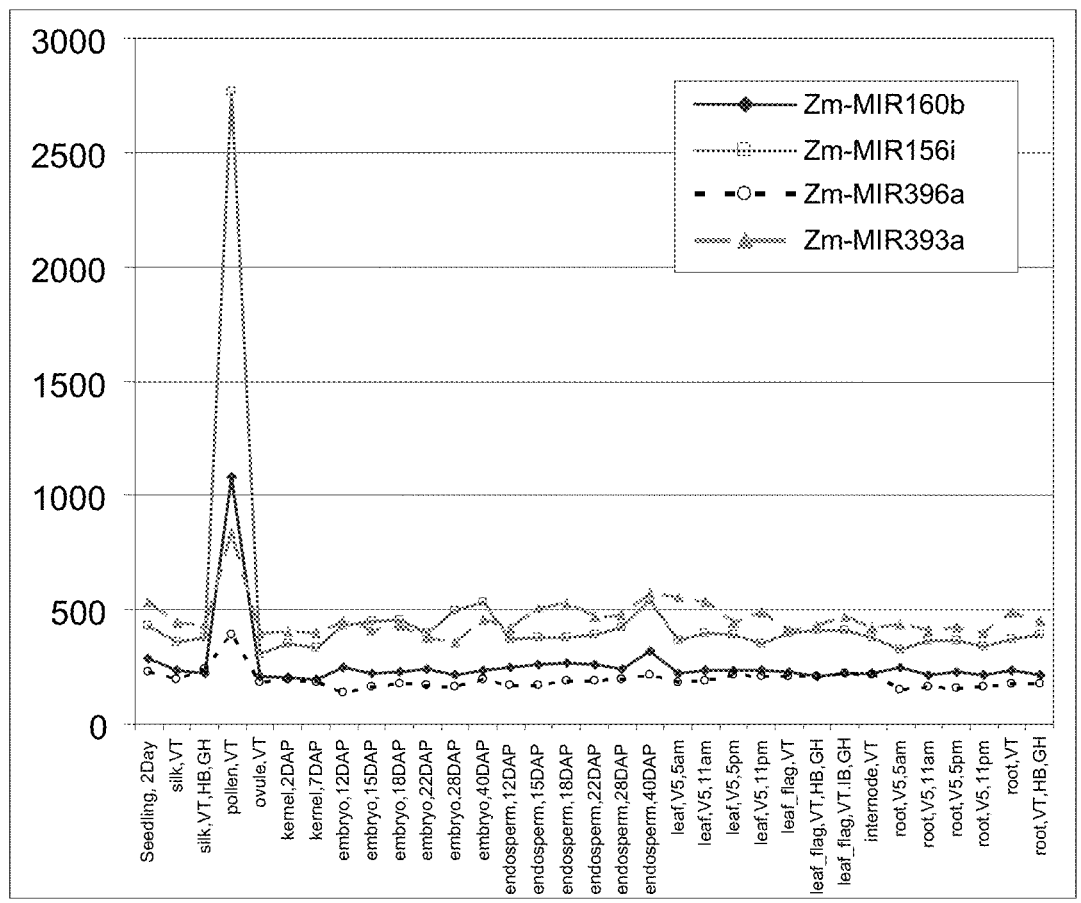

The above procedure was applied to proprietary transcription profiling data from maize. FIGS. 13 and 14 depict the transcription profiles of probeset sequences that were identified as including miRNA genes having the desired expression patterns, i.e., in female reproductive tissue (FIG. 13) or in male reproductive tissue (FIG. 14). Several miRNA genes and examples of their corresponding recognition sites were identified to be useful in making transgenic plants with inducible sterility (Table 6). Two members of the miR166 family, miR166b and miR166d, shared an identical mature miRNA sequence and corresponding recognition sites, but showed different expression patterns, with miR 166b being expressed only in embryo, and miR166d being expressed in ovule, embryo, silk, and root; thus for making inducibly female-sterile plants, miR 166b would be preferred. One particularly preferred embodiment of a miRNA useful for making inducibly female-sterile plants is maize endosperm-specific miR167g (SEQ ID NO. 307), with or without an additional G on the 3' end; embodiments having the additional G on the 3' end are 22-mers ending in GG and have corresponding recognition sites that are also preferably 22-mers where the nucleotide added to the 5' end is preferably mispaired (that is, not a C). In addition to the usefulness of these and similar miRNAs and their corresponding recogition sites for making and using inducibly sterile, transgenic plants, the promoters of these mature miRNAs are useful for driving expression of a transgene for which specific expression in a reproductive tissue is desired, e.g., the miR167g promoter is useful for driving endosperm-specific expression.

TABLE 6

Useful for plants with inducible female sterility

| miR homologue | Mature miRNA | miRNA recognition site(s) | Expression pattern |
|---|---|---|---|
| miR156j | UGACAGAAGAGAGAGAGCACA (SEQ ID NO. 297) | GUGCUCUCUCUCUUCUGUCA (SEQ ID NO. 298) CUGCUCUCUCUCUUCUGUCA (SEQ ID NO. 299) UUGCUUACUCUCUUCUGUCA (SEQ ID NO. 300) CCGCUCUCUCUCUUCUGUCA (SEQ ID NO. 301) | Ovule/early kernel |
| miR159c | CUUGGAUUGAAGGGAGCUCCU (SEQ ID NO. 302) | UGGAGCUCCCUUCAUUCCAAU (SEQ ID NO. 303) UCGAGUUCCCUUCAUUCCAAU (SEQ ID NO. 304) AUGAGCUCUCUUCAAACCAAA (SEQ ID NO. 305) | Ovule/early kernel |

TABLE 6-continued

Useful for plants with inducible female sterility

| miR homologue | Mature miRNA | miRNA recognition site(s) | Expression pattern |
|---|---|---|---|
| | | UGGAGCUCCCUUCAUUCCAAG (SEQ ID NO. 306) UAGAGCUUCCUUCAAACCAAA (SEQ ID NO. 307) UGGAGCUCCAUUCGAUCCAAA (SEQ ID NO. 308) AGCAGCUCCCUUCAAACCAAA (SEQ ID NO. 309) CAGAGCUCCCUUCACUCCAAU (SEQ ID NO. 310) UGGAGCUCCCUUCACUCCAAU (SEQ ID NO. 311) UGGAGCUCCCUUCACUCCAAG (SEQ ID NO. 312) UGGAGCUCCCUUUAAUCCAAU (SEQ ID NO. 313) | |
| miR166b | UCGGACCAGGCUUCAUUCCCC (SEQ ID NO. 314) | UUGGGAUGAAGCCUGGUCCGG (SEQ ID NO. 315) CUGGGAUGAAGCCUGGUCCGG (SEQ ID NO. 316) CUGGAAUGAAGCCUGGUCCGG (SEQ ID NO. 317) CCGGGAUGAAGCCUGGUCCGG (SEQ ID NO. 318) | Embryo |
| miR166d | UCGGACCAGGCUUCAUUCCCC (SEQ ID NO. 314) | UUGGGAUGAAGCCUGGUCCGG (SEQ ID NO. 315) CUGGGAUGAAGCCUGGUCCGG (SEQ ID NO. 316) CUGGAAUGAAGCCUGGUCCGG (SEQ ID NO. 317) CCGGGAUGAAGCCUGGUCCGG (SEQ ID NO. 318) | Embryo/ovule/ root/silk |
| miR167g | UGAAGCUGCCAGCAUGAUCUG (SEQ ID NO. 319) | GAGAUCAGGCUGGCAGCUUGU (SEQ ID NO. 320) UAGAUCAGGCUGGCAGCUUGU (SEQ ID NO. 321) AAGAUCAGGCUGGCAGCUUGU (SEQ ID NO. 322) | Endosperm |
| miR156i | UGACAGAAGAGAGUGAGCAC (SEQ ID NO. 323) | GUGCUCUCUCUCUUCUGUCA (SEQ ID NO. 324) CUGCUCUCUCUCUUCUGUCA (SEQ ID NO. 325) UUGCUUACUCUCUUCUGUCA (SEQ ID NO. 326) CCGCUCUCUCUCUUCUGUCA (SEQ ID NO. 327) | Pollen |
| miR160b-like | UGCCUGGCUCCCUGUAUGCCA (SEQ ID NO. 328) | UGGCAUGCAGGGAGCCAGGCA (SEQ ID NO. 329) AGGAAUACAGGGAGCCAGGCA (SEQ ID NO. 330) GGGUUUACAGGGAGCCAGGCA (SEQ ID NO. 331) AGGCAUACAGGGAGCCAGGCA (SEQ ID NO. 332) | Pollen |
| miR393a | UCCAAAGGGAUCGCAUUGAUCU (SEQ ID NO. 333) | AAACAAUGCGAUCCCUUUGGA (SEQ ID NO. 334) AGACCAUGCGAUCCCUUUGGA (SEQ ID NO. 335) GGUCAGAGCGAUCCCUUUGGC (SEQ ID NO. 336) AGACAAUGCGAUCCCUUUGGA (SEQ ID NO. 337) | Pollen |
| miR396a | UUCCACAGCUUUCUUGAACUG (SEQ ID NO. 338) | UCGUUCAAGAAAGCCUGUGGAA (SEQ ID NO. 339) CCGUUCAAGAAAGCCUGUGGAA (SEQ ID NO. 340) UCGUUCAAGAAAGCAUGUGGAA (SEQ ID NO. 341) | Pollen |

TABLE 6-continued

Useful for plants with inducible female sterility

| miR homologue | Mature miRNA | miRNA recognition site(s) | Expression pattern |
|---|---|---|---|
| | | ACGUUCAAGAAAGCUUGUGGAA (SEQ ID NO. 342) CCGUUCAAGAAAGCCUGUGGAA (SEQ ID NO. 343) | |

Example 7

This is a non-limiting example of methods for making a recombinant DNA construct, useful in making an inducibly sterile, transgenic plant, that transcribes to RNA including: (a) at least one exogenous miRNA recognition site recognizable by a mature miRNA that is specifically expressed in reproductive tissue of the plant; and (b) messenger RNA encoding a protein imparting tolerance to an herbicide; wherein the mature miRNA specifically suppresses expression of the protein in the reproductive tissue, and wherein sterility of the transgenic plant is inducible by application of the herbicide to the plant. A non-limiting example of a method to design a miRNA recognition site for use in such a recombinant DNA construct is illustrated here, wherein the plant is maize and the protein imparting tolerance to an herbicide is 5-enolpyruvylshikimate-3-phosphate synthase; analogous methods are useful with other plants and other proteins.

This method includes the steps of:

(a) Selecting a unique target sequence of at least 18 nucleotides specific to the messenger RNA encoding 5-enolpyruvylshikimate-3-phosphate synthase (EPSPS). One approach is to use a BLAST search (e.g., of both maize cDNA and genomic DNA databases) to identify EPSPS orthologues and any potential matches to unrelated genes, thereby avoiding unintentional silencing of non-target sequences.

(b) Analyzing the messenger RNA for undesirable sequences (e.g., matches to sequences from non-target species, especially animals), and score each potential 19-mer segment for GC content, Reynolds score (see Reynolds et al. (2004) *Nature Biotechnol.*, 22:326-330), and functional asymmetry characterized by a negative difference in free energy ("ΔΔG") (see Khvorova et al. (2003) *Cell*, 115:209-216). Preferably 19-mers are selected that have all or most of the following characteristics: (1) a Reynolds score >4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene. Preferably multiple (3 or more) 19-mers are selected for testing.

(c) Determining the reverse complement of the selected 19-mers to use in making a synthetic 21-mer miRNA; the additional nucleotide at position 20 is preferably matched to the selected target sequence, and the nucleotide at position 21 is preferably chosen to be unpaired to prevent transitivity.

(d) Testing the synthetic miRNAs, for example, in a transient *Nicotiana benthamiana* assay for miRNA expression and target repression.

(e) Cloning the most effective miRNAs into a construct for stable transformation of maize (see the sections under the headings "Making and Using Recombinant DNA Constructs" and "Making and Using Transgenic Plant Cells and Transgenic Plants").

Example 8

This example describes making inducibly sterile, transgenic plants and their use in producing hybrid seed. More specifically, this example describes the production of hybrid maize seed from an inducibly male sterile, transgenic maize parent plant and an inducibly female sterile, transgenic maize parent plant, wherein the sterility is induced by application of the herbicide glyphosate the the parent plants.

Recombinant DNA constructs are designed to transcribe to (a) an exogenous miRNA recognition site recognizable by a mature miRNA that is specifically expressed in reproductive tissue of the plant; and (b) messenger RNA encoding a protein (5-enolpyruvylshikimate-3-phosphate synthase) imparting tolerance to an herbicide (glyphosate); wherein the mature miRNA specifically suppresses expression of the protein in the reproductive tissue, and wherein sterility of the transgenic plant is inducible by application of the herbicide to the plant. Each recombinant DNA construct includes sequence that transcribes to messenger RNA encoding 5-enolpyruvylshikimate-3-phosphate synthase from *Agrobacterium tumefaciens* strain CP4 ("EPSPS-CP4"), (SEQ ID NO. 344)
ATGCTTCACGGTGCAAGCAGCCGTCCAGCAACTGCTCGTAAGTCCTCTGG

TCTTTCTGGAACCGTCCGTATTCCAGGTGACAAGTCTATCTCCCACAGGT

CCTTCATGTTTGGAGGTCTCGCTAGCGGTGAAACTCGTATCACCGGTCTT

TTGGAAGGTGAAGATGTTATCAACACTGGTAAGGCTATGCAAGCTATGGG

TGCCAGAATCCGTAAGGAAGGTGATACTTGGATCATTGATGGTGTTGGTA

ACGGTGGACTCCTTGCTCCTGAGGCTCCTCTCGATTTCGGTAACGCTGCA

ACTGGTTGCCGTTTGACTATGGGTCTTGTTGGTGTTTACGATTTCGATAG

CACTTTCATTGGTGACGCTTCTCTCACTAAGCGTCCAATGGGTCGTGTGT

TGAACCCACTTCGCGAAATGGGTGTGCAGGTGAAGTCTGAAGACGGTGAT

CGTCTTCCAGTTACCTTGCGTGGACCAAAGACTCCAACGCCAATCACCTA

CAGGGTACCTATGGCTTCCGCTCAAGTGAAGTCCGCTGTTCTGCTTGCTG

GTCTCAACACCCCAGGTATCACCACTGTTATCGAGCCAATCATGACTCGT

GACCACACTGAAAAGATGCTTCAAGGTTTTGGTGCTAACCTTACCGTTGA

GACTGATGCTGACGGTGTGCGTACCATCCGTCTTGAAGGTCGTGGTAAGC

TCACCGGTCAAGTGATTGATGTTCCAGGTGATCCATCCTCTACTGCTTTC

CCATTGGTTGCTGCCTTGCTTGTTCCAGGTTCCGACGTCACCATCCTTAA

CGTTTTGATGAACCCAACCCGTACTGGTCTCATCTTGACTCTGCAGGAAA

TGGGTGCCGACATCGAAGTGATCAACCCACGTCTTGCTGGTGGAGAAGAC

GTGGCTGACTTGCGTGTTCGTTCTTCTACTTTGAAGGGTGTTACTGTTCC

-continued

```
AGAAGACCGTGCTCCTTCTATGATCGACGAGTATCCAATTCTCGCTGTTG

CAGCTGCATTCGCTGAAGGTGCTACCGTTATGAACGGTTTGGAAGAACTC

CGTGTTAAGGAAAGCGACCGTCTTTCTGCTGTCGCAAACGGTCTCAAGCT

CAACGGTGTTGATTGCGATGAAGGTGAGACTTCTCTCGTCGTGCGTGGTC

GTCCTGACGGTAAGGGTCTCGGTAACGCTTCTGGAGCAGCTGTCGCTACC

CACCTCGATCACCGTATCGCTATGAGCTTCCTCGTTATGGGTCTCGTTTC

TGAAAACCCTGTTACTGTTGATGATGCTACTATGATCGCTACTAGCTTCC

CAGAGTTCATGGATTTGATGGCTGGTCTTGGAGCTAAGATCGAACTCTCC

GACACTAAGGCTGCTTGA.
```

For convenience in cloning, each recombinant DNA construct also includes a 3' untranslated region (3' UTR) spacer sequence located between the messenger RNA and a terminator,

```
(SEQ ID NO. 345, with SacI and BamHI restriction
            sites indicated by lowercase font)
TgagctcAAGAATTCGAGCTCGGTACCggatccTCTAGCTAG,
``` which allows insertion of a miRNA recognition site between the SacI and BamHI restriction sites.

The recombinant DNA construct for inducible male sterility includes the sequence,

```
(SEQ ID NO. 346, with SacI and BamHI restriction
            sites indicated by lowercase font)
TgagctcAAGAATTCGAAGACAATGCGATCCCUUUGGAGCTCGGTACCgg atccTCTAGCTAG,
``` which contains a synthetic miRNA recognition site (indicated by underlined text), designed to be recognized by a miR393, which is highly expressed in pollen (see Example 6) and is a member of a relatively small miRNA family (reducing the possibility that other members of the same miRNA family will suppress EPSPS-CP4 in tissues other than pollen).

The recombinant DNA construct for inducible female sterility includes the sequence,

```
(SEQ ID NO. 347, with SacI and BamHI restriction
            sites indicated by lowercase font)
TgagctcAAGAATTCGATCCGCTTTCTCTCTTCTGTCAGCTCGGTACCgg atccTCTAGCTAG,
``` which contains a synthetic miRNA recognition site (indicated by underlined text), designed to be recognized by a miR156j, which is highly expressed in ovule and early kernel (see Example 6). This miRNA recognition site includes a unique base at position 14, which can be preferentially matched to a target sequence to improve specificity for miR156j recognition. Pairing to the 3' end of the miRNA is reduced (relative to endogenous targets), improving specificity for miR156j recognition. This reduces the likelihood that other members of the miR156 family will suppress EPSPS-CP4 in tissues other than ovule and early kernel.

Each of the two recombinant DNA constructs (for inducible male sterility and for inducible female sterility) is individually transformed into maize as described under "Making and Using Transgenic Plant Cells and Transgenic Plants". Briefly, a vector for plant transformation is prepared for each of the recombinant DNA constructs as described under "Making and Using Recombinant DNA Constructs", and used to transform maize plant tissue using *Agrobacterium*-mediated transformation and glyphosate selection. Transgenic plants from each transgenic insertion event are grown to maturity and progeny seed are produced by routine selfing or crossing (as described under "Making and Using Transgenic Plant Cells and Transgenic Plants"). The progeny seed optionally include other recombinant DNA for imparting additional traits (e.g., in the case of transformed plants, traits including herbicide resistance, pest resistance, cold germination tolerance, water deficit tolerance, and the like). From these progeny seed are selected transgenic seed to be grown into a first parent plant (containing in its genome the recombinant DNA construct for inducible male sterility) and transgenic seed to be grown into a second parent plant (containing in its genome the recombinant DNA construct for inducible female sterility).

A mixed planting is made in the field, with a ratio of transgenic maize seed having the construct for inducible male sterility to transgenic seed having the construct for inducible male sterility of between about 1:4 to about 1:10. The transgenic maize seed is allowed to germinate, thereby providing first parent plants with inducible male sterility (i.e., parent plants to be pollinated) and second parent plants with inducible female sterility (i.e., pollinating parent plants). At the appropriate stage(s) of plant development, the herbicide glyphosate is applied to the first and second parent plants by spraying an amount effective in inducing male sterility in the first parent plants and female sterility in the second parent plants. Seed collected from the field is hybrid seed produced from ovules of the first parent plant that were pollinated by pollen of the second parent plant.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of preventing expression of a messenger RNA in male reproductive tissue of a plant, comprising the inclusion of at least one exogenous miRNA recognition site in the sequence of said messenger RNA,
   wherein said at least one exogenous miRNA recognition site is recognizable by an endogenous mature miRNA that is endogenously and specifically expressed in male reproductive tissue of said plant, wherein said male reproductive tissue is at least one tissue selected from the group consisting of pollen, male gametes, anthers, stamens, filaments, and tassels whereby said expression of said messenger RNA in said male reproductive tissue is prevented, and wherein said messenger RNA is expressed under the control of a constitutive promoter.

2. The method of claim 1, wherein said messenger RNA encodes at least one insecticidal protein or protein fragment, or at least one protein imparting tolerance to an herbicide, or both.

3. The method of claim 1, wherein said at least one exogenous miRNA recognition site is located within at least one of:

(a) the 5' untranslated region of said messenger RNA;

(b) the 3' untranslated region of said messenger RNA; and (c) the coding region of said messenger RNA.

4. The method of claim 1, wherein said messenger RNA encodes at least one protein imparting tolerance to a systemic herbicide.

5. The method of claim 1, wherein said protein imparting tolerance to a systemic herbicide is at least one protein selected from the group consisting of an 5-enolpyruvylshikimate-3-phosphate synthase, the 5-enolpyruvylshikimate-3-phosphate synthase from *Agrobacterium tumefaciens* strain CP4, glyphosate oxidoreductase, glyphosate acetyltransferase, glyphosate decarboxylase, pat, bar, dicamba monooxygenase, 2,2-dichloropropionic acid dehalogenase, acetohydroxyacid synthase, acetolactate synthase, haloarylnitrilase, modified acetyl-coenzyme A carboxylase, dihydropteroate synthase, 32 kDa photosystem II polypeptide, anthranilate synthase, dihydrodipicolinic acid synthase, phytoene desaturase, hydroxyphenyl pyruvate dioxygenase, modified protoporphyrinogen oxidase I, and aryloxyalkanoate dioxygenase.

6. The method of claim 1, wherein:
    (a) said endogenous mature miRNA is a miR156i having the sequence of SEQ ID NO:323; or
    (b) said at least one exogenous miRNA recognition site has the sequence of any one of SEQ ID NOs:324-327.

7. The method of claim 1, wherein said plant is selected from the group consisting of wheat, oat, barley, maize, rye, triticale, rice, ornamental and forage grasses, sorghum, millet, sugarcane, quinoa, amaranth, buckwheat, alfalfa, vetch, clover, cotton, canola, rapeseed, brassicas, safflower, soybean, flax, sugarbeet, and sunflower.

8. A plant in which expression of a messenger RNA has been prevented in male reproductive tissue by the method of claim 1.

9. A messenger RNA comprising a recombinant RNA molecule which comprises:
    (a) a transgene encoding a protein, and
    (b) at least one exogenous miRNA recognition site recognizable by an endogenous mature miRNA that is endogenously and specifically expressed in male reproductive tissue of a plant,
    wherein said male reproductive tissue is at least one tissue selected from the group consisting of pollen, male gametes, anthers, stamens, filaments, and tassels, and wherein said messenger RNA is expressed under the control of a constitutive promoter.

10. The messenger RNA of claim 9, wherein:
    (a) said transgene encodes at least one insecticidal protein or protein fragment, or at least one protein imparting tolerance to an herbicide, or both;
    (b) said transgene encodes at least one protein imparting tolerance to a systemic herbicide; or
    (c) said transgene encodes at least one protein selected from the group consisting of an 5-enolpyruvylshikimate-3-phosphate synthase, the 5-enolpyruvylshikimate-3-phosphate synthase from *Agrobacterium tumefaciens* strain CP4, glyphosate oxidoreductase, glyphosate acetyltransferase, glyphosate decarboxylase, pat, bar, dicamba monooxygenase, 2,2-dichloropropionic acid dehalogenase, acetohydroxyacid synthase, acetolactate synthase, haloarylnitrilase, modified acetyl-coenzyme A carboxylase, dihydropteroate synthase, 32 kDa photosystem II polypeptide, anthranilate synthase, dihydrodipicolinic acid synthase, phytoene desaturase, hydroxyphenyl pyruvate dioxygenase, modified protoporphyrinogen oxidase I, and aryloxyalkanoate dioxygenase.

11. A plant cell containing the messenger RNA of claim 9.

12. The messenger RNA of claim 9, wherein said at least one exogenous miRNA recognition site is located within at least one of:
    (i) a region 5' to coding sequence of said transgene;
    (ii) a region 3' to coding sequence of said transgene; and
    (iii) the coding region of said transgene.

13. The messenger RNA of claim 9, wherein:
    (a) said endogenous mature miRNA is a miR156i having the sequence of SEQ ID NO:323; or
    (b) said at least one exogenous miRNA recognition site has the sequence of any one of SEQ ID NOs:324-327.

* * * * *

SEQUENCE LISTING

```
<160> NUMBER OF SEQ ID NOS: 347

<210> SEQ ID NO 1
<211> LENGTH: 20
<212> TYPE: DNA
<213> ORGANISM: artificial sequence
<220> FEATURE:
```

<223> OTHER INFORMATION: Synthetic construct

<400> SEQUENCE: 1
gtgctcactc tcttctgtca                                                    20

<210> SEQ ID NO 2
<211> LENGTH: 21
<212> TYPE: DNA
<213> ORGANISM: artificial sequence
<220> FEATURE:
<223> OTHER INFORMATION: Synthetic construct

<400> SEQUENCE: 2
tagagctccc ttcaatccaa a                                                  21

<210> SEQ ID NO 3
<211> LENGTH: 21
<212> TYPE: DNA
<213> ORGANISM: artificial sequence
<220> FEATURE:
<223> OTHER INFORMATION: Synthetic construct

<400> SEQUENCE: 3
tggcatccag ggagccaggc a                                                  21

<210> SEQ ID NO 4
<211> LENGTH: 21
<212> TYPE: DNA
<213> ORGANISM: artificial sequence
<220> FEATURE:
<223> OTHER INFORMATION: Synthetic construct

<400> SEQUENCE: 4
ctggatgcag aggtttatcg a                                                  21

<210> SEQ ID NO 5
<211> LENGTH: 21
<212> TYPE: DNA
<213> ORGANISM: artificial sequence
<220> FEATURE:
<223> OTHER INFORMATION: Synthetic construct

<400> SEQUENCE: 5
tgcacgtgcc ctgcttctcc a                                                  21

<210> SEQ ID NO 6
<211> LENGTH: 21
<212> TYPE: DNA
<213> ORGANISM: artificial sequence
<220> FEATURE:
<223> OTHER INFORMATION: Synthetic construct

<400> SEQUENCE: 6
ggggaatgaa gcctggtccg a                                                  21

<210> SEQ ID NO 7
<211> LENGTH: 21
<212> TYPE: DNA
<213> ORGANISM: artificial sequence
<220> FEATURE:
<223> OTHER INFORMATION: Synthetic construct

<400> SEQUENCE: 7
tagatcatgc tggcagcttc a                                                  21

```
<210> SEQ ID NO 8
<211> LENGTH: 21
<212> TYPE: DNA
<213> ORGANISM: artificial sequence
<220> FEATURE:
<223> OTHER INFORMATION: Synthetic construct

<400> SEQUENCE: 8
ttcccgacct gcaccaagcg a                                              21

<210> SEQ ID NO 9
<211> LENGTH: 21
<212> TYPE: DNA
<213> ORGANISM: artificial sequence
<220> FEATURE:
<223> OTHER INFORMATION: Synthetic construct

<400> SEQUENCE: 9
tcggcaagtc atccttggct g                                              21

<210> SEQ ID NO 10
<211> LENGTH: 21
<212> TYPE: DNA
<213> ORGANISM: artificial sequence
<220> FEATURE:
<223> OTHER INFORMATION: Synthetic construct

<400> SEQUENCE: 10
gatattggcg cggctcaatc a                                              21

<210> SEQ ID NO 11
<211> LENGTH: 21
<212> TYPE: DNA
<213> ORGANISM: artificial sequence
<220> FEATURE:
<223> OTHER INFORMATION: Synthetic construct

<400> SEQUENCE: 11
ctgcagcatc atcaagattc t                                              21

<210> SEQ ID NO 12
<211> LENGTH: 21
<212> TYPE: DNA
<213> ORGANISM: artificial sequence
<220> FEATURE:
<223> OTHER INFORMATION: Synthetic construct

<400> SEQUENCE: 12
ggcgctatcc ctcctgagct t                                              21

<210> SEQ ID NO 13
<211> LENGTH: 21
<212> TYPE: DNA
<213> ORGANISM: artificial sequence
<220> FEATURE:
<223> OTHER INFORMATION: Synthetic construct

<400> SEQUENCE: 13
gatcaatgcg atccctttgg a                                              21

<210> SEQ ID NO 14
<211> LENGTH: 22
<212> TYPE: DNA
<213> ORGANISM: artificial sequence
<220> FEATURE:
<223> OTHER INFORMATION: Synthetic construct
```

<400> SEQUENCE: 14
tggggtcctt acaaggtcaa ga                                          22

<210> SEQ ID NO 15
<211> LENGTH: 20
<212> TYPE: DNA
<213> ORGANISM: artificial sequence
<220> FEATURE:
<223> OTHER INFORMATION: Synthetic construct

<400> SEQUENCE: 15
ggaggtggac agaatgccaa                                             20

<210> SEQ ID NO 16
<211> LENGTH: 21
<212> TYPE: DNA
<213> ORGANISM: artificial sequence
<220> FEATURE:
<223> OTHER INFORMATION: Synthetic construct

<400> SEQUENCE: 16
gagttccccc aaacacttca c                                           21

<210> SEQ ID NO 17
<211> LENGTH: 21
<212> TYPE: DNA
<213> ORGANISM: artificial sequence
<220> FEATURE:
<223> OTHER INFORMATION: Synthetic construct

<400> SEQUENCE: 17
catcaacgct gcgctcaatg a                                           21

<210> SEQ ID NO 18
<211> LENGTH: 21
<212> TYPE: DNA
<213> ORGANISM: artificial sequence
<220> FEATURE:
<223> OTHER INFORMATION: Synthetic construct

<400> SEQUENCE: 18
cgggggcgac ctgagaacac a                                           21

<210> SEQ ID NO 19
<211> LENGTH: 21
<212> TYPE: DNA
<213> ORGANISM: artificial sequence
<220> FEATURE:
<223> OTHER INFORMATION: Synthetic construct

<400> SEQUENCE: 19
agccagggaa gaggcagtgc a                                           21

<210> SEQ ID NO 20
<211> LENGTH: 20
<212> TYPE: RNA
<213> ORGANISM: Arabidopsis thaliana

<400> SEQUENCE: 20
gugcucucuc ucuucuguca                                             20

<210> SEQ ID NO 21
<211> LENGTH: 20
<212> TYPE: RNA
<213> ORGANISM: Arabidopsis thaliana -continued

```
<400> SEQUENCE: 21
cugcucucuc ucuucuguca                                              20

<210> SEQ ID NO 22
<211> LENGTH: 20
<212> TYPE: RNA
<213> ORGANISM: Arabidopsis thaliana

<400> SEQUENCE: 22
uugcuuacuc ucuucuguca                                              20

<210> SEQ ID NO 23
<211> LENGTH: 20
<212> TYPE: RNA
<213> ORGANISM: Arabidopsis thaliana

<400> SEQUENCE: 23
ccgcucucuc ucuucuguca                                              20

<210> SEQ ID NO 24
<211> LENGTH: 21
<212> TYPE: RNA
<213> ORGANISM: Arabidopsis thaliana

<400> SEQUENCE: 24
uggagcuccc uucauuccaa u                                            21

<210> SEQ ID NO 25
<211> LENGTH: 21
<212> TYPE: RNA
<213> ORGANISM: Arabidopsis thaliana

<400> SEQUENCE: 25
ucgaguuccc uucauuccaa u                                            21

<210> SEQ ID NO 26
<211> LENGTH: 21
<212> TYPE: RNA
<213> ORGANISM: Arabidopsis thaliana

<400> SEQUENCE: 26
augagcucuc uucaaaccaa a                                            21

<210> SEQ ID NO 27
<211> LENGTH: 21
<212> TYPE: RNA
<213> ORGANISM: Arabidopsis thaliana

<400> SEQUENCE: 27
uggagcuccc uucauuccaa g                                            21

<210> SEQ ID NO 28
<211> LENGTH: 21
<212> TYPE: RNA
<213> ORGANISM: Arabidopsis thaliana

<400> SEQUENCE: 28
uagagcuucc uucaaaccaa a                                            21

<210> SEQ ID NO 29
<211> LENGTH: 21
<212> TYPE: RNA
```

<213> ORGANISM: Arabidopsis thaliana

<400> SEQUENCE: 29
uggagcucca uucgauccaa a          21

<210> SEQ ID NO 30
<211> LENGTH: 21
<212> TYPE: RNA
<213> ORGANISM: Arabidopsis thaliana

<400> SEQUENCE: 30
agcagcuccc uucaaaccaa a          21

<210> SEQ ID NO 31
<211> LENGTH: 21
<212> TYPE: RNA
<213> ORGANISM: Phaseolus vulgaris

<400> SEQUENCE: 31
cagagcuccc uucacuccaa u          21

<210> SEQ ID NO 32
<211> LENGTH: 21
<212> TYPE: RNA
<213> ORGANISM: Vitis vinifera

<400> SEQUENCE: 32
uggagcuccc uucacuccaa u          21

<210> SEQ ID NO 33
<211> LENGTH: 21
<212> TYPE: RNA
<213> ORGANISM: Hordeum vulgare

<400> SEQUENCE: 33
uggagcuccc uucacuccaa g          21

<210> SEQ ID NO 34
<211> LENGTH: 21
<212> TYPE: RNA
<213> ORGANISM: Oryza sativa

<400> SEQUENCE: 34
uggagcuccc uuuaauccaa u          21

<210> SEQ ID NO 35
<211> LENGTH: 21
<212> TYPE: RNA
<213> ORGANISM: Arabidopsis thaliana

<400> SEQUENCE: 35
uggcaugcag ggagccaggc a          21

<210> SEQ ID NO 36
<211> LENGTH: 21
<212> TYPE: RNA
<213> ORGANISM: Arabidopsis thaliana

<400> SEQUENCE: 36
aggaauacag ggagccaggc a          21

<210> SEQ ID NO 37
<211> LENGTH: 21

```
<212> TYPE: RNA
<213> ORGANISM: Arabidopsis thaliana

<400> SEQUENCE: 37
ggguuuacag ggagccaggc a                                     21

<210> SEQ ID NO 38
<211> LENGTH: 21
<212> TYPE: RNA
<213> ORGANISM: Oryza sativa

<400> SEQUENCE: 38
aggcauacag ggagccaggc a                                     21

<210> SEQ ID NO 39
<211> LENGTH: 21
<212> TYPE: RNA
<213> ORGANISM: Lotus corniculatus var. japonicus

<400> SEQUENCE: 39
aagcauacag ggagccaggc a                                     21

<210> SEQ ID NO 40
<211> LENGTH: 21
<212> TYPE: RNA
<213> ORGANISM: Arabidopsis thaliana

<400> SEQUENCE: 40
accugaugua aucacuuuca a                                     21

<210> SEQ ID NO 41
<211> LENGTH: 21
<212> TYPE: RNA
<213> ORGANISM: Arabidopsis thaliana

<400> SEQUENCE: 41
cccggaugua aucacuuuca g                                     21

<210> SEQ ID NO 42
<211> LENGTH: 21
<212> TYPE: RNA
<213> ORGANISM: Arabidopsis thaliana

<400> SEQUENCE: 42
uuguuacuuu caaugcauug a                                     21

<210> SEQ ID NO 43
<211> LENGTH: 21
<212> TYPE: RNA
<213> ORGANISM: Arabidopsis thaliana

<400> SEQUENCE: 43
cccugaugua uuuacuuuca a                                     21

<210> SEQ ID NO 44
<211> LENGTH: 21
<212> TYPE: RNA
<213> ORGANISM: Arabidopsis thaliana

<400> SEQUENCE: 44
uagucacguu caaugcauug a                                     21

<210> SEQ ID NO 45
```

-continued

```
<211> LENGTH: 21
<212> TYPE: RNA
<213> ORGANISM: Arabidopsis thaliana

<400> SEQUENCE: 45
cccugaugua uucacuuuca g                                              21

<210> SEQ ID NO 46
<211> LENGTH: 21
<212> TYPE: RNA
<213> ORGANISM: Arabidopsis thaliana

<400> SEQUENCE: 46
cccugauguu guuacuuuca g                                              21

<210> SEQ ID NO 47
<211> LENGTH: 21
<212> TYPE: RNA
<213> ORGANISM: Arabidopsis thaliana

<400> SEQUENCE: 47
uagucacuuu cagcgcauug a                                              21

<210> SEQ ID NO 48
<211> LENGTH: 21
<212> TYPE: RNA
<213> ORGANISM: Arabidopsis thaliana

<400> SEQUENCE: 48
uccaaaugua gucacuuuca g                                              21

<210> SEQ ID NO 49
<211> LENGTH: 21
<212> TYPE: RNA
<213> ORGANISM: Arabidopsis thaliana

<400> SEQUENCE: 49
uccaaaugua gucacuuuca a                                              21

<210> SEQ ID NO 50
<211> LENGTH: 21
<212> TYPE: RNA
<213> ORGANISM: Arabidopsis thaliana

<400> SEQUENCE: 50
uccaaaugua gucacuuuca g                                              21

<210> SEQ ID NO 51
<211> LENGTH: 21
<212> TYPE: RNA
<213> ORGANISM: Arabidopsis thaliana

<400> SEQUENCE: 51
uccaaaugua gucacuuuca a                                              21

<210> SEQ ID NO 52
<211> LENGTH: 21
<212> TYPE: RNA
<213> ORGANISM: Arabidopsis thaliana

<400> SEQUENCE: 52
uuguaacuuu cagugcauug a                                              21
```

```
<210> SEQ ID NO 53
<211> LENGTH: 21
<212> TYPE: RNA
<213> ORGANISM: Arabidopsis thaliana

<400> SEQUENCE: 53
uagucacguu caaugcauug a                                              21

<210> SEQ ID NO 54
<211> LENGTH: 21
<212> TYPE: RNA
<213> ORGANISM: Arabidopsis thaliana

<400> SEQUENCE: 54
uuguuacuuu cagugcauug a                                              21

<210> SEQ ID NO 55
<211> LENGTH: 21
<212> TYPE: RNA
<213> ORGANISM: Arabidopsis thaliana

<400> SEQUENCE: 55
cccugauguu gucacuuuca c                                              21

<210> SEQ ID NO 56
<211> LENGTH: 21
<212> TYPE: RNA
<213> ORGANISM: Arabidopsis thaliana

<400> SEQUENCE: 56
uuguuacuua caaugcauug a                                              21

<210> SEQ ID NO 57
<211> LENGTH: 21
<212> TYPE: RNA
<213> ORGANISM: Arabidopsis thaliana

<400> SEQUENCE: 57
uagucuuuuu caacgcauug a                                              21

<210> SEQ ID NO 58
<211> LENGTH: 22
<212> TYPE: RNA
<213> ORGANISM: Arabidopsis thaliana

<400> SEQUENCE: 58
cuggaugcag agguauuauc ga                                             22

<210> SEQ ID NO 59
<211> LENGTH: 22
<212> TYPE: RNA
<213> ORGANISM: Populus tremula

<400> SEQUENCE: 59
cuggaugcag aggucuuauc ga                                             22

<210> SEQ ID NO 60
<211> LENGTH: 22
<212> TYPE: RNA
<213> ORGANISM: Oryza sativa

<400> SEQUENCE: 60
cuggaugcag agguuuuauc ga                                             22
```

```
<210> SEQ ID NO 61
<211> LENGTH: 23
<212> TYPE: RNA
<213> ORGANISM: Arabidopsis thaliana

<400> SEQUENCE: 61
aucgaguucc aaguccucuu caa                                              23

<210> SEQ ID NO 62
<211> LENGTH: 23
<212> TYPE: RNA
<213> ORGANISM: Arabidopsis thaliana

<400> SEQUENCE: 62
aucgaguucc agguccucuu caa                                              23

<210> SEQ ID NO 63
<211> LENGTH: 23
<212> TYPE: RNA
<213> ORGANISM: Arabidopsis thaliana

<400> SEQUENCE: 63
aucgaguucc aaguuuucuu caa                                              23

<210> SEQ ID NO 64
<211> LENGTH: 21
<212> TYPE: RNA
<213> ORGANISM: Arabidopsis thaliana

<400> SEQUENCE: 64
agcacguacc cugcuucucc a                                                21

<210> SEQ ID NO 65
<211> LENGTH: 21
<212> TYPE: RNA
<213> ORGANISM: Arabidopsis thaliana

<400> SEQUENCE: 65
uuuacgugcc cugcuucucc a                                                21

<210> SEQ ID NO 66
<211> LENGTH: 21
<212> TYPE: RNA
<213> ORGANISM: Arabidopsis thaliana

<400> SEQUENCE: 66
agcacguguc cuguuucucc a                                                21

<210> SEQ ID NO 67
<211> LENGTH: 21
<212> TYPE: RNA
<213> ORGANISM: Arabidopsis thaliana

<400> SEQUENCE: 67
ucuacgugcc cugcuucucc a                                                21

<210> SEQ ID NO 68
<211> LENGTH: 21
<212> TYPE: RNA
<213> ORGANISM: Arabidopsis thaliana

<400> SEQUENCE: 68
cucacgugac cugcuucucc g                                                21
```

<210> SEQ ID NO 69
<211> LENGTH: 21
<212> TYPE: RNA
<213> ORGANISM: Oryza sativa

<400> SEQUENCE: 69
cgcacgugac cugcuucucc a                                              21

<210> SEQ ID NO 70
<211> LENGTH: 21
<212> TYPE: RNA
<213> ORGANISM: Medicago truncatula

<400> SEQUENCE: 70
cuuacguguc cugcuucucc a                                              21

<210> SEQ ID NO 71
<211> LENGTH: 21
<212> TYPE: RNA
<213> ORGANISM: Glycine max

<400> SEQUENCE: 71
cuuacgugcc cugcuucucc a                                              21

<210> SEQ ID NO 72
<211> LENGTH: 21
<212> TYPE: RNA
<213> ORGANISM: Lycopersicum esculentum

<400> SEQUENCE: 72
gccacgugca cugcuucucc a                                              21

<210> SEQ ID NO 73
<211> LENGTH: 21
<212> TYPE: RNA
<213> ORGANISM: Arabidopsis thaliana

<400> SEQUENCE: 73
uugggaugaa gccugguccg g                                              21

<210> SEQ ID NO 74
<211> LENGTH: 21
<212> TYPE: RNA
<213> ORGANISM: Arabidopsis thaliana

<400> SEQUENCE: 74
cugggaugaa gccugguccg g                                              21

<210> SEQ ID NO 75
<211> LENGTH: 21
<212> TYPE: RNA
<213> ORGANISM: Arabidopsis thaliana

<400> SEQUENCE: 75
cuggaaugaa gccugguccg g                                              21

<210> SEQ ID NO 76
<211> LENGTH: 21
<212> TYPE: RNA
<213> ORGANISM: Populus tremula

<400> SEQUENCE: 76

```
ccgggaugaa gccugguccg g                                          21

<210> SEQ ID NO 77
<211> LENGTH: 21
<212> TYPE: RNA
<213> ORGANISM: Arabidopsis thaliana

<400> SEQUENCE: 77
gagaucaggc uggcagcuug u                                          21

<210> SEQ ID NO 78
<211> LENGTH: 21
<212> TYPE: RNA
<213> ORGANISM: Arabidopsis thaliana

<400> SEQUENCE: 78
uagaucaggc uggcagcuug u                                          21

<210> SEQ ID NO 79
<211> LENGTH: 21
<212> TYPE: RNA
<213> ORGANISM: Oryza sativa

<400> SEQUENCE: 79
aagaucaggc uggcagcuug u                                          21

<210> SEQ ID NO 80
<211> LENGTH: 21
<212> TYPE: RNA
<213> ORGANISM: Arabidopsis thaliana

<400> SEQUENCE: 80
uucccgagcu gcaucaagcu a                                          21

<210> SEQ ID NO 81
<211> LENGTH: 21
<212> TYPE: RNA
<213> ORGANISM: Arabidopsis thaliana

<400> SEQUENCE: 81
aagggaaguc auccuuggcu g                                          21

<210> SEQ ID NO 82
<211> LENGTH: 21
<212> TYPE: RNA
<213> ORGANISM: Arabidopsis thaliana

<400> SEQUENCE: 82
acgggaaguc auccuuggcu a                                          21

<210> SEQ ID NO 83
<211> LENGTH: 21
<212> TYPE: RNA
<213> ORGANISM: Arabidopsis thaliana

<400> SEQUENCE: 83 agggaaguc auccuuggcu a                                           21

<210> SEQ ID NO 84
<211> LENGTH: 21
<212> TYPE: RNA
<213> ORGANISM: Arabidopsis thaliana

<400> SEQUENCE: 84
```
aggcaaauca ucuuuggcuc a                                               21

<210> SEQ ID NO 85
<211> LENGTH: 21
<212> TYPE: RNA
<213> ORGANISM: Arabidopsis thaliana

<400> SEQUENCE: 85
gcggcaauuc auucuuggcu u                                               21

<210> SEQ ID NO 86
<211> LENGTH: 21
<212> TYPE: RNA
<213> ORGANISM: Arabidopsis thaliana

<400> SEQUENCE: 86
ccggcaaauc auucuuggcu u                                               21

<210> SEQ ID NO 87
<211> LENGTH: 21
<212> TYPE: RNA
<213> ORGANISM: Arabidopsis thaliana

<400> SEQUENCE: 87
aagggaaguc auccuuggcu a                                               21

<210> SEQ ID NO 88
<211> LENGTH: 21
<212> TYPE: RNA
<213> ORGANISM: Zea mays

<400> SEQUENCE: 88
guggcaacuc auccuuggcu c                                               21

<210> SEQ ID NO 89
<211> LENGTH: 21
<212> TYPE: RNA
<213> ORGANISM: Vitis vinifera

<400> SEQUENCE: 89
ugggcaauuc auccuuggcu u                                               21

<210> SEQ ID NO 90
<211> LENGTH: 21
<212> TYPE: RNA
<213> ORGANISM: Oryza sativa

<400> SEQUENCE: 90
auggcaaauc auccuuggcu u                                               21

<210> SEQ ID NO 91
<211> LENGTH: 21
<212> TYPE: RNA
<213> ORGANISM: Glycine max

<400> SEQUENCE: 91
uagggaaguc auccuuggcu c                                               21

<210> SEQ ID NO 92
<211> LENGTH: 21
<212> TYPE: RNA
<213> ORGANISM: Gossypium hirsutum

```
<400> SEQUENCE: 92
cugggaaguc auccuuggcu c                                              21

<210> SEQ ID NO 93
<211> LENGTH: 21
<212> TYPE: RNA
<213> ORGANISM: Arabidopsis thaliana

<400> SEQUENCE: 93
gauauuggcg cggcucaauc a                                              21

<210> SEQ ID NO 94
<211> LENGTH: 21
<212> TYPE: RNA
<213> ORGANISM: Arabidopsis thaliana

<400> SEQUENCE: 94
cugcagcauc aucaggauuc u                                              21

<210> SEQ ID NO 95
<211> LENGTH: 21
<212> TYPE: RNA
<213> ORGANISM: Arabidopsis thaliana

<400> SEQUENCE: 95
cagcagcauc aucaggauuc u                                              21

<210> SEQ ID NO 96
<211> LENGTH: 21
<212> TYPE: RNA
<213> ORGANISM: Arabidopsis thaliana

<400> SEQUENCE: 96
augcagcauc aucaggauuc u                                              21

<210> SEQ ID NO 97
<211> LENGTH: 21
<212> TYPE: RNA
<213> ORGANISM: Arabidopsis thaliana

<400> SEQUENCE: 97
uggcagcauc aucaggauuc u                                              21

<210> SEQ ID NO 98
<211> LENGTH: 21
<212> TYPE: RNA
<213> ORGANISM: Arabidopsis thaliana

<400> SEQUENCE: 98
uuguagcauc aucaggauuc c                                              21

<210> SEQ ID NO 99
<211> LENGTH: 21
<212> TYPE: RNA
<213> ORGANISM: Arabidopsis thaliana

<400> SEQUENCE: 99
uugcagcauc aucaggauuc c                                              21

<210> SEQ ID NO 100
<211> LENGTH: 21
<212> TYPE: RNA
<213> ORGANISM: Arabidopsis thaliana
```

<400> SEQUENCE: 100 caggggggacc cuucagucca a                                                                 21

<210> SEQ ID NO 101
<211> LENGTH: 21
<212> TYPE: RNA
<213> ORGANISM: Arabidopsis thaliana

<400> SEQUENCE: 101 gaggggucccc cuucagucca u                                                                 21

<210> SEQ ID NO 102
<211> LENGTH: 21
<212> TYPE: RNA
<213> ORGANISM: Arabidopsis thaliana

<400> SEQUENCE: 102 gaggggucccc cuucagucca g                                                                 21

<210> SEQ ID NO 103
<211> LENGTH: 21
<212> TYPE: RNA
<213> ORGANISM: Arabidopsis thaliana

<400> SEQUENCE: 103 aaggggguacc cuucagucca g                                                                 21

<210> SEQ ID NO 104
<211> LENGTH: 21
<212> TYPE: RNA
<213> ORGANISM: Arabidopsis thaliana

<400> SEQUENCE: 104 uaggggggacc cuucagucca a                                                                 21

<210> SEQ ID NO 105
<211> LENGTH: 21
<212> TYPE: RNA
<213> ORGANISM: Oryza sativa

<400> SEQUENCE: 105
gaggggaccc cuucagucca g                                                                  21

<210> SEQ ID NO 106
<211> LENGTH: 21
<212> TYPE: RNA
<213> ORGANISM: Oryza sativa

<400> SEQUENCE: 106
ucggggcaca cuucagucca a                                                                  21

<210> SEQ ID NO 107
<211> LENGTH: 21
<212> TYPE: RNA
<213> ORGANISM: Arabidopsis thaliana

<400> SEQUENCE: 107
aaacaaugcg aucccuuugg a                                                                  21

<210> SEQ ID NO 108
<211> LENGTH: 21
<212> TYPE: RNA

```
<213> ORGANISM: Arabidopsis thaliana

<400> SEQUENCE: 108
agaccaugcg aucccuuugg a                                          21

<210> SEQ ID NO 109
<211> LENGTH: 21
<212> TYPE: RNA
<213> ORGANISM: Arabidopsis thaliana

<400> SEQUENCE: 109
ggucagagcg aucccuuugg c                                          21

<210> SEQ ID NO 110
<211> LENGTH: 21
<212> TYPE: RNA
<213> ORGANISM: Arabidopsis thaliana

<400> SEQUENCE: 110
agacaaugcg aucccuuugg a                                          21

<210> SEQ ID NO 111
<211> LENGTH: 21
<212> TYPE: RNA
<213> ORGANISM: Arabidopsis thaliana

<400> SEQUENCE: 111
ggagguugac agaaugccaa a                                          21

<210> SEQ ID NO 112
<211> LENGTH: 21
<212> TYPE: RNA
<213> ORGANISM: Arabidopsis thaliana

<400> SEQUENCE: 112
gaguuccucc aaacacuuca u                                          21

<210> SEQ ID NO 113
<211> LENGTH: 21
<212> TYPE: RNA
<213> ORGANISM: Arabidopsis thaliana

<400> SEQUENCE: 113
gaguuccucc aaacucuuca u                                          21

<210> SEQ ID NO 114
<211> LENGTH: 21
<212> TYPE: RNA
<213> ORGANISM: Arabidopsis thaliana

<400> SEQUENCE: 114
aaguucuccc aaacacuuca a                                          21

<210> SEQ ID NO 115
<211> LENGTH: 22
<212> TYPE: RNA
<213> ORGANISM: Arabidopsis thaliana

<400> SEQUENCE: 115
ucguucaaga aagccugugg aa                                         22

<210> SEQ ID NO 116
<211> LENGTH: 22
```

```
<212> TYPE: RNA
<213> ORGANISM: Arabidopsis thaliana

<400> SEQUENCE: 116
ccguucaaga aagccugugg aa                                              22

<210> SEQ ID NO 117
<211> LENGTH: 22
<212> TYPE: RNA
<213> ORGANISM: Arabidopsis thaliana

<400> SEQUENCE: 117
ucguucaaga aagcaugugg aa                                              22

<210> SEQ ID NO 118
<211> LENGTH: 22
<212> TYPE: RNA
<213> ORGANISM: Arabidopsis thaliana

<400> SEQUENCE: 118
acguucaaga aagcuugugg aa                                              22

<210> SEQ ID NO 119
<211> LENGTH: 22
<212> TYPE: RNA
<213> ORGANISM: Arabidopsis thaliana

<400> SEQUENCE: 119
ccguucaaga aagccugugg aa                                              22

<210> SEQ ID NO 120
<211> LENGTH: 21
<212> TYPE: RNA
<213> ORGANISM: Arabidopsis thaliana

<400> SEQUENCE: 120
aaucaaugcu gcacucaaug a                                               21

<210> SEQ ID NO 121
<211> LENGTH: 21
<212> TYPE: RNA
<213> ORGANISM: Arabidopsis thaliana

<400> SEQUENCE: 121
agucaacgcu gcacuuaaug a                                               21

<210> SEQ ID NO 122
<211> LENGTH: 21
<212> TYPE: RNA
<213> ORGANISM: Arabidopsis thaliana

<400> SEQUENCE: 122
aaucaaugcu gcacuuaaug a                                               21

<210> SEQ ID NO 123
<211> LENGTH: 21
<212> TYPE: RNA
<213> ORGANISM: Arabidopsis thaliana

<400> SEQUENCE: 123 aaggguuuc cugagaucac a                                                21

<210> SEQ ID NO 124
```

```
<211> LENGTH: 22
<212> TYPE: RNA
<213> ORGANISM: Arabidopsis thaliana

<400> SEQUENCE: 124 ugcggguvgac cugggaaaca ua                                          22

<210> SEQ ID NO 125
<211> LENGTH: 22
<212> TYPE: RNA
<213> ORGANISM: Arabidopsis thaliana

<400> SEQUENCE: 125
aaggugugac cugagaauca ca                                           22

<210> SEQ ID NO 126
<211> LENGTH: 22
<212> TYPE: RNA
<213> ORGANISM: Arabidopsis thaliana

<400> SEQUENCE: 126
gugauuuuuc ucaacaagcg aa                                           22

<210> SEQ ID NO 127
<211> LENGTH: 22
<212> TYPE: RNA
<213> ORGANISM: Arabidopsis thaliana

<400> SEQUENCE: 127
gugauuuuuc ucuacaagcg aa                                           22

<210> SEQ ID NO 128
<211> LENGTH: 22
<212> TYPE: RNA
<213> ORGANISM: Arabidopsis thaliana

<400> SEQUENCE: 128
gugauuuuuc ucuccaagcg aa                                           22

<210> SEQ ID NO 129
<211> LENGTH: 21
<212> TYPE: RNA
<213> ORGANISM: Arabidopsis thaliana

<400> SEQUENCE: 129
uagggcauau cuccuuuggc a                                            21

<210> SEQ ID NO 130
<211> LENGTH: 21
<212> TYPE: RNA
<213> ORGANISM: Arabidopsis thaliana

<400> SEQUENCE: 130
uugggcaaau cuccuuuggc a                                            21

<210> SEQ ID NO 131
<211> LENGTH: 21
<212> TYPE: RNA
<213> ORGANISM: Arabidopsis thaliana

<400> SEQUENCE: 131
ucgagcaaau cuccuuuggc a                                            21
```

```
<210> SEQ ID NO 132
<211> LENGTH: 21
<212> TYPE: RNA
<213> ORGANISM: Arabidopsis thaliana

<400> SEQUENCE: 132
uagagcaaau cuccuuuggc a                                              21

<210> SEQ ID NO 133
<211> LENGTH: 21
<212> TYPE: RNA
<213> ORGANISM: Arabidopsis thaliana

<400> SEQUENCE: 133
uagggcaaau cuucuuuggc a                                              21

<210> SEQ ID NO 134
<211> LENGTH: 21
<212> TYPE: RNA
<213> ORGANISM: Oryza sativa

<400> SEQUENCE: 134
uagggcaaau cuccuuuggc a                                              21

<210> SEQ ID NO 135
<211> LENGTH: 21
<212> TYPE: RNA
<213> ORGANISM: Oryza sativa

<400> SEQUENCE: 135
cugggcaaau cuccuuuggc a                                              21

<210> SEQ ID NO 136
<211> LENGTH: 21
<212> TYPE: RNA
<213> ORGANISM: Oryza sativa

<400> SEQUENCE: 136
ucgggcaaau cuccuuuggc a                                              21

<210> SEQ ID NO 137
<211> LENGTH: 21
<212> TYPE: RNA
<213> ORGANISM: Oryza sativa

<400> SEQUENCE: 137
ccgggcaaau cuccuuuggc a                                              21

<210> SEQ ID NO 138
<211> LENGTH: 21
<212> TYPE: RNA
<213> ORGANISM: Populus tremula

<400> SEQUENCE: 138
gcgggcaaau cuucuuuggc a                                              21

<210> SEQ ID NO 139
<211> LENGTH: 21
<212> TYPE: RNA
<213> ORGANISM: Medicago truncatula

<400> SEQUENCE: 139
aagggcaaau cuccuuuggc a                                              21
```

<210> SEQ ID NO 140
<211> LENGTH: 21
<212> TYPE: RNA
<213> ORGANISM: Triticum aestivum

<400> SEQUENCE: 140
uagggcaaau cccuuuggc g                                              21

<210> SEQ ID NO 141
<211> LENGTH: 21
<212> TYPE: RNA
<213> ORGANISM: Triticum aestivum

<400> SEQUENCE: 141
cugggcaaau cccuuuggc g                                              21

<210> SEQ ID NO 142
<211> LENGTH: 21
<212> TYPE: RNA
<213> ORGANISM: Triticum aestivum

<400> SEQUENCE: 142
uucggcaaau cccuuuggc a                                              21

<210> SEQ ID NO 143
<211> LENGTH: 22
<212> TYPE: RNA
<213> ORGANISM: Arabidopsis thaliana

<400> SEQUENCE: 143
ggaguuugug cgugaaucua au                                            22

<210> SEQ ID NO 144
<211> LENGTH: 22
<212> TYPE: RNA
<213> ORGANISM: Arabidopsis thaliana

<400> SEQUENCE: 144
cuugucuauc ccuccugagc ua                                            22

<210> SEQ ID NO 145
<211> LENGTH: 22
<212> TYPE: RNA
<213> ORGANISM: Sorghum bicolor

<400> SEQUENCE: 145
uaugucuauc ccuucugagc ug                                            22

<210> SEQ ID NO 146
<211> LENGTH: 22
<212> TYPE: RNA
<213> ORGANISM: Saccharum officinarum

<400> SEQUENCE: 146
uaugucuauc ccuucugagc ua                                            22

<210> SEQ ID NO 147
<211> LENGTH: 22
<212> TYPE: RNA
<213> ORGANISM: Zea mays

<400> SEQUENCE: 147
uaugucuauc ccuucugagc ug                                            22

-continued

<210> SEQ ID NO 148
<211> LENGTH: 22
<212> TYPE: RNA
<213> ORGANISM: Oryza sativa

<400> SEQUENCE: 148
ucggucuauc ccuccugagc ug                                      22

<210> SEQ ID NO 149
<211> LENGTH: 22
<212> TYPE: RNA
<213> ORGANISM: Pennisetum glaucum

<400> SEQUENCE: 149
uuagucuauc ccuccugagc ua                                      22

<210> SEQ ID NO 150
<211> LENGTH: 22
<212> TYPE: RNA
<213> ORGANISM: Vitis vinifera

<400> SEQUENCE: 150
auugccuauc ccuccugagc ug                                      22

<210> SEQ ID NO 151
<211> LENGTH: 22
<212> TYPE: RNA
<213> ORGANISM: Theobroma cacao

<400> SEQUENCE: 151
ccuugcuauc ccuccugagc ug                                      22

<210> SEQ ID NO 152
<211> LENGTH: 22
<212> TYPE: RNA
<213> ORGANISM: Lycopersicum esculentum

<400> SEQUENCE: 152
cuugucuauc ccuccugagc ug                                      22

<210> SEQ ID NO 153
<211> LENGTH: 22
<212> TYPE: RNA
<213> ORGANISM: Zea mays

<400> SEQUENCE: 153
cccuucuauc ccuccugagc ua                                      22

<210> SEQ ID NO 154
<211> LENGTH: 22
<212> TYPE: RNA
<213> ORGANISM: Populus tremula

<400> SEQUENCE: 154
cuugucuauc ccuccugagc ua                                      22

<210> SEQ ID NO 155
<211> LENGTH: 22
<212> TYPE: RNA
<213> ORGANISM: Oryza sativa

<400> SEQUENCE: 155

```
cccuucuauc ccuccugagc ua                                         22

<210> SEQ ID NO 156
<211> LENGTH: 22
<212> TYPE: RNA
<213> ORGANISM: Triticum aestivum

<400> SEQUENCE: 156
cccuucuauc ccuccugagc ua                                         22

<210> SEQ ID NO 157
<211> LENGTH: 22
<212> TYPE: RNA
<213> ORGANISM: Hordeum vulgare

<400> SEQUENCE: 157 ccuucuauc ccuccugagc ua                                          22

<210> SEQ ID NO 158
<211> LENGTH: 22
<212> TYPE: RNA
<213> ORGANISM: Populus tremula

<400> SEQUENCE: 158
ccugucuauc ccuccugagc ua                                         22

<210> SEQ ID NO 159
<211> LENGTH: 22
<212> TYPE: RNA
<213> ORGANISM: Mesembryanthemum crystallinum

<400> SEQUENCE: 159
ugugucuauc ccuccugagc ua                                         22

<210> SEQ ID NO 160
<211> LENGTH: 21
<212> TYPE: RNA
<213> ORGANISM: Arabidopsis thaliana

<400> SEQUENCE: 160
ugacaaacau cucguccca a                                           21

<210> SEQ ID NO 161
<211> LENGTH: 21
<212> TYPE: RNA
<213> ORGANISM: Arabidopsis thaliana

<400> SEQUENCE: 161
ugacaaacau cucguuccua a                                          21

<210> SEQ ID NO 162
<211> LENGTH: 21
<212> TYPE: RNA
<213> ORGANISM: Arabidopsis thaliana

<400> SEQUENCE: 162
ccaagggaag aggcagugca u                                          21

<210> SEQ ID NO 163
<211> LENGTH: 21
<212> TYPE: RNA
<213> ORGANISM: Arabidopsis thaliana

<400> SEQUENCE: 163
```

-continued accagugaag aggcugugca g                                    21

<210> SEQ ID NO 164
<211> LENGTH: 21
<212> TYPE: RNA
<213> ORGANISM: Arabidopsis thaliana

<400> SEQUENCE: 164
gccagggaag aggcagugca u                                    21

<210> SEQ ID NO 165
<211> LENGTH: 21
<212> TYPE: RNA
<213> ORGANISM: Arabidopsis thaliana

<400> SEQUENCE: 165
gccggugaag aggcugugca a                                    21

<210> SEQ ID NO 166
<211> LENGTH: 21
<212> TYPE: RNA
<213> ORGANISM: Arabidopsis thaliana

<400> SEQUENCE: 166
gccggugaag aggcugugca g                                    21

<210> SEQ ID NO 167
<211> LENGTH: 21
<212> TYPE: RNA
<213> ORGANISM: Arabidopsis thaliana

<400> SEQUENCE: 167
agggucuugc aaggucaaga a                                    21

<210> SEQ ID NO 168
<211> LENGTH: 21
<212> TYPE: RNA
<213> ORGANISM: Arabidopsis thaliana

<400> SEQUENCE: 168
aaggucuugc aaggucaaga a                                    21

<210> SEQ ID NO 169
<211> LENGTH: 21
<212> TYPE: RNA
<213> ORGANISM: Oryza sativa

<400> SEQUENCE: 169
gaggucuugc aaggucaaga a                                    21

<210> SEQ ID NO 170
<211> LENGTH: 21
<212> TYPE: RNA
<213> ORGANISM: Oryza sativa

<400> SEQUENCE: 170
acggucuugc aaggucaaga a                                    21

<210> SEQ ID NO 171
<211> LENGTH: 21
<212> TYPE: RNA
<213> ORGANISM: Arabidopsis thaliana

<400> SEQUENCE: 171
agaacuagag aaagcauugg a					21

<210> SEQ ID NO 172
<211> LENGTH: 21
<212> TYPE: RNA
<213> ORGANISM: Arabidopsis thaliana

<400> SEQUENCE: 172
agaguaagau ggagcuugau a					21

<210> SEQ ID NO 173
<211> LENGTH: 21
<212> TYPE: RNA
<213> ORGANISM: Arabidopsis thaliana

<400> SEQUENCE: 173
agauggugga aaugggauau c					21

<210> SEQ ID NO 174
<211> LENGTH: 21
<212> TYPE: RNA
<213> ORGANISM: Arabidopsis thaliana

<400> SEQUENCE: 174
uuguugaucg uaugguagaa g					21

<210> SEQ ID NO 175
<211> LENGTH: 21
<212> TYPE: RNA
<213> ORGANISM: Arabidopsis thaliana

<400> SEQUENCE: 175
gguauucgag uaucugcaaa a					21

<210> SEQ ID NO 176
<211> LENGTH: 1242
<212> TYPE: DNA
<213> ORGANISM: artificial sequence
<220> FEATURE:
<223> OTHER INFORMATION: Synthetic construct

<400> SEQUENCE: 176
acacgctgaa accatcttcc acacactcaa gccacactat tggagaacac acagggacaa		60 cacaccataa ccgccgccgc cggtagaaga tggcgcccac cgtgatgatg gcctcgtcgg		120 ccaccgccgt cgctccgttc caggggctca gtccaccgc cagcctcccc gtcgcccgcc		180 gctcctccag aagcctcggc aacgtcagca acggcggaag gatccggtgc atgcaggtgt		240 ggccggccta cggcaacaag aagttcgaga cgctgtcgta cctgccgccg ctgtcgaccg		300 gcgggcgcat ccgctgcatg caggccatgg ccttcttcaa ccgggtgatc accctcacgg		360 tgccgtcgtc agacgtggtc aactactcgg agatctacca ggtggctcct cagtatgtca		420 accaggccct gaccctggcc aagtacttcc agggcgccat cgacggcagc accctgaggt		480 tcgacttcga gaaggcgtta cagatcgcca acgacatccc gcaggccgcg gtggtcaaca		540 ccctgaacca gaccgtccag caggggaccg tccaggtcag cgtcatgatc gacaagatcg		600 tggacatcat gaagaatgtc ctgtccatcg tgatagacaa caagaagttt tgggatcagg		660 tcacggctgc catcaccaac accttcacga acctgaacag ccaggagtcg gaggcctgga		720 tcttctatta caaggaggac gcccacaaga cgtcctacta ttacaacatc ctcttcgcca		780

```
tccaggacga agagacgggt ggcgtgatgg ccacgctgcc catcgccttc gacatcagtg      840
tggacatcga gaaggagaag gtcctgttcg tgaccatcaa ggacactgag aattacgccg      900
tcaccgtcaa ggcgatcaac gtggtccagg cactccagtc tagcagggat tctaaggtgg      960
ttgatgcgtt caaatcgcca cggcacttac cccggaagag gcataagatt tgctctaact     1020
cgtgatgact gctggatgca gaggtattat cgatgcgttt ggacgtatgc tcattcaggt     1080
tggagccaat ttggttgatg tgtgtgcgag ttcttgcgag tctgatgaga catctctgta     1140
ttgtgtttct ttccccagtg ttttctgtac ttgtgtaatc ggctaatcgc caacagattc     1200
ggcgatgaat aaatgagaaa taaattgttc tgattttgag tg                        1242
```

<210> SEQ ID NO 177
<211> LENGTH: 956
<212> TYPE: DNA
<213> ORGANISM: artificial sequence
<220> FEATURE:
<223> OTHER INFORMATION: Synthetic construct

<400> SEQUENCE: 177

```
acacgctgac aagctgactc tagcagatcc tctagaacca tcttccacac actcaagcca       60
cactattgga gaacacacag ggacaacaca ccataagatc caagggaggc ctccgccgcc      120
gccggtagaa gtgatcaacc atggccttct tcaaccgggt gatcaccctc acggtgccgt      180
cgtcagacgt ggtcaactac tcggagatct accaggtggc tcctcagtat gtcaaccagg      240
ccctgaccct ggccaagtac ttccagggcg ccatcgacgg cagcaccctg aggttcgact      300
tcgagaaggc gttacagatc gccaacgaca tcccgcaggc cgcggtggtc aacaccctga      360
accagaccgt ccagcagggg accgtccagg tcagcgtcat gatcgacaag atcgtggaca      420
tcatgaagaa tgtcctgtcc atcgtgatag acaacaagaa gttttgggat caggtcacgg      480
ctgccatcac caacaccttc acgaacctga cagccagga gtcggaggcc tggatcttct      540
attacaagga ggacgcccac aagacgtcct actattacaa catcctcttc gccatccagg      600
acgaagagac gggtggcgtg atggccacgc tgcccatcgc cttcgacatc agtgtggaca      660
tcgagaagga gaaggtcctg ttcgtgacca tcaaggacac tgagaattac gccgtcaccg      720
tcaaggcgat caacgtggtc caggcactcc agtctagcag ggattctaag gtggttgatg      780
cgttcaaatc gccacggcac ttaccccgga agaggcataa gatttgctct aactcgtgat      840
gaatgtacgt gccctgcttc tccatctgca tgcgtttgga cgtatgctca ttcaggttgg      900
agccaatttg gttgatgtgt gtgcgagttc ttgcgagtct gatgagacat ctctgt         956
```

<210> SEQ ID NO 178
<211> LENGTH: 22
<212> TYPE: DNA
<213> ORGANISM: Zea mays

<400> SEQUENCE: 178

```
tgaagctgcc agcatgatct gg                                                22
```

<210> SEQ ID NO 179
<211> LENGTH: 1683
<212> TYPE: DNA
<213> ORGANISM: Zea mays

<400> SEQUENCE: 179

```
atgtattgct gatgacgctg cgccttcttg ttttttgct gcaactttga gaaagataga       60
```

```
tccatctgca tgctttttc cgctgctatg gtgtatggtt gtgtgctgca gattttggat      120
ctgacttgtg agaaccgtcg acggacccct gcacacagta cgtgagacga tcgaggagga      180
tggaggcacg cagtacgttt tgttctcgat ctctgctaca gcatgtcatc ttaattaagc      240
ctactggttg catgcatggg tgaggattat tcatcgctaa gtttccatgt acgtagcata      300
ctatcacatg tacaatgaaa taggcaaata gcctagacgt tcttctcatg acgaccatgt      360
ctgccaatta aatatattgc aggtagtaaa cctcaagtac tgatagccat taattcttgg      420
ttggagttcg acagagaaga tcgaaaagac atgtatagaa tactgatcgt ctgatcatat      480
cgtccctacc tatctgtctg tctctaccaa agtgggctac agtacgttag ctagctgtct      540
cttcgaagac actgatagga tgtttgatta caagtccaac ggaaccactt gactgcatac      600
ggttaccact tactcatgca agaaaaaaaa ttgcatttc aaattcgaac cccaagtcgt      660
ctagtgtagg gtcttatgtt cataaccagg tgggataaca aacatattaa tcgatctgca      720
tatatatata tatacacaaa agggctacac agattacaga tgcagtgcat agaacctaat      780
tgcaggtggg ggaccccggc cctccccegg tggacaataa aaaaaatcca gtttccaagc      840
ccaagctata ggtaggcagt ccagagcggt ggtcttgtca ctttcttact tccaaaacca      900
ggccactgtt gatgtaggct ggctggctgg ctcatgtgcc acagttgctg ttcgttatta      960
actgtagtaa acatcagtgt ggacgggcgc cagaatttca gatctcggta cgtatgctgt     1020
gtggattcag cgttatttga acaccgtaat aatgctctcc agcagattgt gaattgtgaa     1080
tacagttcgt agagaacact atttataatg cagacgttat gtttacatag tttagtttaa     1140
aatgggagat aagatagaag agatagaatg agtaattggc tggagatcaa atcgtgcata     1200
ttattgtgca aaacactgtt tttccatata gtggagtttt aaagtatggg acgagagagc     1260
agatagcaaa tcgtgtatat ggtcgtgcaa atattatata tgtggttgtg caaaactccg     1320
aaatttgaaa taggagacac agttgataat tctacgctct acgcacgggc ggcggactgc     1380
actactagtt catcggatgc gttagcgtgc cactcctcat cttgtttcct tgtacgtact     1440
agtgcaatcc gtcagccgca cggctccagt ccactccagt ccagcaacag cgtcacctcc     1500
agctccgaaa ggcttatcct tgcaacaaac atcgtacgaa aaaggcgcag acaaaagaa      1560 aatggatcga aatgcaacaa ataaaaaagg gcatcaaaat acgctgcgag tgagcgagac     1620
gttggcctcc ccatcccata tatatatagc tatagctatc cctcggttct tcaattcatt     1680
cct                                                                   1683

<210> SEQ ID NO 180
<211> LENGTH: 674
<212> TYPE: DNA
<213> ORGANISM: Zea mays

<400> SEQUENCE: 180
acgtatgctg tgtggattca gcgttatttg aacaccgtaa taatgctctc cagcagattg       60
tgaattgtga atacagttcg tagagaacac tatttataat gcagacgtta tgtttacata      120
gtttagttta aaatgggaga taagatagaa gagatagaat gagtaattgg ctggagatca      180
aatcgtgcat attattgtgc aaaacactgt ttttccatat agtggagttt taaagtatgg      240
gacgagagag cagatagcaa atcgtgtata tggtcgtgca aatattatat atgtggttgt      300
gcaaaactcc gaaatttgaa ataggagaca cagttgataa ttctacgctc tacgcacggg      360
cggcggactg cactactagt tcatcggatg cgttagcgtg ccactcctca tcttgtttcc      420
ttgtacgtac tagtgcaatc cgtcagccgc acggctccag tccactccag tccagcaaca      480
```

```
gcgtcacctc cagctccgaa aggcttatcc ttgcaacaaa catcgtacga aaaaggcgca    540
ggacaaaaga aaatggatcg aaatgcaaca aataaaaaag gcatcaaaa tacgctgcga     600 gtgagcgaga cgttggcctc cccatcccat atatatatag ctatagctat ccctcggttc    660
ttcaattcat tcct                                                      674
```

<210> SEQ ID NO 181
<211> LENGTH: 6
<212> TYPE: DNA
<213> ORGANISM: artificial sequence
<220> FEATURE:
<223> OTHER INFORMATION: Synthetic construct

<400> SEQUENCE: 181

```
tgtctc                                                                 6
```

<210> SEQ ID NO 182
<211> LENGTH: 768
<212> TYPE: DNA
<213> ORGANISM: Zea mays

<400> SEQUENCE: 182

```
tcagcgttat ttgaacaccg taaagcctct ccggcagatt gtaatacac agttgtggag      60 aacgctattt ataacgcaga cactatttat aatgcagatg tgtaaaagtg aaatttaaaa    120
tagtagatga gataggagag atagaatgag taaactgctg gagagcaaat cgtgcatatg    180
atcgtgcaaa acaccgtttt tcgtagagtg aagtttaaaa tagcaggtga gagagtagat    240
aggatgagta agctgatgga gagcaaatat tgtatatacg tggtcggtgc aatagagtga    300
aatttgaaat aactgacaca gttttggtgc gtggaaatag acgaggataa ttctagtgca    360
atccgcactg ccagtggacc ccgcccgacg ataattctac gcacgggcgg cgcactgcac    420
tactagttca tcgatcggat gcgttagcgt gcccctcctc atattgtttc cttgtacgta    480
ctagtgcaat ccgtcagccg cacggctcca gtccactcca gtccagcaac agcgtcacct    540
ccagctccga aaggcttatc cttgcaacaa acatcgtacg aaaaggcgc aggaaaarga    600 aaagtgtcga aatacgacat aaaaaaagca tcaaaatacg ctgcgagtga gygagacatt    660
ggcctcccca tcccatatat atatagctat agctayccct cggttcttca attcatctat    720
cccccgctct ctccatctct ctacccttc tctctctcgg atagctag                  768
```

<210> SEQ ID NO 183
<211> LENGTH: 407
<212> TYPE: DNA
<213> ORGANISM: Zea mays

<400> SEQUENCE: 183

```
tttgaaataa ctgacacagt tttggtgcgt ggaaatagac gaggataatt ctagtgcaat     60
ccgcactgcc agtggacccc gcccgacgat aattctacgc acgggcggcg cactgcacta    120
ctagttcatc gatcggatgc gttagcgtgc ccctcctcat attgtttcct tgtacgtact    180
agtgcaatcc gtcagccgca cggctccagt ccactccagt ccagcaacag cgtcacctcc    240
agctccgaaa ggcttatcct tgcaacaaac atcgtacgaa aaggcgcag gaaaargaaa    300 agtgtcgaaa tacgacataa aaaagcatc aaaatacgct gcgagtgagy gagacattgg    360 cctcccccatc ccatatatat atagctatag ctayccctcg gttcttc                 407
```

<210> SEQ ID NO 184

```
<211> LENGTH: 21
<212> TYPE: RNA
<213> ORGANISM: Glycine max

<400> SEQUENCE: 184
ugagaccaaa ugagcagcug a                                              21

<210> SEQ ID NO 185
<211> LENGTH: 20
<212> TYPE: RNA
<213> ORGANISM: Glycine max

<400> SEQUENCE: 185
gcugcucauc uguucucagg                                                20

<210> SEQ ID NO 186
<211> LENGTH: 762
<212> TYPE: DNA
<213> ORGANISM: Glycine max

<400> SEQUENCE: 186
aaaattcatt acattgataa aacacaattc aaaagatcaa tgttccactt catgcaaaga     60
catttccaaa atatgtgtag gtagagggggt tttacaggat cgtcctgaga ccaaatgagc   120
agctgaccac atgatgcagc tatgtttgct attcagctgc tcatctgttc tcaggtcgcc   180
cttgttggac tgtccaactc ctactgattg cggatgcact tgccacaaat gaaaatcaaa   240 gcgagggaa aagaatgtag agtgtgacta cgattgcatg catgtgattt aggtaattaa    300
gttacatgat tgtctaattg tgtttatgga attgtatatt ttcagaccag gcacctgtaa   360
ctaattatag gtaccatacc ttaaaataag tccaactaag tccatgtctg tgatttttta   420
gtgtcacaaa tcacaatcca ttgccattgg ttttttaatt tttcattgtc tgttgtttaa   480
ctaactctag cttttttagct gcttcaagta cagattcctc aaagtggaaa atgttctttg   540
aagtcaataa aaagagcttt gatgatcatc tgcattgtct aagttggata aactaattag   600
agagaacttt tgaactttgt ctaccaaata tctgtcagtg tcatctgtca gttctgcaag   660
ctgaagtgtt gaatccacga ggtgcttgtt gcaaagttgt gatattaaaa gacatctacg   720
aagaagttca agcaaaactc tttttggcaa aaaaaaaaaa aa                      762

<210> SEQ ID NO 187
<211> LENGTH: 21
<212> TYPE: RNA
<213> ORGANISM: Glycine max

<400> SEQUENCE: 187
uagaagcucc ccauguucuc a                                              21

<210> SEQ ID NO 188
<211> LENGTH: 19
<212> TYPE: RNA
<213> ORGANISM: Glycine max

<400> SEQUENCE: 188
gagcaugggu aacuucuau                                                 19

<210> SEQ ID NO 189
<211> LENGTH: 346
<212> TYPE: DNA
<213> ORGANISM: Glycine max
<220> FEATURE:
<221> NAME/KEY: unsure
```

```
<222> LOCATION: (1)..(346)
<223> OTHER INFORMATION: unsure at all n locations

<400> SEQUENCE: 189
ttttctccta actttgagag catgggtaac ttctatttt atctctgncc ccntttcctt    60
catcttttct tcaacctta ttcgttcctt tttcaactgt taaaaggcct gactatgttg   120
aggaaattaa gaaatgggt tgttgccga tgccagcaga atagaagctc cccatgttct   180
caccgttagc agaaacggg tgttatctgg ataagaccgc caggttccat tcccttgttt   240
gccagcacca ccatcacttc ttcactctag tatccgattt ttttaaagga tcgttgtccc   300
ttgccttctg gtggacttct atggagaagt ttcttcacac cctatg               346

<210> SEQ ID NO 190
<211> LENGTH: 21
<212> TYPE: RNA
<213> ORGANISM: Glycine max

<400> SEQUENCE: 190
uguugcgggu aucuuugccu c                                             21

<210> SEQ ID NO 191
<211> LENGTH: 20
<212> TYPE: RNA
<213> ORGANISM: Glycine max

<400> SEQUENCE: 191
ggcguagauc cccacaacag                                               20

<210> SEQ ID NO 192
<211> LENGTH: 434
<212> TYPE: RNA
<213> ORGANISM: Glycine max

<400> SEQUENCE: 192
aacacuaggg uuugcauucc uccuuuagcc gcaacccaua uucuaagcuu ccuuucuccu    60
acuguucugu gucgggccag caaaacuguu gcgggguaucu uugccucuga aggaaaguug  120
ugccuauuau uauggcuuau ugcuuagug gcguagauc cccacaacagu uaugcuugca   180 cugccuuuug ucuccgagac uaacaaauuu gauuguaugu ucucuuguug cuaaacuuuu   240
gauuuugacc cgaacugcau gaggcaugaa aguuucauag ugguucaacc acaguaaaau   300
aggauggucu guuuaugucu ggguuuuaua agaauuuua gaucugucuu gauuacugga   360 ccauggaug aacacccugu ugguguugaa aaaguagcuu cagccuucug gauguggua   420 ugagcuuucg augc                                                     434

<210> SEQ ID NO 193
<211> LENGTH: 21
<212> TYPE: RNA
<213> ORGANISM: Glycine max

<400> SEQUENCE: 193
ugcgaguguc uucgccucug a                                             21

<210> SEQ ID NO 194
<211> LENGTH: 21
<212> TYPE: RNA
<213> ORGANISM: Glycine max

<400> SEQUENCE: 194
```

```
ggaggcguag auacucacac c                                             21

<210> SEQ ID NO 195
<211> LENGTH: 439
<212> TYPE: DNA
<213> ORGANISM: Glycine max

<400> SEQUENCE: 195
aattagggtt ctctggtcct cccgccccg gtgctggcat tctcaagcca gtgaaatcgg    60
tgcgagtgtc ttcgcctctg agagagatac tatgagatct caagcctcgg aggcgtagat  120
actcacacct ctttttctgg ctatctcacc actgctcttt tccgccgggg cacgaaggtc  180
cttcgcctca ccaaatttcg ttctttaaat ttcacctata tatgtgtata tttttaataa  240
taataattag gtttaaaggg aaaaaaagtc gcttcttaat cctttattca ttgtatgcag  300
aacgatttga ttcgtgatga taatgtatgg atctgtatag tcggttgctc tagtatccaa  360
taatttgatt tctaacaaat taatatgtag tggccttctt ggacatgaaa aaaattcttg  420 aaaattgggtt gttaggtta                                              439

<210> SEQ ID NO 196
<211> LENGTH: 22
<212> TYPE: RNA
<213> ORGANISM: Glycine max

<400> SEQUENCE: 196
uugccgauuc cacccauucc ua                                            22

<210> SEQ ID NO 197
<211> LENGTH: 20
<212> TYPE: RNA
<213> ORGANISM: Glycine max

<400> SEQUENCE: 197
gcugcucauc uguucucagg                                               20

<210> SEQ ID NO 198
<211> LENGTH: 495
<212> TYPE: DNA
<213> ORGANISM: Glycine max

<400> SEQUENCE: 198
gactagatgt gaatgtgatt catattcata gagagagaaa gggaaaggga gaagagcttg    60
aggaagtgat gggagatggg agggtcggta aagaatatat ctgagactcg actcaatctc  120
gatctctctc agtgttgtgt tgttttgttt atccttttgc cgattccacc cattcctatg  180
atttccttcg gttcctctct ttccactctc ctctccgctc tttcctcttg ttatggtaag  240 caccttttctt cttcagatct gctctttata ccatacactt attatagatc taagttttta  300
tggaccttaa ctatcttcct tgatctctta ttaattttaa ccgctctctc tttgttgctg  360
gacatgttac ttcaagataa caaattgctt tttattttt catctttct ctcgttctct    420 tgtttaaggt ttctataaat catcgatgag atacctataa taatatactt attacagaca  480
aaaaaaaaaa aaaaa                                                   495

<210> SEQ ID NO 199
<211> LENGTH: 825
<212> TYPE: DNA
<213> ORGANISM: Glycine max

<400> SEQUENCE: 199
```

```
ctgttctata ttgatagagt gagaaaggga aaggaagaag agcttgagga agtgatggga      60
gatgggaggg tcggtaaagg ataacagcgt ctctatgatt aattgttgtg ttgtttattc     120
ttttgccgat tccacccatt cctatgattt tctttggttc ctttctttcc actctcctct     180
ccgctctcca caatctgtta tggtcatgaa gctgccggtc tgactgggtt acattcaaga     240
caagaaaaaa caacaaatcg cttctttctt ttttcgtctt ttctttcctt tttcttgttt     300
aaggcttaac aaattatctc agctctagta gatgtagatt attacagaca gatgctagtt     360
aattagctag ctccacaaga tgtttaaaaa tgtgatctat ccatatcaag ctggaccaaa     420
tccaaataat tttactggag cttttctttc ttggtaaaag ctggacattt ttaaaggttt     480
gggtgccact ataacgccac caaagttttc tttcttgatt tttaaccaag ttacattttt     540
ttccctaaat tattccagcg ctaataaata ctgaattttc tgttttttt ataaaagaa      600 ttttacatta aattctttga aaataatttc attttggttg ttaatatttt ttttagttc     660 ataacaaatt aacgaatttt gtatttattt tttataaaa aattattaga aaataacata      720
ttaaatcaag caaaaaaatg tatttattta aaataaaaaa gtgaaggaaa aaattattta     780
aaaccaacac accaacatat tttaactttt ttattaaact aaacg                     825

<210> SEQ ID NO 200
<211> LENGTH: 21
<212> TYPE: RNA
<213> ORGANISM: Glycine max

<400> SEQUENCE: 200
ccagcugcuc auuggucac u                                                 21

<210> SEQ ID NO 201
<211> LENGTH: 21
<212> TYPE: RNA
<213> ORGANISM: Glycine max

<400> SEQUENCE: 201
agaggacaug gggagguucu a                                                21

<210> SEQ ID NO 202
<211> LENGTH: 21
<212> TYPE: RNA
<213> ORGANISM: Glycine max

<400> SEQUENCE: 202
ucagcugcuc aucuguucuc a                                                21

<210> SEQ ID NO 203
<211> LENGTH: 21
<212> TYPE: RNA
<213> ORGANISM: Glycine max

<400> SEQUENCE: 203
ccagcugcuc auuggucac u                                                 21

<210> SEQ ID NO 204
<211> LENGTH: 21
<212> TYPE: RNA
<213> ORGANISM: Glycine max

<400> SEQUENCE: 204
ucagcucuuc uuuggucuc u                                                 21
```

```
<210> SEQ ID NO 205
<211> LENGTH: 21
<212> TYPE: RNA
<213> ORGANISM: Glycine max

<400> SEQUENCE: 205
ucagcuacug aucggucuc a                                              21

<210> SEQ ID NO 206
<211> LENGTH: 21
<212> TYPE: RNA
<213> ORGANISM: Glycine max

<400> SEQUENCE: 206
ucagcuguuc cuuuguucuc u                                             21

<210> SEQ ID NO 207
<211> LENGTH: 21
<212> TYPE: RNA
<213> ORGANISM: Glycine max

<400> SEQUENCE: 207
ucagcuguuc cuuuguucuc u                                             21

<210> SEQ ID NO 208
<211> LENGTH: 21
<212> TYPE: RNA
<213> ORGANISM: Glycine max

<400> SEQUENCE: 208
guagcuucuc acuuggucuu a                                             21

<210> SEQ ID NO 209
<211> LENGTH: 21
<212> TYPE: RNA
<213> ORGANISM: Glycine max

<400> SEQUENCE: 209
uuagcugcuu cuucggucuc u                                             21

<210> SEQ ID NO 210
<211> LENGTH: 21
<212> TYPE: RNA
<213> ORGANISM: Glycine max

<400> SEQUENCE: 210
uuagaugcuu guuuggucuu u                                             21

<210> SEQ ID NO 211
<211> LENGTH: 21
<212> TYPE: RNA
<213> ORGANISM: Glycine max

<400> SEQUENCE: 211
ugagaacaug gggagccucu a                                             21

<210> SEQ ID NO 212
<211> LENGTH: 21
<212> TYPE: RNA
<213> ORGANISM: Glycine max

<400> SEQUENCE: 212
agaggacaug gggagauucu a                                             21
```

<210> SEQ ID NO 213
<211> LENGTH: 21
<212> TYPE: RNA
<213> ORGANISM: Glycine max

<400> SEQUENCE: 213
agaggacaug gggagguucu a         21

<210> SEQ ID NO 214
<211> LENGTH: 21
<212> TYPE: RNA
<213> ORGANISM: Glycine max

<400> SEQUENCE: 214
ugagaacaug ggaaucuucu a         21

<210> SEQ ID NO 215
<211> LENGTH: 21
<212> TYPE: RNA
<213> ORGANISM: Glycine max

<400> SEQUENCE: 215
aaagaacaug gggagccucu a         21

<210> SEQ ID NO 216
<211> LENGTH: 21
<212> TYPE: RNA
<213> ORGANISM: Glycine max

<400> SEQUENCE: 216
ugagaacaug ggggauuucu a         21

<210> SEQ ID NO 217
<211> LENGTH: 21
<212> TYPE: RNA
<213> ORGANISM: Glycine max

<400> SEQUENCE: 217
ugugaaggug gggagcuucu u         21

<210> SEQ ID NO 218
<211> LENGTH: 21
<212> TYPE: RNA
<213> ORGANISM: Glycine max

<400> SEQUENCE: 218
ggagaacaug cagagcuucu g         21

<210> SEQ ID NO 219
<211> LENGTH: 21
<212> TYPE: RNA
<213> ORGANISM: Glycine max

<400> SEQUENCE: 219
ugagaaacug gggagcuuuu c         21

<210> SEQ ID NO 220
<211> LENGTH: 20
<212> TYPE: RNA
<213> ORGANISM: Glycine max

<400> SEQUENCE: 220
ugagaacugg ugagcuucug                                              20

<210> SEQ ID NO 221
<211> LENGTH: 20
<212> TYPE: RNA
<213> ORGANISM: Glycine max

<400> SEQUENCE: 221
ugaguacugg ggagcuucuc                                              20

<210> SEQ ID NO 222
<211> LENGTH: 21
<212> TYPE: RNA
<213> ORGANISM: Glycine max

<400> SEQUENCE: 222
ugagagcaug gguaacuucu a                                            21

<210> SEQ ID NO 223
<211> LENGTH: 20
<212> TYPE: RNA
<213> ORGANISM: Glycine max

<400> SEQUENCE: 223
ugagcacugg ggagcuucuc                                              20

<210> SEQ ID NO 224
<211> LENGTH: 20
<212> TYPE: RNA
<213> ORGANISM: Glycine max

<400> SEQUENCE: 224
ugagcacugg ggagcuucuc                                              20

<210> SEQ ID NO 225
<211> LENGTH: 20
<212> TYPE: RNA
<213> ORGANISM: Glycine max

<400> SEQUENCE: 225
ugagcacugg ggagcuucuc                                              20

<210> SEQ ID NO 226
<211> LENGTH: 21
<212> TYPE: RNA
<213> ORGANISM: Glycine max

<400> SEQUENCE: 226
ugagaacaug ggaacuuucu a                                            21

<210> SEQ ID NO 227
<211> LENGTH: 21
<212> TYPE: RNA
<213> ORGANISM: Glycine max

<400> SEQUENCE: 227
ugagagcaug gguaacuucu a                                            21

<210> SEQ ID NO 228
<211> LENGTH: 21
<212> TYPE: RNA
<213> ORGANISM: Glycine max

<400> SEQUENCE: 228

-continued ugagaaccug guaagcuucu g               21

<210> SEQ ID NO 229
<211> LENGTH: 21
<212> TYPE: RNA
<213> ORGANISM: Glycine max

<400> SEQUENCE: 229
ugagaacauc gaaagcuucu u               21

<210> SEQ ID NO 230
<211> LENGTH: 21
<212> TYPE: RNA
<213> ORGANISM: Glycine max

<400> SEQUENCE: 230
ugaggacaag gggagcuuau g               21

<210> SEQ ID NO 231
<211> LENGTH: 21
<212> TYPE: RNA
<213> ORGANISM: Glycine max

<400> SEQUENCE: 231
cuaaaacaug gggagcuucu u               21

<210> SEQ ID NO 232
<211> LENGTH: 21
<212> TYPE: RNA
<213> ORGANISM: Glycine max

<400> SEQUENCE: 232
ugaggaaaua gggaguuucu g               21

<210> SEQ ID NO 233
<211> LENGTH: 21
<212> TYPE: RNA
<213> ORGANISM: Glycine max

<400> SEQUENCE: 233
ugagaacaua gugaguuuuu u               21

<210> SEQ ID NO 234
<211> LENGTH: 21
<212> TYPE: RNA
<213> ORGANISM: Glycine max

<400> SEQUENCE: 234
uaggaucgug gggagcuucu c               21

<210> SEQ ID NO 235
<211> LENGTH: 21
<212> TYPE: RNA
<213> ORGANISM: Glycine max

<400> SEQUENCE: 235
uaggaucgug gggagcuucu c               21

<210> SEQ ID NO 236
<211> LENGTH: 21
<212> TYPE: RNA
<213> ORGANISM: Glycine max

```
<400> SEQUENCE: 236
uaggaucgug gggagcuucu c                                              21

<210> SEQ ID NO 237
<211> LENGTH: 21
<212> TYPE: RNA
<213> ORGANISM: Glycine max

<400> SEQUENCE: 237
gaugaauaug gggaguuucu a                                              21

<210> SEQ ID NO 238
<211> LENGTH: 21
<212> TYPE: RNA
<213> ORGANISM: Glycine max

<400> SEQUENCE: 238
ggggcaagga cauccgcaac g                                              21

<210> SEQ ID NO 239
<211> LENGTH: 21
<212> TYPE: RNA
<213> ORGANISM: Glycine max

<400> SEQUENCE: 239
aaggcaaagu ugcccgcgac g                                              21

<210> SEQ ID NO 240
<211> LENGTH: 21
<212> TYPE: RNA
<213> ORGANISM: Glycine max

<400> SEQUENCE: 240
gaggcaaaga ugcgagcaac g                                              21

<210> SEQ ID NO 241
<211> LENGTH: 21
<212> TYPE: RNA
<213> ORGANISM: Glycine max

<400> SEQUENCE: 241
gcggcaaaga uacucacaac c                                              21

<210> SEQ ID NO 242
<211> LENGTH: 21
<212> TYPE: RNA
<213> ORGANISM: Glycine max

<400> SEQUENCE: 242
aacgcaaaga gaccuguaac a                                              21

<210> SEQ ID NO 243
<211> LENGTH: 21
<212> TYPE: RNA
<213> ORGANISM: Glycine max

<400> SEQUENCE: 243
aaggcaaaga ugccagcgac g                                              21

<210> SEQ ID NO 244
<211> LENGTH: 21
<212> TYPE: RNA
<213> ORGANISM: Glycine max
```

```
<400> SEQUENCE: 244
gagccaaaga gacccgugac g                                              21

<210> SEQ ID NO 245
<211> LENGTH: 21
<212> TYPE: RNA
<213> ORGANISM: Glycine max

<400> SEQUENCE: 245
aaggcauaga uagucgcagc a                                              21

<210> SEQ ID NO 246
<211> LENGTH: 21
<212> TYPE: RNA
<213> ORGANISM: Glycine max

<400> SEQUENCE: 246
aaggcaaaga ugccagcaau g                                              21

<210> SEQ ID NO 247
<211> LENGTH: 21
<212> TYPE: RNA
<213> ORGANISM: Glycine max

<400> SEQUENCE: 247
uagggaaaga uacauguaac a                                              21

<210> SEQ ID NO 248
<211> LENGTH: 21
<212> TYPE: RNA
<213> ORGANISM: Glycine max

<400> SEQUENCE: 248
gaggcaaagu uguucgcaau g                                              21

<210> SEQ ID NO 249
<211> LENGTH: 21
<212> TYPE: RNA
<213> ORGANISM: Glycine max

<400> SEQUENCE: 249
caggcaaaga ugucugcaau u                                              21

<210> SEQ ID NO 250
<211> LENGTH: 21
<212> TYPE: RNA
<213> ORGANISM: Glycine max

<400> SEQUENCE: 250
uagguaugga uacuugcaac a                                              21

<210> SEQ ID NO 251
<211> LENGTH: 21
<212> TYPE: RNA
<213> ORGANISM: Glycine max

<400> SEQUENCE: 251
aaggcaaagc ugcccgcgau g                                              21

<210> SEQ ID NO 252
<211> LENGTH: 21
<212> TYPE: RNA
```

```
<213> ORGANISM: Glycine max

<400> SEQUENCE: 252
ucaggggagg agacacucgc a                                              21

<210> SEQ ID NO 253
<211> LENGTH: 21
<212> TYPE: RNA
<213> ORGANISM: Glycine max

<400> SEQUENCE: 253
uuagaggcaa agacacucgu c                                              21

<210> SEQ ID NO 254
<211> LENGTH: 21
<212> TYPE: RNA
<213> ORGANISM: Glycine max

<400> SEQUENCE: 254
ucagaggaga agauacucgu g                                              21

<210> SEQ ID NO 255
<211> LENGTH: 21
<212> TYPE: RNA
<213> ORGANISM: Glycine max

<400> SEQUENCE: 255
ucagaggaga agacacgcgc a                                              21

<210> SEQ ID NO 256
<211> LENGTH: 21
<212> TYPE: RNA
<213> ORGANISM: Glycine max

<400> SEQUENCE: 256
ucagagggga agacacacgc u                                              21

<210> SEQ ID NO 257
<211> LENGTH: 21
<212> TYPE: RNA
<213> ORGANISM: Glycine max

<400> SEQUENCE: 257
ucagagggga agacacacgc u                                              21

<210> SEQ ID NO 258
<211> LENGTH: 21
<212> TYPE: RNA
<213> ORGANISM: Glycine max

<400> SEQUENCE: 258
ucagagguga ggacacacgc u                                              21

<210> SEQ ID NO 259
<211> LENGTH: 21
<212> TYPE: RNA
<213> ORGANISM: Glycine max

<400> SEQUENCE: 259
ccagaggcgg augcauucgc a                                              21

<210> SEQ ID NO 260
<211> LENGTH: 21
```

```
<212> TYPE: RNA
<213> ORGANISM: Glycine max

<400> SEQUENCE: 260
acagaggcag ggacacuugc a                                              21

<210> SEQ ID NO 261
<211> LENGTH: 21
<212> TYPE: RNA
<213> ORGANISM: Glycine max

<400> SEQUENCE: 261
gcagagguga agaagcuugc a                                              21

<210> SEQ ID NO 262
<211> LENGTH: 21
<212> TYPE: RNA
<213> ORGANISM: Glycine max

<400> SEQUENCE: 262
uuagaggaga ggauacucgc g                                              21

<210> SEQ ID NO 263
<211> LENGTH: 21
<212> TYPE: RNA
<213> ORGANISM: Glycine max

<400> SEQUENCE: 263
gcagagguga agaagcuugc a                                              21

<210> SEQ ID NO 264
<211> LENGTH: 21
<212> TYPE: RNA
<213> ORGANISM: Glycine max

<400> SEQUENCE: 264
ucagaggcaa agauacccgc a                                              21

<210> SEQ ID NO 265
<211> LENGTH: 21
<212> TYPE: RNA
<213> ORGANISM: Glycine max

<400> SEQUENCE: 265 uuagaggga agacacgcgc u                                               21

<210> SEQ ID NO 266
<211> LENGTH: 21
<212> TYPE: RNA
<213> ORGANISM: Glycine max

<400> SEQUENCE: 266
ucagagggga agacacccgu g                                              21

<210> SEQ ID NO 267
<211> LENGTH: 21
<212> TYPE: RNA
<213> ORGANISM: Glycine max

<400> SEQUENCE: 267
ucagaggcua agagacuugu a                                              21

<210> SEQ ID NO 268
```

```
<211> LENGTH: 21
<212> TYPE: RNA
<213> ORGANISM: Glycine max

<400> SEQUENCE: 268
ucagagggga agacacgcgu g                                              21

<210> SEQ ID NO 269
<211> LENGTH: 21
<212> TYPE: RNA
<213> ORGANISM: Glycine max

<400> SEQUENCE: 269
ucagagggga agacacccgu g                                              21

<210> SEQ ID NO 270
<211> LENGTH: 21
<212> TYPE: RNA
<213> ORGANISM: Glycine max

<400> SEQUENCE: 270
ucagagggga agacacacgu u                                              21

<210> SEQ ID NO 271
<211> LENGTH: 21
<212> TYPE: RNA
<213> ORGANISM: Glycine max

<400> SEQUENCE: 271
ucagagggga agacacacgu u                                              21

<210> SEQ ID NO 272
<211> LENGTH: 21
<212> TYPE: RNA
<213> ORGANISM: Glycine max

<400> SEQUENCE: 272
ucagggguga agacacacgu a                                              21

<210> SEQ ID NO 273
<211> LENGTH: 21
<212> TYPE: RNA
<213> ORGANISM: Glycine max

<400> SEQUENCE: 273
ucagagggga agacacccgu g                                              21

<210> SEQ ID NO 274
<211> LENGTH: 21
<212> TYPE: RNA
<213> ORGANISM: Glycine max

<400> SEQUENCE: 274
ucagaaacga agacgcucgu u                                              21

<210> SEQ ID NO 275
<211> LENGTH: 21
<212> TYPE: RNA
<213> ORGANISM: Glycine max

<400> SEQUENCE: 275
uccgagggga agauacucgu u                                              21
```

```
<210> SEQ ID NO 276
<211> LENGTH: 21
<212> TYPE: RNA
<213> ORGANISM: Glycine max

<400> SEQUENCE: 276
uccgagggga agauacucgu c                                              21

<210> SEQ ID NO 277
<211> LENGTH: 21
<212> TYPE: RNA
<213> ORGANISM: Glycine max

<400> SEQUENCE: 277
uccgagggga agauacucgu c                                              21

<210> SEQ ID NO 278
<211> LENGTH: 21
<212> TYPE: RNA
<213> ORGANISM: Glycine max

<400> SEQUENCE: 278
gcagaggcug uggcacucgc a                                              21

<210> SEQ ID NO 279
<211> LENGTH: 21
<212> TYPE: RNA
<213> ORGANISM: Glycine max

<400> SEQUENCE: 279
uuagaggcga ggacacacgu u                                              21

<210> SEQ ID NO 280
<211> LENGTH: 21
<212> TYPE: RNA
<213> ORGANISM: Glycine max

<400> SEQUENCE: 280
uccgaggaga agauacucgu u                                              21

<210> SEQ ID NO 281
<211> LENGTH: 21
<212> TYPE: RNA
<213> ORGANISM: Glycine max

<400> SEQUENCE: 281
ucaguggcga aggcguucgu c                                              21

<210> SEQ ID NO 282
<211> LENGTH: 21
<212> TYPE: RNA
<213> ORGANISM: Glycine max

<400> SEQUENCE: 282
uuagagguga uggcacucgu g                                              21

<210> SEQ ID NO 283
<211> LENGTH: 22
<212> TYPE: RNA
<213> ORGANISM: Glycine max

<400> SEQUENCE: 283
ggggaauggg uggaaacggc aa                                             22
```

```
<210> SEQ ID NO 284
<211> LENGTH: 22
<212> TYPE: RNA
<213> ORGANISM: Glycine max

<400> SEQUENCE: 284
ugggaugggu gggaugggu aa                                                    22

<210> SEQ ID NO 285
<211> LENGTH: 22
<212> TYPE: RNA
<213> ORGANISM: Glycine max

<400> SEQUENCE: 285
ugggaugggu gggaugggu aa                                                    22

<210> SEQ ID NO 286
<211> LENGTH: 22
<212> TYPE: RNA
<213> ORGANISM: Glycine max

<400> SEQUENCE: 286
auggaacugg uggaauuggc aa                                                   22

<210> SEQ ID NO 287
<211> LENGTH: 22
<212> TYPE: RNA
<213> ORGANISM: Glycine max

<400> SEQUENCE: 287
cgggaaaggu uggaauuggc aa                                                   22

<210> SEQ ID NO 288
<211> LENGTH: 22
<212> TYPE: RNA
<213> ORGANISM: Glycine max

<400> SEQUENCE: 288 uaggaaugggu uggauuuugc aa                                                  22

<210> SEQ ID NO 289
<211> LENGTH: 20
<212> TYPE: RNA
<213> ORGANISM: Glycine max

<400> SEQUENCE: 289
ggaaugggug gcgugggcaa                                                      20

<210> SEQ ID NO 290
<211> LENGTH: 22
<212> TYPE: RNA
<213> ORGANISM: Glycine max

<400> SEQUENCE: 290
caggaaaggg gggaguuggc aa                                                   22

<210> SEQ ID NO 291
<211> LENGTH: 22
<212> TYPE: RNA
<213> ORGANISM: Glycine max

<400> SEQUENCE: 291
uagcaauggg uuggaucggu ga                                                   22
```

-continued

<210> SEQ ID NO 292
<211> LENGTH: 22
<212> TYPE: RNA
<213> ORGANISM: Glycine max

<400> SEQUENCE: 292
guugaauggg uggaauugga aa                    22

<210> SEQ ID NO 293
<211> LENGTH: 22
<212> TYPE: RNA
<213> ORGANISM: Glycine max

<400> SEQUENCE: 293
guugaauggg uggaauugga aa                    22

<210> SEQ ID NO 294
<211> LENGTH: 22
<212> TYPE: RNA
<213> ORGANISM: Glycine max

<400> SEQUENCE: 294
aaggaauugg gggaauuggu ac                    22

<210> SEQ ID NO 295
<211> LENGTH: 22
<212> TYPE: RNA
<213> ORGANISM: Glycine max

<400> SEQUENCE: 295
cacgaguggg gggaaucggc gg                    22

<210> SEQ ID NO 296
<211> LENGTH: 22
<212> TYPE: RNA
<213> ORGANISM: Glycine max

<400> SEQUENCE: 296
guggaauggg uggucuuggu aa                    22

<210> SEQ ID NO 297
<211> LENGTH: 21
<212> TYPE: RNA
<213> ORGANISM: Zea mays

<400> SEQUENCE: 297
ugacagaaga gagagagcac a                     21

<210> SEQ ID NO 298
<211> LENGTH: 20
<212> TYPE: RNA
<213> ORGANISM: artificial sequence
<220> FEATURE:
<223> OTHER INFORMATION: Synthetic construct

<400> SEQUENCE: 298
gugcucucuc ucuucuguca                       20

<210> SEQ ID NO 299
<211> LENGTH: 20
<212> TYPE: RNA
<213> ORGANISM: artificial sequence
<220> FEATURE:

<223> OTHER INFORMATION: Synthetic construct

<400> SEQUENCE: 299
cugcucucuc ucuucuguca                                           20

<210> SEQ ID NO 300
<211> LENGTH: 20
<212> TYPE: RNA
<213> ORGANISM: artificial sequence
<220> FEATURE:
<223> OTHER INFORMATION: Synthetic construct

<400> SEQUENCE: 300
uugcuuacuc ucuucuguca                                           20

<210> SEQ ID NO 301
<211> LENGTH: 20
<212> TYPE: RNA
<213> ORGANISM: artificial sequence
<220> FEATURE:
<223> OTHER INFORMATION: Synthetic construct

<400> SEQUENCE: 301
ccgcucucuc ucuucuguca                                           20

<210> SEQ ID NO 302
<211> LENGTH: 21
<212> TYPE: RNA
<213> ORGANISM: Zea mays

<400> SEQUENCE: 302
cuuggauuga agggagcucc u                                         21

<210> SEQ ID NO 303
<211> LENGTH: 21
<212> TYPE: RNA
<213> ORGANISM: artificial sequence
<220> FEATURE:
<223> OTHER INFORMATION: Synthetic construct

<400> SEQUENCE: 303
uggagcuccc uucauuccaa u                                         21

<210> SEQ ID NO 304
<211> LENGTH: 21
<212> TYPE: RNA
<213> ORGANISM: artificial sequence
<220> FEATURE:
<223> OTHER INFORMATION: Synthetic construct

<400> SEQUENCE: 304
ucgaguuccc uucauuccaa u                                         21

<210> SEQ ID NO 305
<211> LENGTH: 21
<212> TYPE: RNA
<213> ORGANISM: artificial sequence
<220> FEATURE:
<223> OTHER INFORMATION: Synthetic construct

<400> SEQUENCE: 305
augagcucuc uucaaaccaa a                                         21

<210> SEQ ID NO 306
<211> LENGTH: 21

```
<212> TYPE: RNA
<213> ORGANISM: artificial sequence
<220> FEATURE:
<223> OTHER INFORMATION: Synthetic construct

<400> SEQUENCE: 306
uggagcuccc uucauuccaa g                                              21

<210> SEQ ID NO 307
<211> LENGTH: 21
<212> TYPE: RNA
<213> ORGANISM: artificial sequence
<220> FEATURE:
<223> OTHER INFORMATION: Synthetic construct

<400> SEQUENCE: 307
uagagcuucc uucaaaccaa a                                              21

<210> SEQ ID NO 308
<211> LENGTH: 21
<212> TYPE: RNA
<213> ORGANISM: artificial sequence
<220> FEATURE:
<223> OTHER INFORMATION: Synthetic construct

<400> SEQUENCE: 308
uggagcucca uucgauccaa a                                              21

<210> SEQ ID NO 309
<211> LENGTH: 21
<212> TYPE: RNA
<213> ORGANISM: artificial sequence
<220> FEATURE:
<223> OTHER INFORMATION: Synthetic construct

<400> SEQUENCE: 309
agcagcuccc uucaaaccaa a                                              21

<210> SEQ ID NO 310
<211> LENGTH: 21
<212> TYPE: RNA
<213> ORGANISM: artificial sequence
<220> FEATURE:
<223> OTHER INFORMATION: Synthetic construct

<400> SEQUENCE: 310
cagagcuccc uucacuccaa u                                              21

<210> SEQ ID NO 311
<211> LENGTH: 21
<212> TYPE: RNA
<213> ORGANISM: artificial sequence
<220> FEATURE:
<223> OTHER INFORMATION: Synthetic construct

<400> SEQUENCE: 311
uggagcuccc uucacuccaa u                                              21

<210> SEQ ID NO 312
<211> LENGTH: 21
<212> TYPE: RNA
<213> ORGANISM: artificial sequence
<220> FEATURE:
<223> OTHER INFORMATION: Synthetic construct

<400> SEQUENCE: 312
```
uggagcuccc uucacuccaa g                                              21

<210> SEQ ID NO 313
<211> LENGTH: 21
<212> TYPE: RNA
<213> ORGANISM: artificial sequence
<220> FEATURE:
<223> OTHER INFORMATION: Synthetic construct

<400> SEQUENCE: 313
uggagcuccc uuuaauccaa u                                              21

<210> SEQ ID NO 314
<211> LENGTH: 21
<212> TYPE: RNA
<213> ORGANISM: Zea mays

<400> SEQUENCE: 314
ucggaccagg cuucauuccc c                                              21

<210> SEQ ID NO 315
<211> LENGTH: 21
<212> TYPE: RNA
<213> ORGANISM: artificial sequence
<220> FEATURE:
<223> OTHER INFORMATION: Synthetic construct

<400> SEQUENCE: 315
uugggaugaa gccugguccg g                                              21

<210> SEQ ID NO 316
<211> LENGTH: 21
<212> TYPE: RNA
<213> ORGANISM: artificial sequence
<220> FEATURE:
<223> OTHER INFORMATION: Synthetic construct

<400> SEQUENCE: 316
cugggaugaa gccugguccg g                                              21

<210> SEQ ID NO 317
<211> LENGTH: 21
<212> TYPE: RNA
<213> ORGANISM: artificial sequence
<220> FEATURE:
<223> OTHER INFORMATION: Synthetic construct

<400> SEQUENCE: 317
cuggaaugaa gccugguccg g                                              21

<210> SEQ ID NO 318
<211> LENGTH: 21
<212> TYPE: RNA
<213> ORGANISM: artificial sequence
<220> FEATURE:
<223> OTHER INFORMATION: Synthetic construct

<400> SEQUENCE: 318
ccgggaugaa gccugguccg g                                              21

<210> SEQ ID NO 319
<211> LENGTH: 21
<212> TYPE: RNA
<213> ORGANISM: Zea mays

<400> SEQUENCE: 319
ugaagcugcc agcaugaucu g                                                    21

<210> SEQ ID NO 320
<211> LENGTH: 21
<212> TYPE: RNA
<213> ORGANISM: artificial sequence
<220> FEATURE:
<223> OTHER INFORMATION: Synthetic construct

<400> SEQUENCE: 320
gagaucaggc uggcagcuug u                                                    21

<210> SEQ ID NO 321
<211> LENGTH: 21
<212> TYPE: RNA
<213> ORGANISM: artificial sequence
<220> FEATURE:
<223> OTHER INFORMATION: Synthetic construct

<400> SEQUENCE: 321
uagaucaggc uggcagcuug u                                                    21

<210> SEQ ID NO 322
<211> LENGTH: 21
<212> TYPE: RNA
<213> ORGANISM: artificial sequence
<220> FEATURE:
<223> OTHER INFORMATION: Synthetic construct

<400> SEQUENCE: 322
aagaucaggc uggcagcuug u                                                    21

<210> SEQ ID NO 323
<211> LENGTH: 20
<212> TYPE: RNA
<213> ORGANISM: Zea mays

<400> SEQUENCE: 323
ugacagaaga gagugagcac                                                      20

<210> SEQ ID NO 324
<211> LENGTH: 20
<212> TYPE: RNA
<213> ORGANISM: artificial sequence
<220> FEATURE:
<223> OTHER INFORMATION: Synthetic construct

<400> SEQUENCE: 324
gugcucucuc ucuucuguca                                                      20

<210> SEQ ID NO 325
<211> LENGTH: 20
<212> TYPE: RNA
<213> ORGANISM: artificial sequence
<220> FEATURE:
<223> OTHER INFORMATION: Synthetic construct

<400> SEQUENCE: 325
cugcucucuc ucuucuguca                                                      20

<210> SEQ ID NO 326
<211> LENGTH: 20
<212> TYPE: RNA
<213> ORGANISM: artificial sequence
<220> FEATURE:

<223> OTHER INFORMATION: Synthetic construct

<400> SEQUENCE: 326
uugcuuacuc ucuucuguca                                          20

<210> SEQ ID NO 327
<211> LENGTH: 20
<212> TYPE: RNA
<213> ORGANISM: artificial sequence
<220> FEATURE:
<223> OTHER INFORMATION: Synthetic construct

<400> SEQUENCE: 327
ccgcucucuc ucuucuguca                                          20

<210> SEQ ID NO 328
<211> LENGTH: 21
<212> TYPE: RNA
<213> ORGANISM: Zea mays

<400> SEQUENCE: 328
ugccuggcuc ccuguaugcc a                                        21

<210> SEQ ID NO 329
<211> LENGTH: 21
<212> TYPE: RNA
<213> ORGANISM: artificial sequence
<220> FEATURE:
<223> OTHER INFORMATION: Synthetic construct

<400> SEQUENCE: 329
uggcaugcag ggagccaggc a                                        21

<210> SEQ ID NO 330
<211> LENGTH: 21
<212> TYPE: RNA
<213> ORGANISM: artificial sequence
<220> FEATURE:
<223> OTHER INFORMATION: Synthetic construct

<400> SEQUENCE: 330
aggaauacag ggagccaggc a                                        21

<210> SEQ ID NO 331
<211> LENGTH: 21
<212> TYPE: RNA
<213> ORGANISM: artificial sequence
<220> FEATURE:
<223> OTHER INFORMATION: Synthetic construct

<400> SEQUENCE: 331
ggguuuacag ggagccaggc a                                        21

<210> SEQ ID NO 332
<211> LENGTH: 21
<212> TYPE: RNA
<213> ORGANISM: artificial sequence
<220> FEATURE:
<223> OTHER INFORMATION: Synthetic construct

<400> SEQUENCE: 332
aggcauacag ggagccaggc a                                        21

<210> SEQ ID NO 333
<211> LENGTH: 22

```
<212> TYPE: RNA
<213> ORGANISM: Zea mays

<400> SEQUENCE: 333
uccaaaggga ucgcauugau cu                                              22

<210> SEQ ID NO 334
<211> LENGTH: 21
<212> TYPE: RNA
<213> ORGANISM: artificial sequence
<220> FEATURE:
<223> OTHER INFORMATION: Synthetic construct

<400> SEQUENCE: 334
aaacaaugcg aucccuuugg a                                               21

<210> SEQ ID NO 335
<211> LENGTH: 21
<212> TYPE: RNA
<213> ORGANISM: artificial sequence
<220> FEATURE:
<223> OTHER INFORMATION: Synthetic construct

<400> SEQUENCE: 335
agaccaugcg aucccuuugg a                                               21

<210> SEQ ID NO 336
<211> LENGTH: 21
<212> TYPE: RNA
<213> ORGANISM: artificial sequence
<220> FEATURE:
<223> OTHER INFORMATION: Synthetic construct

<400> SEQUENCE: 336
ggucagagcg aucccuuugg c                                               21

<210> SEQ ID NO 337
<211> LENGTH: 21
<212> TYPE: RNA
<213> ORGANISM: artificial sequence
<220> FEATURE:
<223> OTHER INFORMATION: Synthetic construct

<400> SEQUENCE: 337
agacaaugcg aucccuuugg a                                               21

<210> SEQ ID NO 338
<211> LENGTH: 21
<212> TYPE: RNA
<213> ORGANISM: Zea mays

<400> SEQUENCE: 338
uuccacagcu uucuugaacu g                                               21

<210> SEQ ID NO 339
<211> LENGTH: 22
<212> TYPE: RNA
<213> ORGANISM: artificial sequence
<220> FEATURE:
<223> OTHER INFORMATION: Synthetic construct

<400> SEQUENCE: 339
ucguucaaga aagccugugg aa                                              22

<210> SEQ ID NO 340
```

```
<211> LENGTH: 22
<212> TYPE: RNA
<213> ORGANISM: artificial sequence
<220> FEATURE:
<223> OTHER INFORMATION: Synthetic construct

<400> SEQUENCE: 340
ccguucaaga aagccugugg aa                                              22

<210> SEQ ID NO 341
<211> LENGTH: 22
<212> TYPE: RNA
<213> ORGANISM: artificial sequence
<220> FEATURE:
<223> OTHER INFORMATION: Synthetic construct

<400> SEQUENCE: 341
ucguucaaga aagcaugugg aa                                              22

<210> SEQ ID NO 342
<211> LENGTH: 22
<212> TYPE: RNA
<213> ORGANISM: artificial sequence
<220> FEATURE:
<223> OTHER INFORMATION: Synthetic construct

<400> SEQUENCE: 342
acguucaaga aagcuugugg aa                                              22

<210> SEQ ID NO 343
<211> LENGTH: 22
<212> TYPE: RNA
<213> ORGANISM: artificial sequence
<220> FEATURE:
<223> OTHER INFORMATION: Synthetic construct

<400> SEQUENCE: 343
ccguucaaga aagccugugg aa                                              22

<210> SEQ ID NO 344
<211> LENGTH: 1368
<212> TYPE: DNA
<213> ORGANISM: Agrobacterium tumefaciens

<400> SEQUENCE: 344
atgcttcacg gtgcaagcag ccgtccagca actgctcgta agtcctctgg tctttctgga    60
accgtccgta ttccaggtga caagtctatc tcccacaggt ccttcatgtt tggaggtctc   120
gctagcggtg aaactcgtat caccggtctt ttggaaggtg aagatgttat caacactggt   180
aaggctatgc aagctatggg tgccagaatc cgtaaggaag gtgatacttg gatcattgat   240
ggtgttggta acggtggact ccttgctcct gaggctcctc tcgatttcgg taacgctgca   300
actggttgcc gtttgactat gggtcttgtt ggtgtttacg atttcgatag cactttcatt   360
ggtgacgctt ctctcactaa gcgtccaatg ggtcgtgtgt tgaacccact tcgcgaaatg   420
ggtgtgcagg tgaagtctga agacggtgat cgtcttccag ttaccttgcg tggaccaaag   480
actccaacgc caatcaccta cagggtacct atggcttccg ctcaagtgaa gtccgctgtt   540
ctgcttgctg gtctcaacac cccaggtatc accactgtta tcgagccaat catgactcgt   600
gaccacactg aaaagatgct tcaaggtttt ggtgctaacc ttaccgttga gactgatgct   660
gacggtgtgc gtaccatccg tcttgaaggt cgtggtaagc tcaccggtca agtgattgat   720
gttccaggtg atccatcctc tactgctttc ccattggttg ctgccttgct tgttccaggt   780
```

```
tccgacgtca ccatccttaa cgttttgatg aacccaaccc gtactggtct catcttgact    840
ctgcaggaaa tgggtgccga catcgaagtg atcaacccac gtcttgctgg tggagaagac    900
gtggctgact tgcgtgttcg ttcttctact ttgaagggtg ttactgttcc agaagaccgt    960
gctccttcta tgatcgacga gtatccaatt ctcgctgttg cagctgcatt cgctgaaggt   1020
gctaccgtta tgaacggttt ggaagaactc cgtgttaagg aaagcgaccg tctttctgct   1080
gtcgcaaacg gtctcaagct caacggtgtt gattgcgatg aaggtgagac ttctctcgtc   1140
gtgcgtggtc gtcctgacgg taagggtctc ggtaacgctt ctggagcagc tgtcgctacc   1200
cacctcgatc accgtatcgc tatgagcttc ctcgttatgg gtctcgtttc tgaaaaccct   1260
gttactgttg atgatgctac tatgatcgct actagcttcc cagagttcat ggatttgatg   1320
gctggtcttg gagctaagat cgaactctcc gacactaagg ctgcttga               1368
```

<210> SEQ ID NO 345
<211> LENGTH: 42
<212> TYPE: DNA
<213> ORGANISM: artificial sequence
<220> FEATURE:
<223> OTHER INFORMATION: Synthetic construct

<400> SEQUENCE: 345

```
tgagctcaag aattcgagct cggtaccgga tcctctagct ag                       42
```

<210> SEQ ID NO 346
<211> LENGTH: 63
<212> TYPE: DNA
<213> ORGANISM: artificial sequence
<220> FEATURE:
<223> OTHER INFORMATION: Synthetic construct

<400> SEQUENCE: 346

```
tgagctcaag aattcgaaga caatgcgatc ccuuuggagc tcggtaccgg atcctctagc    60
tag                                                                  63
```

<210> SEQ ID NO 347
<211> LENGTH: 63
<212> TYPE: DNA
<213> ORGANISM: artificial sequence
<220> FEATURE:
<223> OTHER INFORMATION: Synthetic construct

<400> SEQUENCE: 347

```
tgagctcaag aattcgatcc gctttctctc ttctgtcagc tcggtaccgg atcctctagc    60
tag                                                                  63
```